(12) United States Patent
Lee et al.

(10) Patent No.: US 8,207,166 B2
(45) Date of Patent: Jun. 26, 2012

(54) SUBSTITUTED PYRAZOLYL UREA DERIVATIVES USEFUL IN THE TREATMENT OF CANCER

(75) Inventors: Wendy Lee, South San Francisco, CA (US); Gaetan Ladouceur, Guilford, CT (US); Jacques Dumas, Waltham, MA (US); Roger Smith, Madison, CT (US); Shihong Ying, Orange, CT (US); Gan Wang, Wallingford, CT (US); Zhi Chen, Lyndhurst, NJ (US); Qingjie Liu, Orange, CT (US); Holia Mokdad, Guilford, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

(21) Appl. No.: 12/941,841

(22) Filed: Nov. 8, 2010

(65) Prior Publication Data

US 2011/0136809 A1   Jun. 9, 2011

Related U.S. Application Data

(62) Division of application No. 11/579,093, filed as application No. PCT/US2005/015106 on May 2, 2005, now Pat. No. 7,838,524.

(60) Provisional application No. 60/566,445, filed on Apr. 30, 2004.

(51) Int. Cl.
*A61K 31/5377* (2006.01)
*A61K 31/4439* (2006.01)
*A61K 31/454* (2006.01)
*A61K 31/497* (2006.01)

(52) U.S. Cl. .......... 514/235.8; 514/253.01; 514/326; 514/341; 546/194; 546/272.7; 546/275.4; 544/124; 544/360

(58) Field of Classification Search ............ 514/235.8, 514/253.01, 326, 341; 544/124, 360; 546/194, 546/272.7, 275.4
See application file for complete search history.

(56) References Cited

U.S. PATENT DOCUMENTS

| | | | |
|---|---|---|---|
| 3,284,433 A | 11/1966 | Becker et al. |
| 3,424,760 A | 1/1969 | Helsley et al. |
| 3,424,761 A | 1/1969 | Helsley et al. |
| 3,424,762 A | 1/1969 | Helsley et al. |
| 3,547,940 A | 12/1970 | Brantley |
| 3,646,059 A | 2/1972 | Brantley |
| 3,743,498 A | 7/1973 | Brantley |
| 3,754,887 A | 8/1973 | Brantley |
| 3,823,161 A | 7/1974 | Lesser |
| 3,828,001 A | 8/1974 | Broad et al. |
| 4,001,256 A | 1/1977 | Callahan et al. |
| 4,009,847 A | 3/1977 | Aldrich et al. |
| 4,062,861 A | 12/1977 | Yukinaga et al. |
| 4,111,680 A | 9/1978 | Yukinaga et al. |
| 4,116,671 A | 9/1978 | Yukinaga et al. |
| 4,173,637 A | 11/1979 | Nishiyama et al. |
| 4,173,638 A | 11/1979 | Nishiyama et al. |
| 4,212,981 A | 7/1980 | Yukinaga et al. |
| 4,240,820 A | 12/1980 | Dickore et al. |
| 4,405,644 A | 9/1983 | Kabbe et al. |
| 4,437,878 A | 3/1984 | Acker et al. |
| 4,468,380 A | 8/1984 | O'Doherty et al. |
| 4,526,997 A | 7/1985 | O'Doherty et al. |
| 4,623,662 A | 11/1986 | DeVries |
| 4,808,588 A | 2/1989 | King |
| 4,820,871 A | 4/1989 | Kissener et al. |
| 4,983,605 A | 1/1991 | Kondo et al. |
| 5,059,614 A | 10/1991 | Lepage et al. |
| 5,162,360 A | 11/1992 | Creswell et al. |
| 5,185,358 A | 2/1993 | Creswell et al. |
| 5,312,820 A | 5/1994 | Ashton et al. |
| 5,447,957 A | 9/1995 | Adams et al. |
| 5,559,137 A | 9/1996 | Adams et al. |
| 5,597,719 A | 1/1997 | Freed et al. |
| 5,658,903 A | 8/1997 | Adams et al. |
| 5,710,094 A | 1/1998 | Minami et al. |
| 6,022,884 A | 2/1998 | Mantlo et al. |

(Continued)

FOREIGN PATENT DOCUMENTS

DE    511 468 C1    10/1930

(Continued)

OTHER PUBLICATIONS

Golub et al. Science (1999), vol. 286 531-537.*
Lala et al. Cancer and Metastasis Reviews (1998), 17(1), 91-106.*
Abstract of EP 16,371, Oct. 1, 1980.
Abstract of EP 0405233A1, Tetsuo Sekiya et al.
Abstract of WO 9822103, Hedge May 28, 1998, Philip et al.
Chemical Abstract, vol. 116, No. 21, May 25, 1992, (pp. 741-742) N 116:214456.
Tarzia, G. et al., "Synthesis and anit-inflammatory properties of some pyrrolo(1H,3H) [3,4d]pyrimidin-2-ones and pyrrolo(1H,6H)[3,4-d]pyrimidin-2-ones," *Chemical Abstracts*, vol. 91, 1979, 91:74558.

(Continued)

*Primary Examiner* — Rebecca Anderson
*Assistant Examiner* — Samantha Shterengarts
(74) *Attorney, Agent, or Firm* — Millen, White, Zelano & Branigan, PC

(57) ABSTRACT

The present invention relates to compounds of formula (I), pharmaceutical compositions which contain them and methods for treating cancer using compounds of formula (I).

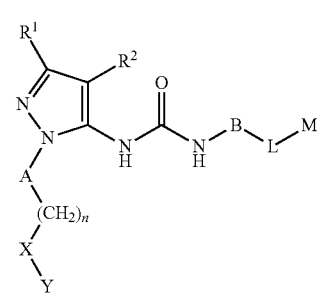

(I)

6 Claims, No Drawings

U.S. PATENT DOCUMENTS

| | | | |
|---|---|---|---|
| 5,773,459 A | 6/1998 | Tang et al. |
| 5,780,483 A | 7/1998 | Widdowson et al. |
| 5,808,080 A | 9/1998 | Bell et al. |
| 5,886,044 A | 3/1999 | Widdowson et al. |
| 5,891,895 A | 4/1999 | Shiraishi et al. |
| 6,005,008 A | 12/1999 | Widdowson et al. |
| 6,015,908 A | 1/2000 | Widdowson et al. |
| 6,080,763 A | 6/2000 | Regan et al. |
| 6,093,742 A | 7/2000 | Salituro et al. |
| 6,133,319 A | 10/2000 | Widdowson |
| 6,174,901 B1 | 1/2001 | Mantlo et al. |
| 6,187,799 B1 | 2/2001 | Wood et al. |
| 6,211,373 B1 | 4/2001 | Widdowson et al. |
| 6,218,539 B1 | 4/2001 | Widdowson |
| 6,262,113 B1 | 7/2001 | Widdowson et al. |
| 6,271,261 B1 | 8/2001 | Widdowson |
| 6,297,381 B1 | 10/2001 | Cirillo et al. |
| 6,329,415 B1 | 12/2001 | Cirillo et al. |
| 6,333,341 B1 | 12/2001 | Mantlo et al. |
| 6,339,045 B1 | 1/2002 | Kanno et al. |
| 6,344,476 B1 | 2/2002 | Ranges et al. |
| 6,358,945 B1 | 3/2002 | Breitfelder et al. |
| 6,372,773 B1 | 4/2002 | Regan |
| 6,380,218 B1 | 4/2002 | Marfat et al. |
| 6,492,393 B1 | 12/2002 | Breitfelder et al. |
| 6,525,046 B1 | 2/2003 | Cirillo et al. |
| 6,583,282 B1 | 6/2003 | Zhang et al. |
| 6,608,052 B2 | 8/2003 | Breitfelder et al. |
| 6,916,814 B2 | 7/2005 | Moss |
| 7,041,669 B2 * | 5/2006 | Cirillo et al. ............... 514/236.5 |
| 7,329,670 B1 | 2/2008 | Dumas et al. |
| 2002/0065283 A1 | 5/2002 | McMahon et al. |
| 2002/0065296 A1 | 5/2002 | Dumas et al. |
| 2002/0165349 A1 | 11/2002 | Kirsch et al. |
| 2002/0165394 A1 | 11/2002 | Dumas et al. |
| 2002/0173507 A1 | 11/2002 | Santora et al. |
| 2003/0125359 A1 | 7/2003 | Lyons et al. |
| 2003/0144278 A1 | 7/2003 | Riedl et al. |
| 2003/0207872 A1 | 11/2003 | Riedl et al. |
| 2003/0207914 A1 | 11/2003 | Dumas et al. |
| 2003/0232400 A1 | 12/2003 | Radka et al. |
| 2004/0023961 A1 | 2/2004 | Dumas |
| 2004/0209905 A1 | 10/2004 | Kubo et al. |

FOREIGN PATENT DOCUMENTS

| | | |
|---|---|---|
| DE | 35 29 247 A1 | 2/1987 |
| DE | 3529247 A1 | 2/1987 |
| DE | 35 40 377 A1 | 5/1987 |
| EP | 0016371 A1 | 10/1980 |
| EP | 0202538 A1 | 11/1986 |
| EP | 0335156 A1 | 10/1989 |
| EP | 0379915 A1 | 8/1990 |
| EP | 0405233 A1 | 1/1991 |
| EP | 0709225 A1 | 5/1996 |
| EP | 0709225 B1 | 5/1996 |
| EP | 0860433 A1 | 8/1998 |
| FR | 1 457 172 A | 9/1966 |
| GB | 1590870 | 6/1981 |
| IR | 26555 | 1/2000 |
| JP | 51-080862 A | 7/1976 |
| JP | 54-032468 A | 9/1979 |
| JP | 61020039 A | 7/1984 |
| LB | 6124 | 1/2000 |
| WO | WO 94/18170 A1 | 8/1994 |
| WO | WO 95/31451 A1 | 11/1995 |
| WO | WO 95/33458 A1 | 12/1995 |
| WO | WO 96/25157 A1 | 8/1996 |
| WO | WO 96/40673 A1 | 12/1996 |
| WO | WO 97/29743 A1 | 8/1997 |
| WO | WO 98/45268 A1 | 10/1998 |
| WO | WO 98/52558 A1 | 11/1998 |
| WO | WO 98/52559 A1 | 11/1998 |
| WO | WO 99/00357 A1 | 1/1999 |
| WO | WO 99/23091 A1 | 5/1999 |
| WO | WO 99/32106 A1 | 7/1999 |
| WO | WO 99/32110 A1 | 7/1999 |
| WO | WO 99/32111 A1 | 7/1999 |
| WO | WO 99/32436 A1 | 7/1999 |
| WO | WO 99/32455 A1 | 7/1999 |
| WO | WO 99/32463 A1 | 7/1999 |
| WO | WO 99/62890 A1 | 12/1999 |
| WO | WO 00/26203 A1 | 5/2000 |
| WO | WO 00/41698 A1 | 7/2000 |
| WO | WO 00/42012 A1 | 7/2000 |
| WO | WO 00/43366 A1 | 7/2000 |
| WO | WO 00/43384 A1 | 7/2000 |
| WO | WO 00/55139 | 9/2000 |
| WO | WO 00/55152 A1 | 9/2000 |
| WO | WO 00/56331 A1 | 9/2000 |
| WO | WO 00/71532 A1 | 11/2000 |
| WO | WO 01/04115 A2 | 1/2001 |
| WO | WO 01/07411 A1 | 2/2001 |
| WO | WO 01/12188 | 2/2001 |
| WO | WO 01/36403 A1 | 5/2001 |
| WO | WO 02/07747 A1 | 1/2002 |
| WO | WO 02/07772 | 1/2002 |
| WO | WO 02/10141 A1 | 2/2002 |
| WO | WO 02/14281 A1 | 2/2002 |
| WO | WO 02/14311 A2 | 2/2002 |
| WO | WO 02/18346 A1 | 3/2002 |
| WO | WO 02/32872 A1 | 4/2002 |
| WO | WO 02/44156 A2 | 6/2002 |
| WO | WO 02/44158 A1 | 6/2002 |
| WO | WO 02/062763 A2 | 8/2002 |
| WO | WO 02/083628 A1 | 10/2002 |
| WO | WO 02/083642 A1 | 10/2002 |
| WO | WO 02/085857 A2 | 10/2002 |
| WO | WO 02/085859 A1 | 10/2002 |
| WO | WO 2002/085857 A2 | 10/2002 |
| WO | WO 03/005999 A | 1/2003 |
| WO | WO 03/005999 A2 | 1/2003 |
| WO | WO 03/047523 A1 | 6/2003 |
| WO | WO 2004/019941 A1 | 7/2003 |
| WO | WO 03/068223 | 8/2003 |
| WO | WO 03/068223 A | 8/2003 |
| WO | WO 03/068228 A1 | 8/2003 |
| WO | WO 03/068229 A1 | 8/2003 |
| WO | WO 03/068746 A1 | 8/2003 |
| WO | WO 2003/094626 A | 9/2003 |
| WO | WO 03/082272 A2 | 10/2003 |
| WO | WO 2004/078746 A2 | 9/2004 |
| WO | WO 2004/078747 A1 | 9/2004 |
| WO | WO 2004/113274 A | 12/2004 |
| WO | WO 2005/002673 A1 | 1/2005 |
| WO | WO 2005/009367 A | 2/2005 |
| WO | WO 2005/009961 A2 | 2/2005 |
| WO | WO 2005/019192 A1 | 3/2005 |
| WO | WO 2005/047283 A1 | 5/2005 |
| WO | WO 2005/048948 A2 | 6/2005 |
| WO | WO 2005/075425 A2 | 8/2005 |
| WO | WO 2005/089443 A | 9/2005 |
| WO | WO 2005/110994 A2 | 11/2005 |
| WO | WO 2006/026501 | 3/2006 |
| WO | WO 2006/034797 A | 4/2006 |
| WO | WO 2006/105844 A1 | 10/2006 |
| WO | WO 2007/015947 A | 2/2007 |
| WO | WO 2007/039403 A1 | 4/2007 |
| WO | WO 2007/064872 A2 | 6/2007 |
| WO | WO 2007/096393 A1 | 8/2007 |
| WO | WO 2007/096395 A1 | 8/2007 |

OTHER PUBLICATIONS

XP-002918005, White, A. D., et al., "Heterocyclic Ureas: Inhibitors of Acyl-CoA:Cholesterol O-Acyltransferase as Hypochelesterolemic Agents," *J. Med. Chem.* 1996, 39, pp. 4382-4395.

XP-000941493, Forbes, Ian T., "N-(1-Methyl-5-indolyl)-N -(3-methyl-5-isothiazolyl)urea: A Novel, High-Affinity 5-HT$_{2B}$ Receptor Antagonist," *Journal of Medicinal Chem.* vol. 38, No. 6, Mar. 17, 1995, pp. 855-857.

XP-000943551, Boulton, A. J., et al., "Heterocyclic Rearrangements. Part X. A Generalised Monocyclic Rearrangement," *J. Chem. Soc.* (C), 1967, pp. 2005-2007.

W. Kolch, et al., "Raf-1 protein kinase is required for growth of induced NIH/3T3 cells," *Letters to Nature*, vol. 349, Jan. 31, 1991, pp. 426-428.

M. Fridman, et al., "The Minimal Fragments of c-Raf-1 and NF1 That Can Suppress v-HaRas-Induced Malignant Phenotype," *The Journal of Biological Chemistry*, vol. 269, No. 48, Dec. 2, 1994, pp. 30105-30108.

G. L. Bolton, et al., Chapter 17. *Ras* Oncogene Directed Approaches in Cancer Chemotherapy, *Annual Reports in Medicinal Chemistry*, vol. 29, 1994, pp. 165-174.

J. L. Bos, "*ras* Oncogenes in Human Cancer: A Review," *Cancer Research*, vol. 49, Sep. 1, 1989, pp. 4682-4689.

Michaelis, Justus, *Liebigs Ann. Chem.* (JLACBF) 397, 1913, p. 143.

International search report for International Application No. PCT/US98/27265.

International search report for International Application No. PCT/US02/12064 dated Sep. 20, 2002, Omega-Carboxypyridyl Substituted Dephenyl Ureas as Raf Kinase Inhibitors, publication No. 02/085859, publication date Oct. 31, 2002.

Publication No. US 2001/0011136 A1, Publication Date: Aug. 2, 2001, Riedl et al.

Publication No. US 2001/0016659 A1, Publication Date: Aug. 23, 2001, Riedl et al.

Publication No. US 2001/0027202 A1, Publication Date: Oct. 4, 2001, Riedl et al.

Publication No. US 2002/0165394 A1, Publication Date: Nov. 7, 2002, Dumas et al.

Publication No. US 2002/0042517 A1, Publication Date: Apr. 11, 2002, Uday et al.

Publication No. US 2001/0034447 A1, Publication Date: Oct. 25, 2001, Riedl et al.

Publication No. US 2001/0011135 A1, Publication Date: Aug. 2, 2001, Riedl et al.

Publication No. US 2002/0103253 A1, Publication Date: Aug. 1, 2002, Ranges et al.

Publication No. US 2001/0006975 A1, Publication Date: Jul. 5, 2001, Wood et al.

Publication No. US 2002/0062763 A1, Publication Date: May 30, 2002, Macholdt et al.

Publication No. US 2002/0085859 A1, Publication Date: Jul. 4, 2002, Hashimoto et al.

Publication No. US 2002/0137774 A1, Publication Date: Sep. 26, 2002, Riedl et al.

XP-001145518 # 4956 Potent *Raf* Kinase Inhibitors from the Diphenylurea Class: Structure Activity Relationships, B. Riedl et al., Bayer Corporation.

XP-001145779 "Antitumor Activity of a C-raf Antisense Oligonucleotide in Combination with Standard Chemotherapeutic Agents against Various Human Tumors Transplanted Subcutaneously into Nude Mice," Thomas Geiger et al., vol. 3, 1179-1185, Jul. 1997.

XP-001145481 #2921 "Phase I and Pharmacokinetic Study of the Raf Kinase Inhibitor Bay 43/9006 in Patients with Locally Advanced or Metastic Cancer," Dirk Strumberg et al., Bayer AG.

XP-002232130, "A Phase I Trial of H-ras Antisense Oligonucleotide ISIS 2503 Administered as a Continuous Intravenous Infusion in Patients with Advanced Carcinoma," C. Casey Cunningham et al., 2001 *American Cancer Society*, vol. 92, No. 5, pp. 1265-1271.

Duam et al., "The Ins and Outs of Raf Kinases," TIBS 19, Nov. 1994, pp. 474-480.

Campbell et al., "Increasing Complexity of Ras Signaling," *Oncogene*, 1998, vol. 17, pp. 1395-1413.

Bolton et al., "Ras Oncogene Directed Approaches in Cancer Chemotherapy," *Annual Reports in Medicinal Chemistry*, vol. 29, pp. 165-174.

Stein, Jay H., MD, Internal Medicine, 4th Edition, 1994, pp. 699-715.

Bos et al., "Ras Oncogenes in Human Cancer: A Review," *Cancer Research*, Sep. 1, 1989, vol. 49, pp. 4682-4689.

Lyons et al., "Discovery of a novel Raf Kinase Inhibitor," *Endocrine-Related Cancer*, 2001, vol. 8, pp. 219-225.

Lowinger et al., "Design and Discovery of Small Molecules Targeting Raf-1 Kinase," *Current Pharmaceutical Design*, 2002, vol. 8, pp. 2269-2278.

Dumas et al., "Recent Developments in the Discovery of Protein Kinase Inhibitors from the Urea Class," *Current Opinion in Drug Discovery & Development*, 2004, vol. 7, No. 5, pp. 600-616.

Dumas et al., "Protein Kinase Inhibitors from the Urea Class," *Current Opinion in Drug Discovery & Development*, 2002, vol. 5, No. 5, pp. 718-727.

Lowinger et al., "Discovery of Novel Class of Potent Raf Kinase Inhibitors: Structure Activity Relationships," *Clinical Cancer Research*, Nov. 2000, vol. 6, p. 4533s.

Hotte et al., "BAY 43-9006: Early Clinical Data in Patients with Advanced Solid Malignancies," *Current Pharmaceutical Design*, 2002, vol. 8, pp. 2249-2253.

Lee et al., "BAY-43-9006: Bayer/Onyx," *Current Opinion in Investigational Drugs*, 2003, vol. 4, No. 6, pp. 757-763.

Sorbara et al., "BAY-43-9006," *Drugs of the Future*, 2002, vol. 27, No. 12, pp. 1141-1147.

Khire et al., "Omega-Carboxypyridyl Substituted Ureas as Raf Kinase Inhibitors: SAR of the Amid Substituent," *Bioorg. Med. Chem. Lett.*, 2004, vol. 14, pp. 783-786.

Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis," *Cancer Research*,. Oct. 1, 2004, vol. 64, pp. 7099-7109.

Smith, et al., "Discovery of Heterocyclic Ureas as a New Class of Raf Kinase Inhibitors: Identification of a Second Generation Lead by a Combinatorial Chemistry Approach." *Bioorganic & Medicinal Chemistry Letters*, 2001, vol. 11, pp. 2775-2778.

Spronsen et al., "Novel Treatment Strategies in Clear-Cell Metastatic renal Cell Carcinoma," *Anti-Cancer Drugs*, 2005, vol. 16, pp. 709-717.

Thaimattam et al., "3D-QSAR CoMFA, CoMSIA Studies on Substituted Ureas as Raf-1 Kinase Inhibitors and its Confirmation with Structure-Based Studies," *Bioorganic & Medicinal Chemistry*, 2004, vol. 12, pp. 6415-6425.

Danson et al., "Improving Outcomes in Advanced Malignant Melanoma," *Drugs*, 2005, vol. 65, No. 6, pp. 733-743.

Hubbard, "Oncogenic Mutations in B-Raf: Some Losses Yield Gains," Skirball Institute of Biomolecular Medicine and Department of Pharmacology, New York University School of Medicine, New York, NY.

Thompson et al., "Recent Progress in Targeting the Raf/MEK/ERK Pathway with Inhibitors in Cancer Drug Discovery," *Curr. Opin. Pharmacol.*, Aug. 2005, vol. 5, No. 4, pp. 350-356.

Wan et al., "Mechanism of Activation of the RAF-ERK Signaling Pathway by Oncogenic Mutations of B-RAF," *cell*, Mar. 19, 2004, vol. 116, pp. 855-867.

XP-002086152, Hanson et al., "Pulmonary-Allergy, Dermatological, Gastrointestinal & Arthritis, Inhibitors of p38 Kinase," Exp. Opin. Ther. Patents, 1997, vol. 7, No. 7, pp. 729-733.

Regan et al., "Pyrazole Urea-Based Inhibitors of p38 MAP Kinase: from Lead Compound to Clinical Candidate," *J. Med. Chem.*, 2002, vol. 45, pp. 2994-3008.

XP-002103155, Wilson et al., "The Structural Basis for the Specificity of Pyridinylimidazole Inhibitors of p38 MAP Kinase," *Chemistry & Biology*, 1997, vol. 4, No. 6, pp. 423-431.

Hanson, "Inhibitors of p38 Kinase," *Expert Opinion on Therapeutic Patents*, Jul. 1997, vol. 7, No. 7, pp. 729-733(5).

Garcia-Lopez et al., "New routes for the Synthesis of Pyrrolo[3,2-d]-and [2,3-d]-Pyrimidine Systems Starting from a Common Pyrrole Derivative," *Journal of the Chemical Society*, Perkin Transactions 1: Organic and Bio-Organic Chemistry (1972-1999), 1978, pp. 483-487.

02-022650, Patent Abstracts of Japan, Jan. 25, 1990.

02-023337, Patent Abstracts of Japan, Jan. 25, 1990.

XP-000676688, WisSner et al., "Analogues of Platelet Activating Factor. 7. Bis-Aryl Amide and Bis-Aryl Urea Receptor Antagonists of PAF," *J. Med. Chem.*, 1992, vol. 35, pp. 4779-4789.

Ravi et al., "Activated RAF-1 Causes Growth Arrest in Human Small Cell Lung Cancer Cells," *J. Clinical. Investigation*, pp. 153-159.

Lemoine, "Overview of ras oncogenes and their clinical potential," Chapter 10, pp. 85-91.

Drug: *Facts and Comparisons*, 1994 Edition, pp. 2703-2705.

XP-001093697, Carling et al., "1-(3-Cyanobenzylpiperidin-4-yl)-5-Methyl-4-Phenyl-1,3-Dihydroimidazol-2-One: A Selective High- Affinity Antagonist for the Human Dopamine $D_4$ Receptor with Excellent Selectivity over Ion Channels," *J. Med. Chem.*, 1999, vol. 42, pp. 2706-2715.
XP-001062441, Eisenhauer et al., "Impact of New Non-Cytotoxics in the Treatment in Ovarian Cancer," *International J. Gynecol Cancer*, 2001, vol. 11, Supplement 1, pp. 68-72.
913, XP-001152608, Kubo et al., "Synthesis and Structure-Activity Relationship of Quinazoline-Urea Derivatives as Novel Orally Active VEGF Receptor Tyrosine Kinase Selective Inhibitors," Proceedings of the American Association of Cancer Res., 2002, vol. 43, p. 182.
Dumas et al., "1-Phenyl-5-Pyrazolyl Ureas: Potent and Selective p38 Kinase Inhibitors," *Bioorganic & Medicinal Chemistry Letters*, 2000, vol. 10, pp. 2051-2054.
4956, XP-001145518, Riedl et al., "Potent Raf Kinase Inhibitors from the Diphenylurea Class: Structure Activity Relationships," Bayer Corporation.
XP-001145779, Geiger et al., "Antitumor Activity of a C-raf Antisense Oligonucleotide in Combination with Standard Chemotherapeutic Agents against Various Human Tumors Transplanted Subcutaneously into Nude Mice," *Clinical Cancer Research*, Jul. 1997, vol. 3, pp. 1179-1185.
XP-002232130, Cunningham et al., "A Phase I Trial of H-ras Antisense Oligonucleotide ISIS 2503 Administered as a Continuous Intravenous Infusion in Patients with Advanced Carcinoma," *American Cancer Society*, Sep. 2001, vol. 92, No. 5, pp. 1265-1271.
Blanco et al., "p38 MAPK Signaling Cascades: Ancient Roles and New Functions," *Bioassays*, 2000, vol. 22, pp. 637-645.
Madwed et al., "Pharmacological Evaluation of BIRB 796, a Selective Inhibitor of p38 MAP Kinase (MAPK), in Animal Models of Endotoxic Shock, Inflammation and Arthritis," Inflammation Res., 2001, vol. 50, p. S184.
Ridley et al., "Actions of IL-1 are Selectively Controlled by p38 Mitogen-Activated Protein Kinase, Regulation of Prostaglandin H Synthase-2, Metalloproteinases, and IL-6 at Different Levels," *The Journal of Immunology*, 1997, vol. 158, pp. 3165-3173.
Wild, Hanno, "Substructure #1," 1996, pp. 1-107.
Raez et al., "New Developments in chemotherapy for advanced non-small lung cancer," *Current Opinion in Oncology*, vol. 18, 2006, pp. 156-161.
Cortes et al., "Targeting the Microtubules in Breast Cancer Beyond Taxanes: The Epothilones," *The Oncologist*, 2007, vol. 12, pp. 271-280.
Kuefer et al., "Translational research in renal cell cancer. Illustrated by the example of the vascular endothelial growth factor pathway," *Der Urologe*, 2006, vol. 45, No. 3, pp. 328, 330-335.
Leuner et al., "Inmproving drug solubility for oral delivery using solic dispersions," *European Journal of Pharmaceutics and Biopharmaceutics*.
Luo et al., "Enhancement of radiation effects by pXLG-mENDO in a lung carcinoma model," *I.J. Radiation Oncology Biology Physics*, 2005, vol. 63, No. 2, pp. 553-564.
Hardmann et al., "Goodman & Gilman's The Pharmacological Basis of Therapeutics," 9th ed., 1996, pp. 51 and 57-58.
Stella, Valentino J, Expert Opinion of Therapeutic Patents, Prodrugs as therapeutics, 2004 1(3): 277-280.
Wolff et al. (Burger's Medicinal Chemistry, 5th Ed., vol. 1, pp. 975-977, 1994).
Testa, Bernard, Biochemical Pharmacology, Prodrug, Research: futile or fertile? 68 (2004) 2097-2106.
Ettmayer, Peter, Medicinal Chemistry, Lesson Learned from Marketed and Investigational Prodrugs, 47(10) (2004) 2394-2404.
B. P. Monia, et al., "Antitumor activity of a phosphorothioate antisense oligodeoxynucleotide targeted against C-*raf* kinase," *Nature Medicine*, vol. 2, No. 6, Jun. 1996, pp. 668-675.
Ridley, et al., "Actions of IL-1 are Selectively Controlled by p38 Mitogen-Activated Protein Kinase," *The American Association of Immunologists*, 1997, p. 3165-73.
N. S. Magnuson, et al., "The Raf-1 serine/threonine protein kinase," *Cancer Biology*, vol. 5, 1994, pp. 247-253.
G. Daum, et al., "The ins and outs of Raf Kinases,": *TIBS* 19, Nov. 1994, pp. 474-480.

Joseph T. Bruder et al., *Journal of Virology*, Jan. 1997, "Adenovirus Infection Stimulates the Raf/MAPK Signaling Pathway and Induces Interleukin-8 Expression," May 17, 1996, pp. 398-404.
XP-000943598, Foussard-Blanpin, Odette: "Comparative pharmacodynamic study of variously substituted carboxamides of the central nervous ststem" *Ann. Pharm. Fr.* (1982), 40 (4), pp. 339-350.
Avruch et al., "Raf meets Ras: completing the framework of a signal transduction pathway," *TIBS* 19; Jul. 1994; pp. 279-281.
Publication No. US 2002/0065296 A1, Publication Date: May 30, 2002, Dumas et al.
Publication No. US 2002/0128321 A1, Publication Date: Sep. 12, 2002, Widdowson et al.
Publication No. US 2002/0082255 A1, Publication Date: Jun. 27, 2002, Eastwood.
Caplus 72:79046, Abstract of CH 479557, "Tuberculostatic and cancerostatic polybasic ureas," Dr. A. Wander, Oct. 15, 1969.
Caplus 131:58658k, "Inhibition of raf kinase using symmetrical and unsymmetrical substituted diphenyl ureas," Miller, Scott, Jul. 1, 1999.
Caplus 131:87909y, "Inhibition of p38 kinase activity using substituted heterocyclic ureas," Jacques Dumas, Jul. 1, 1999.
Caplus 131:73649b, "Preparation of pyrazolyl aryl ureas and related compounds as p38kinase inhibitor," Jacques Dumas, Jul. 1, 1999.
Jacques Dumas et al., "1-Phenyl-5-pyrazolyl Ureas: Potent and Selective p38 Kinase Inhibitors," *Bioorganic & Medicinal Chemistry Letters*, pp. 2051-2054, May 2, 2000.
Dumas, J.. "CAS Substructure," May 6, 1997, pp. 1-29.
Scott,Bill, "Substructure (Patent Families)," Aug. 11, 1997, pp. 1-19.
Scott, Bill, "Substructure #2," Nov. 25, 1997, pp. 1-3.
"Beilstein number" Collection, 28 pages (1997).
"Beilstein Collection," 4 pages (1997).
Scott, Bill, "Substructure Search," Dec. 2, 1997, pp. 1-51.
Substructure Search, pp. 1-30. (1997).
Derwent World Patents Index Search, pp. 20-26. (1997).
Supplemental search report from the EPO for European application EP 98/963810 dated Dec. 21, 2000, Inhibition of Raf Kinase Using Aryl and Heteroaryl Substituted Heterocyclic Ureas, publication No. 1056725, publication date Dec. 6, 2000.
Supplemental search report from the EPO for European application EP 98/965981 dated Dec. 21, 2000, Inhibition of Raf Kinase Using Substituted Heterocyclic Ureas, publication No. 1047418, publication date Nov. 2, 2000.
International search report for International Application No. PCT/US98/10375 dated Sep. 3, 1998, Inhibition of p38 Kinase Activity by Aryl Ureas, publication No. 98/52558, publication date Nov. 26, 1998.
International search report for International Application No. PCT/US98/10376 dated Jul. 30, 1998, Raf Kinase Inhibitors, publication No. WO 98/52559, publication date Nov. 26, 1998.
International search report for International Application No. PCT/US98/26078 dated Apr. 2, 1999, Inhibition of Raf Kinase Using Substituted Heterocyclic Ureas, publication No. WO99/32106, publication date Jul. 1, 1999.
International search report for International Application No. PCT/US98/26079 dated Apr. 12, 1999, Inhibition of p38 Activity Using Aryl and Heteroaryl Substituted Heterocyclic Ureas, publication No. WO99/32110, publication date Jul. 1, 1999.
International search report for International Application No. PCT/US98/26080 dated Apr. 12, 1999, Inhibition of p38 Kinase Using Substituted Heterocyclic Ureas, publication No. WO99/32111, publication date Jul. 1, 1999.
International search report for International Application No. PCT/US98/26082 dated May 12, 1999, Inhibition of Raf Kinase Using Aryl and Heteroaryl Substituted Heterocyclic Ureas, publication No. WO99/32455, publication date Jul. 1, 1999.
Bergstralh et al., "Microtubule stabilizing agents: Their molecular signaling consequences and the potential for enhancement by drug combination," *Cancer Treatment Reviews*, 2006, vol. 32, pp. 166-179.
Bando et al., "Association between intratumoral free and total VEGF, soluble VEGRF-1, VEGFR-2 and prognosis in breast cancer" *British Journal of Cancer*, 2005, vol. 92, pp. 553-561.

Foekens et al., "High Tumor Levels of Vascular Endothelial Growth Factor Predict Poor Response to Systemic Therapy in Advanced Breast Cancer," *Cander Research*, 2001, vol. 61, pp. 5407-5414.

Forbes et al., "N-(1-Methyl-5-indolyl)-N'-(3-methyl-5-isothiazolyl)urea: A Novel, High-Affinity 5-$HT_{2B}$ Receptor Antagonist" *Journal of Medicinal Chemistry*, 1995, vol. 38, No. 6, pp. 854-857.

Gomez-Esquer et al., "mRNA expression of the angiogenesis markers VEGF and CD105 (endoglin) in human breast cancer," *US National Library of Medicine*, 2004, vol. 24, No. 3a, pp. 1581-1585, XP002455577.

Gura, "Systems for identifying new drugs are often faulty." *Science*, 1997, vol. 278 (5340), pp. 1041-1042.

Quinglong et al., "Soluble Vascular Endothelial Growth Factor Receptor 1, and Not Receptor 2, Is an Independent Prognostic Factor in Acute Myeloid Leukemia and Myelodysplastic Syndromes," *Wiley InterScience*, 2004, vol. 100, No. 9, pp. 1884-1891.

Dumas et al., "Synthesis and Pharmacological Characterization of a Potent, Orally Active p38 Kinase Inhibitor," *Bioorganic & Medicinal Chemistry Letters*, 2002, vol. 12, pp. 1559-1562.

Johnson et al., "Relationships between drug activity in NCI preclinical in vitro and in vivo models and early clinical trials," *British Journal of Cancer*, 2001, vol. 84, No. 10, pp. 1424-1431.

\* cited by examiner

SUBSTITUTED PYRAZOLYL UREA DERIVATIVES USEFUL IN THE TREATMENT OF CANCER

FIELD OF THE INVENTION

This invention relates to novel compounds, pharmaceutical compositions containing such compounds and the use of those compounds or compositions for treating hyper-proliferative and angiogenesis disorders, as a sole agent or in combination with other active ingredients, e.g., cytotoxic therapies.

BACKGROUND OF THE INVENTION

To support progressive tumor growth beyond the size of 1-2 mm$^3$, it is recognized that tumor cells require a functional stroma, a support structure consisting of fibroblast, smooth muscle cells, endothelial cells, extracellular matrix proteins, and soluble factors (Folkman, J., *Semin Oncol*, 2002. 29(6 Suppl 16), 15-8). Tumors induce the formation of stromal tissues through the secretion of soluble growth factors such as PDGF and transforming growth factor-beta (TGF-beta), which in turn stimulate the secretion of complimentary factors by host cells such as fibroblast growth factor (FGF), epidermal growth factor (EGF), and vascular endothelial growth factor (VEGF). These stimulatory factors induce the formation of new blood vessels, or angiogenesis, which brings oxygen and nutrients to the tumor and allows it to grow and provides a route for metastasis. It is believed some therapies directed at inhibiting stroma formation will inhibit the growth of epithelial tumors from a wide variety of histological types. (George, D. *Semin Oncol*, 2001. 28(5 Suppl 17), 27-33; Shaheen, R. M., et al., *Cancer Res*, 2001. 61(4), 1464-8; Shaheen, R. M., et al. *Cancer Res*, 1999. 59(21), 5412-6). However, because of the complex nature and the multiple growth factors involved in angiogenesis process and tumor progression, an agent targeting a single pathway may have limited efficacy. It is desirable to provide treatment against a number of key signaling pathways utilized by tumors to induce angiogenesis in the host stroma. These include PDGF, a potent stimulator of stroma formation (Ostman, A. and C. H. Heldin, *Adv Cancer Res*, 2001, 80, 1-38), FGF, a chemoattractant and mitogen for fibroblasts and endothelial cells, and VEGF, a potent regulator of vascularization.

PDGF is another key regulator of stromal formation which is secreted by many tumors in a paracrine fashion and is believed to promote the growth of fibroblasts, smooth muscle and endothelial cells, promoting stroma formation and angiogenesis. PDGF was originally identified as the v-sis oncogene product of the simian sarcoma virus (Heldin, C. H., et al., *J Cell Sci Suppl*, 1985, 3, 65-76). The growth factor is made up of two peptide chains, referred to as A or B chains which share 60% homology in their primary amino acid sequence. The chains are disulfide cross linked to form the 30 kDa mature protein composed of either AA, BB or AB homo- or heterodimmers. PDGF is found at high levels in platelets, and is expressed by endothelial cells and vascular smooth muscle cells. In addition, the production of PDGF is up regulated under low oxygen conditions such as those found in poorly vascularized tumor tissue (Kourembanas, S., et al., *Kidney Int*, 1997, 51(2), 438-43). PDGF binds with high affinity to the PDGF receptor, a 1106 amino acid 124 kDa transmembrane tyrosine kinase receptor (Heldin, C. H., A. Ostman, and L. Ronnstrand, *Biochim Biophys Acta*, 1998. 1378(1), 79-113). PDGFR is found as homo- or heterodimer chains which have 30% homology overall in their amino acid sequence and 64% homology between their kinase domains (Heldin, C. H., et al. *Embo J*, 1988, 7(5), 1387-93). PDGFR is a member of a family of tyrosine kinase receptors with split kinase domains that includes VEGFR2 (KDR), VEGFR3 (Flt4), c-Kit, and FLT3. The PDGF receptor is expressed primarily on fibroblast, smooth muscle cells, and pericytes and to a lesser extent on neurons, kidney mesangial, Leydig, and Schwann cells of the central nervous system. Upon binding to the receptor, PDGF induces receptor dimerization and undergoes auto- and trans-phosphorylation of tyrosine residues which increase the receptors' kinase activity and promotes the recruitment of downstream effectors through the activation of SH2 protein binding domains. A number of signaling molecules form complexes with activated PDGFR including PI-3-kinase, phospholipase C-gamma, src and GAP (GTPase activating protein for p21-ras) (Soskic, V., et al. *Biochemistry*, 1999, 38(6), 1757-64). Through the activation of PI-3-kinase, PDGF activates the Rho signaling pathway inducing cell motility and migration, and through the activation of GAP, induces mitogenesis through the activation of p21-ras and the MAPK signaling pathway.

In adults, it is believed the major function of PDGF is to facilitate and increase the rate of wound healing and to maintain blood vessel homeostasis (Baker, E. A. and D. J. Leaper, *Wound Repair Regen*, 2000. 8(5), 392-8; Yu, J., A. Moon, and H. R. Kim, *Biochem Biophys Res Commun*, 2001. 282(3), 697-700). PDGF is found at high concentrations in platelets and is a potent chemoattractant for fibroblast, smooth muscle cells, neutrophils and macrophages. In addition to its role in wound healing PDGF is known to help maintain vascular homeostasis. During the development of new blood vessels, PDGF recruits pericytes and smooth muscle cells that are needed for the structural integrity of the vessels. PDGF is thought to play a similar role during tumor neovascularization. As part of its role in angiogenesis PDGF controls interstitial fluid pressure, regulating the permeability of vessels through its regulation of the interaction between connective tissue cells and the extracellular matrix. Inhibiting PDGFR activity can lower interstitial pressure and facilitate the influx of cytotoxics into tumors improving the anti-tumor efficacy of these agents (Pietras, K., et al. *Cancer Res*, 2002. 62(19), 5476-84; Pietras, K., et al. *Cancer Res*, 2001. 61(7), 2929-34).

PDGF can promote tumor growth through either the paracrine or autocrine stimulation of PDGFR receptors on stromal cells or tumor cells directly, or through the amplification of the receptor or activation of the receptor by recombination. Over expressed PDGF can transform human melanoma cells and keratinocytes (Forsberg, K., et al. *Proc Natl Acad Sci USA.*, 1993. 90(2), 393-7; Skobe, M. and N. E. Fusenig, *Proc Natl Acad Sci USA*, 1998. 95(3), 1050-5), two cell types that do not express PDGF receptors, presumably by the direct effect of PDGF on stroma formation and induction of angiogenesis. This paracrine stimulation of tumor stroma is also observed in carcinomas of the colon, lung, breast, and prostate (Bhardwaj, B., et al. *Clin Cancer Res*, 1996, 2(4), 773-82; Nakanishi, K., et al. *Mod Pathol*, 1997, 10(4), 341-7; Sundberg, C., et al. *Am J Pathol*, 1997, 151(2), 479-92; Lindmark, G., et al. *Lab Invest*, 1993, 69(6), 682-9; Vignaud, J. M., et al, *Cancer Res*, 1994, 54(20), 5455-63) where the tumors express PDGF, but not the receptor. The autocrine stimulation of tumor cell growth, where a large faction of tumors analyzed express both the ligand PDGF and the receptor, has been reported in glioblastomas (Fleming, T. P., et al. *Cancer Res*, 1992, 52(16), 4550-3), soft tissue sarcomas (Wang, J., M. D. Coltrera, and A. M. Gown, *Cancer Res*, 1994, 54(2), 560-4) and cancers of the ovary (Henriksen, R., et al. *Cancer Res*, 1993, 53(19), 4550-4), prostate (Fudge, K., C. Y. Wang, and M. E. Stearns, *Mod Pathol*, 1994, 7(5), 549-54), pancreas (Funa, K., et al. *Cancer Res*, 1990, 50(3), 748-53) and lung (Antoniades, H. N., et al., *Proc Natl Acad Sci USA*, 1992, 89(9), 3942-6). Ligand independent activation of the receptor is found to a lesser extent but has been reported in chronic myelomonocytic leukemia (CMML) where the a chromosomal translocation event forms a fusion protein between the Ets-like transcription factor TEL and the PDGF receptor. In addition, activating mutations in PDGFR have been found in gastrointestinal stromal tumors in which c-Kit activation is not involved (Heinrich, M. C., et al., *Science*, 2003, 9, 9).

Certain PDGFR inhibitors will interfere with tumor stromal development and are believed to inhibit tumor growth and metastasis.

Another major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in homodimeric forms due to alternative RNA splicing. The VEGF isoforms are reported to be highly specific for vascular endothelial cells (for reviews, see: Farrara et al. *Endocr. Rev.* 1992, 13, 18; Neufield et al. *FASEB J.* 1999, 13, 9).

VEGF expression is reported to be induced by hypoxia (Shweiki et al. *Nature* 1992, 359, 843), as well as by a variety of cytokines and growth factors, such as interleukin-1, interleukin-6, epidermal growth factor and transforming growth factor. To date, VEGF and the VEGF family members have been reported to bind to one or more of three transmembrane receptor tyrosine kinases (Mustonen et al. *J. Cell Biol.*, 1995, 129, 895), VEGF receptor-1 (also known as flt-1 (fms-like tyrosine kinase-1)), VEGFR-2 (also known as kinase insert domain containing receptor (KDR); the murine analogue of KDR is known as fetal liver kinase-1 (flk-1)), and VEGFR-3 (also known as flt-4). KDR and flt-1 have been shown to have different signal transduction properties (Waltenberger et al. *J. Biol. Chem.* 1994, 269, 26988); Park et al. *Oncogene* 1995, 10, 135). Thus, KDR undergoes strong ligand-dependant tyrosine phosphorylation in intact cells, whereas flt-1 displays a weak response. Thus, binding to KDR is believed to be a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. It is believed regulation of the VEGF-mediated signal transduction cascade by some agents can provide a useful mode for control of abnormal angiogenesis and/or hyperpermeability processes.

The vascular endothelial growth factors (VEGF, VEGF-C, VEGF-D) and their receptors (VEGFR2, VEGFR3) are not only key regulators of tumor angiogenesis, but also lymphangiogenesis. VEGF, VEGF-C and VEGF-D are expressed in most tumors, primarily during periods of tumor growth and, often at substantially increased levels. VEGF expression is stimulated by hypoxia, cytokines, oncogenes such as ras, or by inactivation of tumor suppressor genes (McMahon, G. *Oncologist* 2000, 5(Suppl. 1), 3-10; McDonald, N. Q.; Hendrickson, W. A. *Cell* 1993, 73, 421-424)

The biological activities of the VEGFs are mediated through binding to their receptors. It is believed VEGFR3 (also called Flt-4) is predominantly expressed on lymphatic endothelium in normal adult tissues and that VEGFR3 function is needed for new lymphatic vessel formation, but not for maintenance of the pre-existing lymphatics. VEGFR3 is also upregulated on blood vessel endothelium in tumors. Recently VEGF-C and VEGF-D, ligands for VEGFR3, have been identified as regulators of lymphangiogenesis in mammals. Lymphangiogenesis induced by tumor-associated lymphangiogenic factors could promote the growth of new vessels into the tumor, providing tumor cells access to systemic circulation. Cells that invade the lymphatics could find their way into the bloodstream via the thoracic duct. Tumor expression studies have allowed a direct comparison of VEGF-C, VEGF-D and VEGFR3 expression with clinicopathological factors that relate directly to the ability of primary tumors to spread (e.g., lymph node involvement, lymphatic invasion, secondary metastases, and disease-free survival). In many instances, these studies demonstrate a statistical correlation between the expression of lymphangiogenic factors and the ability of a primary solid tumor to metastasize (Skobe, M. et al. *Nature Med.* 2001, 7(2), 192-198; Stacker, S. A. et al. *Nature Med.* 2001, 7(2), 186-191; Makinen, T. et al. *Nature Med.* 2001, 7(2), 199-205; Mandriota, S. J. et al. *EMBO J.* 2001, 20(4), 672-82; Karpanen, T. et al. *Cancer Res.* 2001, 61(5), 1786-90; Kubo, H. et al. *Blood* 2000, 96(2), 546-53).

Hypoxia appears to be an important stimulus for VEGF production in malignant cells. Activation of p38 MAP kinase is required for VEGF induction by tumor cells in response to hypoxia (Blaschke, F. et al. *Biochem. Biophys. Res. Commun.* 2002, 296, 890-896; Shemirani, B. et al. *Oral Oncology* 2002, 38, 251-257). In addition to its involvement in angiogenesis through regulation of VEGF secretion, p38 MAP kinase promotes malignant cell invasion, and migration of different tumor types through regulation of collagenase activity and urokinase plasminogen activator expression (Laferriere, J. et al. *J. Biol. Chem.* 2001, 276, 33762-33772; Westermarck, J. et al. *Cancer Res.* 2000, 60, 7156-7162; Huang, S. et al. *J. Biol. Chem.* 2000, 275, 12266-12272; Simon, C. et al. *Exp. Cell Res.* 2001, 271, 344-355).

The receptor tyrosine kinase Trk-A is another target of interest for the preparation of medicines directed at the treatment and prevention of cancer. TrkA is the high affinity receptor of the nerve growth factor (NGF). The expression of TrkA and NGF in tumors is believed to be implicated in the proliferation and metastasis of tumors such as pancreatic, prostate and also breast, as well as in angiogenesis. TrkA expression is reported in pancreatic, breast, ovarian, and prostate tumors. Recent studies demonstrate that human prostate and pancreatic tumor cells can secrete NGF, which, along with its receptor, TrkA, creates an autocrine loop that promotes the growth and survival of these tumor cells (Ruggeri, B. A. et al, *Curr. Med. Chem.* 1999, 6:845-857; Weeraratna, A. T. et al., *The Prostate* 2000, 45:140-148). Inhibition of the NGF-TrkA signaling pathway by small molecule TrkA inhibitors (Miknyoczki, S. J. et al., *Clin. Cancer Res.* 1999, 5: 2205-2212; George, D. J. et al., *Cancer Res.* 1999, 59: 2395-2401; Weeraratna, A. T. et al, *Clin. Cancer Res.* 2001, 7: 2237-2245) and anti-NGF antibodies (Miknyoczki, S. J. et al., *Clin. Cancer Res.* 2002, 8:1924-1931) has been postulated to inhibit not only growth, but also metastasis of neuroendocrine tumors in xenograft models. In addition, NGF has been shown to induce proliferation of endothelial cells (Cantarella, G. et al., *FASEB J.* 2002, 16: 1307). These cells, which form new vascular networks to feed the growing tumor, also express VEGFR2 tyrosine kinase receptors. Activation of these receptors by their ligands leads to endothelial cell proliferation, migration, and vessel formation and stabilization (Albo, D. et al., *Curr. Pharm. Des.* 2004, 10:27-37; Thurston, G., *Cell Tissue Res.* 2003, 31:61-68).

Certain diarylureas have been described as having activity as serine-threonine kinase and/or as tyrosine kinase inhibitors. The utility of these diarylureas as an active ingredient in pharmaceutical compositions for the treatment of cancer, angiogenesis disorders, and inflammatory disorders has been demonstrated. See Redman et al., *Bioorg. Med. Chem. Lett.* 2001, 11, 9-12; Smith et al., *Bioorg. Med. Chem. Lett.* 2001, 11, 2775-2778; Dumas et al., *Bioorg. Med. Chem. Lett.* 2000, 10, 2047-2050; Dumas et al., *Bioorg. Med. Chem. Lett.* 2000, 10, 2051-2054; Ranges et al., *Book of Abstracts, 220th ACS National Meeting, Washington, D.C., USA, MEDI* 149; Dumas et al., *Bioorg. Med. Chem. Lett.* 2002, 12, 1559-1562; Lowinger et al., *Clin. Cancer Res.* 2000, 6(suppl.), 335; Lyons et al., *Endocr.-Relat. Cancer* 2001, 8, 219-225; Riedl et al., *Book of Abstracts, 92nd AACR Meeting, New Orleans, La., USA,* abstract 4956; Khire et al., *Book of Abstracts, 93rd AACR Meeting, San Francisco, Calif., USA,* abstract 4211; Lowinger et al., *Curr. Pharm. Design* 2002, 8, 99-110; Regan et al., *J. Med. Chem.* 2002, 45, 2994-3008; Pargellis et al., *Nature Struct. Biol.* 2002, 9(4), 268-272; Carter et al., *Book of Abstracts, 92hd AACR Meeting, New Orleans, La., USA,* abstract 4954; Vincent et al., *Book of Abstracts, 38th ASCO Meeting, Orlando, Fla., USA,* abstract 1900; Hilger et al., *Book of Abstracts, 38th ASCO Meeting, Orlando, Fla., USA,* abstract 1916; Moore et al., *Book of Abstracts, 38th ASCO Meeting, Orlando, Fla., USA,* abstract 1816; Strumberg et al., *Book of Abstracts, 38th ASCO Meeting, Orlando, Fla., USA,* abstract 121; Madwed J B: *Book of Abstracts, Protein Kinases: Novel Target Identification and Validation for Therapeutic Development, San Diego, Calif., USA,* March 2002; Roberts et al., *Book of Abstracts, 38th ASCO Meeting, Orlando, Fla., USA,* abstract 473; Tolcher et al., *Book of Abstracts, 38th ASCO Meeting, Orlando, Fla., USA,* abstract 334; and Karp et al., *Book of Abstracts, 38th AACR Meeting, San Francisco, Calif., USA,* abstract 2753.

Despite the advancements in the art, there remains a need for cancer treatments and anti-cancer compounds.

DESCRIPTION OF THE INVENTION

The present invention pertains to:
(i) novel compounds of Formula I below, salts, metabolites and prodrugs thereof, including diastereoisomeric forms,
(ii) pharmaceutical compositions containing compounds of Formula I below or salts, metabolites or prodrugs thereof, including diastereoisomeric forms, and
(iii) use of those compounds of (i) or compositions of (ii) for treating diseases, e.g., hyper-proliferative and angiogenesis disorders, as a sole agent or in combination with other active ingredients, e.g., cytotoxic therapies.

The compounds of Formula I, salts, metabolites and prodrugs thereof, including diastereoisomeric forms (both isolated stereoisomers and mixtures of stereoisomers) are collectively referred to herein as the "compounds of the invention". Formula I is as follows:

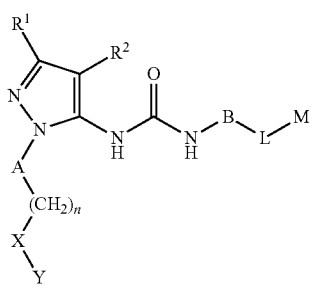

Formula I $R^1$ and $R^2$ are independently selected from:
(a) hydrogen;
(b) $(C_1-C_5)$alkyl, optionally substituted with one or more hydroxy or fluoro; or
(c) halogen.

In a class of compounds of formula I, $R^1$ is $(C_1-C_5)$alkyl and $R^2$ is hydrogen. In a subclass of this class of compounds, $R^1$ is tert-butyl, isopropyl, or cyclopentyl and $R^2$ is hydrogen.

A is phenyl, pyridine, or pyrimidine, optionally substituted with 1 or 2 substituents that are independently selected from $(C_1-C_5)$alkyl, $(C_1-C_5)$alkoxy, $(C_1-C_5)$haloalkyl, $(C_1-C_5)$haloalkoxy, or halogen. Structures for A of formula I which are of particular interest are phenyl and pyridine optionally substituted with 1 or 2 substituents that are independently selected from $(C_1-C_5)$alkyl, $(C_1-C_5)$alkoxy or halogen. Included in the structures for A of formula I which are of particular interest are structures of formulae 1x and 1xx:

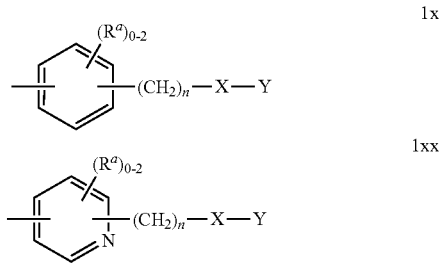

wherein $R^a$ is methyl, ethyl, propyl, butyl, methoxy, ethoxy, propoxy, bromine, chlorine or fluorine.

The structures 1x and 1xx represent that the substituents $R^a$ and the group $-(CH_2)_n-X-Y$ can appear on any carbon atom in the ring which has a valence that is otherwise complete with a hydrogen atom as a substituent. The bond to the pyrazole ring can also be through any carbon atom in the ring which has a valence that is otherwise complete with a hydrogen atom as a substituent.

In a class of compounds of formula I, the pyrazole ring and the group, $-(CH_2)_n-X-Y$ are not bound to contiguous ring carbons of A, but rather have 1 or 2 ring carbons separating them.

B is phenylene or naphthylene, optionally substituted with 1 to 4 substituents that are independently selected from $(C_1-C_5)$alkyl, $(C_1-C_5)$alkoxy, $(C_1-C_5)$haloalkyl, $(C_1-C_5)$haloalkoxy, or halogen. In a class of compounds of formula I, B is phenylene, optionally substituted with 1 to 2 halogen atoms. Structures for B of formula (I) included within this class are those of formula 2x:

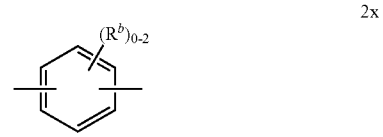

wherein $R^b$ is fluorine or chlorine.

The structure 2x represents that the substituents $R^b$ can appear on any carbon atom in the ring which has a valence that is otherwise complete with a hydrogen atom as a substituent. In addition, both the bond to the urea group, $-NH-C(O)-NH-$, and the bond to the bridging group, L, can be through any carbon atom in the ring which has a valence that is otherwise complete with a hydrogen atom as a substituent.

In a class of compounds of formula (I), the urea group —NH—C(O)—NH— and the bridging group, L, are not bound to contiguous ring carbons of B, but rather have 1 or 2 ring carbons separating them.

A class of structures of interest for B of formula (I) are of the following formulae:

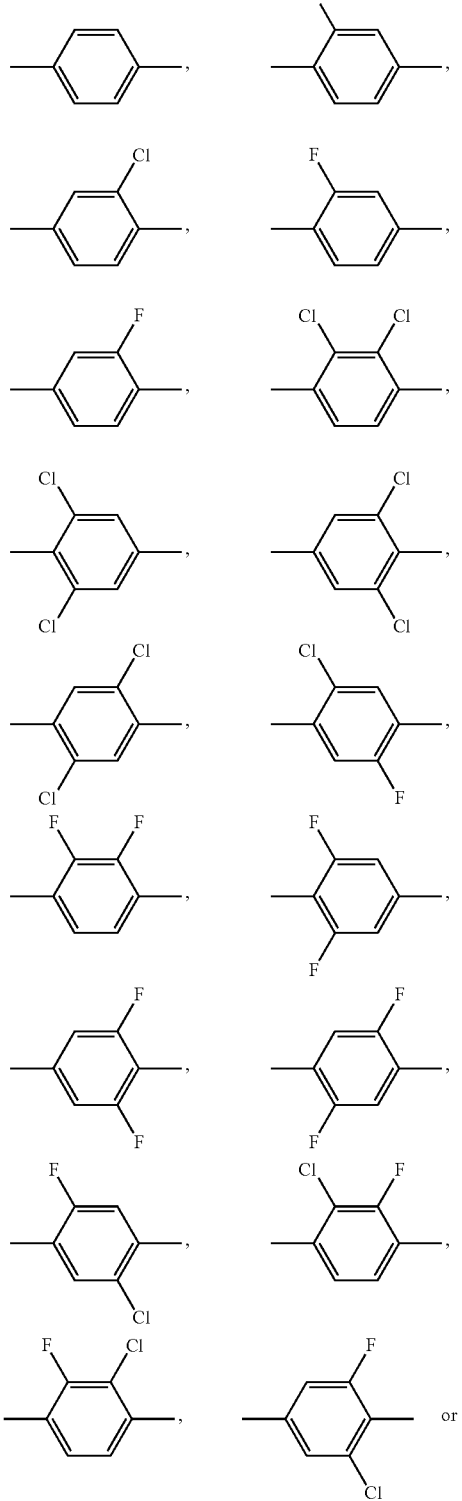

-continued

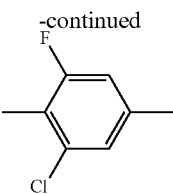

L is a bridging group which is —O—, —S—, or —CH$_2$—.

In a class of compounds of formula I, L is —O—.

M is phenyl, pyridine or pyrimidine, optionally substituted with 1 to 3 substituents that are independently selected from:
(1) (C$_1$-C$_5$)alkyl;
(2) (C$_1$-C$_5$)haloalkyl;
(3) —O—R$^3$;
(4) —NR$^3$R$^4$;
(5) halogen;
(6) —C(O)NR$^3$R$^4$;
(7) cyano;
(8) C(O)R$^3$;
(9) —C≡C—R$^3$; or
(10) nitro.

In a class of compounds of formula I, M is pyridine, optionally substituted with 1 substituent selected from:
(1) (C$_1$-C$_5$)alkyl;
(2) (C$_1$-C$_5$)haloalkyl;
(3) —O—R$^3$;
(4) —NR$^3$R$^4$;
(5) halogen;
(6) —C(O)NR$^3$R$^4$;
(7) cyano;
(8) C(O)R$^3$;
(9) —C≡C—R$^3$; or
(10) nitro.

A subclass of optionally substituted pyridine structures for M of formula (I) are of the following formulae:

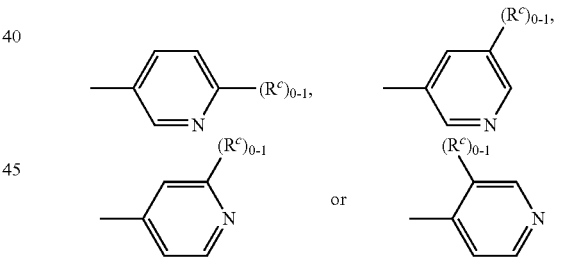

wherein R$^c$ is (C$_1$-C$_5$)alkyl; (C$_1$-C$_5$)haloalkyl; —O—R$^3$; —NR$^3$R$^4$; halogen; —C(O)NR$^3$R$^4$; cyano C(O)R$^3$; —C≡C—R$^3$ or nitro.

In formula I, n is zero or one and

X is:
(1) —O—;
(2) —SO$_2$—;
(3) —NR$^5$—;
(4) —NR$^5$—SO$_2$—;
(5) —N(SO$_2$NR$^7$R$^8$)—;
(6) —SO$_2$—NR$^5$—;
(7) —NR$^5$—C(O)—;
(8) —C(O)—NR$^5$—;
(9) —C(O)—; or
(10) a single bond.

In a class of compounds of formula I, X is —O—; —NR$^5$—; —NR$^5$—C(O)—; —C(O)—NR$^5$— or a single bond.

In formula I above, Y is a linear or branched $C_1$ to $C_6$ alkyl fragment that is substituted with one or two Z groups, where each Z group is independently selected from:

(1) —$OR^6$;
(2) —O—C(O)—$R^6$;
(3) —$NR^7R^8$;
(4) —$SO_2$—$(C_1-C_5)$alkyl;
(5) —C(O)—O—$R^6$;
(6) —NH—C(O)—$R^6$;
(7) —C(O)—$NR^7R^8$; or
(8) a monocyclic, saturated, partially saturated, or aromatic heterocycle of 5-7 ring atoms containing at least one heteroatom selected from N, O, or S, that is optionally substituted with 1 to 3 substituents selected from $(C_1-C_5)$alkyl, $(C_1-C_5)$ haloalkyl, hydroxy, amino, halogen, or oxo;

with the proviso that when n is zero and X is —O—, —$NR^3$—, or a single bond, then Z is not morpholine, piperidine, imidazole, or tetrazole;

with the further proviso that when n is zero and X is a single bond, then Z is not —$NR^7R^8$.

In a class of compounds of formula I, Y is a linear or branched $C_1$ to $C_4$ alkyl fragment ($C_1$ to $C_4$ alkyl chain) that is substituted with one Z group selected from —$OR^6$; —$NR^7R^8$; —NH—C(O)—$R^6$ or —C(O)—$NR^7R^8$. In a subclass of compounds of this invention within this class, Y is methylene, ethylene, n-propylene or n-butylene.

The substituents $R^3$, $R^4$, $R^5$ and $R^6$ are each independently hydrogen or $(C_1-C_5)$alkyl optionally substituted with hydroxy. In a class of compounds of this invention, $R^3$, $R^4$, $R^5$ and $R^6$ are each independently hydrogen, methyl, ethyl, propyl or butyl, optionally substituted with hydroxy.

The substituents $R^7$ and $R^8$ are independently hydrogen, or $(C_1-C_5)$alkyl optionally substituted with hydroxy; or the group —$NR^7R^8$ forms a monocyclic saturated heterocyclic ring having 5 to 7 ring atoms, where, in addition to the nitrogen atom attached to the rest of the molecule, zero to two of the other ring atoms is a hetero atom selected from N, O and S, and the remaining ring atoms are carbon. Examples of such —$NR^7R^8$ monocyclic saturated heterocyclic ring groups include pyrrolidine, piperidine, azepane, morpholine, thiomorpholine, piperazine, and homopiperazine. The —$NR^7R^8$ monocyclic saturated heterocyclic ring group is optionally substituted on a carbon atom with hydroxy.

In a class of compounds of formula I, $R^7$ and $R^8$ are each independently hydrogen, methyl, ethyl, propyl or butyl, optionally substituted with hydroxy.

A class of compounds of this invention within the scope of Formula I are also of Formula II, including the salts, metabolites and prodrugs thereof and diastereoisomeric forms (both isolated stereoisomers and mixtures of stereoisomers) thereof. Formula II is as follows:

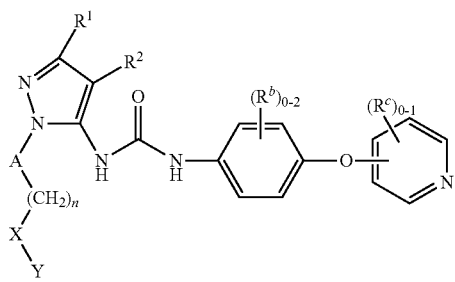

II wherein $R^b$ is fluorine or chlorine and
$R^1$ and $R^2$ are independently selected from:
(a) hydrogen;
(b) $(C_1-C_5)$alkyl, optionally substituted with one or more hydroxy or fluoro; or
(c) halogen.

In a class of compounds of formula II, $R^1$ is $(C_1-C_5)$alkyl and $R^2$ is hydrogen. In a subclass of this class of compounds, $R^1$ is tert-butyl, isopropyl, or cyclopentyl and $R^2$ is hydrogen.

A is phenyl, pyridine, or pyrimidine, optionally substituted with 1 or 2 substituents that are independently $(C_1-C_5)$alkyl, $(C_1-C_5)$alkoxy, $(C_1-C_5)$haloalkyl, $(C_1-C_5)$haloalkoxy, or halogen. In a class of compounds of formula II, Structures for A are phenyl and pyridine optionally substituted with 1 or 2 substituents that are independently $(C_1-C_5)$alkyl, $(C_1-C_5)$ alkoxy or halogen.

Structures of optionally substituted phenyl or pyridinyl moieties for A of formula II which are of particular interest include structures of formulae 1x and 1xx:

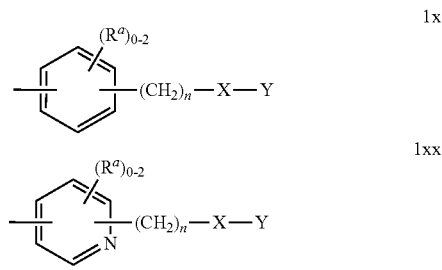

wherein $R^a$ is methyl, ethyl, propyl, butyl, methoxy, ethoxy, propoxy, bromine, chorine or fluorine.

The structures 1x and 1xx represent that the substituents $R^a$ and the group —$(CH_2)_n$—X—Y can appear on any carbon atom in the ring which has a valence that is otherwise complete with a hydrogen atom as a substituent. The bond to the pyrazole ring can also be through any carbon atom in the ring which has a valence that is otherwise complete with a hydrogen atom as a substituent.

In a class of compounds of formula II, the pyrazole ring and the group, —$(CH_2)_n$—X—Y are not bound to contiguous ring carbons of A, but rather have 1 or 2 ring carbons separating them.

Formula II represents that the substituents $R^b$ can appear on any carbon atom in the phenyl ring which has a valence that is otherwise complete with a

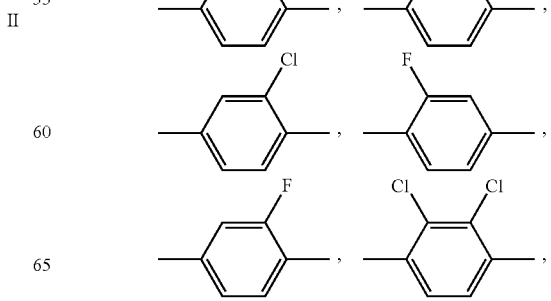

-continued

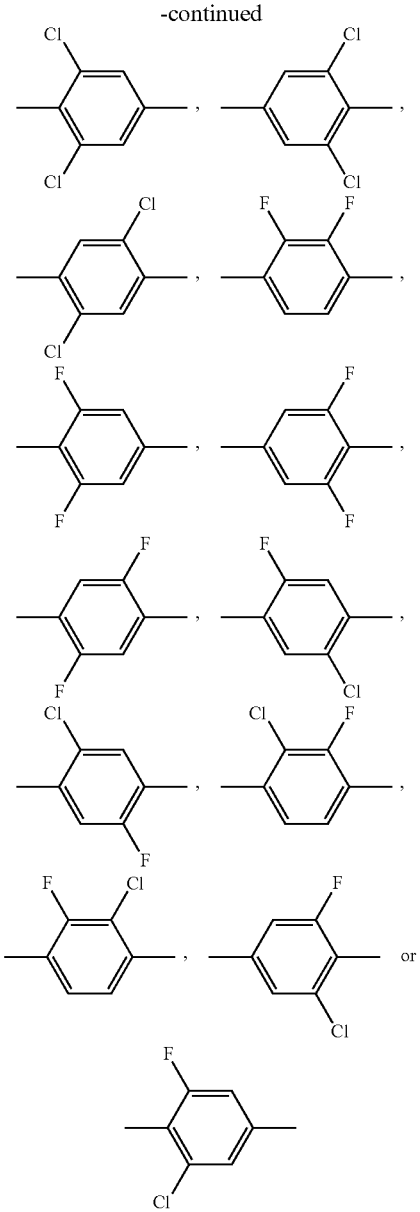

hydrogen atom as a substituent. The following structures illustrate the positions for $R^b$ which are of interest:

$R^c$ is selected from:
(1) $(C_1-C_5)$alkyl;
(2) $(C_1-C_5)$haloalkyl;
(3) —O—$R^3$;
(4) —$NR^3R^4$;
(5) halogen;
(6) —$C(O)NR^3R^4$;
(7) cyano;
(8) $C(O)R^3$;
(9) —C≡C—$R^3$; or
(10) nitro.

Structures which illustrate positions for $R^c$ which are of interest are as follows:

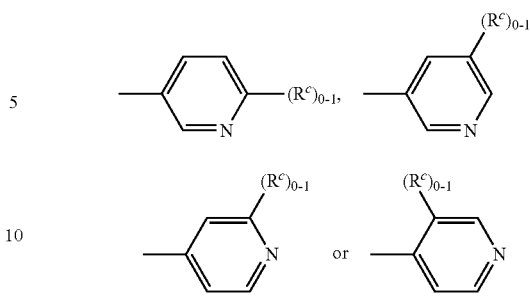

In formula II, n is zero or one and
X is:
(1) —O—;
(2) —$SO_2$—;
(3) —$NR^5$—;
(4) —$NR^5$—$SO_2$—;
(5) —$N(SO_2NR^7R^8)$—;
(6) —$SO_2$—$NR^5$—;
(7) —$NR^5$—C(O)—;
(8) —C(O)—$NR^5$—;
(9) —C(O)—; or
(10) a single bond.

In a class of compounds of formula II, X is —O—; —$NR^5$—; —$NR^5$—C(O)—; —C(O)—$NR^5$— or a single bond.

In formula II above, Y is a linear or branched $C_1$ to $C_6$ alkyl fragment that is substituted with one or two Z groups, where each Z group is independently selected from
(1) —$OR^6$;
(2) —O—C(O)—$R^6$;
(3) —$NR^7R^8$;
(4) —$SO_2$—$(C_1-C_5)$alkyl;
(5) —C(O)—O—$R^6$;
(6) —NH—C(O)—$R^6$;
(7) —C(O)—$NR^7R^8$; or
(8) a monocyclic, saturated, partially saturated, or aromatic heterocycle of 5-7 ring atoms containing at least one heteroatom selected from N, O, or S, that is optionally substituted with 1 to 3 substituents selected from $(C_1-C_5)$alkyl, $(C_1-C_5)$haloalkyl, hydroxy, amino, halogen, or oxo;
with the proviso that when n is zero and X is —O—, —$NR^3$—, or a single bond, then Z is not morpholine, piperidine, imidazole, or tetrazole;
with the further proviso that when n is zero and X is a single bond, then Z is not —$NR^7R^8$.

In a class of compounds of formula II, Y is a linear or branched $C_1$ to $C_4$ alkyl fragment ($C_1$ to $C_4$ alkyl chain) that is substituted with one Z group selected from —$OR^6$; —$NR^7R^8$; —NH—C(O)—$R^6$ or —C(O)—$NR^7R^8$. In a subclass of compounds of this invention within this class, Y is methylene, ethylene, n-propylene or n-butylene.

The substituents $R^3$, $R^4$, $R^5$ and $R^6$ are each independently hydrogen or $(C_1-C_5)$alkyl optionally substituted with hydroxy. In a class of compounds of this invention, $R^3$, $R^4$, $R^5$ and $R^6$ are each independently hydrogen, methyl, ethyl, propyl or butyl, optionally substituted with hydroxy.

The substituents $R^7$ and $R^8$ are independently hydrogen, or $(C_1-C_5)$alkyl optionally substituted with hydroxy; or the group —$NR^7R^8$ forms a monocyclic saturated heterocyclic ring having 5 to 7 ring atoms, where, in addition to the nitrogen atom attached to the rest of the molecule, zero to two of the other ring atoms is a hetero atom selected from N, O and S, and the remaining ring atoms are carbon. Examples of such —NR⁷R⁸ monocyclic saturated heterocyclic ring groups include pyrrolidine, piperidine, azepane, morpholine, thiomorpholine, piperazine, and homopiperazine. The —NR⁷R⁸ monocyclic saturated heterocyclic ring group is optionally substituted on a carbon atom with hydroxy.

In a class of compounds of formula II, $R^7$ and $R^8$ are each independently hydrogen, methyl, ethyl, propyl or butyl, optionally substituted with hydroxy.

A class of compounds of this invention are within the scope of formulae I and II and the scope of formulae III and IV, including the salts, metabolites and prodrugs thereof and diastereoisomeric forms (both isolated stereoisomers and mixtures of stereoisomers) thereof. Formula III and IV are as follows:

III

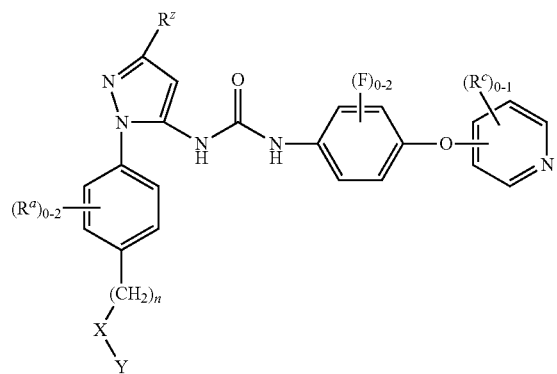

IV

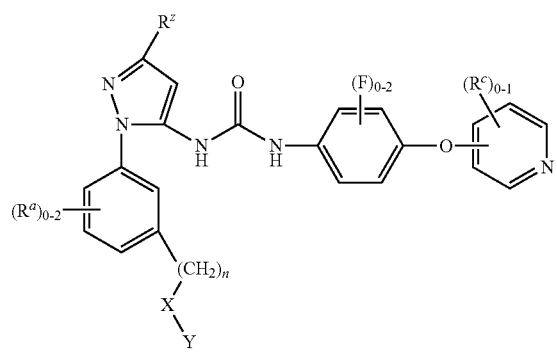

wherein $R^a$ is methyl, ethyl, propyl, butyl, methoxy, ethoxy, propoxy, bromine, chorine or fluorine;

$R^c$ is $(C_1-C_5)$alkyl; $(C_1-C_5)$haloalkyl; —O—R³; —NR³R⁴; halogen; —C(O)NR³R⁴; cyano; C(O)R³; —C≡C—R³; or nitro; and $R^z$ is tert-butyl, isopropyl, or cyclopentyl.

Formulae III and IV each represent that the fluorine substituent can appear on any carbon atom in the ring which has a valence that is otherwise complete with a hydrogen atom as a substituent. The following structures illustrate the positions for fluorine substituent which are of interest:

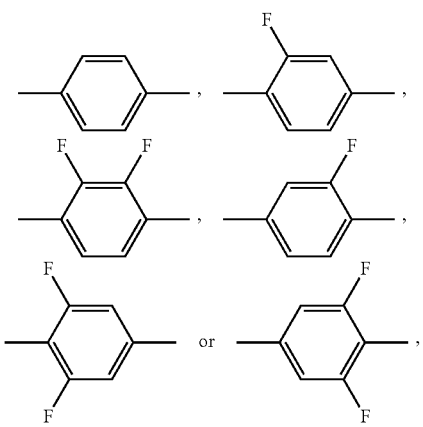

A subclass of optionally substituted pyridine structures for M of formula (I) are of the following formulae:

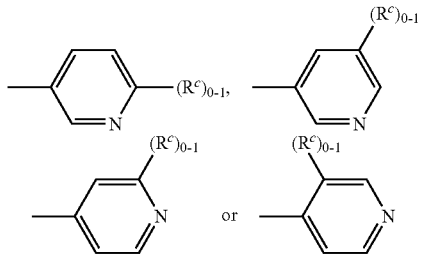

In formulae III and IV, n is zero or one and X is:
(1) —O—;
(2) —SO₂—;
(3) —NR⁵—;
(4) —NR⁵—SO₂—;
(5) —N(SO₂NR⁷R⁸)—;
(6) —SO₂—NR⁵—;
(7) —NR⁵—C(O)—;
(8) —C(O)—NR⁵—;
(9) —C(O)—; or
(10) a single bond.

In a class of compounds of formulae III and IV, X is —O—; —NR⁵—; —NR⁵—C(O)—; —C(O)—NR⁵— or a single bond.

In formulae III and IV above, Y is a linear or branched $C_1$ to $C_6$ alkyl fragment that is substituted with one or two Z groups, where each Z group is independently selected from:
(1) —OR⁶;
(2) —O—C(O)—R⁶;
(3) —NR⁷R⁸;
(4) —SO₂—(C₁-C₅)alkyl;
(5) —C(O)—O—R⁶;
(6) —NH—C(O)—R⁶;
(7) —C(O)—NR⁷R⁸; or
(8) a monocyclic, saturated, partially saturated, or aromatic heterocycle of 5-7 ring atoms containing at least one heteroatom selected from N, O, or S, that is optionally substituted with 1 to 3 substituents selected from (C₁-C₅)alkyl, (C₁-C₅) haloalkyl, hydroxy, amino, halogen, or oxo;
with the proviso that when n is zero and X is —O—, —NR³—, or a single bond, then Z is not morpholine, piperidine, imidazole, or tetrazole;
with the further proviso that when n is zero and X is a single bond, then Z is not —NR⁷R⁸.

In a class of compounds of formulae III and IV, Y is a linear or branched $C_1$ to $C_4$ alkyl fragment ($C_1$ to $C_4$ alkyl chain) that is substituted with one Z group selected from —$OR^6$; —$NR^7R^8$; —NH—C(O)—$R^6$ or —C(O)—$NR^7R^8$. In a subclass of compounds of this invention within this class, Y is methylene, ethylene, n-propylene or n-butylene.

The substituents $R^3$, $R^4$, $R^5$ and $R^6$ are each independently hydrogen or ($C_1$-$C_5$)alkyl optionally substituted with hydroxy. In a class of compounds of this invention, $R^3$, $R^4$, $R^5$ and $R^6$ are each independently hydrogen, methyl, ethyl, propyl or butyl, optionally substituted with hydroxy.

The substituents $R^7$ and $R^8$ are independently hydrogen, or ($C_1$-$C_5$)alkyl optionally substituted with hydroxy; or the group —$NR^7R^8$ forms a monocyclic saturated heterocyclic ring having 5 to 7 ring atoms, where, in addition to the nitrogen atom attached to the rest of the molecule, zero to two of the other ring atoms is a hetero atom selected from N, O and S, and the remaining ring atoms are carbon. Examples of such —$NR^7R^8$ monocyclic saturated heterocyclic ring groups include pyrrolidine, piperidine, azepane, morpholine, thiomorpholine, piperazine, and homopiperazine. The —$NR^7R^8$ monocyclic saturated heterocyclic ring group is optionally substituted on a carbon atom with hydroxy.

In a class of compounds of formulae III and IV I of particular interest, $R^7$ and $R^8$ are each independently selected from hydrogen, methyl, ethyl, propyl or butyl, optionally substituted with hydroxy.

Another class of compounds of this invention within the scope of formula I are
of Formulae V and VI, including the salts, metabolites and prodrugs thereof and diastereoisomeric forms (both isolated stereoisomers and mixtures of stereoisomers) thereof. Formula V and VI are as follows:

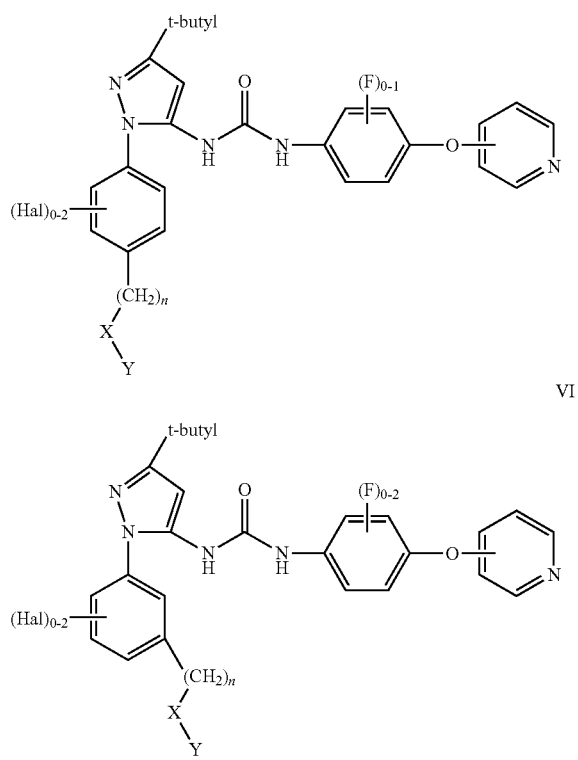

wherein
Hal is bromine, chorine or fluorine;
n is zero or one;
X is: —O—; —$NR^5$—; —$NR^5$—C(O)—; —C(O)—$NR^5$— or a single bond; and
Y is: methylene, ethylene, n-propylene or n-butylene substituted with one Z group
which is: —$OR^6$; —$NR^7R^8$; —NH—C(O)—$R^6$ or —C(O)—$NR^7R^8$;
with the proviso that when n is zero and X is a single bond, then Z is not —$NR^7R^8$.

The substituents $R^5$ and $R^6$ are each independently hydrogen, methyl, ethyl, propyl or butyl, optionally substituted with hydroxy.

The substituents $R^7$ and $R^8$ are each independently hydrogen, methyl, ethyl, propyl or butyl, optionally substituted with hydroxy.

When any moiety is "substituted", it can have up to the highest number of indicated substituents, and each substituent can be located at any available position on the moiety and can be attached through any available atom on the substituent. "Any available position" means any position on the moiety that is chemically accessible through means known in the art or taught herein and that does not create an unduly unstable molecule. When there are two or more substituents on any moiety, each substituent is defined independently of any other substituent and can, accordingly, be the same or different.

The term "optionally substituted" means that the moiety so modified may be either unsubstituted, or substituted with the identified substituent(s).

It is understood that if M is pyridine, the term "$OR^4$", combined with $R^4$=H, represents a 2-, 3-, and 4-hydroxypyridine, but also includes those structures referred to in the art as 1-oxo-pyridine, 1-hydroxy-pyridine and pyridine N-oxide. The same applies if M is a pyrimidine ring.

Where the plural form of the word compounds, salts, and the like, is used herein, this is taken to mean also a single compound, salt, or the like.

The term ($C_1$-$C_5$)alkyl, means straight, branched, or cyclic alkyl groups having from one to five carbon atoms, that may be linear or branched with single or multiple branching. Such groups include methyl, ethyl, n-propyl, isopropyl, n-butyl, isobutyl, sec-butyl, tert-butyl, cyclobutyl, 1-methylcyclopropyl, and the like.

The term ($C_1$-$C_5$)haloalkyl means a ($C_1$-$C_5$)alkyl group as defined above, that is substituted with a least one halogen atom, up to per-halo. The halo substituent(s) include fluoro, chloro, bromo, or iodo. Fluoro, chloro and bromo are preferred, and fluoro and chloro are more preferred. The halogen substituent(s) can be located on any available carbon. When more than one halogen substituent is present on this moiety, they may be the same or different carbon atoms. Examples of such halogenated alkyl substituents include but are not limited to chloromethyl, dichloromethyl, trichloromethyl, fluoromethyl, difluoromethyl, trifluoromethyl, 2,2,2-trifluoroethyl, and 1,1,2,2-tetrafluoroethyl, and the like.

The term ($C_1$-$C_5$)alkoxy means a straight, branched, or cyclic alkoxy group having from one to three saturated carbon atoms that may be linear or branched with single or multiple branching, and includes such groups as methoxy, ethoxy, n-propoxy, isopropoxy, cyclopropyloxy, cyclobutylmethoxy, and the like.

The term ($C_1$-$C_5$)haloalkoxy means a ($C_1$-$C_5$)alkoxy group as defined above, that is substituted with at least one halogen atom, up to per-halo, and includes halogenated groups such as 2,2-dichloroethoxy, trifluoromethoxy, and the like.

Halogen means fluoro, chloro, bromo, or iodo. Fluoro, chloro and bromo are preferred, and fluoro and chloro are more preferred.

The term "monocyclic, saturated, partially saturated, or aromatic heterocycle containing at least one heteroatom selected from N, O, or S" refers to a synthetically accessible, saturated, partially saturated, or aromatic monocyclic ring having 5 to 7 ring atoms, where one to three of these ring atoms is a hetero atom selected from N, O and S, with the remaining ring atoms being carbon. When more than one hetero atom is present in the moiety, they are selected independently from the other(s) so that they may be the same or different. Saturated heterocyclic rings include, but are not limited to, tetrahydropyrane, pyrrolidine, piperidine, azepane, morpholine, thiomorpholine, tetrahydrofuran, tetrahydrothiophene, oxetane, dioxane, and the like. Partially saturated heterocyclic rings include, but are not limited to, dihydrofurane, dihydropyrane, dihydropyridine, dihydrothiophene, and the like. Monocyclic aromatic heterocyclic rings include, but are not limited to pyrrole, furan, thiophene, imidazole, pyrazole, thiazole, oxazole, isoxazole, isothiazole, triazole, tetrazole, thiadiazole, oxadiazole, pyridine, pyrimidine, pyridazine, pyrazine, and triazine.

The compounds of Formula I may contain one or more asymmetric centers, depending upon the location and nature of the various substituents desired. Asymmetric carbon atoms may be present in the (R) or (S) configuration or (R,S) configuration. In certain instances, asymmetry may also be present due to restricted rotation about a given bond, for example, the central bond adjoining two substituted aromatic rings of the specified compounds. Substituents on a ring may also be present in either cis or trans form. It is intended that all such configurations (including enantiomers and diastereomers), are included within the scope of the present invention. Preferred compounds are those with the absolute configuration of the compound of Formula I which produces the more desirable biological activity. Separated, pure or partially purified isomers or racemic mixtures of the compounds of this invention are also included within the scope of the present invention. The purification of said isomers and the separation of said isomeric mixtures can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formula I can likewise be obtained by chiral syntheses utilizing optically active starting materials.

The present invention also relates to useful forms of the compounds as disclosed herein, such as pharmaceutically acceptable salts, metabolites and prodrugs of all the compounds Formula (I). The term "pharmaceutically acceptable salt" refers to a relatively non-toxic, inorganic or organic acid addition salt of a compound of the present invention. For example, see S. M. Berge, et al. "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Certain compounds of this invention can be further modified with labile functional groups that are cleaved after in vivo administration to furnish the parent active agent and the pharmacologically inactive derivatizing (functional) group. These derivatives, commonly referred to as prodrugs, can be used, for example, to alter the physicochemical properties of the active agent, to target the active agent to a specific tissue, to alter the pharmacokinetic and pharmacodynamic properties of the active agent, and to reduce undesirable side effects Prodrugs of the invention include, e.g., the esters of appropriate compounds of this invention, are well-tolerated, pharmaceutically acceptable esters such as alkyl esters including methyl, ethyl, propyl, isopropyl, butyl, isobutyl or pentyl esters. Additional esters such as phenyl($C_1$-$C_5$)alkyl may be used, although methyl ester is preferred.

Methods for synthesizing prodrugs are described in the following reviews on the subject, which are incorporated herein by reference for their description of these methods:

Higuchi, T.; Stella, V. eds. *Prodrugs As Novel Drug Delivery Systems*. ACS Symposium Series. American Chemical Society: Washington, D.C. (1975).

Roche, E. B. *Design of Biopharmaceutical Properties through Prodrugs and Analogs*. American Pharmaceutical Association: Washington, D.C. (1977).

Sinkula, A. A.; Yalkowsky, S. H. *J Pharm Sci.* 1975, 64, 181-210.

Stella, V. J.; Charman, W. N. Naringrekar, V. H. *Drugs* 1985, 29, 455-473.

Bundgaard, H., ed. *Design of Prodrugs*. Elsevier: New York (1985).

Stella, V. J.; Himmelstein, K. J. *J. Med. Chem.* 1980, 23, 1275-1282.

Han, H-K; Amidon, G. L. *AAPS Pharmsci* 2000, 2, 1-11.

Denny, W. A. *Eur. J. Med. Chem.* 2001, 36, 577-595.

Wermuth, C. G. in Wermuth, C. G. ed. *The Practice of Medicinal Chemistry* Academic Press: San Diego (1996), 697-715.

Balant, L. P.; Doelker, E. in Wolff, M. E. ed. *Burgers Medicinal Chemistry And Drug Discovery* John Wiley & Sons: New York (1997), 949-982.

General Preparative Methods

The particular process to be utilized in the preparation of the compounds used in this embodiment of the invention depends upon the specific compound desired. Such factors as the selection of the specific substituents play a role in the path to be followed in the preparation of the specific compounds of this invention. Those factors are readily recognized by one of ordinary skill in the art.

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

All variable groups of these methods are as described in the generic description if they are not specifically defined below. When a variable group or substituent with a given symbol is used more than once in a given structure, it is to be understood that each of these groups or substituents may be independently varied within the range of definitions for that symbol. It is recognized that compounds of the invention with each claimed optional functional group cannot be prepared with each of the below-listed methods. Within the scope of each method optional substituents are used which are stable to the reaction conditions, or the functional groups which may participate in the reactions are present in protected form where necessary, and the removal of such protective groups is completed at appropriate stages by methods well known to those skilled in the art.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in examples.

Specific preparations of diaryl ureas, including pyrazolyl ureas, are already described in the patent literature, and can be adapted to the compounds of the present invention. For example, Miller S. et al, "Inhibition of p38 Kinase using Symmetrical and Unsymmetrical Diphenyl Ureas" PCT Int. Appl. WO 99 32463, Miller, S et al. "Inhibition of raf Kinase using Symmetrical and Unsymmetrical Substituted Diphenyl Ureas" PCT Int. Appl., WO 99 32436, Dumas, J. et al., "Inhibition of p38 Kinase Activity using Substituted Heterocyclic Ureas" PCT Int. Appl., WO 99 32111, Dumas, J. et al., "Method for the Treatment of Neoplasm by Inhibition of raf Kinase using N-Heteroaryl-N'-(hetero)arylureas" PCT Int. Appl., WO 99 32106, Dumas, J. et al., "Inhibition of p38 Kinase Activity using Aryl- and Heteroaryl-Substituted Heterocyclic Ureas" PCT Int. Appl., WO 99 32110, Dumas, J., et al., "Inhibition of raf Kinase using Aryl- and Heteroaryl-Substituted Heterocyclic Ureas" PCT Int. Appl., WO 99 32455, Riedl, B., et al., "O-Carboxy Aryl Substituted Diphenyl Ureas as raf Kinase Inhibitors" PCT Int. Appl., WO 00 42012, Riedl, B., et al., "O-Carboxy Aryl Substituted Diphenyl Ureas as p38 Kinase Inhibitors" PCT Int. Appl., WO 00 41698, Dumas, J. et al. "Heteroaryl ureas containing nitrogen hetero-atoms as p38 kinase inhibitors" U.S. Pat. Appl. Publ., US 20020065296, Dumas, J. et al. "Preparation of N-aryl-N'-[(acylphenoxy)phenyl]ureas as raf kinase inhibitors" PCT Int. Appl., WO 02 62763, Dumas, J. et al. "Inhibition of raf kinase using quinolyl, isoquinolyl or pyridyl ureas" PCT Int. Appl., WO 02 85857, Dumas, J. et al. "Preparation of quinolyl, isoquinolyl or pyridyl-ureas as inhibitors of raf kinase for the treatment of tumors and/or cancerous cell growth" U.S. Pat. Appl. Publ., US 20020165394. All the preceding patent applications are hereby incorporated by reference.

The compounds of Formula I can be synthesized according to the reaction sequence shown in the General Method 1. These compounds can be synthesized by reacting arylamines of Formula III with isocyanates of Formula II.

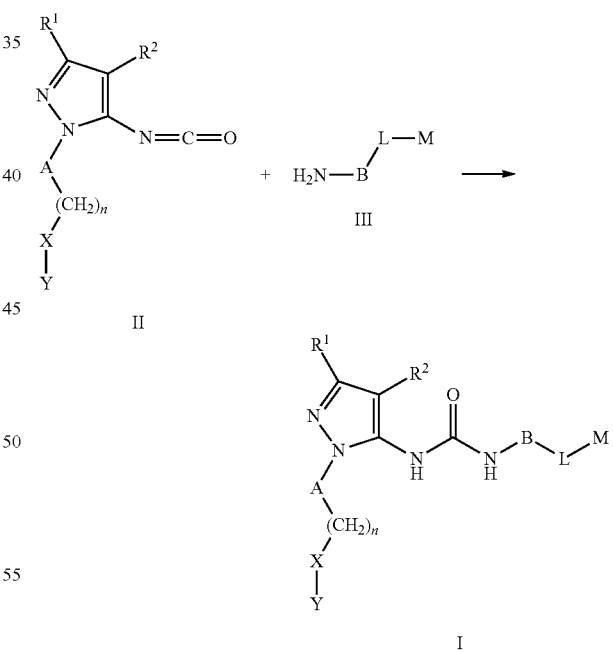

Compounds of Formula II can be synthesized according to methods commonly known to those skilled in the art. For example, isocyanates of Formula II may be prepared in situ or isolated from treatment of amino-pyrazoles of Formula IV with phosgene or a phosgene equivalent such as trichloromethyl chloroformate (diphosgene), bis(trichloromethyl)carbonate (triphosgene), or N,N'-carbonyl-diimidazole (CDI), or N,N'-carbonylditriazole (CDT). Alternatively, compounds of Formula II can be obtained from the corresponding pyrazole-carboxylic acid derivatives via a Curtius-type rearrangement.

Aromatic amines of Formula III are commercially available or can be synthesized according methods commonly known to those skilled in the art. In particular, a large variety of aromatic amines of Formula III has been described in the diaryl urea patent literature cited above.

Alternatively, compounds of Formula I can be prepared according to General Method 2, where 3-aminopyrazoles of Formula IV and amino compounds of Formula III are coupled together to form a urea of Formula I. This process occurs in the presence of a coupling agent such as carbonyldiimidazole, carbonylditriazole, phosgene, diphosgene, triphosgene, and the like. In this process, the isocyanates of Formula II may or may not be formed during the reaction process. The coupling step may be performed in an inert solvent such as dioxane, diethylether, dichloromethane, chloroform, tetrahydrofuran, toluene, and the like, at a temperature selected between 0° C. and reflux. This coupling may be achieved using these reagents alone, or in the presence of an organic or inorganic base as described in the art.

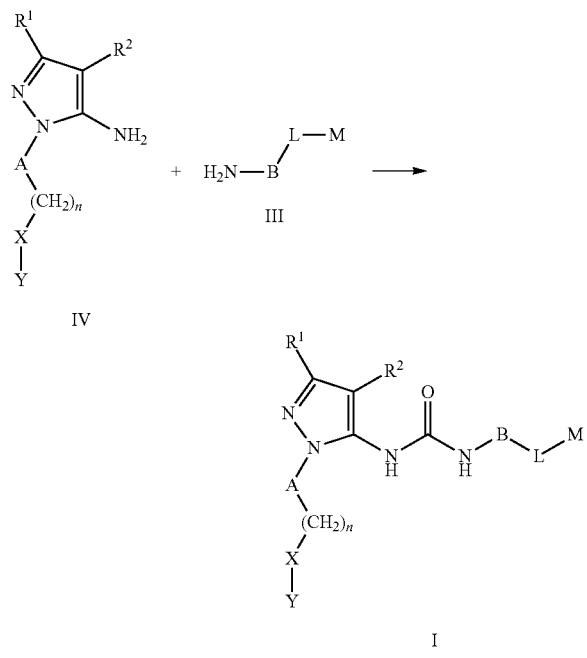

General Method 2

The reaction of the compounds of Formula II with aromatic amines of Formula III is carried out preferably in a solvent. Suitable solvents comprise the customary organic solvents that are inert under the reaction conditions. Non-limiting examples include ethers such as diethyl ether, dioxane, tetrahydrofuran, 1,2-dimethoxy ethane; hydrocarbons such as benzene, toluene, xylene, hexane, cyclohexane, mineral oil fractions; halogenated hydrocarbons such as dichloromethane, trichloromethane, carbon tetrachloride, dichloroethane, trichloro-ethylene, chlorobenzene; alcohols such as methanol, ethanol, n-propanol, isopropanol; esters such as ethyl acetate; ketones such as acetone; nitriles such as acetonitrile; heteroaromatics such as pyridine; polar solvents such as dimethyl formamide and hexamethyl phosphoric acid trisamide; and mixtures of the above-mentioned solvents. Toluene, benzene, and dichloromethane are preferred.

Aromatic amines of Formula III are generally employed in an amount of from 1 to 3 mol per mol of compounds of Formula II; an equimolar amount or slight excess of compounds of Formula III is preferred.

The reaction of the compounds of Formula II with aromatic amines of Formula III is generally carried out within a relatively wide temperature range. In general, they are carried out in a range of from −20 to 200° C., preferably from 0 to 100° C., and more preferably from 25 to 50° C. The steps of this reaction are generally carried out under atmospheric pressure. However, it is also possible to carry them out under super-atmospheric pressure or at reduced pressure (for example, in a range of from 0.5 to 5 bar). The reaction time can generally be varied within a relatively wide range. In general, the reaction is finished after a period of from 2 to 24 hours, preferably from 6 to 12 hours.

3-Aminopyrazoles of Formula IV can be prepared by a variety of methods which will depend on the value of n and the nature of the X and Y linker units, as well as the nature of the Z substituent group(s) on Y.

For example, aminopyrazoles of Formula IV used for the preparation of compounds of Formula I where n=0 or 1 and X is —C(O)—NR$^5$— can be prepared as follows. Carboxylic acids of Formula V are condensed with cyanoketones of Formula VI to afford aminopyrazole intermediates of Formula VII, which are further derivatized by amide formation to aminopyrazoles of Formula IV where n=0 or 1 and X is —C(O)—NR$^5$—, using conventional methods.

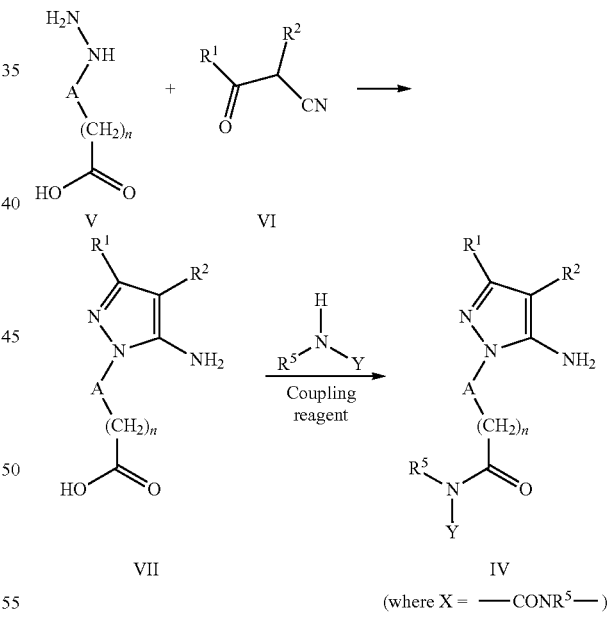

(where X = —CONR$^5$—)

Alternatively, use of an ester of Formula VIII would lead to an aminopyrazole of Formula IX, which can be amidated using an amine of Formula Y—N(R$^5$)H, for example in the presence of trimethylaluminum in an inert solvent. The compounds of Formula V and VIII are commercially available or are prepared by methods described in the scientific literature; for example, an aryl amine H$_2$N-A-(CH$_2$)$_n$—CO$_2$R can be treated with sodium nitrite and then with tin(II) chloride under acidic conditions to provide the corresponding aryl hydrazine of Formula VIII.

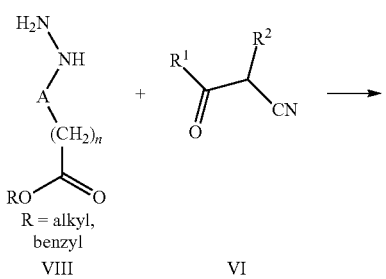

VIII        VI

X can be condensed to aminopyrazoles of Formula XI, which are reduced to the corresponding arylamines of Formula XII (for example, via catalytic hydrogenation, or with the use of iron powder in acetic acid, tin dichloride in DMF, or a similar reducing reagent known in the art). Intermediates of Formula XII can be further elaborated by amide formation with a carboxylic acid such as Y—COOH and a suitable coupling agent to give pyrazoles of Formula IV where n=0 and X is —$NR^5$—C(O)—. Reduction of these compounds provides pyrazoles of Formula IV where n=0 and X is —$NR^5$—. Alternatively, reductive amination of intermediates of Formula XII with an aldehyde also provides pyrazoles of Formula IV where n=0 and X is —$NR^5$— as indicated below.

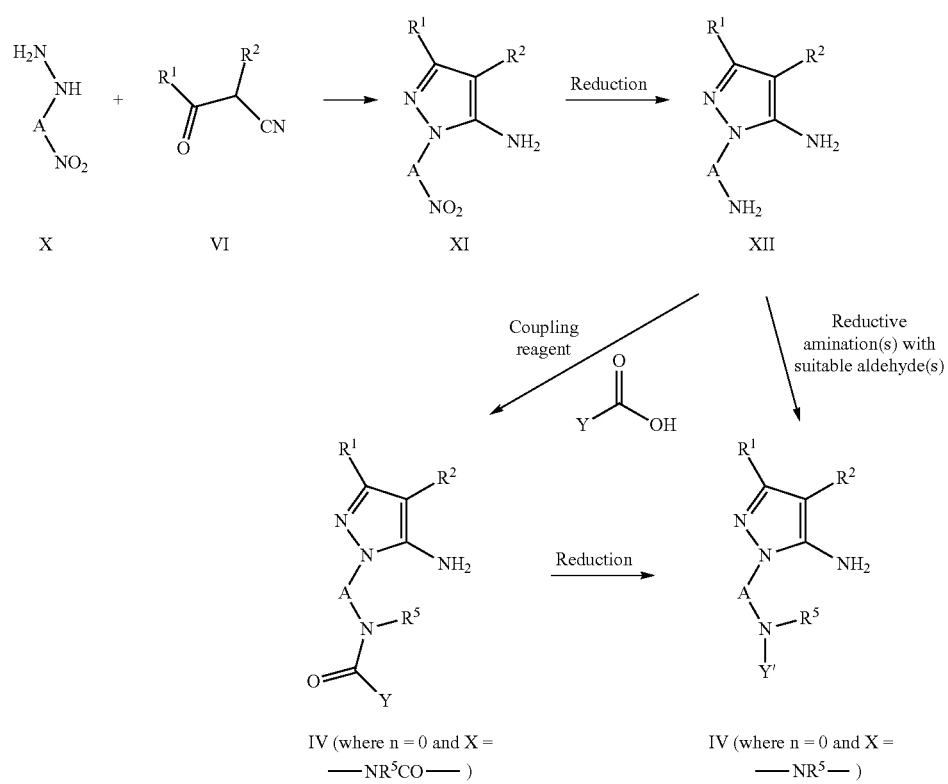

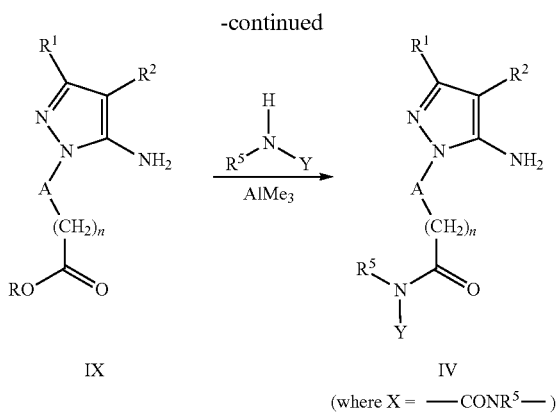

IX

IV
(where X = —$CONR^5$—)

Aminopyrazoles of Formula IV where n=0 and X is —$NR^5$— or —$NR^5$—C(O)— can be prepared in several conventional steps as follows. Nitroaryl-hydrazines of Formula X can be condensed to aminopyrazoles of Formula XI, which Coupling of aminopyrazoles of Formula XII with sulfonyl chlorides such as Y—$SO_2Cl$, usually under basic conditions, provides aminopyrazoles of Formula IV where n=0 and X is —NH—$SO_2$—. These sulfonamides may be further alkylated with a halide reagent such as $R^5$—Br, usually under basic conditions, to give aminopyrazoles of Formula IV where X is —$NR^5$—$SO_2$—.

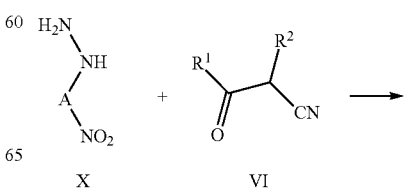

X        VI

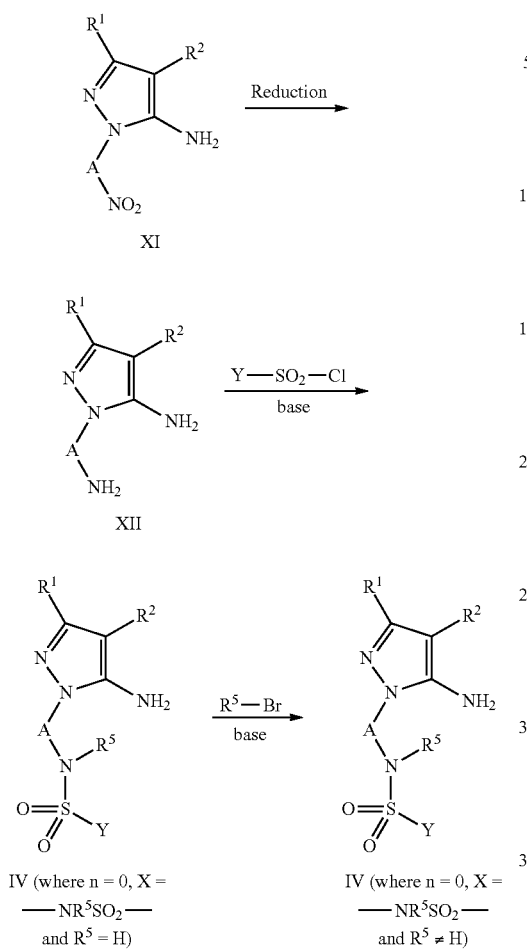
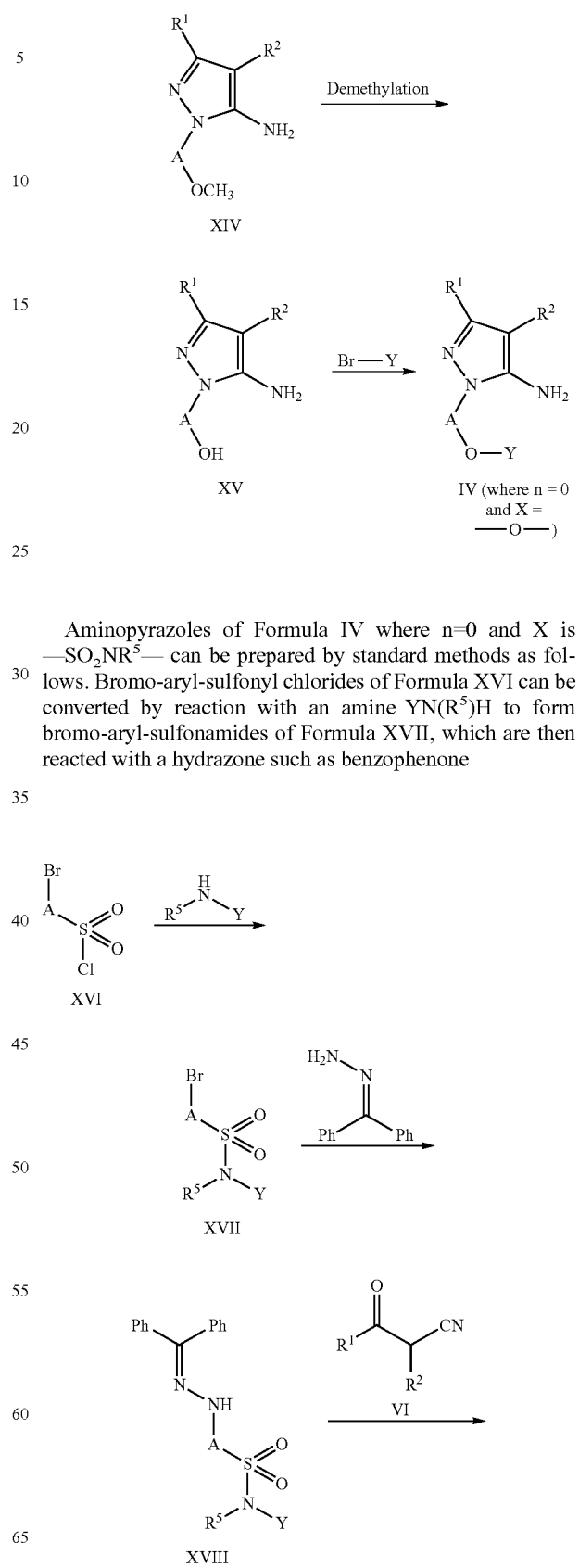

Aminopyrazoles of Formula IV where n=0 and X is —O— can be prepared in several conventional steps as follows. Methoxy-aryl-hydrazines of Formula XIII can be condensed to aminopyrazoles of Formula XIV, which are de-methylated to the corresponding hydroxy compounds of Formula XV (for example, with the use of boron tribromide, methylthiolate in DMF, lithium diphenylphosphide, or an equivalent reagent known in the art). Intermediates of Formula XV can be further elaborated by alkylation, for example with an alkyl halide such as Y—Br, Y—I, or Y—Cl or by a Mitsunobu reaction with an alkanol such as Y—OH, to afford aminopyrazoles of Formula IV where n=0 and X is —O—.

Aminopyrazoles of Formula IV where n=0 and X is —$SO_2NR^5$— can be prepared by standard methods as follows. Bromo-aryl-sulfonyl chlorides of Formula XVI can be converted by reaction with an amine $YN(R^5)H$ to form bromo-aryl-sulfonamides of Formula XVII, which are then reacted with a hydrazone such as benzophenone

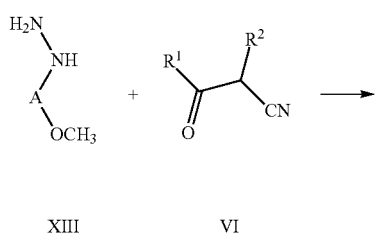

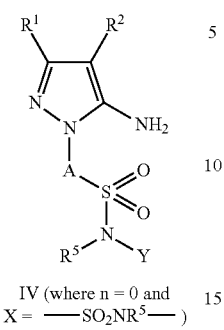

IV (where n = 0 and X = —SO$_2$NR$^5$—)

hydrazone to form the compounds of Formula XVIII. Condensation with cyanoketones of Formula VI provides the desired aminopyrazoles of Formula IV where n=0 and X is —SO$_2$NR$^5$—.

The synthetic transformations described above, which focus on the elaboration of the —X—Y chain, are meant to be applied to prepare 3-aminopyrazole intermediates of Formula IV. However, in many cases, it is also possible to carry out the urea formation at an early stage in the synthesis to lead to key urea intermediates of Formulas IX to XXII. Then, these urea intermediates can be subjected to additional reactions to form the desired —X—Y chains, according to methods similar to those described above.

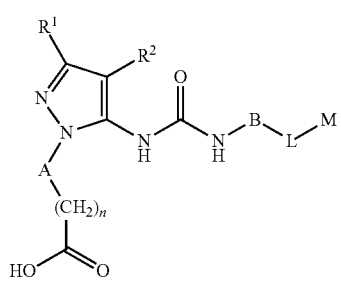

IX

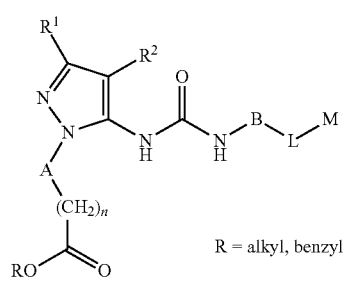

R = alkyl, benzyl

XX

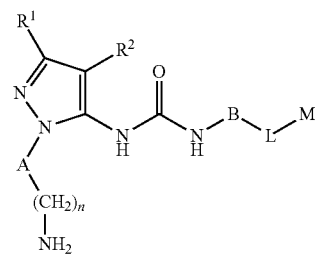

XXI

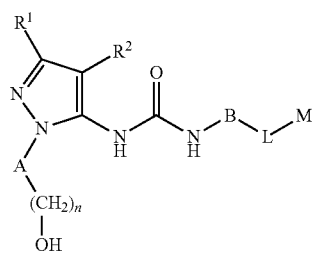

XXII

For example, compounds of Formula I where n=0 and X is —NR$^5$— or —NR$^5$—C(O)— can be prepared as indicated below. In this case, a compound of Formula XXIII in which the group A is substituted with a nitro functionality is reduced (for example, by hydrogenation catalyzed by palladium on carbon) to provide the related amino-substituted compound of Formula XXIV. Intermediates of Formula XXIV can be further elaborated by amide formation with a carboxylic acid such as Y—COOH and a suitable coupling agent to give pyrazoles of Formula I where n=0 and X is —NR$^5$—C(O)—. Reduction of these compounds provides pyrazoles of Formula I where n=0 and X is —NR$^5$—. Alternatively, reductive amination(s) of intermediates of Formula XXIV with an aldehyde(s) also provides pyrazoles of Formula I where n=0 and X is —NR$^5$— as indicated below. Intermediates of Formula XXIV can also be elaborated by treatment with a cyclic anhydride such as succinic or glutaric anhydride, to give pyrazoles of Formula I where n=0, X is —NR$^5$—C(O)—, and the alkyl fragment Y is substituted with Z=—C(O)OH. It is also possible to carry out further reactions on certain compounds of Formula I to produce additional examples of compounds of Formula I. For example, reductive amination (using a suitable aldehyde) of a compound of Formula I where X is —NR$^5$— and R$^5$=H provides a compound of Formula I where X is —NR$^5$— and R$^5$ is not hydrogen. Also, reaction of a compound of Formula I where X is —NR$^5$— and R$^5$=H with a sulfamoyl chloride R$^7$R$^8$N—SO$_2$Cl provides a compound of Formula I where X is —N(SO$_2$NR$^7$R$^8$)—.

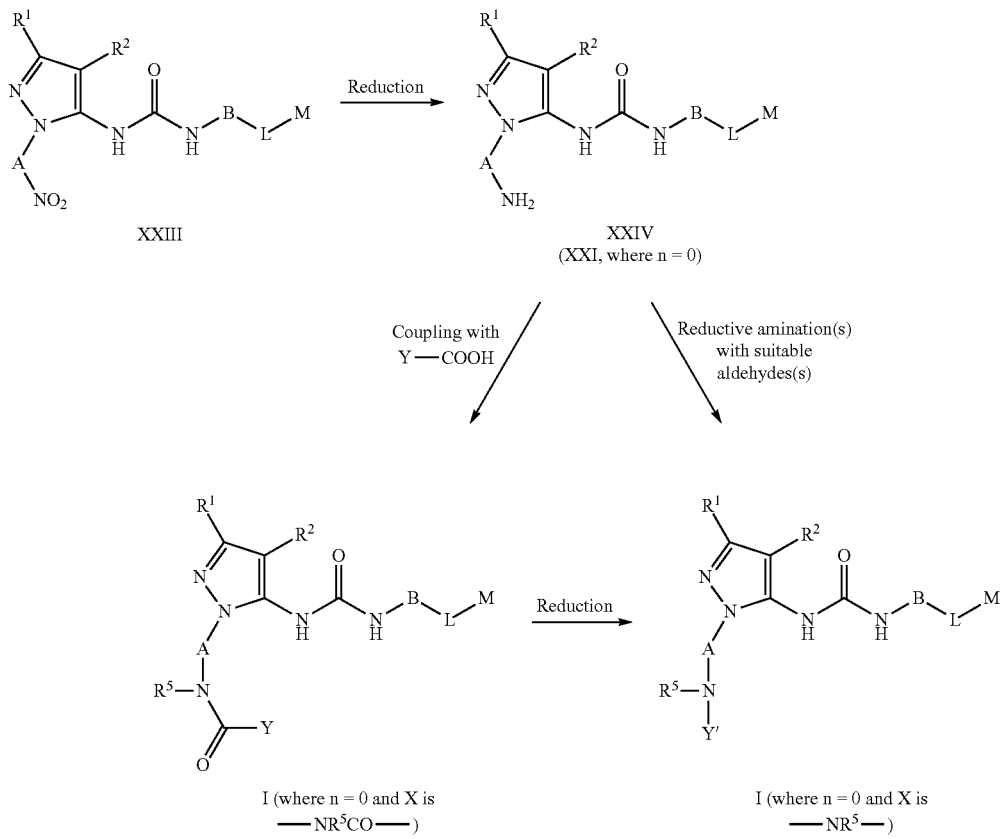

Compounds of Formula I where n=1 and X is —NR⁵— or —NR⁵—C(O)— can be prepared as indicated below. In this case, a compound of Formula XXV in which the group A is substituted with a cyano functionality is reduced (for example, by the use of lithium aluminum hydride) to provide the related aminomethylene-substituted compound of Formula I where n=0, X is a bond, Y is —CH₂— and Z is —NH₂. Then, in a similar manner to that described above, compounds of Formula I where n=1 and X is —NR⁵— or —NR⁵—C(O)— can be prepared by applying standard coupling reactions and/or reductive amination reactions.

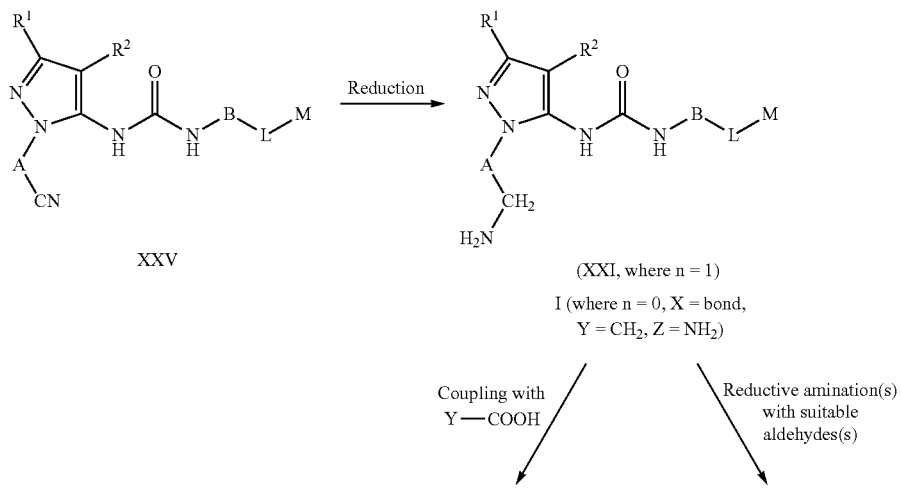

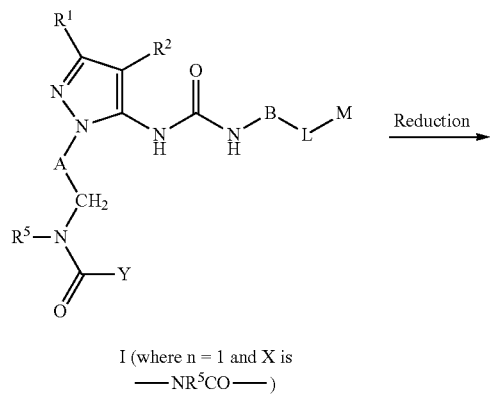

I (where n = 1 and X is
—NR⁵CO—)

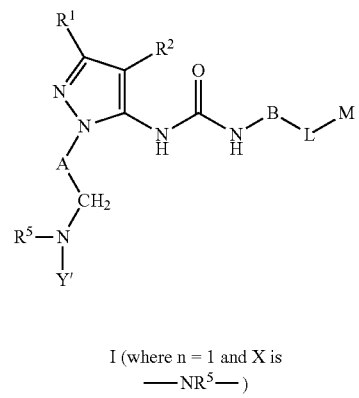

I (where n = 1 and X is
—NR⁵—)

Compounds of Formula I where n=1 and X is —O— can be prepared as indicated in the scheme below. In this case, a compound of Formula XXVI in which the group A is substituted with an ester functionality is reduced (for example, by the use of lithium aluminum hydride) to provide the related hydroxymethylene-substituted compound of Formula I where n=0, X is a bond, Y is —CH₂— and Z is —OH. Then, the hydroxy functionality can be derivatized, for example by conversion to the corresponding methanesulfonate or 4-toluenesulfonate (a compound of Formula XXVII) followed by reaction with Y—OH, to give compounds of Formula I where n=1 and X is —O—.

-continued

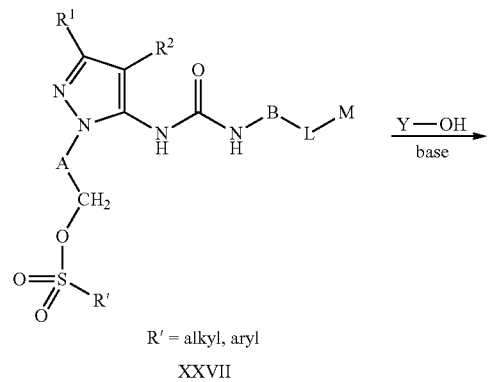

R' = alkyl, aryl

XXVII

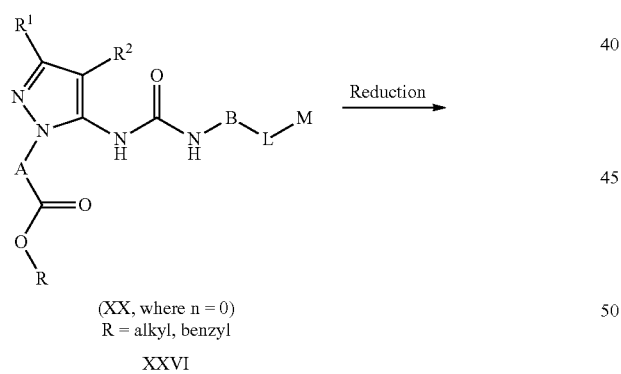

(XX, where n = 0)
R = alkyl, benzyl

XXVI

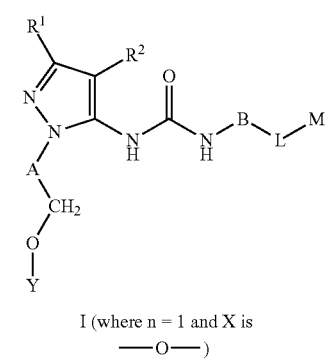

I (where n = 1 and X is
—O—)

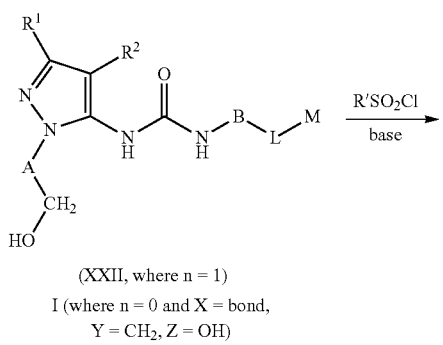

(XXII, where n = 1)
I (where n = 0 and X = bond,
Y = CH₂, Z = OH)

The preparation of several additional examples of compounds of Formula I are illustrated in the following scheme. The ester functionality in a compound of Formula XXVIII can be hydrolyzed under standard conditions to form the compound of Formula I where n=0, X is a bond, Y is CH₂, and Z=C(O)OH. This compound of Formula I can be converted to various other examples of compounds of Formula I by reduction and amide-coupling reactions as indicated in the scheme. For example, an amide-coupling reaction with an amine R⁷R⁸NH gives a compound of Formula I where n=0, X is a bond, Y is CH₂, and Z=—C(O)NR⁷R⁸, and a subsequent reduction reaction provides a compound of Formula I where n=0, X is a bond, Y is CH₂CH₂, and Z=—NR⁷R⁸.

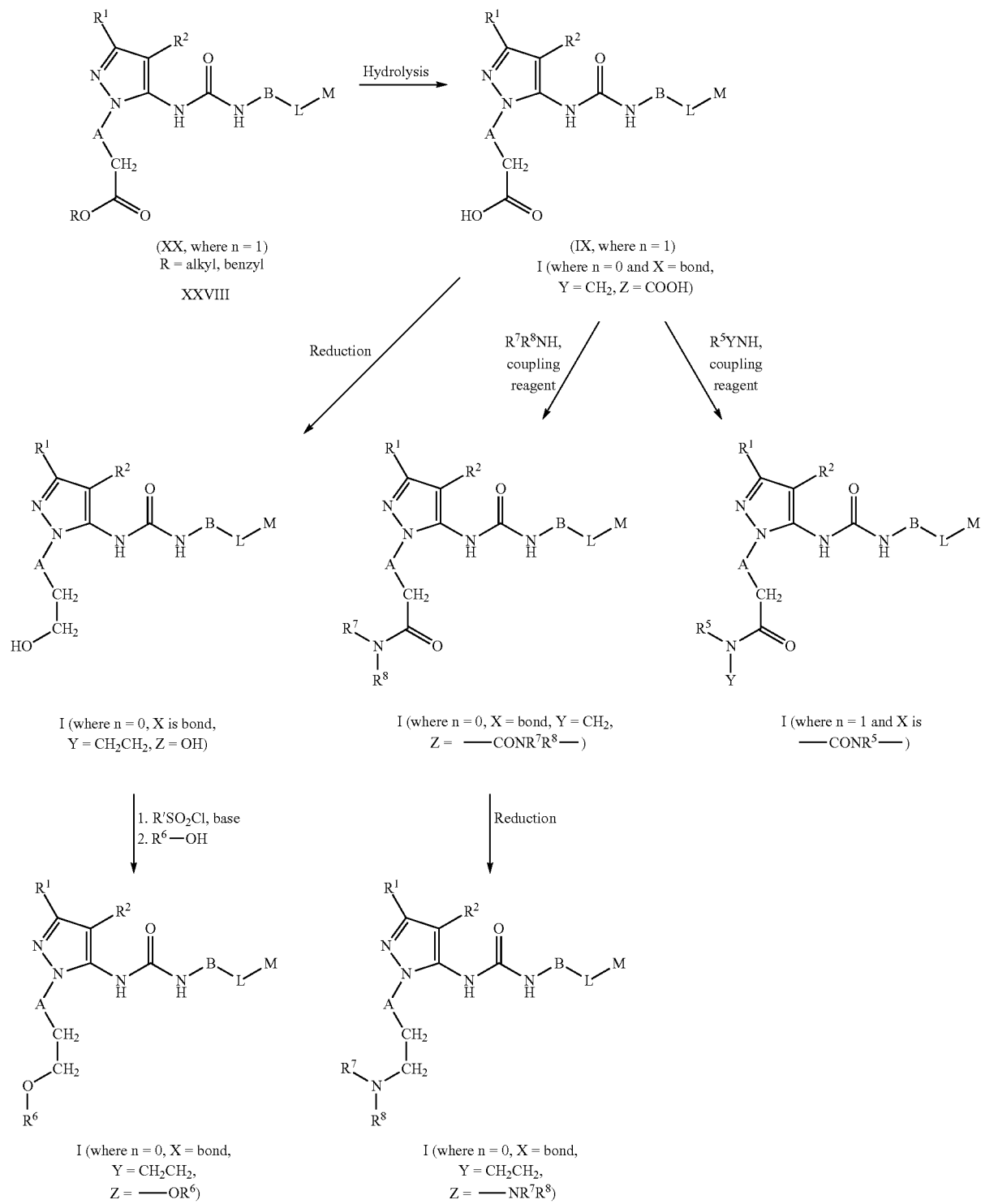

Synthetic transformations that may be employed in the synthesis of compounds of Formula I and in the synthesis of intermediates involved in the synthesis of compounds of Formula I are known by or accessible to one skilled in the art. Collections of synthetic transformations may be found in compilations, such as:

J. March. *Advanced Organic Chemistry,* 4th ed.; John Wiley: New York (1992)

R. C. Larock. *Comprehensive Organic Transformations,* 2nd ed.; Wiley-VCH: New York (1999)

F. A. Carey; R. J. Sundberg. *Advanced Organic Chemistry,* 2nd ed.; Plenum Press: New York (1984)

T. W. Greene; P. G. M. Wuts. *Protective Groups in Organic Synthesis,* 3rd ed.; John Wiley: New York (1999)

L. S. Hegedus. *Transition Metals in the Synthesis of Complex Organic Molecules*, 2nd ed.; University Science Books: Mill Valley, Calif. (1994)

L. A. Paquette, Ed. *The Encyclopedia of Reagents for Organic Synthesis*; John Wiley: New York (1994)

A. R. Katritzky; O. Meth-Cohn; C. W. Rees, Eds. *Comprehensive Organic Functional Group Transformations*; Pergamon Press: Oxford, UK (1995)

G. Wilkinson; F. G A. Stone; E. W. Abel, Eds. *Comprehensive Organometallic Chemistry*; Pergamon Press: Oxford, UK (1982)

B. M. Trost; I. Fleming. *Comprehensive Organic Synthesis*; Pergamon Press: Oxford, UK (1991)

A. R. Katritzky; C. W. Rees Eds. *Comprehensive Heterocylic Chemistry*; Pergamon Press: Oxford, UK (1984)

A. R. Katritzky; C. W. Rees; E. F. V. Scriven, Eds. *Comprehensive Heterocylic Chemistry II*; Pergamon Press: Oxford, UK (1996)

C. Hansch; P. G. Sammes; J. B. Taylor, Eds. *Comprehensive Medicinal Chemistry*: Pergamon Press: Oxford, UK (1990).

In addition, recurring reviews of synthetic methodology and related topics include *Organic Reactions*; John Wiley: New York; *Organic Syntheses*; John Wiley: New York; *Reagents for Organic Synthesis*: John Wiley: New York; *The Total Synthesis of Natural Products*; John Wiley: New York; *The Organic Chemistry of Drug Synthesis*; John Wiley: New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include *Chemical Abstracts*, which may be searched using either CAS OnLine or SciFinder, *Handbuch der Organischen Chemie* (Beilstein), which may be searched using SpotFire, and REACCS.

Compositions of the Compounds of this Invention

This invention also relates to pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC$—$CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:
- 50 mg/mL of the desired, water-insoluble compound of this invention
- 5 mg/mL sodium carboxymethylcellulose
- 4 mg/mL TWEEN 80
- 9 mg/mL sodium chloride
- 9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Hyper-Proliferative Disorders

The present invention relates to a method for using the compounds described above (Compounds of Formula I, salts thereof, stereoisomers thereof, esters thereof, etc.) and compositions thereof, to treat mammalian hyper-proliferative disorders. This method comprises administering to a mammal in need thereof, including a human, an amount of a compound of this invention, (Compounds of Formula I or a pharmaceutically acceptable salt, isomer, or ester thereof; etc.) which is effective to treat the disorder. Hyper-proliferative disorders include but are not limited, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalamic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity (Aiello et al. *New Engl. J. Med.* 1994, 331, 1480; Peer et al. *Lab. Invest.* 1995, 72, 638), age-related macular degeneration (AMD; see, Lopez et al. *Invest. Opththalmol. Vis. Sci.* 1996, 37, 855), neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, compounds of the present invention can be utilized to treat and/or prevent any of the aforementioned angiogenesis disorders.

Based upon standard laboratory techniques known to evaluate compounds useful for the treatment of hyper-proliferative disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. It should be noted that the choice of dosing schedules is particularly important to maximize the efficacy and safety of drugs for the treatment of proliferative disorders such as cancer. Clinically useful dosing schedules will range from three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

The compounds of this invention can be administered as the sole pharmaceutical agent or in combination with one or more other pharmaceutical agents where the combination causes no unacceptable adverse effects. For example, the compounds of this invention can be combined with known anti-hyper-proliferative or other indication agents, and the like, as well as with admixtures and combinations thereof.

The additional pharmaceutical agent can be aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depo-medrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulphate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofuran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, BAY 43-9006, avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

Optional anti-hyper-proliferative agents which can be added to the composition include but are not limited to compounds listed on the cancer chemotherapy drug regimens in the 11$^{th}$ Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

Generally, the use of cytotoxic and/or cytostatic agents in combination with a compound or composition of the present invention will serve to:
(1) yield better efficacy in reducing the growth of a tumor or even eliminate the tumor as compared to administration of either agent alone,
(2) provide for the administration of lesser amounts of the administered chemo-therapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

EXAMPLES

Abbreviations aq aqueous
min minute(s)
h hour(s)
ADDP 1,1'-(Azodicarbonyl)dipiperidine
DMA N,N-Dimethyl acetamide
DMF N,N-Dimethyl formamide
DCM Dichloromethane
DCE 1,2-Dichloroethane
EtOAc Ethyl acetate
EtOH Ethanol
MeOH Methanol
THF Tetrahydrofuran
DMSO Dimethyl sulphoxide
MTBE Methyl tert-butyl ether
HPLC High pressure liquid chromatography
MPLC Medium pressure liquid chromatography
LC-MS Liquid chromatography—coupled mass spectroscopy
RT Retention time
NMR Nuclear resonance spectroscopy
TLC Thin layer chromatography
ES Electrospray
CDT 1,1'-Carbonylditriazole
CDI 1,1'-Carbonyldiimidazole
HOBT 1-Hydroxybenzotriazole
EDCl 1-[3-(Dimethylamino)propyl]-3-ethylcarbodiimide hydrochloride
TMSCl Trimethylsilyl chloride
Et$_3$N Triethylamine
NH$_4$Cl Ammonium chloride
Na$_2$SO$_4$ Sodium sulfate
MgSO$_4$ Magnesium sulfate
HEPES N-(2-hydroxyethyl)-piperazine-N'-(2-ethane sulfonic acid)

The percentage yields reported in the following examples are based on the starting component that was used in the lowest molar amount.
LC-MS: HPLC—electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2×23 mm, 120 A), and a Micromass LCZ single quadrupole mass spectrometer with z-spray electrospray ionization. Spectra were scanned from 120-1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in acetonitrile with 0.02% TFA at 1.5 mL/min. Samples were eluted as follows: 90% A for 0.5 minutes ramped to 95% B over 3.5 minutes and held at 95% B for 0.5 minutes, and then the column was brought back to initial conditions over 0.1 minutes. Total run time was 4.8 minutes.
Preparative HPLC: Preparative HPLC was carried out in reversed phase mode, eluting with aqueous acetonitrile containing 0.5% TFA, typically using a Gilson HPLC system equipped with two Gilson 322 pumps, a Gilson 215 Autosampler, a Gilson diode array detector, and a YMC Pro C-18 column (20×150 mm, 120 A). Gradient elution was used with Buffer A as water with 0.1% TFA and Buffer B as acetonitrile with 0.1% TFA. Sample was dissolved in MeOH or MeOH/DMSO with concentration about 50 mg/mL. Injection volume was about 2-3 mL/injection. Sample was typically eluted as follows: 10-90% B over 15 minutes with flow rate of 25 mL/min, hold 2 minutes, back to 10% B. The desired fraction(s) were collected by UV monitoring at 254 or 220 nm and evaporated by using a GeneVac centrifugal vacuum instrument.

Preparative MPLC: Preparative medium pressure liquid chromatography (MPLC) was carried out by standard silica gel "flash chromatography" techniques (e.g., Still, W. C. et al. *J. Org. Chem.* 1978, 43, 2923-5), or by using silica gel cartridges and devices such as the Biotage Flash systems. A variety of eluting solvents were used, as described in the experimental protocols.

Preparation of Intermediates

Preparation of 5-tert-butyl-2-(4-nitro-phenyl)-2H-pyrazol-3-ylamine

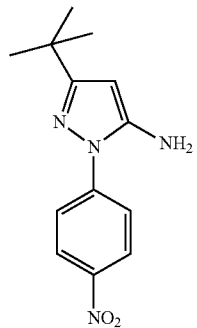

To a solution of 4,4-dimethyl-3-oxopentanenitrile (20.4 g, 163 mmol) and 4-nitrophenylhydrazine (25.0 g, 163 mmol) in anhydrous EtOH (300 mL) was added acetic acid (3.4 mL, 60 mL) dropwise. The reaction was stirred at reflux under $N_2$ for 18 h. The reaction mixture was cooled to room temperature and concentrated at reduced pressure. The residue was partitioned between EtOAc (500 mL) and aqueous saturated NaHCO$_3$ solution (300 mL). The organic layer was washed with water and brine, dried over Na$_2$SO$_4$, and concentrated at reduced pressure. The crude residue was purified by MPLC (eluting with 80:20 hexanes/EtOAc) to give 36.0 g (85%) of the desired product. $^1$H-NMR (DMSO-d$_6$) δ 8.28 (d, J=6.9 Hz, 2H), 7.93 (d, J=6.9 Hz, 2H), 5.55 (s, 2H), 5.46 (s, 1H), 1.20 (s, 9H); MS LC-MS [M+H]$^+$=261, RT=2.74 min.

Preparation of 4-(5-amino-3-tert-butyl-pyrazol-1-yl)-benzonitrile

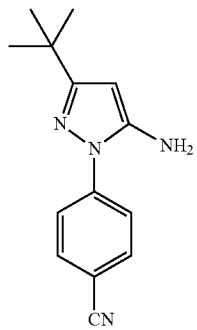

The title compound was prepared (85% yield) in the same manner as described for 5-tert-butyl-2-(4-nitro-phenyl)-2H-pyrazol-3-ylamine, replacing 4-nitrophenylhydrazine with 4-cyanophenylhydrazine. MS LC-MS [M+H]$^+$=241, RT=2.39 min.

Preparation of 4-(5-amino-3-tert-butyl-pyrazol-1-yl)benzoic acid

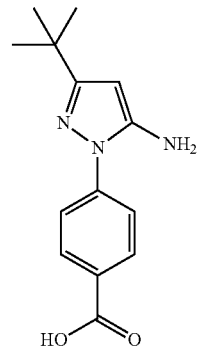

A mixture of 4,4-dimethyl-3-oxo-pentanenitrile (4.52 g, 36.15 mmol), 4-hydrazinobenzoic acid (5.00 g, 32.86 mmol), and acetic acid (2 mL) in EtOH/THF (1:1) was refluxed for 16 h. After cooling, the solvent was concentrated at reduced pressure, and the crude was re-dissolved in EtOAc. The organic layer was washed with aqueous saturated Na$_2$CO$_3$ solution and brine, dried over MgSO$_4$, filtered, and concentrated to half its volume. The resulting residue was filtered, and the solids were washed with cold EtOAc and dried under high vacuum to afford the title compound as a white solid (8.4 g, 99%). $^1$H-NMR (DMSO-d$_6$) δ 12.91 (s, 1H), 7.99 (d, J=6.0 Hz, 2H), 7.75 (d, J=9.0 Hz, 2H), 5.42 (s, 1H), 5.39 (s, 2H), 1.21 (s, 9H); MS LC-MS [M+H]$^+$=260, RT=1.83 min.

Preparation of 4-(5-amino-3-tert-butyl-pyrazol-1-yl)benzoic acid methyl ester

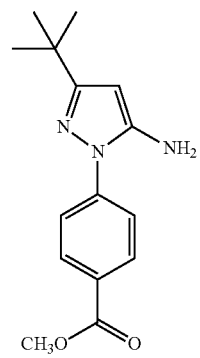

To anhydrous methanol at 0° C. was added dropwise TMSCl (12.57 g, 115.0 mmol). After 10 minutes a solution of 4-(5-amino-3-tert-butyl-pyrazol-1-ylbenzoic acid (3.00 g, 11.57 mmol) in anhydrous methanol was added dropwise, and the reaction mixture was stirred at 80° C. for 16 h. The volatile solvent was removed and the crude was partitioned between EtOAc and aqueous saturated Na$_2$CO$_3$ solution. The organic layer was washed with water and brine, dried over MgSO$_4$, and concentrated at reduced pressure. The resultant solid was triturated from hexane, filtered, and dried under high vacuum to afford 2.23 g (71%) of the title compound as a white solid. $^1$H-NMR (DMSO-$d_6$) δ 8.07 (d, J=9.0 Hz, 2H), 7.87 (d, J=12.0 Hz, 2H), 5.57 (s, 1H), 4.97 (s, 2H), 3.90 (s, 3H), 1.26 (s, 9H); MS LC-MS [M+H]$^+$=274, RT=2.74 min.

Preparation of 4-(3-tert-butyl-5-phenoxycarbonylamino-pyrazol-1-yl)-benzoic acid methyl ester

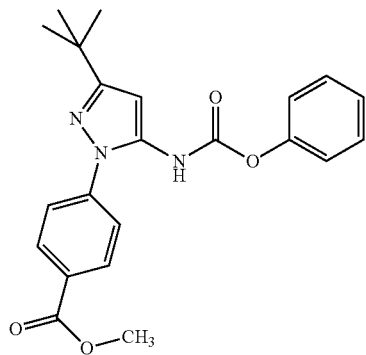

To a solution of 4-(5-amino-3-tert-butyl-pyrazol-1-yl)-benzoic acid methyl ester (5.3 g, 19.4 mmol) in anhydrous THF (200 mL) was slowly added phenyl chloroformate (6.81 mL, 54.3 mmol), followed by sodium carbonate (2.1 g, 19.4 mmol). The mixture was stirred at room temperature overnight. Ethyl acetate (500 mL) was added, followed by saturated sodium carbonate (300 mL). The organic layer was washed with saturated sodium carbonate (3×) and brine (1×), dried over MgSO$_4$, and concentrated at reduced pressure. The residue was washed with ether to give 4.3 g (56%) of the desired product. $^1$H-NMR (DMSO-$d_6$) δ 10.19 (s, 1H), 8.10 (d, J=9.0 Hz, 2H), 7.73 (d, J=9.0 Hz, 2H), 7.38-7.11 (m, 5H), 6.41 (s, 1H), 3.87 (s, 3H), 1.27 (s, 1H); MS LC-MS [M+H]$^+$= 394.1, RT=3.53 min.

Preparation of 5-tert-butyl-2-(4-methoxyphenyl)-2H-pyrazol-3-ylamine

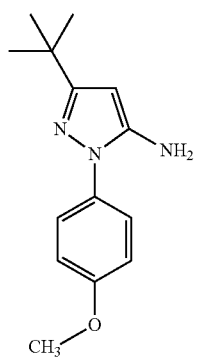

The title compound was prepared in the same manner as described for 4-(5-amino-3-tert-butyl-pyrazol-1-yl)benzoic acid, replacing 4-hydrazinobenzoic acid with 4-methoxyphenylhydrazine. $^1$H-NMR (DMSO-$d_6$) δ 7.40 (d, J=5.1 Hz, 2H), 6.98 (d, J=4.8 Hz, 2H), 5.32 (s, 1H), 5.05 (s, 2H), 3.77 (s, 3H), 1.20 (s, 9H); MS LC-MS [M+H]$^+$=246, RT=1.76 min.

Preparation of 4-(5-amino-3-tert-butyl-pyrazol-1-yl)phenol

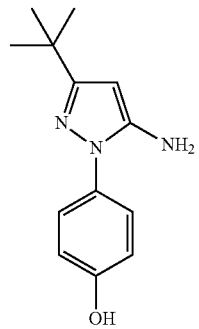

To a stirred solution of 5-tert-butyl-2-(4-methoxyphenyl)-2H-pyrazol-3-ylamine (5.3 g, 21.6 mmol) in anhydrous DCM (43.2 mL) was added aluminum trichloride (14.4 g, 108.0 mmol, 5.0 eq) proportion wise, and the reaction was stirred at reflux for 18 h. The cooled reaction was poured into ethyl acetate, and the organic layer was washed with water and brine, dried over Na$_2$SO$_4$, filtered, and concentrated at reduced pressure. Crystallization from DCM/ether afforded the title compound (2.71 g, 54%) as a white solid. $^1$H-NMR (DMSO-$d_6$) δ 9.47 (s, 1H), 7.21 (d, J=9.0 Hz, 2H), 6.75 (d, J=8.7 Hz, 2H), 5.25 (s, 1H), 4.91 (broad s, 2H), 1.13 (s, 9H); MS LC-MS [M+H]$^+$=232, RT=1.13 min; TLC (35% EtOAc/hex), R$_f$=0.13.

Preparation of 5-tert-butyl-2-[4-(2-methoxyethoxy)phenyl]-2H-pyrazol-3-ylamine

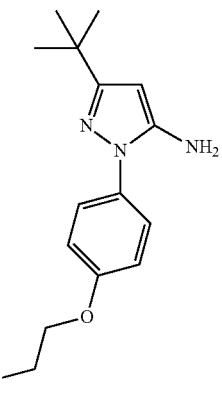

A mixture of 4-(5-amino-3-tert-butyl-pyrazol-1-yl)phenol (500 mg, 2.16 mmol), 2-methoxyethanol (164.5 mg, 2.16 mmol), ADDP (818.2 mg, 3.24 mmol, 1.5 eq), and triphenylphosphine (850.5 mg, 3.24 mmol, 1.5 eq) in anhydrous THF was stirred at ambient temperature under nitrogen for 18 h. The reaction mixture was poured into EtOAc, and the organic layer was washed with water and brine, dried over Na$_2$SO$_4$, filtered, and concentrated at reduced pressure. Purification by MPLC (eluting with 25% EtOAc/hexane) gave an oil which solidified upon standing, 507 mg (81%). $^1$H-NMR (DMSO-$d_6$) δ 7.39 (dd, J=6.6, 2.4 Hz, 2H), 6.97 (dd, J=6.9, 2.7 Hz, 2H), 5.30 (s, 1H), 5.02 (broad s, 2H), 4.09 to 4.06 (m, 2H), 3.65 to 3.62 (m, 2H), 3.28 (s, 3H), 1.16 (s, 9H); MS LC-MS [M+H]$^+$=290, RT=1.35 min.

Preparation of 5-tert-butyl-2-[4-(2-diethylaminoethoxy-phenyl]-2H-pyrazol-3-ylamine

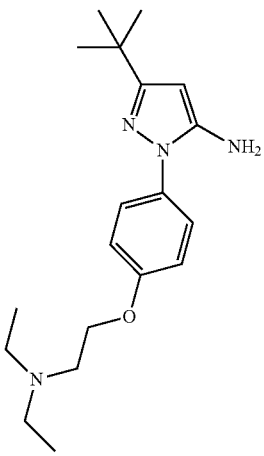

To a solution of 4-(5-amino-3-tert-butyl-pyrazol-1-yl)-phenol (300 mg, 1.30 mmol) in anhydrous 2-butanone (5.2 mL) was added 2-(diethylamino)ethyl chloride hydrochloride (245.5 mg, 1.43 mmol, 1.1 eq), potassium carbonate (448.2 mg, 3.24 mmol, 2.5 eq), and sodium iodide (19.4 mg, 0.13 mmol, 0.1 eq), and the reaction mixture was stirred at 60° C. for 3 days. The cooled reaction was poured into EtOAc, and the organic layer was washed with water and brine, dried over Na$_2$SO$_4$, filtered, and concentrated at reduced pressure. Purification by MPLC (1:4 MeOH/EtOAc) afforded the title compound (133 mg, 31%) as a syrup. $^1$H-NMR (CD$_3$OD) δ 7.35 (d, J=9.3 Hz, 2H), 7.00 (d, J=9.0 Hz, 2H), 5.82 (s, 1H), 4.14 (t, J=5.4 Hz, 2H), 2.96 (t, J=5.7 Hz, 2H), 2.72 (q, J=7.2 Hz, 4H), 1.33 (s, 9H), 1.12 (t, J=7.2 Hz, 6H); MS LC-MS [M+H]$^+$=331, RT=0.33 min.

Preparation of 4-{2-[4-(5-amino-3-tert-butyl-pyrazol-1-yl)-phenoxy]-ethyl}-piperidine-1-carboxylic acid tert-butyl ester

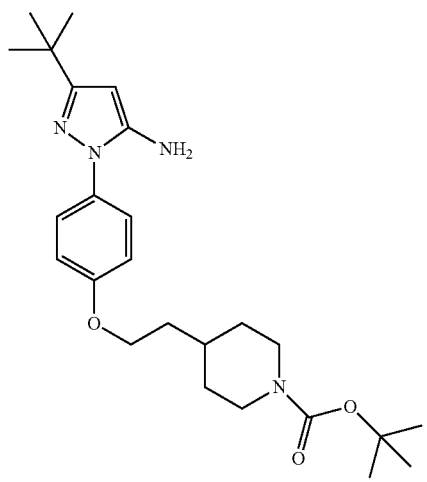

To a solution of 4-(5-amino-3-tert-butyl-pyrazol-1-yl)-phenol (550 mg, 2.4 mmol) and 4-(2-hydroxy-ethyl)-piperidine-1-carboxylic acid tert-butyl ester (505 mg, 2.18 mmol) in 50 mL THF was added ADDP (825 mg, 3.28 mmol) and triphenylphosphine (858 mg, 3.28 mmol). The reaction mixture was stirred at room temperature under nitrogen overnight. The solid was removed by filtration, the filtrate was concentrated and the residue was purified by MPLC (80:20 hexane/EtOAc) to give the desired product 4-{2-[4-(5-amino-3-tert-butyl-pyrazol-1-yl)-phenoxy]-ethyl}-piperidine-1-carboxylic acid tert-butyl ester 800 mg (83%). $^1$H-NMR (DMSO-d$_6$) δ 7.40 (d, 2H), 7.00 (d, 2H), 5.35 (s, 1H), 5.0 (s, 2H), 4.0 (m, 2H), 3.90 (m, 2H), 1.70-1.60 (m, 6H), 1.40 (s, 9H), 1.20 (s, 9H), 1.05 (m, 1H); MS LC-MS [M+H]$^+$=443.3, RT=3.10 min.

Preparation of 5-tert-butyl-2-(3-methoxy-phenyl)-2H-pyrazol-3-ylamine hydrochloride

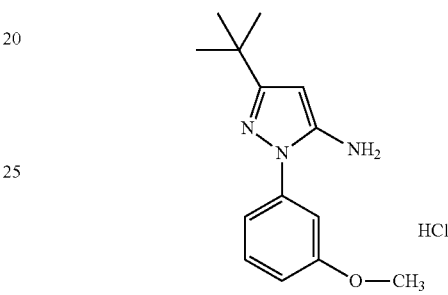

To a solution of 4,4-dimethyl-3-oxo-pentanenitrile (5.0 g, 40 mmol) and 3-methoxy-phenylhydrazine hydrochloride (7.0 g, 40 mmol) in anhydrous ethanol (200 mL) was added acetic acid (1.2 mL). The reaction mixture was heated at reflux overnight, then cooled to room temperature and concentrated at reduced pressure. The residue was combined with ethyl acetate (200 mL), and washed with saturated aq NaHCO$_3$, water, and brine. The solution was dried over Na$_2$SO$_4$, evaporated at reduced pressure and the solid residue was re-dissolved in ethanol (100 mL). A solution of 2M HCl in ether was added and the mixture was stirred for 30 min. The solvent was removed at reduced pressure, the solid residue was triturated and washed with hexane (50 mL) and then dried in a vacuum oven overnight to give the product 5-tert-butyl-2-(3-methoxy-phenyl)-2H-pyrazol-3-ylamine hydrochloride (5.46 g, 56%) as an off-white solid. $^1$H-NMR (DMSO-d$_6$) δ 7.50 (t, 1H), 7.10 (m, 3H), 5.60 (s, 1H), 3.80 (s, 3H), 1.30 (s, 9H); MS LC-MS [M+H]$^+$=246.2, RT=1.90 min.

Preparation of 3-(5-amino-3-tert-butyl-pyrazol-1-yl)-phenol

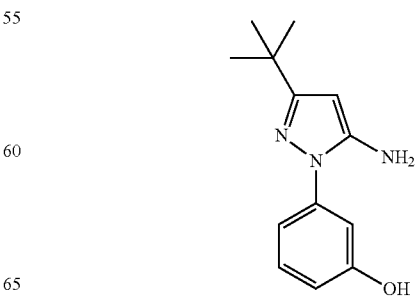

In a 500 mL round bottom flask was added 5-tert-butyl-2-(3-methoxy-phenyl)-2H-pyrazol-3-ylamine hydrochloride (8.42 g, 30 mmol) and pyridinium hydrochloride (13.8 g, 120 mmol). The reaction mixture was heated neat at 195° C. with stirring for 3 h. The mixture was cooled to room temperature, water (300 mL) and EtOAc (300 mL) were added, and then the organic phase was washed with saturated aq NaHCO$_3$ and brine, dried (Na$_2$SO$_4$) and concentrated at reduced pressure. The residue was purified by MPLC (80:20 hexane/EtOAc) to give the product 3-(5-amino-3-tert-butyl-pyrazol-1-yl)-phenol (1.3 g, 19%). $^1$H-NMR (DMSO-d$_6$) δ 7.20 (t, 1H), 7.00 (m, 2H), 6.50 (d, 1H), 5.30 (s, 1H), 5.10 (bs, 2H), 1.30 (s, 9H); MS LC-MS [M+H]$^+$=232.2, RT=0.57 min.

Preparation of 3-[3-(5-amino-3-tert-butyl-pyrazol-1-yl)-phenoxy]-propan-1-ol

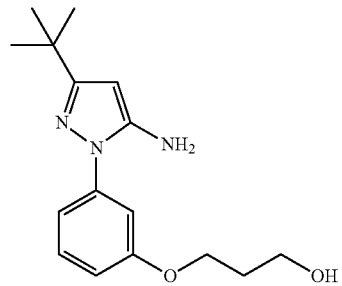

A mixture of 3-(5-amino-3-tert-butyl-pyrazol-1-yl)-phenol (400 mg, 1.73 mmol), 3-chloropropanol (326 mg, 3.46 mmol), potassium carbonate (596 mg, 4.32 mmol) and sodium iodide (77 mg, 0.52 mmol) were combined in n-butanol (6 mL). The reaction mixture was heated at 60° C. for 4 days. The mixture was cooled to room temperature, water (100 mL) and EtOAc (100 mL) were added, and then the organic phase was washed with water and brine, dried (Na$_2$SO$_4$), and concentrated at reduced pressure. The residue was purified by MPLC (80:20 hexane/EtOAc) to give the product 3-[3-(5-amino-3-tert-butyl-pyrazol-1-yl)-phenoxy]-propan-1-ol (400 mg, 80%). $^1$H-NMR (DMSO-d$_6$) δ 7.30 (t, 1H), 7.10 (m, 2H), 6.80 (d, 1H), 5.30 (s, 1H), 5.10 (bs, 2H), 4.0 (t, 2H), 3.60 (t, 3H), 1.80 (m, 2H), 1.30 (s, 9H); MS LC-MS [M+H]$^+$=290.3, RT=1.05 min.

Preparation of 4-bromo-2-methyl-N-(2-morpholin-4-yl-ethyl)benzene sulfonamide

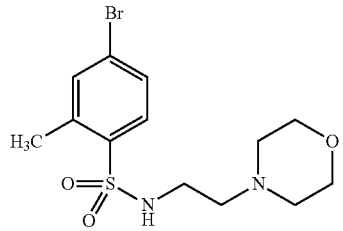

A mixture of 4-bromo-2-methylbenzene sulfonyl chloride (700 mg, 2.6 mmol), 4-(2-aminoethyl)morpholine (372 mg, 2.86 mmol, 1.1 eq), and N,N-diisopropylethylamine (1.0 mL, 5.71 mmol, 2.2 eq) in anhydrous tetrahydrofuran (13 mL, 0.2 M) was stirred at 40° C. under nitrogen for 18 h. Solvent was removed at reduced pressure and the residue was partitioned between EtOAc and water. The organic phase was washed with water and brine, dried over Na$_2$SO$_4$, and concentrated at reduced pressure. The residue was purified by MPLC (eluting with 50% to 75% EtOAc/hexane) to give 939 mg (99%) of the desired product as a white solid. $^1$H-NMR (DMSO-d$_6$) δ 7.73 (d, J=8.4 Hz, 1H), 7.68 (broad s, 1H), 7.65 (dd, J=2.1, 0.6 Hz, 1H), 7.55 (ddd, J=7.3, 2.1, 0.6 Hz, 1H), 3.41 (t, J=4.5 Hz, 4H), 2.88 (t, J=6.3 Hz, 2H), 2.56 (s, 3H), 2.19 (t,=6.6 Hz, 2H), 2.16 to 2.12 (m, 4H); MS LC-MS [M+H]$^+$=363 & 365, RT=1.90 min.

Preparation of 4-bromo-N-(2-morpholin-4-ylethyl)-2-trifluoromethoxy-benzene sulfonamide

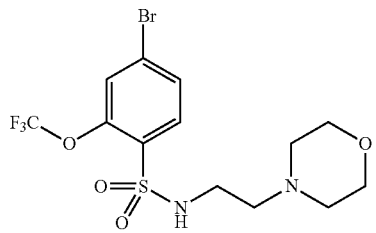

The title compound was prepared in the same manner as described for 4-bromo-2-methyl-N-(2-morpholin-4-yl-ethyl) benzene sulfonamide, replacing 4-bromo-2-methyl-benzene sulfonyl chloride with 4-bromo-2-trifluoromethoxybenzene sulfonyl chloride. $^1$H-NMR (DMSO-d$_6$) δ 7.88 to 7.77 (m, 4H), 3.43 (t, J=4.2 Hz, 4H), 2.99 to 2.97 (broad s, 2H), 2.29 to 2.20 (m, 6H); MS LC-MS [M+H]$^+$=433 & 435, RT=2.03 min.

Preparation of 4-bromo-N-(2-morpholin-4-yl-ethyl)benzene sulfonamide

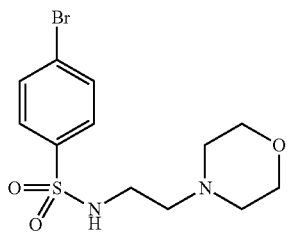

The title compound was prepared in the same manner as described for 4-bromo-2-methyl-N-(2-morpholin-4-yl-ethyl) benzene sulfonamide, replacing 4-bromo-2-methyl-benzene sulfonyl chloride with 4-bromobenzene sulfonyl chloride. $^1$H-NMR (DMSO-d$_6$) δ 7.81 to 7.68 (m, 4H), 7.66 (broad s, 1H), 3.46 (t, J=4.8 Hz, 4H), 2.85 (t, J=6.6 Hz, 2H), 2.28 to 2.21 (m, 6H); MS LC-MS [M+H]$^+$=349 & 351, RT=1.34 min.

Preparation of 3-bromo-N-(2-methoxyethyl)benzene sulfonamide

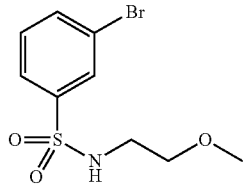

To a solution of 3-bromobenzenesulfonyl chloride (1.00 g, 3.72 mmol) in acetone (10 mL) was added 2-methoxyethylamine (0.97 mL, 11.15 mmol, 3.0 eq) and potassium carbonate (2.57 g, 18.6 mmol, 5.0 eq), and the reaction was stirred at 40° C. for 5 h. The mixture was cooled to room temperature and then partitioned between EtOAc and water, and the organic phase was washed with brine, dried over MgSO$_4$, and concentrated at reduced pressure. The residue was purified by MPLC (20% to 25% EtOAc/hexane) to give 1.05 g (96%) of the desired product as an oil. TLC [30% EtOAc/hexane], Rf=0.33.

Preparation of 4-(5-amino-3-tert-butyl-pyrazol-1-yl)-2-methyl-N-(2-morpholin-4-yl-ethyl)benzene sulfonamide Step 1: Preparation of 4-(N'-benzhydrylidene-hydrazino)-2-methyl-N-(2-morpholin-4-yl-ethyl)-benzene sulfonamide

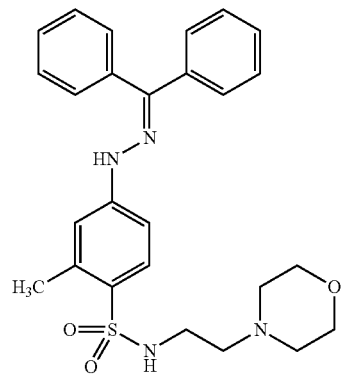

To a degassed solution of 4-bromo-2-methyl-N-(2-morpholin-4-yl-ethyl)benzene-sulfonamide (939 mg, 2.58 mmol), benzophenone hydrazone (558 mg, 2.84 mmol, 1.1 eq), and 9,9-dimethyl-4,5-bis(diphenylphosphino)xanthene (75 mg, 0.13 mmol, 0.05 eq) in anhydrous toluene (13 mL, 0.2M) was added sodium tert-butoxide (596 mg, 6.20 mmol, 2.4 eq) followed by palladium(II) acetate (29 mg, 0.13 mmol, 0.05 eq), and the reaction mixture was stirred at 85° C. under nitrogen for 17 h. The reaction mixture was cooled to room temperature and was partitioned between EtOAc and water. The organic layer was washed with water and brine, dried over Na$_2$SO$_4$, and concentrated at reduced pressure. Purification by MPLC (75% EtOAc/hexane) afforded the title compound (1.00 g, 80%) as a white solid. $^1$H-NMR (DMSO-d$_6$) δ 9.25 (s, 1H), 7.64 to 7.52 (m, 4H), 7.44 to 7.41 (m, 2H), 7.35 to 7.26 (m, 5H), 7.16 to 7.13 (m, 3H), 3.45 (t, J=4.8 Hz, 4H), 2.79 (q, J=6.3 Hz, 2H), 2.47 (s, 3H), 2.21 to 2.15 (m, 6H); MS LC-MS [M+H]$^+$=479, RT=3.15 min.

Step 2: Preparation of 4-(5-amino-3-tert-butyl-pyrazol-1-yl)-2-methyl-N-(2-morpholin-4-yl-ethyl)benzene sulfonamide

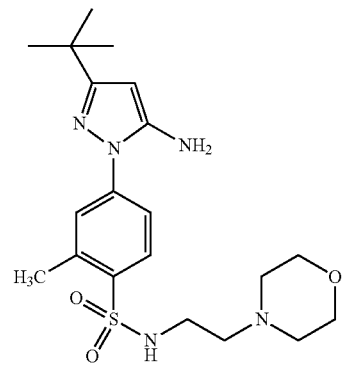

To a solution of 4-(N'-benzhydrylidene-hydrazino)-2-methyl-N-(2-morpholin-4-yl-ethyl)-benzene sulfonamide (1.00 g, 2.09 mmol) and 4,4-dimethyl-3-oxopentanenitrile (392 mg, 3.13 mmol, 1.5 eq) in anhydrous ethanol (10.5 mL, 0.2 M) was added p-toluenebenzene sulfonic acid (402 mg, 4.18 mmol, 2.0 eq), and the reaction mixture was stirred at reflux under nitrogen. After 18 h, concentrated HCl (2 mL) was added and the reaction mixture was stirred at reflux under nitrogen for an additional 4 h. The reaction mixture was cooled to room temperature and concentrated at reduced pressure. The residue was partitioned between EtOAc (500 mL) and aqueous saturated NaHCO$_3$ solution (300 mL). The organic layer was washed with water and brine, dried over Na$_2$SO$_4$, and concentrated at reduced pressure. The residue was purified by MPLC (70% to 90% EtOAc/hexane) to give 799 mg (91%) of the desired product. $^1$H-NMR (DMSO-d$_6$) δ 7.85 (d, J=8.4 Hz, 1H), 7.61 to 7.55 (m, 3H), 5.40 (s, 1H), 5.38 (broad s, 2H), 3.46 (t, J=4.5 Hz, 4H), 2.88 (q, J=6.0 Hz, 2H), 2.60 (s, 3H), 2.27 to 2.18 (m, 6H), 1.20 (s, 9H); MS LC-MS [M+H]$^+$=422, RT=1.95 min.

Preparation of 3-(5-amino-3-tert-butyl-pyrazol-1-yl)-N-(2-methoxyethyl)-benzene sulfonamide Step 1: Preparation of 3-(N'-benzhydrylidenehydrazino)-N-(2-methoxy-ethyl)-benzene sulfonamide

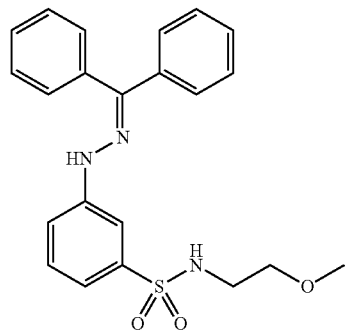

The compound was prepared in the same manner as described for 4-(N'-benzhydrylidenehydrazino)-2-methyl-N-(2-morpholin-4-yl-ethyl)benzene sulfonamide, replacing 4-bromo-2-methyl-N-(2-morpholin-4-yl-ethyl)benzene sulfonamide with 3-bromo-N-(2-methoxyethyl)benzene sulfonamide. ¹H-NMR (DMSO-d₆) δ 9.32 (s, 1H), 7.67 (t, J=2.1 Hz, 1H), 7.63 to 7.48 (m, 4H), 7.46 to 7.41 (m, 3H), 7.39 to 7.26 (m, 6H), 7.15 to 7.12 (m, 1H), 3.29 (t, 5.7 Hz, 2H), 3.15 (s, 3H), 2.87 (q, J=5.7 Hz, 2H); MS LC-MS [M+H]⁺=410, RT=3.50 min.

Step 2: Preparation of 3-(5-amino-3-tert-butyl-pyrazol-1-yl)-N-(2-methoxyethyl)-benzene sulfonamide

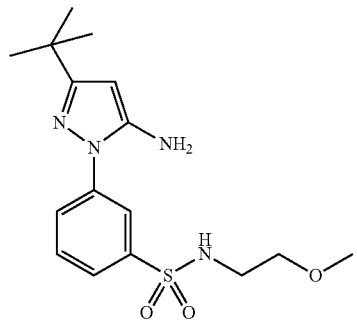

The title compound was prepared in the same manner as described for 4-(N'-benzhydrylidenehydrazino)-2-methyl-N-(2-morpholin-4-yl-ethyl)benzene sulfonamide, replacing 4-(N'-benzhydrylidene-hydrazino)-2-methyl-N-(2-morpholin-4-yl-ethyl)-benzene sulfonamide with 3-(N'-benzhydrylidenehydrazino)-N-(2-methoxyethyl)-benzene sulfonamide. ¹H-NMR (DMSO-d₆) δ 8.00 (s, 1H), 7.86 to 7.79 (m, 2H), 7.63 (dd, J=3.6 Hz, 1.5 Hz, 2H), 5.42 (s, 1H), 5.33 (s, 2H), 3.30 (t, J=5.7 Hz, 2H), 3.14 (s, 3H), 2.91 (q, J=5.7 Hz, 2H), 1.20 (s, 9H); MS LC-MS [M+H]⁺=353, RT=2.50 min.

Preparation of {5-tert-butyl-2-[3-(2-methoxyethyl-sulfamoyl)-phenyl]-2H-pyrazol-3-yl}-carbamic acid phenyl ester

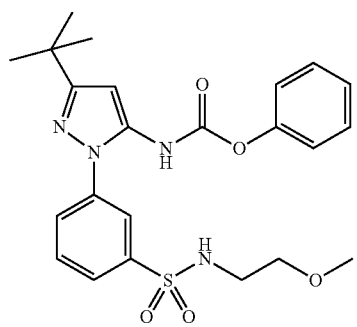

To a mixture of 3-(5-amino-3-tert-butyl-pyrazol-1-yl)-N-(2-methoxyethyl)benzene sulfonamide (940 mg, 2.67 mmol) and solid sodium carbonate (493 mg, 5.87 mmol, 2.2 eq) in anhydrous THF was slowly added phenylchloroformate (0.40 mL, 3.20 mmol, 1.2 eq), and the reaction mixture was stirred at room temperature under nitrogen for 6 h. The reaction mixture was poured into ethyl acetate, and then the organic phase was separated and washed with water and brine, dried over Na₂SO₄, filtered, and concentrated at reduced pressure. Purification by MPLC (35% EtOAc/hexane) afforded the title compound (887 mg, 70%) as a white solid. ¹H-NMR (CD₃OD) δ 10.17 (broad s, 1H), 7.94 (t, J=1.5 Hz, 1H), 7.89 (t, J=6.0 Hz, 1H), 7.81 to 7.69 (m, 3H), 7.34 to 7.29 (m, 2H), 7.19 (t, J=7.2 Hz, 1H), 7.09 (broad s, 2H), 6.38 (s, 1H), 3.25 (t, J=6.0 Hz, 2H), 3.09 (s, 3H), 2.90 (broad s, 2H), 1.26 (s, 9H).

Preparation of ethyl[4-(5-amino-3-tert-butyl-1H-pyrazol-1-yl)phenyl]acetate hydrochloride Step 1. Preparation of ethyl(4-hydrazinophenyl)acetate hydrochloride

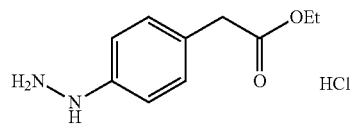

A solution of sodium nitrite (NaNO₂, 4.04 g, 58.6 mmol) in H₂O (20 mL) was added to a cooled (−5° C., ice-salt) solution of ethyl 4-aminophenylacetate (10 g, 55.8 mmol) in conc. HCl (55 mL), at a rate such that the temperature did not exceed 0° C. The mixture was stirred at 0° C. for 10 min and then added portion-wise to a cooled (−5° C., ice-salt) and rapidly-stirred solution of tin(II) chloride (SnCl₂, 39.67 g, 209.2 mmol) in conc. HCl (30 mL), at a rate such that the temperature did not exceed 0° C. The resulting cream-colored suspension was warmed to 25° C. and stirred at room temperature for 2-3 hrs and then was filtered under vacuum. The collected solid was washed with water and ether and then air dried to afford the desired product as a pale solid (HCl salt). Precipitate that formed in the filtrates upon standing for 16 h was collected by filtration, washed with water and ether, and air-dried. The combined solids were obtained in 88% yield (11.28 g). ¹H-NMR (DMSO-d₆) δ 8.85 (broad, 2H), 7.73 (broad, 1H), 7.10 (d, J=8.4 Hz, 2H), 6.82 (d, J=8.4 Hz, 2H), 4.03 (q, J=7.0 Hz, 2H), 3.53 (s, 2H), 1.16 (t, J=7.1 Hz, 3H); MS LC-MS [M+H]⁺=195.0, RT=1.11 min.

Step 2. Preparation of ethyl[4-(5-amino-3-tert-butyl-1H-pyrazol-1-yl)phenyl]acetate hydrochloride

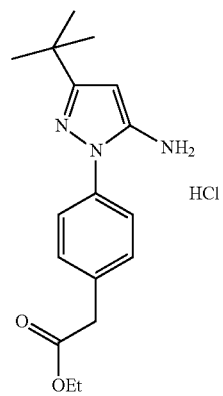

The title compound was prepared in the same manner as described for 5-tert-butyl-2-(4-nitro-phenyl)-2H-pyrazol-3-ylamine, replacing 4-nitrophenylhydrazine with ethyl(4-hydrazinophenyl)acetate hydrochloride (11.98 g, 51.9 mmol). The title compound was obtained as a white solid (HCl salt, 11.95 g) in 68% yield. $^1$H-NMR (DMSO-d$_6$) δ 7.52 (d, J=8.4 Hz, 2H), 7.45 (d, J=8.1 Hz, 2H), 5.59 (s, 1H), 4.08 (q, J=7.1 Hz, 2H), 3.77 (s, 2H), 1.27 (s, 9H), 1.20 (t, J=7.1 Hz, 3H); MS LC-MS [M+H]$^+$=302.3, RT=2.44 min.

Preparation of ethyl(4-{3-tert-butyl-5-[(phenoxycarbonyl)amino]-1H-pyrazol-1-yl}phenyl)acetate

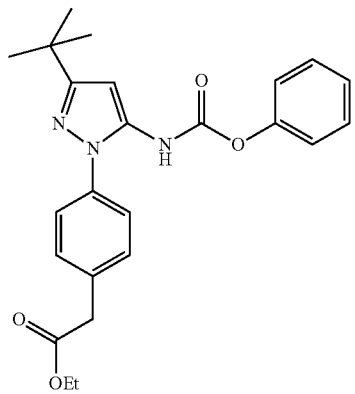

To a suspension of ethyl[4-(5-amino-3-tert-butyl-1H-pyrazol-1-yl)phenyl]acetate (10 g, 33.2 mmol) and K$_2$CO$_3$ (9.17 g, 66.4 mmol) in THF (300 mL) was added phenyl chloroformate (8.61 mL, 66.4 mmol), and the resulting reaction mixture was stirred at room temperature overnight. The mixture was poured into a mixture of water and EtOAc and the organic phase was separated and dried over Na$_2$SO4, concentrated at reduced pressure to afford a brown syrup, which was purified by MPLC (0% to 20% EtOAc in hexane). The desired product was obtained as a white solid (10.6 g) in 76% yield. $^1$H-NMR (CD$_2$Cl$_2$-d$_2$) δ 7.51-7.10 (m, 10H), 6.47 (s, 1H), 4.16 (q, J=7.1 Hz, 2H), 3.71 (s, 2H), 1.37 (s, 9H), 1.28 (t, J=7.0 Hz, 3H).

Preparation of 4-(3-tert-butyl-5-{3-[4-(pyridin-4-yloxy)phenyl]ureido}-pyrazol-1-yl)-benzoic acid methyl ester

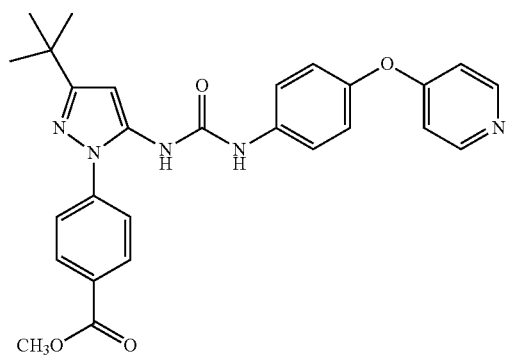

To a suspension of 4-(5-amino-3-tert-butyl-pyrazol-1-yl) benzoic acid methyl ester (1.89 g, 6.93 mmol) in anhydrous DCE (10 mL) was added CDI (1.24 g, 7.62 mmol), and the mixture was stirred at room temperature for 16 h. A suspension of 4-(pyridin-4-yloxy)phenylamine (1.29 g, 6.93 mmol; Dumas et al., U.S. pat. appl. US2002065296 (2002)) in DCE was then added, and the mixture was stirred at room temperature for 4 h. The reaction was diluted into EtOAc. The organic layer was washed with water and brine, dried over MgSO$_4$, filtered, and concentrated at reduced pressure. The crude product was purified by MPLC (15% EtOAc/hexane) to give 2.3 g (68%) of the title compound as a white solid. $^1$H-NMR (acetone-d$_6$) δ 8.64 (s, 1H), 8.44 (d, J=9.0 Hz, 2H), 8.12 (d, J=9.0 Hz, 2H), 8.01 (s, 1H), 7.61 (d, J=9.0 Hz, 2H), 7.81 (d, J=9.0 Hz, 2H), 7.09 (d, J=9.0 Hz, 2H), 6.86 (d, J=6.0 Hz, 2H), 6.48 (s, 1H), 3.91 (s, 3H), 1.34 (s, 9H); MS LC-MS [M+H]$^+$= 486, RT=2.50 min.

Preparation of 4-(3-tert-butyl-5-{3-[2-fluoro-4-(2-methyl-pyridin-4-yloxy)-phenyl]-ureido}-pyrazol-1-yl)-benzoic acid methyl ester

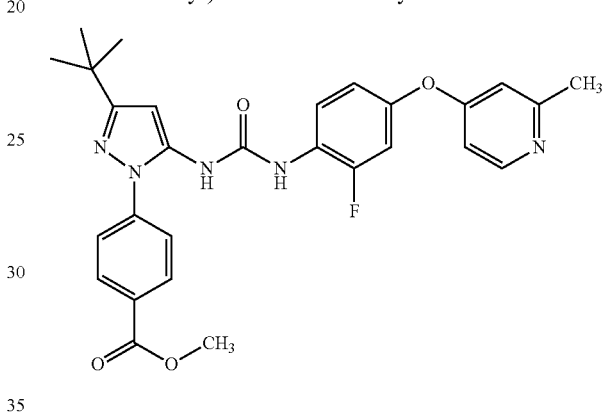

A solution of 4-(3-tert-butyl-5-phenoxycarbonylamino-pyrazol-1-yl)benzoic acid methyl ester (470 mg, 1.19 mmol) and 2-fluoro-4-(2-methyl-pyridin-4-yloxy)-phenylamine (260.69 mg, 1.19 mmol) was stirred at 40° C. overnight. The mixture was cooled to room temperature, and then evaporated at reduced pressure. The residue was purified by MPLC (eluting with 50:50 EtOAc/hexane) to afford the title compound (407 mg, 66%). $^1$H-NMR (DMSO-d$_6$) δ 8.94 (s, 2H), 8.30 (d, J=5.7 Hz, 1H), 8.09 (m, 3H), 7.71 (d, J=5.7 Hz, 2H), 7.20 (d, J=14.7, 1H), 6.94 (d, J=5.4 Hz, 1H), 6.77 (d, J=2.7 Hz, 1H), 6.72 (d, J=5.4 Hz, 1H), 6.42 (s, 1H), 3.87 (s, 3H), 2.38 (s, 3H), 1.27 (s, 9H); MS LC-MS [M+H]$^+$=518.2, RT=2.94 min.

Preparation of 3-(3-tert-butyl-5-{3-[2-fluoro-4-(2-methyl-pyridin-4-yloxy)-phenyl]-ureido}-pyrazol-1-yl)-benzoic acid

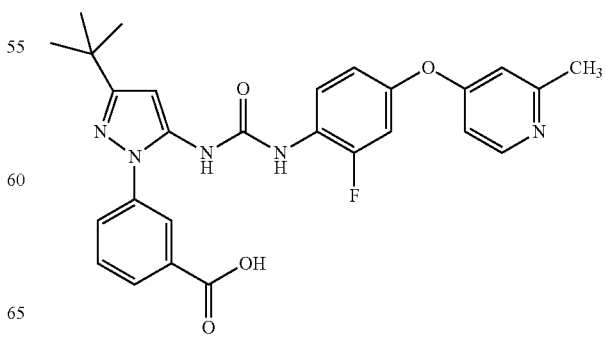

To a solution of 3-(3-tert-butyl-5-{3-[2-fluoro-4-(2-methyl-pyridin-4-yloxy)-phenyl]-ureido}-pyrazol-1-yl)-benzoic acid methyl ester (2.0 g, 4.12 mmol; prepared in a similar manner as described for 4-(3-tert-butyl-5-{3-[2-fluoro-4-(2-methyl-pyridin-4-yloxy)-phenyl]-ureido}-pyrazol-1-yl)-benzoic acid methyl ester) in methanol, was added potassium hydroxide (692 mg, 12.4 mmol) in water. The mixture was stirred at 40° C. overnight, then cooled to room temperature. Methanol was evaporated at reduced pressure, and the aqueous residue neutralized to pH 7 by addition of 2N HCl. The white solid that formed was collected by filtration and dried in vacuo to give the title compound (1.9 g, 98%). $^1$H-NMR (DMSO-d$_6$) δ 8.95 (s, 1H), 8.92 (s, 1H), 8.30 (d, J=5.7 Hz, 1H), 8.11-8.03 (m, 2H), 7.94 (d, 10.2 Hz, 1H), 7.79 (d, J=9.9 Hz, 1H), 7.65 (t, J=7.5 Hz, 1H), 7.18 (J=14.1 Hz, 1H), 6.95 (d, J=12.9 Hz, 1H), 6.75 (m, 2H), 6.39 (s, 1H), 2.39 (s, 3H), 1.89 (s, 9H); MS LC-MS [M+H]$^+$=504.2, RT=2.47 min.

Preparation of 1-[5-tert-butyl-2-(4-nitro-phenyl)-2H-pyrazol-3-yl]-3-[4-(pyridin-4-yloxy)-phenyl]-urea

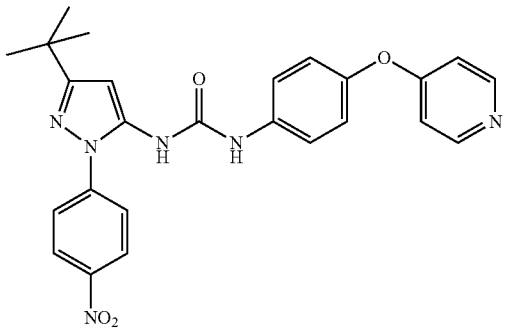

To a solution of 5-tert-butyl-2-(4-nitrophenyl)-2H-pyrazol-3-ylamine (5.0 g, 19.2 mmol) in anhydrous DCE (2 mL) was added CDI (3.5 g, 21.1 mmol), and the reaction was stirred under N$_2$ at room temperature for 18 h. 4-(Pyridin-4-yloxy)phenylamine (3.3 g, 17.7 mmol, Dumas et al., U.S. pat. appl. US2002065296 (2002)) in DCE (12 mL) was added to the reaction, and the solution was stirred under N$_2$ at room temperature for 7 h. The reaction mixture was partitioned between EtOAc (100 mL) and water (100 mL). The organic layer was washed with brine, dried over Na$_2$SO$_4$, and concentrated at reduced pressure. The crude residue was purified by MPLC (1:1 hexanes/EtOAc) to give 5.6 g (68%) of the desired product. $^1$H-NMR (DMSO-d$_6$) δ 9.21 (s, 1H), 8.68 (s, 1H), 8.43 (d, J=6.3 Hz, 2H), 8.36 (d, J=7.2 Hz, 2H), 7.90 (d, J=6.9 Hz, 2H), 7.50 (d, J=6.9 Hz, 2H), 7.09 (d, J=6.6 Hz, 2H), 6.86 (d, J=5.7 Hz, 2H), 6.44 (s, 1H), 1.29 (s, 9H); MS LC-MS [M+H]$^+$=473, RT=2.60 min.

Preparation of 1-[2-(4-aminophenyl)-5-tert-butyl-2H-pyrazol-3-yl]-3-[4-(pyridin-4-yloxy)phenyl]urea

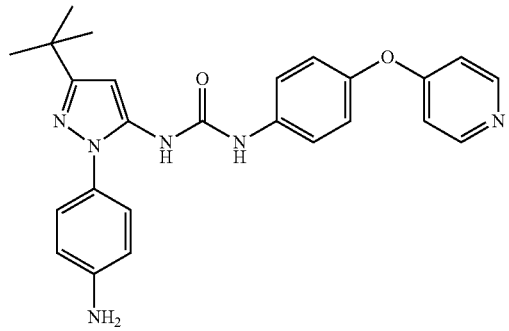

A solution of 1-[5-tert-butyl-2-(4-nitrophenyl)-2H-pyrazol-3-yl]-3-[4-(pyridin-4-yloxy)phenyl]urea (2.5 g, 5.3 mmol) in anhydrous EtOH (40 mL) was added to a round bottle (100 mL) flask containing 10% Pd/C (30 mg). The reaction vessel was fitted with a balloon adapter and charged with hydrogen and evacuated three times until the reaction was under a H$_2$ atmosphere. The reaction mixture was stirred at room temperature for 18 h, and then filtered through a pad of celite. The celite was washed with EtOH (200 mL) and the filtrate was concentrated at reduced pressure. The residue was purified by MPLC (1:1 hexanes/EtOAc) to give 1.8 g (77%) of the desired product. $^1$H-NMR (DMSO-d$_6$) δ 9.16 (s, 1H), 8.42 (d, J=5.4 Hz, 2H), 8.17 (s, 1H), 7.47 (d, J=6.9 Hz, 2H), 7.09 to 7.04 (m, 4H), 6.86 (d, J=5.7 Hz, 2H), 6.64 (d, J=6.6 Hz, 2H), 6.28 (s, 1H), 6.38 (s, 2H), 1.18 (s, 9H); MS LC-MS [M+H]$^+$=443, RT=1.95 min.

Preparation of 1-[5-tert-butyl-2-(4-cyano-phenyl)-2H-pyrazol-3-yl]-3-[4-(pyridin-4-yloxy)-phenyl]urea

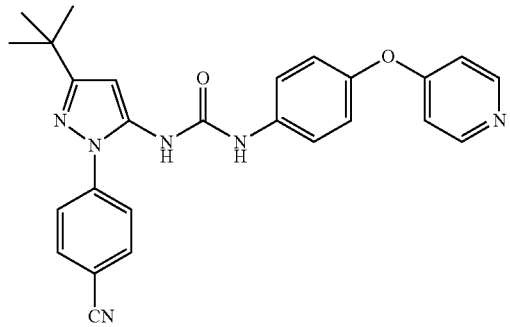

The title compound was prepared by CDI coupling (35% yield) in the same manner as described for 1-[5-tert-butyl-2-(4-nitro-phenyl)-2H-pyrazol-3-yl]-3-[4-(pyridin-4-yloxy)-phenyl]urea, replacing 5-tert-butyl-2-(4-nitrophenyl)-2H-pyrazol-3-ylamine with 1-[5-tert-butyl-2-(4-cyano-phenyl)-2H-pyrazol-3-yl]-3-[4-(pyridin-4-yloxy)-phenyl]urea.
$^1$H-NMR (DMSO-d$_6$) δ 9.18 (s, 1H), 8.60 (s, 1H), 8.41 (d, J=5.4 Hz, 2H), 7.98 (d, J=6.9 Hz, 2H), 7.80 (d, J=6.9 Hz, 2H), 7.48 (d, J=6.6 Hz, 2H), 7.08 (d, J=6.6 Hz, 2H), 6.84 (d, J=5.4 Hz, 2H), 6.40 (s, 1H), 1.26 (s, 9H); MS LC-MS [M+H]$^+$=453, RT=2.37 min.

Preparation of 4-(pyridin-3-yloxy)aniline

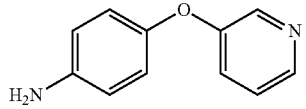

Step 1. Preparation of 3-(4-nitrophenoxy)pyridine

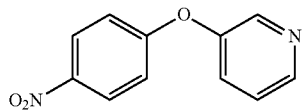

To a solution of 1-fluoro-4-nitrobenzene (50.00 g, 354.36 mmol) in DMF (450 ml) was added 3-hydroxypyridine (33.70 g, 354.36 mmol) under nitrogen. The reaction mixture was heated to 35° C. and then potassium carbonate (102.85 g, 744.15 mmol) was added in one portion. The reaction was very exothermic, and the temperature rapidly increased to 115° C., then gradually increased to 125° C. The mixture was then cooled to 90° C. and stirred at 90° C. for 2 h. The mixture was cooled to room temperature and poured into 2.5 L of water. The mixture was extracted with ethyl acetate (3×), and the combined organic phases were washed with water (3×) and brine (1×), dried over sodium sulfate, and evaporated at reduced pressure. The brown solid residue was stirred in MTBE at reflux, then filtered, and the filtrate was concentrated at reduced pressure to give a yellow crystalline solid that was triturated with ether to give 23.79 g (31%) of the desired product. The brown solids that did not dissolve in MTBE (43.89 g, 57%) were also of sufficient purity for use in the next step (i.e., total yield 88%). $^1$H-NMR (DMSO-d$_6$) δ 8.50 (m, 2H), 8.24 (d, J=9.1 Hz, 2H), 7.67 (ddd, J=8.4, 2.9, 1.3 Hz, 1H), 7.52 (dd, J=8.3, 4.7 Hz, 1H), 7.18 (d, J=9.0 Hz, 2H); MS LC-MS [M+H]$^+$=217, RT=1.67 min. In a subsequent experiment, the potassium carbonate was added to the 1-fluoro-4-nitrobenzene in DMF under nitrogen. To this stirred solution was dropwise added a solution of the 3-hydroxypyridine in DMF, and the exotherm caused the mixture to gradually warm up to 38° C. The reaction mixture was then heated to 60° C. for 2 h. Reaction work up as described above gave the desired product.

Step 2. Preparation of 4-(pyridin-3-yloxy)aniline

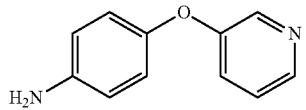

A solution of 3-(4-nitrophenoxy)pyridine (5.00 g, 23.13 mmol) in EtOAc (100 mL) in a 250 ml Parr bottle was purged with nitrogen. To this solution was added EtOAc-moistened 10% Pd/C catalyst (500 mg, 10% by weight). The reaction flask was placed in a Parr hygrogenation apparatus, purged with nitrogen (5×), evacuated, and then pressurized to 40 psi with hydrogen and shaken for 3.5 h. The reaction mixture was then purged with nitrogen, and filtered through a pad of Celite®, rinsing with ethyl acetate (3×) and ethanol (3×). The filtrate was evaporated at reduced pressure to give a brown crystalline residue. The residue was stirred in diethyl ether at room temperature for 16 h and then filtered to provide 4.11 g (95%) of the desired product as light brown crystals. $^1$H-NMR (DMSO-d$_6$) δ 8.21 (m, 2H), 7.30 (ddd, J=8.4, 4.6, 0.7 Hz, 1H), 7.18 (ddd, J=8.4, 2.9, 1.4 Hz, 1H), 6.79 (d, J=8.8 Hz, 2H), 6.58 (d, J=9.0 Hz, 2H), 5.05 (br s, 2H); MS LC-MS [M+H]$^+$=187, RT=1.03 min.

Preparation of 2-fluoro-4-(2-methylpyridin-4-yloxy)phenylamine

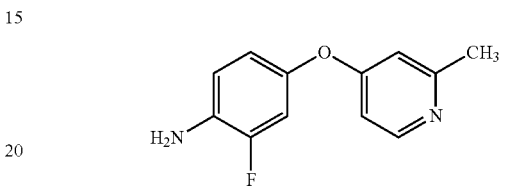

A solution of 4-amino-3-fluorophenol (5.00 g, 39.3 mmol) in anhydrous DMA (100 mL) was treated with potassium tert-butoxide (5.30 g, 47.2 mmol), and the red-brown mixture was stirred at room temperature for 1 h. The mixture was treated with a solution of 4-chloro-2-picoline (5.02 g, 39.3 mmol) in anhydrous DMA (75 mL) and then heated at 100° C. for 17 h. The mixture was cooled to ambient temperature and partitioned between EtOAc (500 mL) and saturated NaCl solution (500 mL). The aqueous phase was back-extracted with EtOAc (300 mL). The combined organic phases were washed with brine, dried over Na$_2$SO$_4$, and concentrated at reduced pressure. Purification through a silica gel plug, eluting with 40% EtOAc/hexane, followed by crystallization from DCM/hexane afforded 4.06 g (47%) of the title compound as a yellow solid. $^1$H-NMR (DMSO-d$_6$) δ 8.24 (d, J=5.4 Hz, 1H), 6.91 (dd, J=12.3, 2.7 Hz, 1H), 6.80 (dd, J=9.6, 8.7 Hz, 1H), 6.72 to 6.62 (m, 3H), 5.15 (broad s, 2H), (2.36 (s, 3H); MS LC-MS [M+H]$^+$=219, RT=0.24 min.

EXAMPLES

Example 1

4-{3-tert-Butyl-5-[({[4-(pyridin-4-yloxy)-phenyl]amino}carbonyl)amino]-1H-pyrazol-1-yl}-N-(2-pyrrolidin-1-ylethyl)benzamide

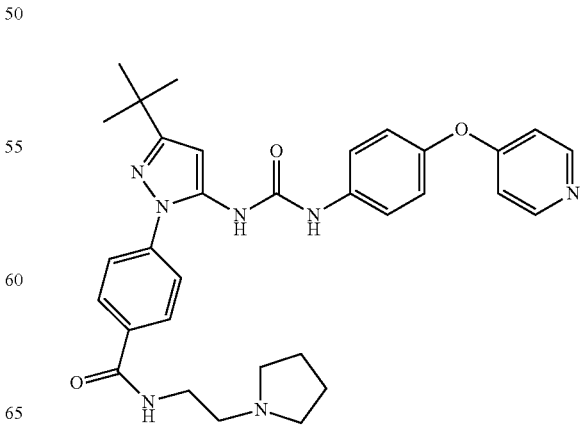

To a solution of 2-pyrrolidin-1-yl-ethylamine in DCE was added trimethyl aluminum (1.03 mmol, 0.51 mL of 2N solution in DCM). After the reaction was stirred at ambient temperature for 30 minutes, a solution of 4-(3-tert-butyl-5-{3-[4-(pyridin-4-yloxy)phenyl]ureido}pyrazol-1-yl}benzoic acid methyl ester (100 mg, 0.21 mmol) in DCE was added, and the reaction mixture was stirred at 80° C. for 16 h. The reaction mixture was quenched with two drops of water, dried over MgSO$_4$, filtered, and evaporated at reduced pressure. Purification using MPLC (eluting with 15% NH$_3$ in MeOH (2N)/EtOAc) afforded 34 mg (29%) of the title compound. $^1$H-NMR (acetone-d$_6$) δ 8.43 (d, J=9.0 Hz, 2H), 7.94 (d, J=9.0 Hz, 2H), 7.69 (d, J=9.0 Hz, 2H), 7.60 (d, J=9.0 Hz, 2H), 7.07 (d, J=9.0 Hz, 2H), 6.84 (d, J=4.0 Hz, 2H), 6.48 (s, 1H), 3.52 (t, J=7.5 Hz, 2H), 2.67 (t, J=3.0 Hz, 2H), 2.50 to 2.64 (m, 4H), 1.70 to 1.72 (m, 4H), 1.31 (s, 9H); MS LC-MS [M+H]$^+$=568, RT=2.48 min.

Example 2

N-{3-tert-Butyl-1-[4-(2-methoxyethoxy)phenyl]-1H-pyrazol-5-yl}-N'-[4-(pyridin-4-yl-oxy)phenyl]urea

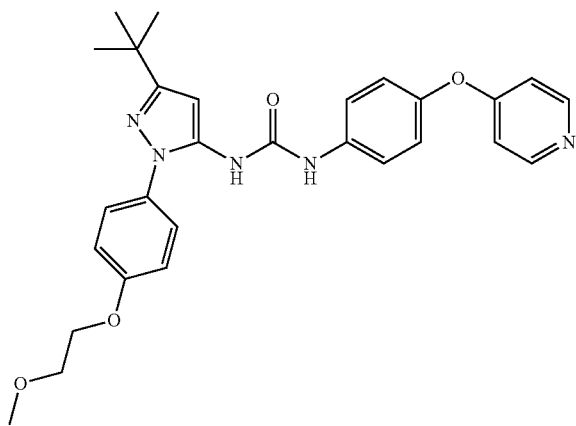

To a solution of 5-tert-butyl-2-[4-(2-methoxyethoxy)phenyl]2H-pyrazol-3-ylamine (75 mg, 0.26 mmol) in anhydrous DCE (1.0 mL) was added CDT (37 mg, 0.31 mmol), and the reaction mixture was stirred at 60° C. for 6 h. A solution of 4-(pyridin-4-yloxy)phenylamine (48 mg, 0.26 mmol) in DCE (1.3 mL) was then added, and the mixture was stirred at 60° C. for 20 h. The reaction mixture was diluted into EtOAc. The organic layer was washed with water and brine, dried over Na$_2$SO$_4$, filtered, and concentrated at reduced pressure. The crude product was purified by HPLC and recrystallized from ether/DCM/hexane to give 45.2 mg (35%) of the title compound as a white solid. $^1$H-NMR (DMSO-d$_6$) δ 9.01 (s, 1H), 8.39 (d, J=4.8 Hz, 2H), 8.28 (s, 1H), 7.46 (d, J=8.4 Hz, 2H), 7.38 (d, J=8.7 Hz, 2H), 7.05 (d, J=8.7 Hz, 4H), 6.84 (d, J=4.8 Hz, 2H), 6.29 (s, 1H), 4.14 to 4.10 (m, 2H), 3.66 to 3.63 (m, 2H), 3.28 (s, 3H), 1.23 (s, 9H); MS LC-MS [M+H]$^+$=502, RT=2.80 min.

Example 3

N-{3-tert-Butyl-1-[4-(2-methoxyethoxy)phenyl]-1H-pyrazol-5-yl}-N'-{2-fluoro-4-[(2-methylpyridin-4-yl)oxy]phenyl}urea

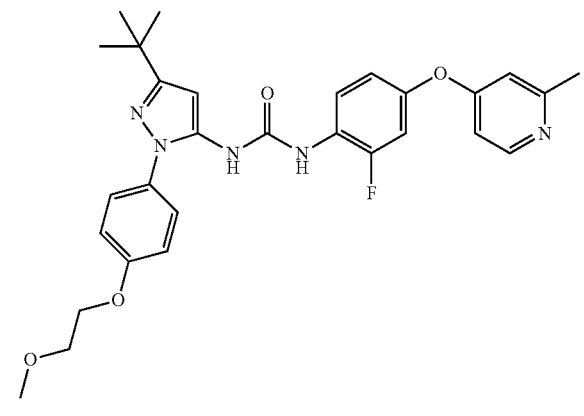

The title compound was prepared in the same manner as described for 1-{5-tert-butyl-2-[4-(2-methoxyethoxy)phenyl]-2H-pyrazol-3-yl}-3-[4-(pyridin-4-yloxy)-phenyl]urea, replacing 4-(pyridin-4-yloxy)phenylamine with 2-fluoro-4-(2-methyl-pyridin-4-yloxy)phenyl-amine. $^1$H-NMR (DMSO-d$_6$) δ 8.96 (s, 1H), 8.74 (s, 1H), 8.29 (d, J=6.0 Hz, 1H), 8.14 (t, J=9.3 Hz, 1H), 7.38 (d, J=9.0 Hz, 2H), 7.18 (d, J=9.0 Hz, 1H), 7.08 (dd, J=11.7, 2.4 Hz, 2H), 6.95 (d, J=7.5 Hz, 1H), 6.76 (d, J=2.4 Hz, 1H), 6.73 to 6.70 (m, 1H), 6.34 (s, 1H), 4.16 to 4.12 (m, 2H), 3.68 to 3.65 (m, 2H), 3.30 (s, 3H), 2.38 (s, 3H), 1.24 (s, 9H); MS LC-MS [M+H]$^+$=534, RT=2.39 min.

Example 4

N-(3-tert-Butyl-1-{4-[2-(diethylamino)ethoxy]phenyl}-1H-pyrazol-5-yl)-N'-[4-(pyridin-4-yloxy)phenyl]urea

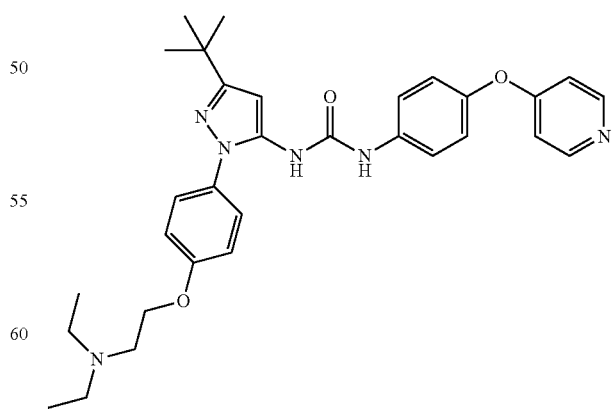

To 4-(pyridin-4-loxy)phenylamine (75.0 mg, 0.40 mmol) in anhydrous THF (4.0 mL) was added triphosgene (48 mg, 0.16 mmol) and N,N'-diisopropylethyl amine (63 mg, 0.48 mmol), and the reaction mixture was stirred at 75° C. for 3 h. A solution of 5-tert-butyl-2-[4-(2-diethylaminoethoxyphenyl]-2H-pyrazol-3-ylamine (133 mg, 0.40 mmol) in anhydrous THF (2.0 mL) was added, and the reaction mixture was stirred at 75° C. for 17 h. The reaction was partitioned between EtOAc and saturated aqueous NH$_4$Cl solution. The organic layer was washed with water and brine, dried over Na$_2$SO$_4$, filtered, and concentrated at reduced pressure. Purification using MPLC (eluting with 10 to 15% MeOH/EtOAc) and crystallization from ether/hexane afforded 65.7 mg (30%) of the title compound as a tan solid. $^1$H-NMR (DMSO-d$_6$) δ 9.08 (s, 1H), 8.40 (dd, J=4.5, 1.8 Hz, 2H), 8.28 (s, 1H), 7.46 (dd, J=6.6, 2.1 Hz, 2H), 7.37 (dd, J=6.9, 2.1 Hz, 2H), 7.08 to 7.02 (m, 4H), 6.84 (dd, J=4.8, 1.8 Hz, 2H), 6.30 (s, 1H), 4.04 (t, J=6.6 Hz, 2H), 2.77 (t, J=5.7 Hz, 2H), 2.53 (q, J=6.9 Hz, 4H), 1.24 (s, 9H), 0.95 (t, J=6.9 Hz, 6H); MS LC-MS [M+H]$^+$=543, RT=2.16 min.

Example 5

1-{5-tert-Butyl-2-[4-(2-piperidin-4-yl-ethoxy)-phenyl]-2H-pyrazol-3-yl}-3-[4-(pyridin-3-yloxy)-phenyl]-urea

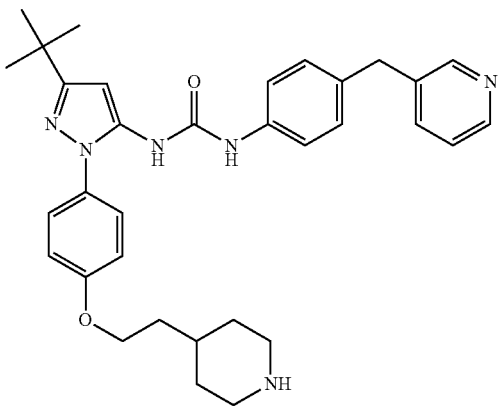

Step 1. 4-{2-[4-(5-Amino-3-tert-butyl-pyrazol-1-yl)-phenoxy]-ethyl}-piperidine-1-carboxylic acid tert-butyl ester was coupled with 4-(pyridin-3-yloxy)phenylamine by reaction with CDI in a similar manner to that described above, to provide the urea 4-{2-[4-(3-tert-butyl-5-{3-[4-(pyridin-3-yloxy)-phenyl]-ureido}-pyrazol-1-yl)-phenoxy]-ethyl}-piperidine-1-carboxylic acid tert-butyl ester (LC-MS [M+H]$^+$= 655, RT=3.51 min).

Step 2. To a solution of 4-{2-[4-(3-tert-butyl-5-{3-[4-(pyridin-3-yloxy)-phenyl]-ureido}-pyrazol-1-yl)-phenoxy]-ethyl}-piperidine-1-carboxylic acid tert-butyl ester (210 mg, 0.32 mmol) in DCM (1 mL) was added trifluoroacetic acid (0.3 mL). The reaction mixture was stirred at room temperature for 16 h, concentrated at reduced pressure, re-dissolved in methanol and purified by preparative HPLC. The HPLC fraction containing the desired product was basified by addition of saturated aq Na$_2$CO$_3$ and then extracted with EtOAc. Evaporation of the solvent at reduced pressure gave the desired product 1-{5-tert-butyl-2-[4-(2-piperidin-4-yl-ethoxy)-phenyl]-2H-pyrazol-3-yl}-3-[4-(pyridin-3-yloxy)-phenyl]-urea (46.6 mg, 26%). 1H-NMR (DMSO-d$_6$) δ 9.20 (s, 1H), 8.30 (m, 3H), 7.45-7.35 (m, 5H), 7.00 (m, 3H), 6.30 (s, 1H), 4.0 (m, 4H), 2.40 (m, 2H), 1.70-1.60 (m, 6H), 1.40 (s, 9H), 1.05 (m, 1H); MS LC-MS [M+H]$^+$=555.3, RT=2.73 min.

Example 6

1-{5-tert-Butyl-2-[3-(3-hydroxy-propoxy)-phenyl]-2H-pyrazol-3-yl}-3-[4-(pyridin-4-yloxy)-phenyl]-urea

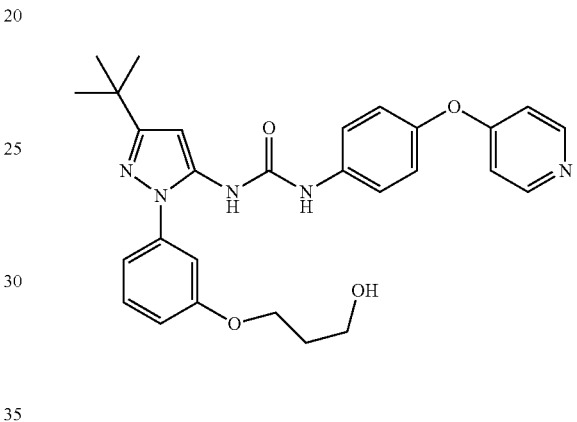

Step 1. To a solution of 3-[3-(5-amino-3-tert-butyl-pyrazol-1-yl)-phenoxy]-propan-1-ol (400 mg, 1.38 mmol) and phenyl chloroformate (324 mg, 2.07 mmol) in THF (14 mL) was added cesium carbonate (673 mg, 2.07 mmol). The mixture was stirred at room temperature for 4 h, additional phenyl chloroformate (108 mg, 0.69 mmol) was added, and then the mixture was stirred for an additional two hours. The reaction mixture was washed with saturated NaHCO$_3$ (3×30 mL), water, brine, dried (Na$_2$SO$_4$), and evaporated at reduced pressure to give the crude carbamate intermediate {5-tert-butyl-2-[3-(3-hydroxy-propoxy)-phenyl]-2H-pyrazol-3-yl}-carbamic acid phenyl ester (500 mg).

Step 2. To a solution of {5-tert-butyl-2-[3-(3-hydroxy-propoxy)-phenyl]-2H-pyrazol-3-yl}-carbamic acid phenyl ester (200 mg, 0.49 mmol) in THF was added 4-(pyridin-4-yloxy)-phenylamine (109 mg, 0.59 mmol). The reaction mixture was heated at 60° C. for 16 h. The reaction mixture was cooled to room temperature, concentrated at reduced pressure, and the residue was dissolved in DMF and methanol. The product was isolated by preparative HPLC, and the HPLC fraction containing the desired product was concentrated at reduced pressure and then partitioned between EtOAc (20 mL) and saturated aq Na$_2$CO$_3$ (10 mL). The organic layer was dried over Na$_2$SO$_4$ and evaporated to give 1-{5-tert-butyl-2-[3-(3-hydroxy-propoxy)-phenyl]-2H-pyrazol-3-yl}-3-[4-(pyridin-4-yloxy)-phenyl]-urea (51.3 mg, 21%). $^1$H-NMR (DMSO-d$_6$) δ 7.50 (d, 2H), 7.10 (m, 5H), 6.90 (d, 2H), 6.70 (m, 3H), 6.40 (s, 1H), 4.0 (t, 2H), 3.60 (t, 3H), 1.80 (m, 2H), 1.30 (s, 9H); MS LC-MS [M+H]$^+$=502.1, RT=2.36 min.

Example 7

N-(4-{3-tert-Butyl-5-[({[4-(pyridin-4-yloxy)-phenyl]amino}carbonyl)amino]-1H-pyrazol-1-yl}phenyl)-3-methoxypropanamide

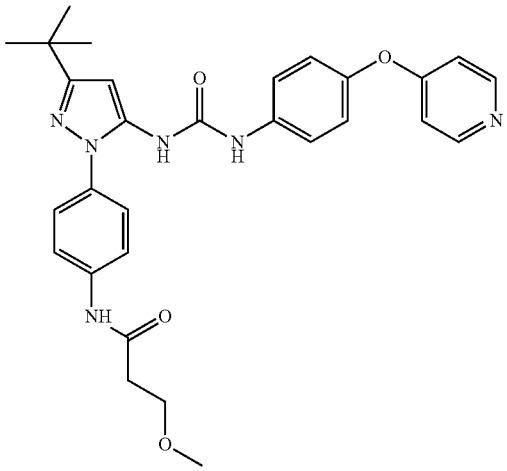

To a solution of 1-[2-(4-aminophenyl)-5-tert-butyl-2H-pyrazol-3-yl]-3-[4-(pyridin-4-yloxy)phenyl]urea (200 mg, 0.45 mmol) and 3-methoxypropionyl chloride (55 mg, 0.45 mmol) in anhydrous THF (5 mL) was added Et$_3$N (69 mg, 0.68 mmol). The reaction was stirred at room temperature for 7 h, and then partitioned between EtOAc (50 mL) and water (50 mL). The organic layer was washed with brine, dried over Na$_2$SO$_4$, and concentrated at reduced pressure. The residue was purified by MPLC (1:1 hexanes/EtOAc) to give 51 mg (21%) of the desired product. $^1$H-NMR (DMSO-d$_6$) δ 10.16 (s, 1H), 9.14 (s, 1H), 8.42 (d, J=4.8 Hz, 2H), 8.34 (s, 1H), 7.74 (d, J=6.9 Hz, 2H), 7.48 (d, J=6.9 Hz, 2H), 7.43 (d, J=8.7 Hz, 2H), 7.08 (d, J=6.6 Hz, 2H), 6.88 (d, J=5.4 Hz, 2H), 6.35 (s, 1H), 3.63 (t, J=6.0 Hz, 2H), 3.33 (s, 3H), 2.57 (t, J=6.0 Hz, 2H), 1.27 (s, 9H); MS LC-MS [M+H]$^+$=529, RT=2.20 min.

Example 8

N-(3-tert-Butyl-1-{4-[(2-methoxyethyl)amino]phenyl}-1H-pyrazol-5-yl)-N'-[4-(pyridin-4-yloxy)phenyl]urea

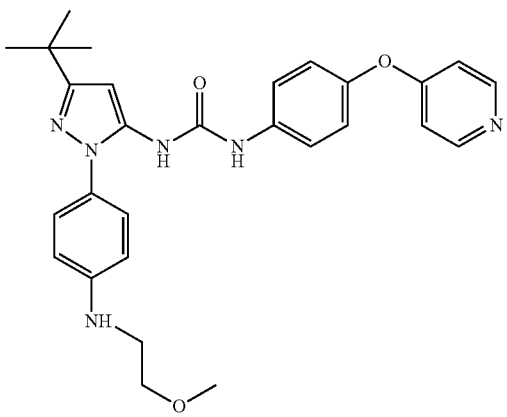

To a solution of N-[4-(3-tert-butyl-5-{[({2-fluoro-4-[(2-methylpyridin-4-yl)oxy]-phenyl}amino)carbonyl]amino}-1H-pyrazol-1-yl)phenyl]-2-methoxyacetamide (500 mg, 0.97 mmol) in anhydrous THF (20 mL) was added borane-methyl sulfide complex (2.0 M solution in THF, 5 mL, 10 mmol), and the reaction was stirred at reflux for 7 h. The reaction mixture was cooled to room temperature, partitioned between EtOAc (50 mL) and water (50 mL), and the organic layer was washed with brine, dried over Na$_2$SO$_4$, and concentrated at reduced pressure. The residue was purified by MPLC (1:1 hexanes/EtOAc) to give 33 mg (7%) of the desired product. $^1$H-NMR (DMSO-d$_6$) δ 8.65 (s, 1H), 8.42 (d, J=4.8 Hz, 2H), 8.34 (s, 1H), 7.58 (d, J=6.6 Hz, 2H), 7.21 (d, J=6.6 Hz, 2H), 7.06 (d, J=6.9 Hz, 2H), 6.84 (d, J=4.8 Hz, 2H), 6.73 (d, J=6.9 Hz, 2H), 6.43 (s, 1H), 5.23 (s, 1H), 3.57 (t, J=5.7 Hz, 2H), 3.35 to 3.30 (m, 5H), 1.32 (s, 9H); MS LC-MS [M+H]$^+$=529, RT=2.20 min.

Example 9

N-[4-(3-tert-Butyl-5-{3-[4-(pyridin-4-yloxy)-phenyl]-ureido}-pyrazol-1-yl)-phenyl]-2,2-dimethylsuccinamic acid

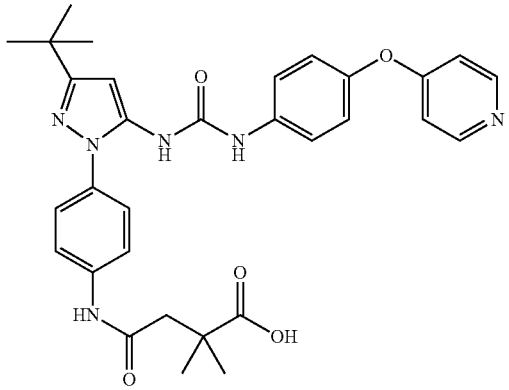

A solution of 1-[2-(4-amino-phenyl)-5-tert-butyl-2H-pyrazol-3-yl]-3-[4-(pyridin-4-yloxy)-phenyl]-urea (208 mg, 0.47 mmol) and 2,2-dimethylsuccinic anhydride (66 mg, 0.52 mmol, 1.1 eq) in 2 mL THF was stirred at room temperature overnight. HPLC analysis indicated that starting material was remaining. The reaction was then heated at 60° C. for 2 days, at which time HPLC analysis indicated the reaction was complete. The reaction mixture was cooled to room temperature, and the resulting suspension was diluted with Et$_2$O. The solid was isolated by filtration to afford the desired product (227 mg, 85%). $^1$H-NMR (DMSO-d$_6$) δ 12.06 (s, 1H), 10.06 (s, 1H), 9.09 (s, 1H), 8.40 (d, J=6.0 Hz, 2H), 8.31 (s, 1H), 7.69 (d, J=9.0 Hz, 2H), 7.47 (d, J=9.0 Hz, 2H), 7.39 (d, J=9.0 Hz, 2H), 7.07 (d, J=9.0 Hz, 2H), 6.85 (dd, J=1.5 & 4.7 Hz, 2H), 6.33 (s, 1H), 2.59 (s, 2H), 1.26 (s, 9H), 1.21 (s, 6H); MS LC-MS [M+H]$^+$=571.3, RT=2.49 min.

Example 10

1-{5-tert-Butyl-2-[4-(4-hydroxy-3,3-dimethyl-butylamino)-phenyl]-2H-pyrazol-3-yl}-3-[4-(pyridin-4-yloxy)-phenyl]-urea

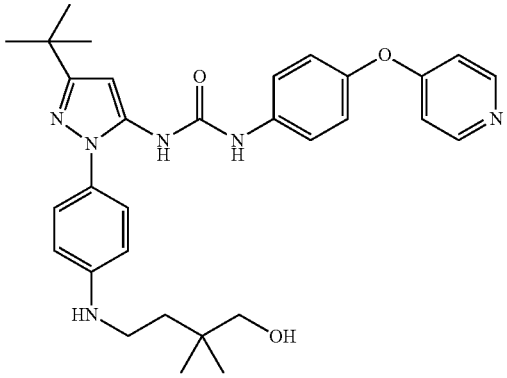

A solution of N-[4-(3-tert-butyl-5-{3-[4-(pyridin-4-yloxy)-phenyl]-ureido}-pyrazol-1-yl)-phenyl]-2,2-dimethyl-succinamic acid (190 mg, 0.33 mmol) in 3 mL THF was treated with borane-methylsulfide complex (2M, 1.0 mL, 2.0 mmol, 6 eq). The reaction mixture was heated at reflux under nitrogen for 4 h. The reaction mixture was then cooled to room temperature, slowly quenched by the addition of 0.6 mL EtOH and 2 mL 2N HCl. The reaction mixture was heated again at reflux for 1 hr, then cooled to room temperature, basified by the addition of 1N NaOH, extracted with DCM, and concentrated at reduced pressure. The crude residue was purified by MPLC (eluting with 2% to 6% MeOH in DCM) to afford 80 mg of semi-pure 1-[2-(4-amino-phenyl)-5-tert-butyl-2H-pyrazol-3-yl]-3-[4-(pyridin-4-yloxy)-phenyl]-urea. Preparative HPLC purification using 5-80% H$_2$O in acetonitrile (containing 0.5% TFA) afforded 33 mg (18%) of the desired product. $^1$H-NMR (DMSO-d$_6$) δ 9.14 (s, 1H), 8.40 (dd, J=1.6 & 4.8 Hz, 2H), 8.17 (s, 1H), 7.47 (d, J=8.9 Hz, 2H), 7.11 (d, J=8.6 Hz, 2H), 7.07 (d, J=9 Hz, 2H), 6.85 (dd, J=1.5 & 4.9 Hz, 2H), 6.62 (d, J=8.9 Hz, 2H), 6.28 (s, 1H), 5.83 (t, J=5.2 Hz, 1H), 4.58 (t, J=5.2 Hz, 1H), 3.14 (d, J=5.4 Hz, 2H), 3.06-3.01 (m, 2H), 1.52-1.48 (m, 2H), 1.25 (s, 9H), 0.87 (s, 6H); MS LC-MS [M+H]$^+$=543.2, RT=2.31 min.

Example 11

1-{5-tert-Butyl-2-[3-(3-hydroxy-propylamino)-phenyl]-2H-pyrazol-3-yl}-3-[4-(pyridin-4-yloxy)-phenyl]-urea

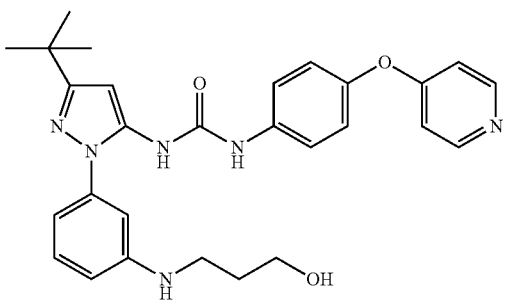

Step 1: To a solution of 1-[2-(3-amino-phenyl)-5-tert-butyl-2H-pyrazol-3-yl]-3-[4-(pyridin-4-yloxy)-phenyl]-urea (100 mg, 0.23 mmol), 3-[(tert-butyldimethylsilyl)oxy]-1-propanal (47 mg, 0.25 mmol, 1.1 eq), and sodium triacetoxyborohydride (67 mg, 0.32 mmol, 1.4 eq) in anhydrous THF (2 mL) was added acetic acid (16 mg, 0.27 mmol, 1.2 eq). The reaction mixture was stirred under N$_2$ at room temperature for 2 h. The reaction mixture was quenched with saturated NaHCO$_3$ and extracted with EtOAc. The combined organic phases were washed with brine, dried over Na$_2$SO$_4$ and concentrated at reduced pressure. The crude residue was purified by MPLC (eluting with 40:60 to 60:40 EtOAc/hexanes) to give 117 mg (84%) of 1-(5-tert-butyl-2-{3-[3-(tert-butyl-dimethyl-silanyloxy)-propylamino]-phenyl}-2H-pyrazol-3-yl)-3-[4-(pyridin-4-yloxy)-phenyl]-urea. $^1$H-NMR (DMSO-d$_6$) δ 9.17 (s, 1H), 8.40 (dd, J=1.5 & 4.6 Hz, 2H), 8.31 (s, 1H), 7.48 (d, J=8.8 Hz, 2H), 7.17 (t, J=8.1 Hz, 1H), 7.07 (d, J=8.8 Hz, 2H), 6.85 (dd, J=1.6 & 4.9 Hz, 2H), 6.61-6.56 (m, 3H), 6.32 (s, 1H), 5.92 (t, J=5.6 Hz, 1H), 3.66 (t, J=6.1 Hz, 2H), 3.07 (q, J=7.5 Hz, 2H), 1.72 (quintet, J=6.8 Hz, 2H), 1.26 (s, 9H), 0.84 (s, 9H), 0.02 (s, 6H); MS LC-MS [M+H]$^+$=615.4, RT=3.28 min.

Step 2: To a solution of 1-(5-tert-butyl-2-{3-[3-(tert-butyl-dimethyl-silanyloxy)-propylamino]-phenyl}-2H-pyrazol-3-yl)-3-[4-(pyridin-4-yloxy)-phenyl]-urea (117 mg, 0.19 mmol) in methanol (2 mL) was added a solution of 10% TFA in H$_2$O (2 mL). The reaction was stirred at room temperature overnight. The mixture was then diluted with DCM, basified by the addition of saturated aq NaHCO$_3$ and extracted with DCM. The combined organic phases were washed with brine, dried over MgSO$_4$, and concentrated at reduced pressure. The crude residue was purified by MPLC (eluting with 4% to 5.5% MeOH in DCM) to give 82 mg (86%) of the desired product 1-{5-tert-butyl-2-[3-(3-hydroxy-propylamino)-phenyl]-2H-pyrazol-3-yl}-3-[4-(pyridin-4-yloxy)-phenyl]-urea. $^1$H-NMR (DMSO-d$_6$) δ 9.18 (s, 1H), 8.40 (dd, J=1.7 & 4.7 Hz, 2H), 8.32 (s, 1H), 7.48 (d, J=9.0 Hz, 2H), 7.17 (t, J=7.9 Hz, 1H), 7.07 (d, J=9.1 Hz, 2H), 6.85 (dd, J=1.5 & 4.7 Hz, 2H), 6.63-6.56 (m, 3H), 6.33 (s, 1H), 5.91 (t, J=5.3 Hz, 1H), 4.47 (t, J=5.1 Hz, 1H), 3.48 (q, J=6.1 Hz, 2H), 3.06 (q, J=6.6 Hz, 2H), 1.69 (quintet, J=6.5 Hz, 2H), 1.26 (s, 9H); MS LC-MS [M+H]$^+$=501.2, RT=2.29 min.

Example 12

N-(3-tert-Butyl-1-{3-[[(dimethylamino)sulfonyl](3-hydroxypropyl)amino]phenyl}-1H-pyrazol-5-yl)-N'-[4-(pyridin-4-yloxy)phenyl]urea

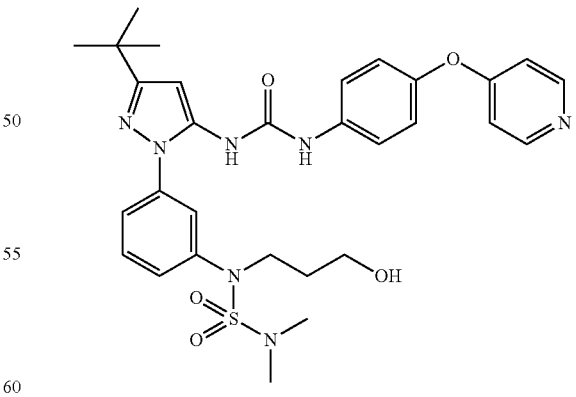

A solution of 1-{5-tert-butyl-2-[3-(3-hydroxy-propylamino)-phenyl]-2H-pyrazol-3-yl}-3-[4-(pyridin-4-yloxy)-phenyl]-urea (100 mg, 0.21 mmol) in THF (1 mL) was treated with dimethylsulfamoyl chloride (90 mg, 0.62 mmol, 3 eq) followed by DIEA (30 mg, 0.21 mmol, 1 eq). The reaction mixture was stirred at 40° C. overnight. The mixture was evaporated at reduced pressure, and the product was isolated by MPLC (eluting with 1% to 4% MeOH in DCM) to afford 57 mg (46%) of desired product. $^1$H-NMR (DMSO-d$_6$) δ 9.08 (s, 1H), 8.40-8.38 (m, 3H), 7.54-7.36 (m, 6H), 7.05 (d, J=8.9 Hz, 2H), 6.84 (d, J=5.6 Hz, 2H), 6.32 (s, 1H), 4.45 (t, J=4.6 Hz, 1H), 3.64 (t, J=7.0 Hz, 2H), 3.33-3.28 (m, 2H), 2.70 (s, 6H), 1.49-1.45 (m, 2H), 1.29 (s, 9H); MS LC-MS [M+H]$^+$=608.2, RT=2.45 min.

Example 13

1-(2-{3-[Bis-(2-hydroxy-ethyl)-amino]-phenyl}-5-tert-butyl-2H-pyrazol-3-yl)-3-[4-(pyridin-4-yloxy)-phenyl]-urea

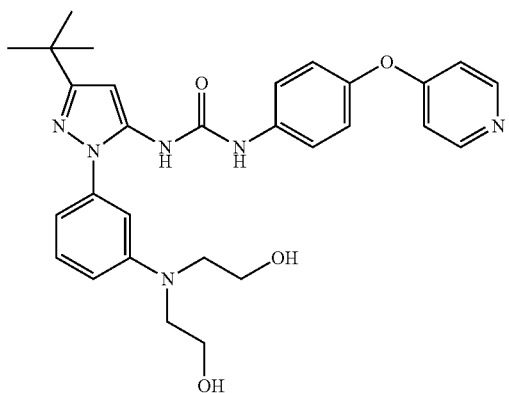

Step 1: To a solution of 1-[2-(3-amino-phenyl)-5-tert-butyl-2H-pyrazol-3-yl]-3-[4-(pyridin-4-yloxy)-phenyl]-urea (124 mg, 0.28 mmol), (tert-butyldimethylsilyloxy)acetaldehyde (135 mg, 0.70 mmol, 2.5 eq), and sodium triacetoxyborohydride (178 mg, 0.84 mmol, 3 eq) in anhydrous THF (2 mL) was added acetic acid (20 mg, 0.34 mmol, 1.2 eq). The reaction was stirred under N$_2$ at room temperature for 2 h. The reaction mixture was quenched with saturated aq NaHCO$_3$ and extracted with EtOAc. The combined organic phases were washed with brine, dried over Na$_2$SO$_4$ and concentrated at reduced pressure. The residue was purified by MPLC (eluting with 45:55 to 65:35 EtOAc/hexanes) to give 153 mg (72%) of 1-[2-(3-{bis-[2-(tert-butyl-dimethyl-silanyloxy)-ethyl]-amino}-phenyl)-5-tert-butyl-2H-pyrazol-3-yl]-3-[4-(pyridin-4-yloxy)-phenyl]-urea. $^1$H-NMR (DMSO-d$_6$) δ 9.17 (s, 1H), 8.39 (d, J=6.3 Hz, 2H), 8.31 (s, 1H), 7.47 (d, J=9.0 Hz, 2H), 7.24 (t, J=7.9 Hz, 1H), 7.07 (d, J=9 Hz, 2H), 6.84 (d, J=6.1 Hz, 2H), 6.72-6.66 (m, 3H), 6.33 (s, 1H), 3.72 (t, J=5.8 Hz, 4H), 3.49 (t, J=5.9 Hz, 4H), 1.26 (s, 9H), 0.82 (s, 18H), −0.01 (s, 12H); MS LC-MS [M+H]$^+$=760.3, RT=4.10 min.

Step 2: To a solution of 1-[2-(3-{bis-[2-(tert-butyl-dimethyl-silanyloxy)-ethyl]-amino}-phenyl)-5-tert-butyl-2H-pyrazol-3-yl]-3-[4-(pyridin-4-yloxy)-phenyl]-urea (153 mg, 0.20 mmol) in methanol (2 mL) was added a solution of 10% TFA in H$_2$O (2 mL). The reaction was stirred at room temperature for 4 h. The mixture was then diluted with DCM, basified by addition of saturated NaHCO$_3$ and extracted with DCM. The combined organic phases were washed with brine, dried over MgSO$_4$, and concentrated at reduced pressure. The residue was purified by MPLC (eluting with 3% to 6% MeOH in DCM) to give 35 mg (36%) of the desired product. $^1$H-NMR (DMSO-d$_6$) δ 9.17 (s, 1H), 8.40 (dd, J=1.5 & 4.7 Hz, 2H), 8.32 (s, 1H), 7.48 (d, J=8.8 Hz, 2H), 7.26-7.22 (m, 1H), 7.07 (d, J=9.1 Hz, 2H), 6.85 (dd, J=1.5 & 4.7 Hz, 2H), 6.71-6.69 (m, 2H), 6.63 (d, J=7.9 Hz, 1H), 6.34 (s, 1H), 4.76 (t, J=5.4 Hz, 2H), 3.54 (q, J=5.7 Hz, 4H), 3.43 (t, J=5.7 Hz, 4H), 1.26 (s, 9H); MS LC-MS [M+H]$^+$=531.2, RT=2.27 min.

Example 14

1-[2-(4-Aminomethyl-phenyl)-5-tert-butyl-2H-pyrazol-3-yl]-3-[4-(pyridin-4-yloxy)-phenyl]urea

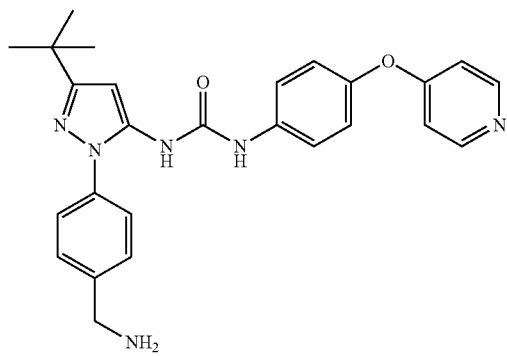

To a solution of 1-[5-tert-butyl-2-(4-cyano-phenyl)-2H-pyrazol-3-yl]-3-[4-(pyridin-4-yloxy)phenyl]urea (4.0 g, 8.8 mmol) in anhydrous THF (20 mL) was added a solution of lithium aluminum hydride in THF (1M, 9.7 mL, 9.7 mmol) with stirring at 0° C. under nitrogen, and then the reaction mixture was stirred at room temperature for 5 h. The excess lithium aluminum hydride was quenched by dropwise addition of EtOAc (5 mL) followed by EtOH (5 mL) and then 10% aqueous KHSO$_4$ solution (5 mL). The reaction mixture was stirred at room temperature for an additional 10 min, and was then filtered through a pad of Celite® filter agent. The Celite® was washed with EtOH (50 mL) and the filtrate was concentrated at reduced pressure. The residue was purified by MPLC (80:20 CH$_2$Cl$_2$/MeOH) to give 3.2 g (79%) of the desired product. $^1$H-NMR (DMSO-d$_6$) δ 9.38 (s, 1H), 8.41 (dd, J=1.5, 4.8 Hz, 2H), 7.49 to 7.46 (m, 6H), 7.07 (d, J=6.9 Hz, 2H), 6.85 (dd, J=1.8, 4.8 Hz, 2H), 6.32 (s, 1H), 3.82 (s, 2H), 1.26 (s, 9H); MS LC-MS [M+H]$^+$=457, RT=1.96 min.

Example 15

N-[4-(3-tert-Butyl-5-{3-[4-(pyridin-4-yloxy)-phenyl]-ureido}-pyrazol-1-yl)-benzyl]-2-methoxy-acetamide

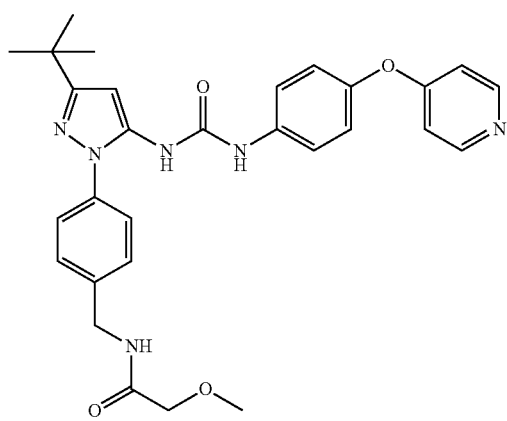

To a solution of 1-[2-(4-aminomethyl-phenyl)-5-tert-butyl-2H-pyrazol-3-yl]-3-[4-(pyridin-4-yloxy)phenyl]urea (400 mg, 0.88 mmol) in THF (20 mL) was added N,N-diisopropylethylamine (0.23 mL, 1.31 mmol). A solution of 3-methoxypropionyl chloride (95 mg, 0.88 mmol) in THF (1 mL) was added to the solution at 0° C. under $N_2$ and the reaction mixture was stirred at room temperature for 3 h. The reaction mixture was concentrated at reduced pressure and dissolved in EtOAc (100 mL). The solution was washed with water and brine, dried over $Na_2SO_4$, and concentrated at reduced pressure. The residue was purified by MPLC (50:50 hexanes/EtOAc) to give 240 mg (52%) of the desired product. $^1$H-NMR (DMSO-$d_6$) δ 9.16 (s, 1H), 8.42 to 8.40 (m, 4H), 7.50 to 7.37 (m, 6H), 7.08 (d, J=8.7 Hz, 2H), 6.85 (d, J=6.0 Hz, 2H), 6.34 (s, 1H), 4.33 (d, J=6.0 Hz, 2H), 3.86 (s, 2H), 3.26 (s, 3H), 1.25 (s, 9H); MS LC-MS [M+H]$^+$=529, RT=2.29 min.

Example 16

1-(5-tert-Butyl-2-{4-[(2-methoxy-ethylamino)-methyl]-phenyl}-2H-pyrazol-3-yl)-3-[4-(pyridin-4-yloxy)phenyl]urea

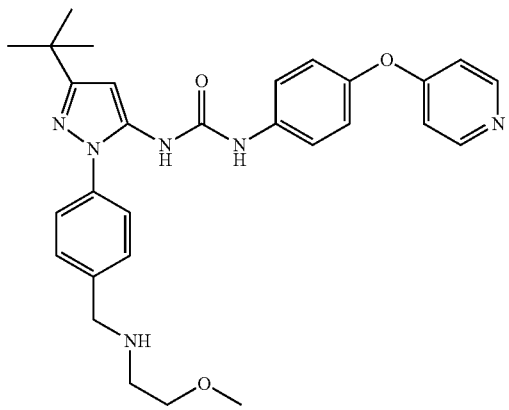

To a solution of N-[4-(3-tert-butyl-5-{3-[4-(pyridin-4-yloxy)-phenyl]-ureido}-pyrazol-1-yl)-benzyl]-2-methoxy-acetamide (200 mg, 0.38 mmol) in anhydrous THF (10 mL) was added borane-methyl sulfide complex (2.0 M solution in THF, 1 mL, 2 mmol), and the reaction was stirred at reflux for 7 h. The reaction mixture was cooled to room temperature, partitioned between EtOAc (50 mL) and water (50 mL), and then the organic layer was separated and washed with brine, dried over $Na_2SO_4$, and concentrated at reduced pressure. The residue was purified by MPLC (90:10 $CH_2Cl_2$/MeOH) to give 30 mg (15%) of the desired product. $^1$H-NMR (DMSO-$d_6$) δ 8.79 (s, 1H), 8.42 (d, J=4.8 Hz, 2H), 7.61 to 7.46 (m, 7H), 7.06 (d, J=6.6 Hz, 2H), 6.84 (d, J=4.5 Hz, 2H), 6.44 (s, 1H), 3.85 (s, 2H), 3.49 (t, J=5.7 HZ, 2H), 3.29 (s, 3H), 2.81 (t, J=5.7 Hz, 2H), 1.31 (s, 9H); MS LC-MS [M+H]$^+$=515, RT=2.02 min.

Example 17

1-[2-(4-{[Bis-(2-hydroxy-ethyl-amino]-methyl}-phenyl)-5-tert-butyl-2H-pyrazo-3-yl]-3-[4-(pyridin-4-yloxy)phenyl]urea Step 1. 1-{2-[4-({bis-[2-(tert-Butyl-dimethyl-silanyloxy)-ethyl]-amino}-methyl)-phenyl]-5-tert-butyl-2H-pyrazo-3-yl}-3-[4-(pyridin-4-yloxy)phenyl]urea

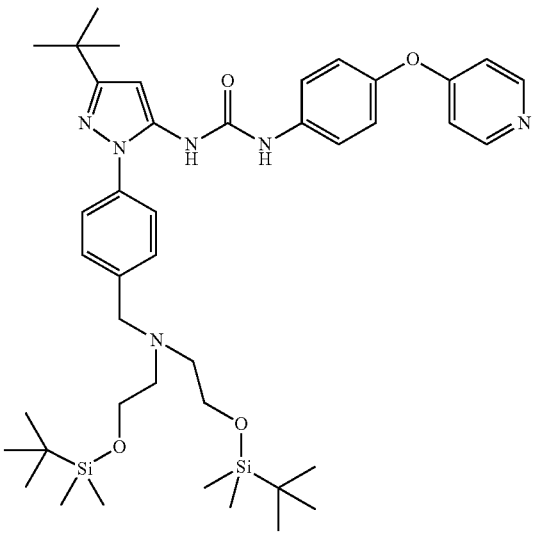

To a solution of 1-[2-(4-aminomethyl-phenyl)-5-tert-butyl-2H-pyrazol-3-yl]-3-[4-(pyridin-4-yloxy)phenyl]urea (200 mg, 0.44 mmol) and sodium triacetoxyborohydride (186 mg, 0.88 mmol) in anhydrous THF (3 mL) was added tert-butyldimethylsilyloxy)acetaldehyde (153 mg, 0.88 mmol) and acetic acid (53 mg, 0.88 mmol), and then the reaction mixture was stirred at room temperature for 2 h. The reaction mixture was partitioned between EtOAc (20 mL) and water (10 mL), and the organic layer was washed with brine, dried over $Na_2SO_4$, and concentrated at reduced pressure. The residue was purified by MPLC (50:50 hexanes/EtOAc) to give 160 mg (47%) of the desired product. $^1$H-NMR (DMSO-$d_6$) δ 8.48 (s, 1H), 8.36 (d, J=4.5 Hz, 2H), 7.78 (s, 1H), 7.54 (d, J=6.6 Hz, 2H), 7.53 to 7.40 (m, 4H), 7.01 (d, J=6.6 Hz, 2H), 6.79 (d, J=5.7 Hz, 2H), 6.38 (s, 1H), 3.76 (s, 2H), 3.70 (t, J=6.3 Hz, 4H), 2.67 (t, J=6.3 Hz, 4H), 1.26 (s, 9H), 0.83 (s, 18H), 0.00 (s, 12H); MS LC-MS [M+H]$^+$=773, RT=3.39 min.

Step 2. 1-[2-(4-{[Bis-(2-hydroxy-ethyl-amino]-methyl}-phenyl)-5-tert-butyl-2H-pyrazo-3-yl]-3-[4-(pyridin-4-yloxy)phenyl]urea

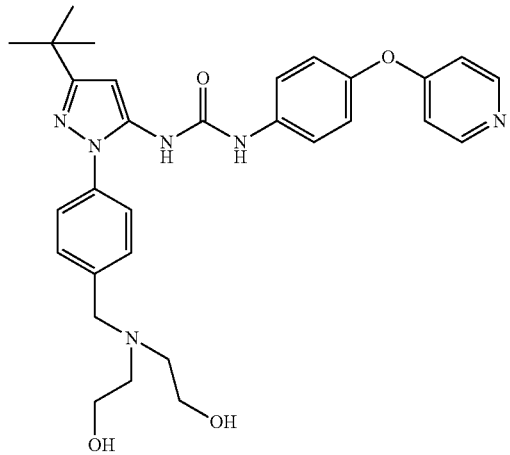

To a solution of 1-{2-[4-({bis-[2-(tert-butyl-dimethyl-silanyloxy)-ethyl]-amino}-methyl)-phenyl]-5-tert-butyl-2H-pyrazo-3-yl}-3-[4-(pyridin-4-yloxy)phenyl]urea (160 mg, 0.21 mmol) in methanol (5 mL) was added 10% aqueous TFA solution (5 mL), and then the reaction mixture was stirred at room temperature for 4 h. The reaction mixture was partitioned between EtOAc (20 mL) and saturated aq NaHCO$_3$ (20 mL), and then the organic layer was washed with brine, dried over Na$_2$SO$_4$, and concentrated at reduced pressure. The residue was purified by MPLC (90:10 CH$_2$Cl$_2$/MeOH) to give 34 mg (30%) of the desired product. $^1$H-NMR (DMSO-d$_6$) δ 9.12 (s, 1H), 8.42 to 8.40 (m, 3H), 7.50 to 7.42 (m, 6H), 7.08 (d, J=6.9 Hz, 2H), 6.85 (d, J=6.3 Hz, 2H), 6.35 (s, 1H), 4.39 (b, 2H), 3.69 (s, 2H), 3.45 (m, 4H), 2.54 (m, 4H), 1.24 (s, 9H); MS LC-MS [M+H]$^+$=545, RT=2.03 min.

Example 18

2-Amino-N-[4-(3-tert-butyl-5-{3-[4-(pyridin-4-yloxy)-phenyl]-ureido}-pyrazol-1-yl)-benzyl]-acetamide Step 1. {[4-(3-tert-Butyl-5-{3-[4-(pyridin-4-yloxy)-phenyl]-ureido}-pyrazol-1-yl)-benzylcarbamoyl]-methyl}-carbamic acid tert-butyl ester

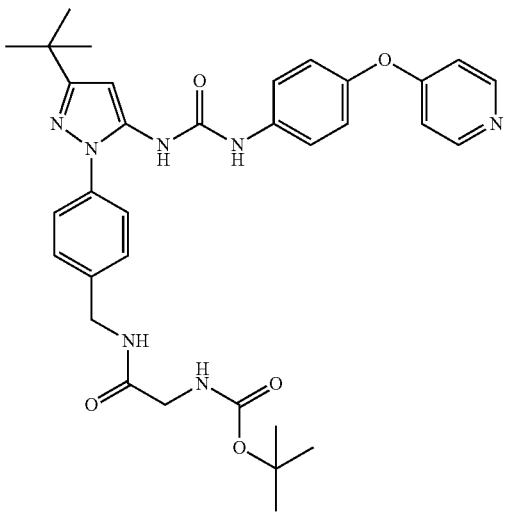

To a solution of N-Boc-glycine (260 mg, 1.48 mmol), EDCl (283 mg, 148 mmol) and HOBT (200 mg, 1.48 mmol) in THF/acetonitrile (50:50, 5 mL) was added N,N-diisopropylethylamine (380 mg, 2.96 mmol), and the resulting reaction mixture was stirred at room temperature for 1 h. Then, 1-[2-(4-aminomethyl-phenyl)-5-tert-butyl-2H-pyrazol-3-yl]-3-[4-(pyridin-4-yloxy)phenyl]urea (450 mg, 0.99 mmol) was added to the solution and the reaction mixture was stirred at 50° C. for 18 h. The reaction mixture was cooled to room temperature, concentrated at reduced pressure, and the residue was dissolved in EtOAc (20 mL). The solution was washed with water and brine, dried over Na$_2$SO$_4$, and concentrated at reduced pressure. The residue was purified by preparative TLC (50:50 hexanes/EtOAc) to give 65 mg (11%) of the desired product. $^1$H-NMR (DMSO-d$_6$) δ 8.68 (s, 1H), 8.42 (d, J=6.3 Hz, 2H), 7.98 (s, 1H), 7.82 (b, 1H), 7.61 (d, J=6.9 Hz, 2H), 7.50 (d, J=8.4 Hz, 2H), 7.42 (d, J=8.4 Hz, 2H), 7.08 (d, J=6.6 Hz, 2H), 6.80 (d, J=6.3 Hz, 2H), 6.46 (s, 1H), 4.48 (d, J=6.0 Hz, 2H), 3.78 (d, J=5.7 Hz, 2H), 1.35 (s, 9H), 1.30 (s, 9H); MS LC-MS [M+H]$^+$=614, RT=2.89 min.

Step 2. 2-Amino-N-[4-(3-tert-butyl-5-{3-[4-(pyridin-4-yloxy)-phenyl]-ureido}-pyrazol-1-yl)-benzyl]-acetamide

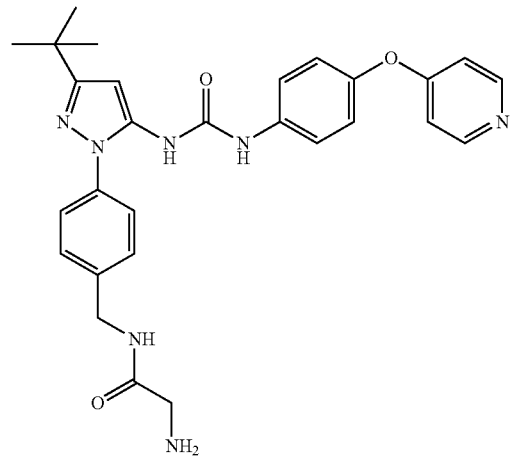

To a solution of {[4-(3-tert-butyl-5-{3-[4-(pyridin-4-yloxy)-phenyl]-ureido}-pyrazol-1-yl)-benzylcarbamoyl]-methyl}-carbamic acid tert-butyl ester (60 mg, 0.10 mmol) in THF (5 mL) was added TFA (3 mL), and the resulting mixture was stirred at room temperature for 18 h. The reaction mixture was partitioned between EtOAc (20 mL) and saturated NaHCO$_3$ aqueous solution (20 mL), and the organic layer was removed and washed with brine, dried over Na$_2$SO$_4$, and concentrated at reduced pressure. The residue was purified by preparative TLC (90:10 CH$_2$Cl$_2$/MeOH) to give 10 mg (20%) of the desired product. $^1$H-NMR (DMSO-d$_6$) δ 8.72 (s, 1H), 8.32 (d, J=5.7 Hz, 2H), 8.02 (s, 1H), 7.53 to 7.30 (m, 6H), 6.96 (d, J=6.6 Hz, 2H), 6.73 (d, J=6.3 Hz, 2H), 6.32 (s, 1H), 4.36 (s, 2H), 3.70 (S, 2H), 1.18 (s, 9H); MS LC-MS [M+H]$^+$=513, RT=2.01 min.

Example 19

3-(3-tert-Butyl-5-{3-[2-fluoro-4-(2-methyl-pyridin-4-yloxy)-phenyl]-ureido}-pyrazol-1-yl)-N-(2,2-dimethyl-[1,3]dioxolan-4-ylmethyl)-benzamide

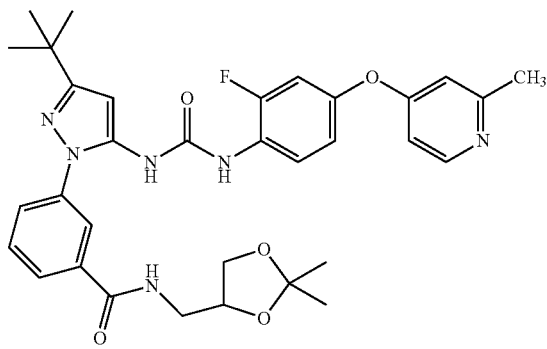

A mixture of 3-(3-tert-butyl-5-{3-[2-fluoro-4-(2-methyl-pyridin-4-yloxy)-phenyl]-ureido}-pyrazol-1-yl)-benzoic acid (300.0 mg, 0.60 mmol), 1-(2,2-dimethyl-1,3-dioxolan-4-yl)methanamine (93.8 mg, 0.71 mmol), 1-[3-(dimethylamino)propyl]-3-ethylcarbodiimide hydrochloride (136.6 mg, 0.71 mmol), 4-dimethylaminopyridine (87.3 mg, 0.71 mmol) and 1-hydroxybenzotriazole (96.6 mg, 0.71 mmol) in THF and DCM was stirred at room temperature overnight.

Ethyl acetate and water were added, and the organic phase was washed with brine, dried over MgSO₄. and evaporated at reduced pressure. HPLC purification (10-90% aqueous acetonitrile) afforded pure title compound (270 mg, 73%). ¹H-NMR (DMSO-d$_6$) δ 8.93 (s, 1H), 8.88 (s, 1H), 8.72 (t, J=6.07.66 (m, 2H), 8.30 (d, J=5.7 Hz), 8.13 (t, J=9.0 Hz, 1H), 7.98 (s, 1H), 7.89 (d, J=9.0 Hz, 1H), 7.69 (m, 2H), 7.19 (d, J=14.7 Hz, 1H), 6.96 (d, J=10.2 Hz, 1H), 6.76 (s, 1H), 6.72 (d, J=5.7 Hz, 1H), 6.41 (s, 1H), 3.95 (t, J=6.3 Hz, 1H), 3.68 (t, J=6.0 Hz, 1H) 3.28-3.45 (m, 2H), 1.314 (s, 3H), 1.27 (s, 9H), 1.22 (s, 3H); MS LC-MS [M+H]⁺=617.3, RT=2.54 min.

Example 20

3-(3-tert-Butyl-5-{3-[4-(pyridin-4-yloxy)-phenyl]-ureido}-pyrazol-1-yl)-N-(2,2-dimethyl-[1,3]dioxolan-4-ylmethyl-benzamide

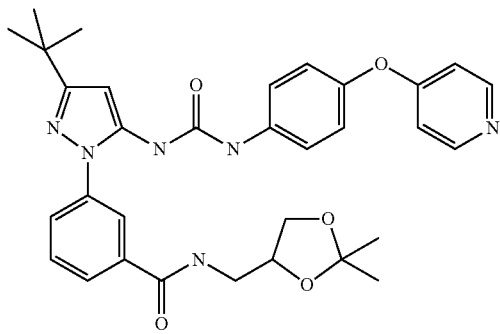

This compound was prepared in a similar manner as described for 3-(3-tea-butyl-5-{3-[2-fluoro-4-(2-methyl-pyridin-4-yloxy)-phenyl]-ureido}-pyrazol-1-yl)-N-(2,2-dimethyl-[1,3]dioxolan-4-ylmethyl)-benzamide. MS LC-MS [M+H]⁺=585.3, RT=2.59 min.

Example 21

3-(3-tert-Butyl-5-{[({2-fluoro-4-[(2-methylpyridin-4-yl)oxy]phenyl}amino)carbonyl]-amino}-1H-pyrazol-1-yl)-N-(2,3-dihydroxypropyl)benzamide

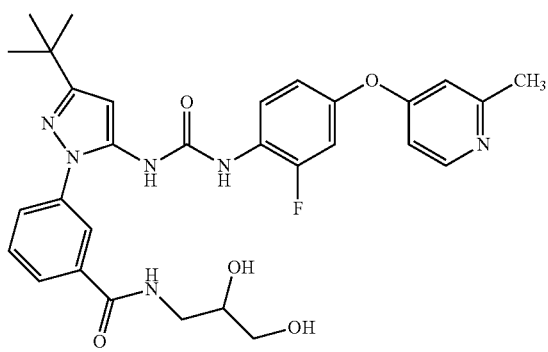

A mixture of 3-(3-tert-butyl-5-{3-[2-fluoro-4-(2-methyl-pyridin-4-yloxy)-phenyl]-ureido}-pyrazol-1-yl)-benzoic acid (100 mg, 0.20 mmol), 3-aminopropane-1,2-diol (22 mg, 0.24 mmol), 1-[3-(dimethylamino)propyl]-3-ethylcarbodiimide hydrochloride (46 mg, 0.24 mmol), 4-dimethylaminopyridine (29 mg, 0.24 mmol) and 1-hydroxybenzotriazole (32 mg, 0.24 mmol) in THF and DCM was stirred at room temperature overnight. Ethyl acetate and water were added, and the organic phase was washed with brine, dried over MgSO₄, and evaporated at reduced pressure. HPLC purification (10-90% aqueous acetonitrile) afforded pure title compound (23 mg, 20%). ¹H-NMR (DMSO-d$_6$) δ 8.97 (s, 1H), 8.91 (s, 1H), 8.55 (t, J=5.7 Hz, 1H), 8.29 (d, J=7.2 Hz, 1H), 8.11 (t, J=9.0 Hz, 1H), 7.98 (s, 1H), 7.89 (d, J=7.2 Hz, 1H), 7.64-7.58 (m, 2H), 7.18 (d, J=9.0 Hz, 1H), 6.94 (d, J=12.0 Hz, 1H), 6.76 (s, 1H), 4.81 (s, 1H), 4.57 (s, 1H), 3.62 (t, J=5.7 Hz, 1H). 3.40 (m, 2H), 3.18 (m, 2H), 2.36 (s, 3H), 1.80 (s, 9H); MS LC-MS [M+H]⁺=577.3, RT=1.54 min.

Example 22

3-(3-tert-Butyl-5-{3-[4-(pyridin-4-yloxy)-phenyl]-ureido}-pyrazol-1-yl)-N-(2,3-dihydroxy-propyl)benzamide

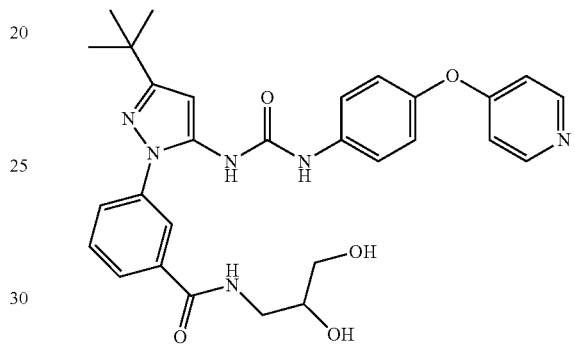

To a solution of 3-(3-tert-butyl-5-{3-[4-(pyridin-4-yloxy)-phenyl]-ureido}-pyrazol-1-yl)-N-(2,2-dimethyl-[1,3]dioxolan-4-ylmethyl-benzamide (120 mg, 0.21 mmol) in acetone, 2N HCl (0.2 mL, 0.4 mmol) was added. The mixture was stirred at room temperature overnight. EtOAc was added, and the organic layer was washed with brine, dried over MgSO₄, and evaporated at reduced pressure. HPLC purification (10-90% aq acetonitrile) afforded pure title compound (36.5 mg, 33%). ¹H-NMR (DMSO-d$_6$) δ 9.19 (s, 1H), 8.54 (s, 4H), 7.99 (s, 1H), 7.87 (d, J=10.5 Hz, 1H), 7.68-7.49 (m, 4H), 7.15-7.07 (m, 4H), 6.37 (s, 1H), 3.71-3.11 (m, 5H), 1.20 (s, 9H); MS LC-MS [M+H]⁺=545.3, RT=2.21 min.

Example 23

1-[5-tert-Butyl-2-(4-hydroxymethyl-phenyl)-2H-pyrazol-3-yl]-3-[2-fluoro-4-(2-methyl-pyridin-4-yloxy)-phenyl]-urea

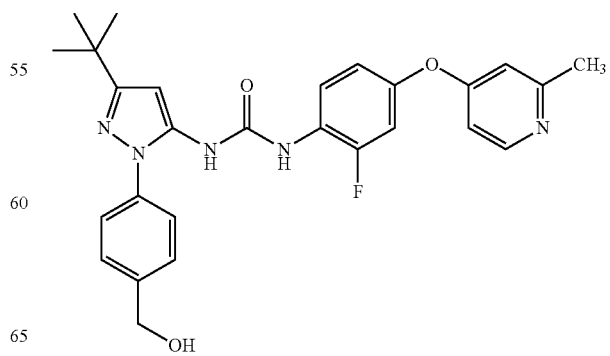

To a solution of 4-(3-tert-butyl-5-{3-[2-fluoro-4-(2-methyl-pyridin-4-yloxy)-phenyl]-ureido}-pyrazol-1-yl)-benzoic acid methyl ester (700 mg, 1.35 mmol) in anhydrous THF at 0° C. was slowly added a 1N solution of lithium aluminum hydride in THF (0.95 mL, 0.95 mmol). The mixture was stirred at room temperature for 15 minutes, and then water was added dropwise to quench the reaction. The mixture was extracted with EtOAc, and the combined organic phases were dried over MgSO$_4$ and evaporated at reduced pressure. The residue was purified by HPLC (10% to 90% aq acetonitrile) to afford 600 mg (90%) of the title compound as a white solid. $^1$H-NMR (DMSO-d$_6$) δ 8.97 (s, 1H), 8.79 (s, 1H), 8.29 (d, J=5.7 Hz, 1H), 8.13 (t, J=9.0 Hz, 1H), 7.46 (m, 4H), 7.18 (d, J=14.7 Hz, 1H), 6.95 (d, J=10.2 Hz, 1H), 6.76 (d, J=2.1 Hz, 1H), 6.71 (d, J=5.4 Hz, 1H), 6.36 (s, 1H), 5.30 (t, J=5.7 Hz, 2H), 2.38 (s, 3H), 1.25 (s, 9H); MS LC-MS [M+H]$^+$= 490.2, RT=2.41 min.

Example 24

1-{5-tert-Butyl-2-[4-(2-methoxy-ethoxymethyl)-phenyl]-2H-pyrazol-3-yl}-3-[2-fluoro-4-(2-methyl-pyridin-4-yloxy)-phenyl]-urea

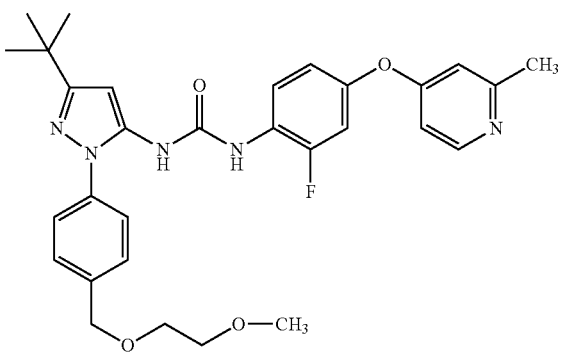

To a solution of 1-[5-tert-butyl-2-(4-hydroxymethyl-phenyl)-2H-pyrazol-3-yl]-3-[2-fluoro-4-(2-methyl-pyridin-4-yloxy)-phenyl]-urea (170 mg, 0.35 mmol) in anhydrous THF was added K$_2$CO$_3$ (52 mg, 0.38 mmol) followed by methanesulfonyl chloride (30 μL, 0.38 mmol). The mixture was stirred at room temperature for one day, and then 2-methoxy-ethanol (213 mg, 3.5 mmol) was added. The mixture was stirred at room temperature overnight, then EtOAc was added followed by saturated Na$_2$CO$_3$. The organic layer was washed with saturated Na$_2$CO$_3$ and brine, dried over MgSO$_4$ and evaporated at reduced pressure. Purification by HPLC (10% to 90% aq acetonitrile afforded pure product (10 mg, 5%). $^1$H-NMR (CD$_3$OD) δ 8.17 (d, J=6.0 Hz, 1H), 8.01 (t, J=9.3 Hz, 1H), 7.48-7.37 (m, 4H), 6.93-6.69 (m, 4H), 6.36 (s, 1H), 4.54 (s, 2H), 3.58 (m, 2H), 3.50 (m, 2H), 3.28 (s, 3H), 2.37 (s, 3H), 1.25 (s, 9H); MS LC-MS [M+H]$^+$=548.1, RT=2.69 min.

Example 25

4-(3-tert-Butyl-5-{3-[2-fluoro-4-(2-methyl-pyridin-4-yloxy)phenyl]ureido}pyrazol-1-yl)-2-methyl-N-(2-morpholin-4-yl-ethyl)benzene-sulfonamide

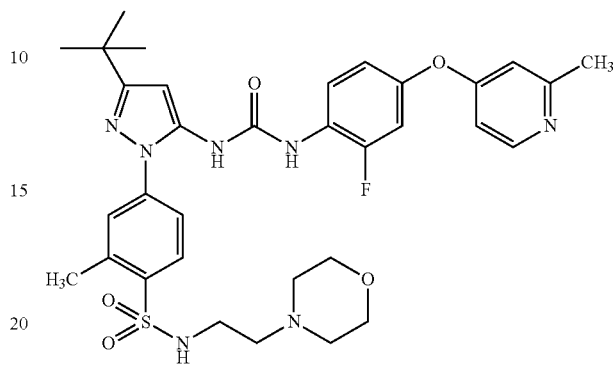

To a solution of 4-(5-amino-3-tert-butyl-pyrazol-1-yl)-2-methyl-N-(2-morpholin-4-yl-ethyl)benzenesulfonamide (150 mg, 0.36 mmol) in anhydrous DCE (1 mL) was added CDT (64 mg, 0.39 mmol, 1.1 eq), and the reaction was stirred under nitrogen at 50° C. for 18 h. A solution of 2-fluoro-4-(2-methyl-pyridin-4-yloxy)phenylamine (86 mg, 0.39 mmol, 1.1 eq) in anhydrous THF (1 mL) was added to the reaction, and the solution was stirred under at 50° C. for 3 days. The reaction mixture was partitioned between EtOAc (50 mL) and water (50 mL). The organic layer was washed with brine, dried over Na$_2$SO$_4$, and concentrated at reduced pressure. The crude product was purified by HPLC and recrystallized from DCM/hexane to give 55 mg (23%) of the title compound as a white solid. $^1$H-NMR (DMSO-d$_6$) δ 8.92 (d, J=14.4 Hz, 2H), 8.30 (d, J=5.7 Hz, 1H), 8.07 (t, J=9 Hz, 1H), 7.95 (d, J=8.4 Hz, 1H), 7.68 (t, J=6 Hz, 1H), 7.58 to 7.51 (m, 2H), 7.25 (dd, J=11.4, 2.4 Hz, 1H), 6.97 to 6.92 (m, 1H), 6.77 (d, J=2.4 Hz, 1H), 6.74 to 6.70 (m, 1H), 6.41 (s, 1H), 3.45 (t, J=4.5 Hz, 4H), 2.93 (q, J=6H, 2H), 2.65 (s, 3H), 2.39 (s, 3H), 2.25 (t, J=6.9 Hz, 2H), 2.20 to 2.17 (m, 4H), 1.27 (s, 9H); MS LC-MS [M+H]$^+$=666, RT=2.26 min.

Example 26

Ethyl(4-{3-tert-butyl-5-[({[4-(pyridin-4-yloxy)phenyl]amino}carbonyl)amino]-1H-pyrazol-1-yl}phenyl)acetate

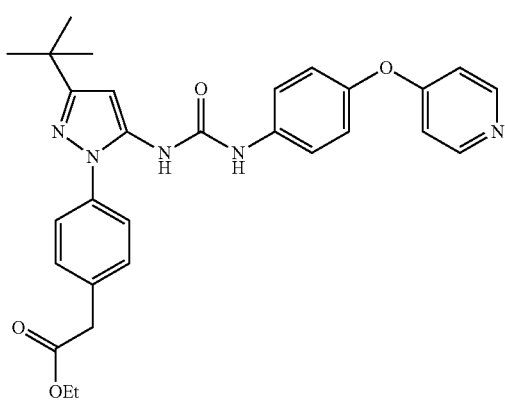

A mixture of ethyl(4-{3-tert-butyl-5-[(phenoxycarbonyl) amino]-1H-pyrazol-1-yl}phenyl)acetate (3.0 g, 7.12 mmol) and 4-(pyridin-4-yloxy)aniline (1.26 g, 6.78 mmol) in THF (50 mL) was heated at 60° C. overnight. The reaction mixture was cooled to room temperature and then evaporated at reduced pressure to afford a brown syrup, which was purified by MPLC (25:75 to 70:30 EtOAc/hexane). The desired product was obtained as a white solid (2.42 g) in 70% yield. $^1$H-NMR (CD$_2$Cl$_2$-d$_2$) δ 8.35 (m, 2H), 8.06 (s, 1H), 7.42 (m, 4H), 7.33 (s, 1H), 7.28 (d, J=8.3 Hz, 2H), 6.99 (d, J=8.8 Hz, 2H), 6.88 (d, J=5.8 Hz, 2H), 6.35 (s, 1H), 4.12 (q, J=7.1 Hz, 2H), 3.63 (s, 2H), 1.31 (s, 9H), 1.27 (t, J=7.1 Hz, 3H); MS LC-MS [M+H]$^+$=514.2, RT=2.66 min.

Example 27

(4-{3-tert-Butyl-5-[({[4-(pyridin-4-yloxy)phenyl] amino}carbonyl)amino]-1H-pyrazol-1-yl}phenyl) acetic acid

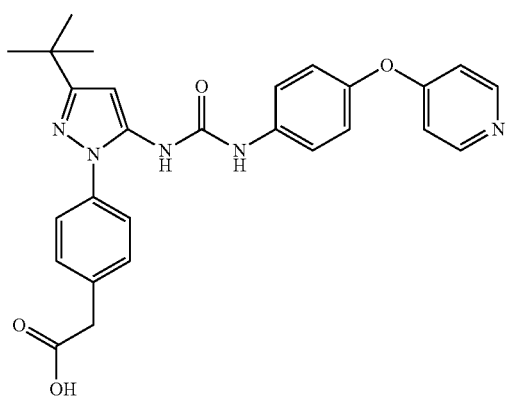

To a suspension of ethyl(4-{3-tert-butyl-5-[({[4-(pyridin-4-yloxy)phenyl]-amino}carbonyl)amino]-1H-pyrazol-1-yl}phenyl)acetate (2.42 g, 4.72 mmol) in THF/H$_2$O/EtOH (3:1:1, 50 mL) was added LiOH (0.34 g, 14.15 mmol) and the resulting reaction mixture was stirred at room temperature for 2.5 h. The mixture was evaporated at reduced pressure to afford a syrup-type residue. The residue was dissolved in 1N HCl, and then the acidity was adjusted to pH ~7. The mixture was washed with EtOAc, and then the aqueous phase was acidified to pH 5-6. The white precipitate that formed was collected by filtration, washed with water and hexane, and air-dried to afford the product as a white solid (2.1 g) in 92% yield. $^1$H-NMR (DMSO-d$_6$) δ 12.45 (broad, 1H), 9.64 (broad, 1H), 8.98 (broad, 1H), 8.38 (dd, JJ=1.6 Hz, 4.7 Hz, 2H), 7.51-7.42 (m, 4H), 7.36 (d, J=8.3 Hz, 2H), 7.05 (dd, JJ=2.1 Hz, 6.9 Hz, 2H), 6.84 (dd, JJ=1.6 Hz, 4.7 Hz, 2H), 6.31 (s, 1H), 3.58 (s, 2H), 1.27 (s, 9H); MS LC-MS [M+H]$^+$=486.2, RT=2.39 min.

Example 28

N-{3-tert-butyl-1-[4-(2-hydroxyethyl)phenyl]-1H-pyrazol-5-yl}-N'-[4-(pyridin-4-yloxy)-phenyl]urea

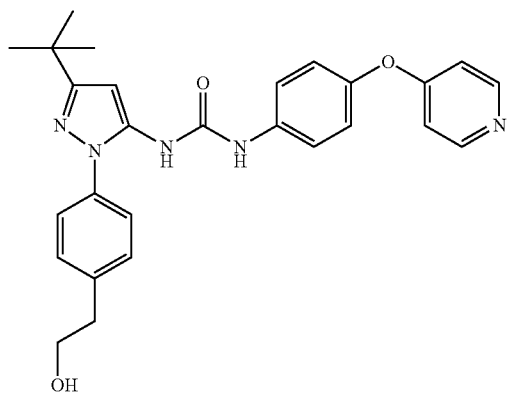

To a solution of (4-{3-tert-butyl-5-[({[4-(pyridin-4-yloxy) phenyl]amino}-carbonyl)amino]-1H-pyrazol-1-yl}phenyl) acetic acid (100 mg, 0.21 mmol) in THF (4 mL) was added borane-methyl sulfite complex (0.51 mL, 2M in THF) dropwise with stirring at room temperature. The resulting reaction mixture was heated at reflux for 2 h, then cooled to room temperature and quenched by the addition of EtOH/1N HCl. The resulting mixture was heated at reflux for 1 h. The mixture was cooled to room temperature and evaporated at reduced pressure, and the residue was dissolved in a mixture of EtOAc and saturated NaHCO$_3$. The organic phase was dried over Na$_2$SO$_4$, concentrated, and purified by MPLC (50:50 hexane/EtOAc). The desired product was obtained as a white solid (50 mg) in 51% yield. $^1$H-NMR (DMSO-d$_6$) δ 9.12 (s, 1H), 8.39 (m, 3H), 7.48 (d, J=9.0 Hz, 2H), 7.40-7.33 (m, 4H), 7.07 (d, J=8.8 Hz, 2H), 6.85 (m, 2H), 6.34 (s, 1H), 4.69 (t, J=5.1 Hz, 1H), 3.64 (m, 2H), 2.78 (t, J=7.1 Hz, 2H), 1.27 (s, 9H); MS LC-MS [M+H]$^+$=472.2, RT=2.35 min.

Example 29

N-[3-tert-Butyl-1-(4-{2-[(3S)-3-hydroxypyrrolidin-1-yl]-2-oxoethyl}phenyl)-1H-pyrazol-5-yl]-N'-[4-(pyridin-4-yloxy)phenyl]urea

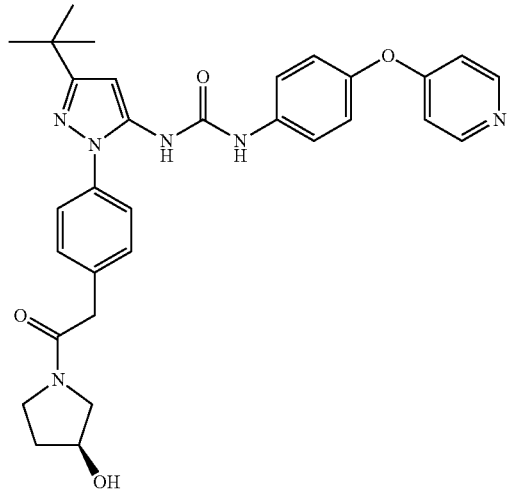

A mixture of (4-{3-tert-butyl-5-[({[4-(pyridin-4-yloxy)phenyl]amino}carbonyl)-amino]-1H-pyrazol-1-yl}phenyl)acetic acid (150 mg, 0.31 mmol), (S)-3-pyrrolidinol (54 mg, 0.62 mmol), 1-(3-dimethylaminopropyl)-3-ethylcarbodiimide hydrochloride (EDCl, 71 mg, 0.37 mmol), 1-hydroxybenzotrazole hydrate (HOBT, 50 mg, 0.37 mmol), and triethylamine (0.09 mL, 0.62 mmol) in THF/$CH_2Cl_2$ (1/1, 6 mL) was stirred at room temperature overnight. The mixture was evaporated at reduced pressure, and the residue was dissolved in $CH_2Cl_2$/MeOH and purified by MPLC (EtOAc/Hexane/MeOH). $^1$H-NMR (DMSO-$d_6$) δ 9.13 (s, 1H), 8.04 (m, 3H), 7.50-7.34 (m, 6H), 7.07 (d, J=8.9 Hz, 2H), 6.85 (dd, JJ=1.8 Hz, 4.8 Hz, 2H), 6.35 (s, 1H), 4.97 (dd, JJ=3.8 Hz, 44.1 Hz, 1H), 4.27 (broad d, J=30.7 Hz, 1H), 3.70-3.56 (m, 4H), 3.44-3.27 (m, 2H), 1.95-1.73 (m, 2H), 1.27 (s, 9H); MS LC-MS [M+H]$^+$=555.2, RT=2.28 min.

Example 30

N-[3-tert-Butyl-1-(4-{2-[(3S)-3-hydroxypyrrolidin-1-yl]ethyl}phenyl)-1H-pyrazol-5-yl]-N'-[4-(pyridin-4-yloxy)phenyl]urea

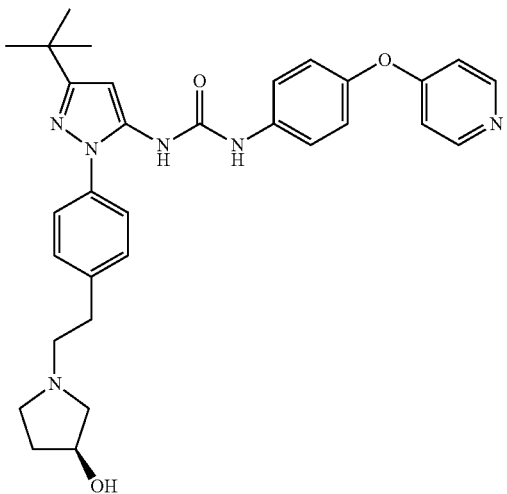

The title compound was prepared in the same manner as described for N-{3-tert-butyl-1-[4-(2-hydroxyethyl)phenyl]-1H-pyrazol-5-yl}-N'-[4-(pyridin-4-yloxy)phenyl]urea, replacing (4-{3-tert-butyl-5-[({[4-(pyridin-4-yloxy)phenyl]amino}carbonyl)amino]-1H-pyrazol-1-yl}phenyl)acetic acid with N-[3-tert-butyl-1-(4-{2-[(3S)-3-hydroxypyrrolidin-1-yl]-2-oxoethyl}phenyl)-1H-pyrazol-5-yl]-N'-[4-(pyridin-4-yloxy)phenyl]urea (90 mg, 0.16 mmol). The title compound was purified by HPLC, the TFA salt isolated from HPLC was neutralized, and the title compound was obtained as a white solid (25 mg) in 29% yield. $^1$H-NMR (DMSO-$d_6$) δ 9.11 (broad, 1H), 8.39 (m, 3H), 7.47 (d, J=8.8 Hz, 2H), 7.37 (m, 4H), 7.07 (d, J=8.9 Hz, 2H), 6.84 (m, 2H), 6.34 (s, 1H), 4.67 (d, J=4.5 Hz, 1H), 4.16 (broad, 1H), 2.76 (m, 2H), 2.61 (m, 2H), 2.48 (m, 1H), 2.34 (m, 1H), 1.96 (broad, 1H), 1.52 (broad, 1H); MS LC-MS [M+H]$^+$=541.2, RT=2.04 min.

Example 31

Methyl N-[(4-{3-tert-butyl-5-[({[4-(pyridin-4-yloxy)phenyl]amino}carbonyl)amino]-1H-pyrazol-1-yl}phenyl)acetyl]-L-serinate

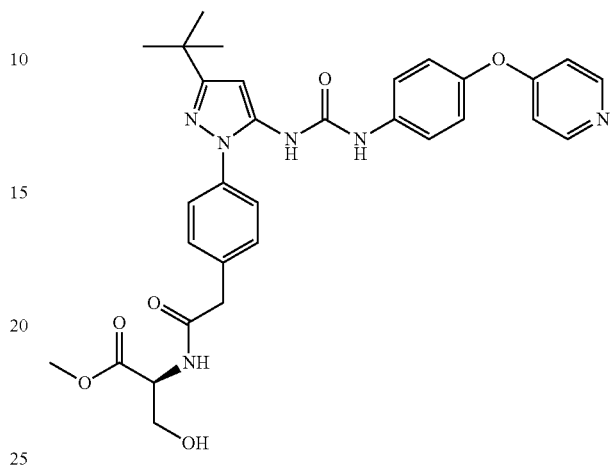

The title compound was prepared in the same manner as described for N-[3-tert-butyl-1-(4-{2-[(3S)-3-hydroxypyrrolidin-1-yl]-2-oxoethyl}phenyl)-1H-pyrazol-5-yl]-N'-[4-(pyridin-4-yloxy)phenyl]urea, replacing (S)-3-pyrrolidinol with L-serine methyl ester hydrochloride. The desired product was purified by MPLC (EtOAc/hexane/MeOH) and obtained as a solid (150 mg) in 62% yield. A sample of this material was purified further by HPLC and the TFA salt isolated from HPLC was neutralized to provide the title compound. $^1$H-NMR (DMSO-$d_6$) δ 9.12 (s, 1H), 8.50 (d, J=7.9 Hz, 1H) 8.40 (m, 3H), 7.50-7.38 (m, 6H), 7.07 (d, J=8.7 Hz, 2H), 6.85 (m, 2H), 6.34 (s, 1H), 5.10 (t, J=5.4 Hz, 1H), 4.35 (m, 1H), 3.72 (m, 1H), 3.61 (m, 6H), 1.27 (s, 9H); MS LC-MS [M+H]$^+$= 587.2, RT=2.27 min.

Example 32

N-[(4-{3-tert-Butyl-5-[({[4-(pyridin-4-yloxy)phenyl]amino}carbonyl)amino]-1H-pyrazol-1-yl}phenyl)acetyl]-L-serine

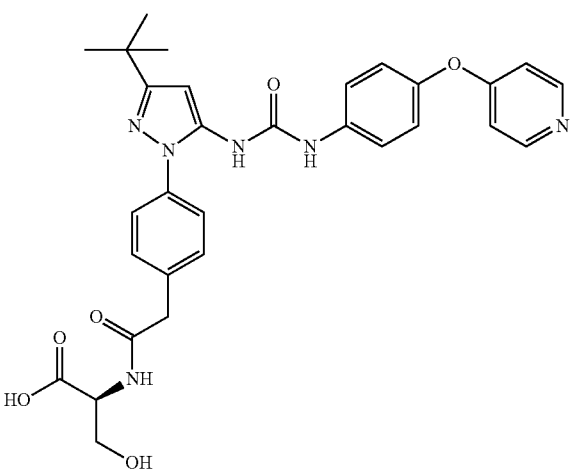

The title compound was prepared in the same manner as described for (4-{3-tert-butyl-5-[({[4-(pyridin-4-yloxy)phenyl]amino}carbonyl)amino]-1H-pyrazol-1-yl}phenyl)acetic acid. The title compound was obtained as a pale solid in 78% yield. $^1$H-NMR (DMSO-$d_6$) δ 12.59 (broad, 1H), 9.15 (s, 1H), 8.40 (m, 2H), 8.34 (d, J=7.6 Hz, 1H), 7.48 (d, J=9.0 Hz, 2H), 7.41 (s, 4H), 7.07 (d, J=8.9 Hz, 2H), 6.85 (m, 2H), 6.35 (s, 1H), 5.05 (broad, 1H), 4.27 (m, 1H), 3.70 (m, 1H), 3.61 (m, 3H), 1.27 (s, 9H); MS LC-MS [M+H]$^+$=573.1, RT=2.22 min.

Example 33

2-(4-{3-tert-Butyl-5-[({[4-(pyridin-4-yloxy)phenyl]amino}carbonyl)amino]-1H-pyrazol-1-yl}phenyl)-N-[2-hydroxy-1-(hydroxymethyl)ethyl]acetamide

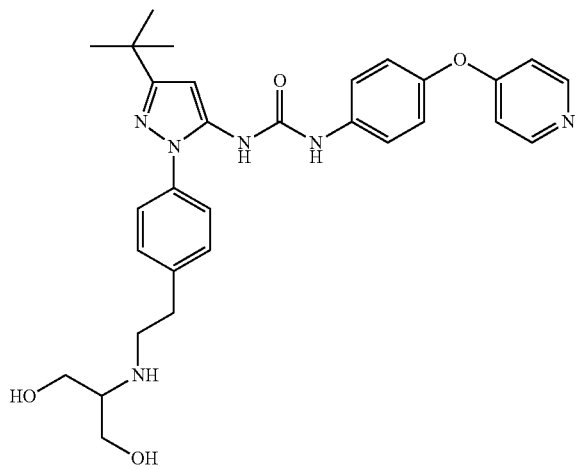

The title compound was prepared in the same manner as described for N-[3-tert-butyl-1-(4-{2-[(3S)-3-hydroxypyrrolidin-1-yl]ethyl}phenyl)-1H-pyrazol-5-yl]-N'-[4-(pyridin-4-yloxy)phenyl]urea, and was obtained as a white solid in 24% yield. $^1$H-NMR (DMSO-$d_6$) δ 9.11 (s, 1H), 8.39 (m, 3H), 7.48 (d, J=9.0 Hz, 2H), 7.38 (m, 4H), 7.07 (d, J=9.2 Hz, 2H), 6.85 (m, 2H), 6.34 (s, 1H), 4.38 (t, J=5.4 Hz, 2H), 3.40-3.27 (m, 4H), 2.84 (m, 2H), 2.75 (m, 2H), 2.54 (m, 1H), 1.60 (broad, 1H), 1.27 (s, 9H); MS LC-MS [M+H]$^+$=545.3, RT=2.14 min.

BIOLOGICAL ASSAY EXAMPLES

Flk-1 (Murine VEGFR-2) Biochemical Assay

This assay was performed in 96-well opaque plates (Costar 3915) in the TR-FRET format. Reaction conditions are as follows: 10 μM ATP, 25 nM poly GT-biotin, 2 nM Eu-labelled phospho-Tyr Ab (PY20 Perkin Elmer), 10 nM APC (Perkin Elmer), 7 nM Flk-1 (kinase domain), 1% DMSO, 50 mM HEPES pH 7.5, 10 mM MgCl$_2$, 0.1 mM EDTA, 0.015% BRIJ, 0.1 mg/mL BSA, 0.1% mercapto-ethanol). Reaction is initiated upon addition of enzyme. Final reaction volume in each well is 100 μL. Plates are read at both 615 and 665 nM on a Perkin Elmer Victor V Multilabel counter at about 1.5-2.0 hours after reaction initiation. Signal is calculated as a ratio: (665 nm/615 nm)*10000 for each well.

The compounds of Formula I tested in this VEGFR2 kinase assay showed significant inhibitory activity (IC$_{50}$<10 μM). The compounds of Examples 1 to 33 showed inhibition of VEGFR2 kinase activity in this assay with IC$_{50}$<300 nM.

Trk-A FRET Biochemical Assay

This assay uses the N-terminal HIS-tagged intracellular kinase domain of human recombinant Trk-A in 96-well plates. This involves a biotinylated-poly-GluTyr substrate and an Eu-labelled anti-phosphotyrosine antibody for detection of kinase activity in a homogeneous time-resolved FRET format. The Trk-A biochemical FRET assay protocol is as follows: 10 mM stock solution of test compounds are diluted to 1 mM in 100% DMSO. These stocks are diluted with 100% DMSO by a factor of 5, in a total of 7 steps to create an 8-point IC$_{50}$ curve. The diluted compounds are combined 1:4 with distilled water to form the 25× dilution plate for the assay.

A 2 μL aliquot of compound from the 25× dilution plate is added with 23 μL of assay buffer (50 mM HEPES pH 7.0, 5 mM MnCl$_2$, 0.1% BSA, 0.5 mM vanadate, 0.1% β-mercaptoethanol) into a 96-well, half volume opaque (black) plate (Costar #3694). ATP is added to all wells except the negative controls (5 microliters of 40 μM). Five microliters of 2.2 μg/mL poly(GluTyr)-biotin (CIS US #61GTOBLB) and 15 μL of 6.66 nM Trk-A diluted in assay buffer are added to the plate to start the reaction.

After 60 min. at room temperature, the assay is stopped with addition of 5 μL of 0.5M EDTA. 25 μL each of 340 ng/mL PY20 cryptate antibody (CIS US #61Y20KLA) and 40 nM streptavidin labelled APC (SA-XL-CIS US #611SAXLB) are added in development buffer (50 mM HEPES pH7.0, 0.8M KF, 0.1% BSA). The assay plate sits at room temperature for at least one hour, then is read on a Perkin Elmer Victor 2 instrument at 615 and 665 nM emission. A ratio of these two numbers is used in the calculations of the data.

The compounds of Examples 1 to 243 showed significant inhibition of Trk-A kinase activity in this assay (IC$_{50}$<1 μM). The compounds of Examples 1 to 33 showed inhibition of Trk-A kinase activity in this assay with IC$_{50}$<200 nM.

It is believed that one skilled in the art, using the preceding information and information available in the art, can utilize the present invention to its fullest extent. It should be apparent to one of ordinary skill in the art that changes and modifications can be made to this invention without departing from the spirit or scope of the invention as it is set forth herein. The topic headings set forth above and below are meant as guidance where certain information can be found in the application, but are not intended to be the only source in the application where information on such topic can be found.

All publications and patents cited above are incorporated herein by reference.

Additional compounds as listed below and illustrated in Table 1 were prepared as described above by choosing the appropriate starting materials or intermediates, and using the processes described as in Examples 1 to 33 or other standard chemical processes known in the art.

1. 4-{3-tert-butyl-5-[({[4-(pyridin-4-yloxy)phenyl]amino}carbonyl)amino]-1H-pyrazol-1-yl}-N-(2-pyrrolidin-1-ylethyl)benzamide
2. N-{3-tert-butyl-1-[4-(2-methoxyethoxy)phenyl]-1H-pyrazol-5-yl}-N'-[4-(pyridin-4-yloxy)phenyl]urea
3. N-{3-tert-butyl-1-[4-(2-methoxyethoxy)phenyl]-1H-pyrazol-5-yl}-N'-{2-fluoro-4-[(2-methylpyridin-4-yl)oxy]phenyl}urea
4. N-(3-tert-butyl-1-{4-[2-(diethylamino)ethoxy]phenyl}-1H-pyrazol-5-yl)-N'-[4-(pyridin-4-yloxy)phenyl]urea
5. N-{3-tert-butyl-1-[4-(2-piperidin-4-ylethoxy)phenyl]-1H-pyrazol-5-yl}-N'-[4-(pyridin-3-yloxy)phenyl]urea
6. N-{3-tert-butyl-1-[3-(3-hydroxypropoxy)phenyl]-1H-pyrazol-5-yl}-N'-[4-(pyridin-4-yloxy)phenyl]urea 7. N-(4-{3-tert-butyl-5-[({[4-(pyridin-4-yloxy)phenyl]amino}carbonyl)amino]-1H-pyrazol-1-yl}phenyl)-3-methoxypropanamide
8. N-(3-tert-butyl-1-{4-[(2-methoxyethyl)amino]phenyl}-1H-pyrazol-5-yl)-N'-[4-(pyridin-4-yloxy)phenyl]urea
9. 4-[(4-{3-tert-butyl-5-[({[4-(pyridin-4-yloxy)phenyl]amino}carbonyl)amino]-1H-pyrazol-1-yl}phenyl)amino]-2,2-dimethyl-4-oxobutanoic acid
10. N-(3-tert-butyl-1-{4-[(4-hydroxy-3,3-dimethylbutyl)amino]phenyl}-1H-pyrazol-5-yl)-N'-[4-(pyridin-4-yloxy)phenyl]urea
11. N-(3-tert-butyl-1-{3-[(3-hydroxypropyl)amino]phenyl}-1H-pyrazol-5-yl)-N'-[4-(pyridin-4-yloxy)phenyl]urea
12. N-(3-tert-butyl-1-{3-[[(dimethylamino)sulfonyl](3-hydroxypropyl)amino]phenyl}-1H-pyrazol-5-yl)-N'-[4-(pyridin-4-yloxy)phenyl]urea
13. N-(1-{3-[bis(2-hydroxyethyl)amino]phenyl}-3-tert-butyl-1H-pyrazol-5-yl)-N'-[4-(pyridin-4-yloxy)phenyl]urea
14. N-{1-[4-(aminomethyl)phenyl]-3-tert-butyl-1H-pyrazol-5-yl}-N'-[4-(pyridin-4-yloxy)-phenyl]urea
15. N-(4-{3-tert-butyl-5-[({[4-(pyridin-4-yloxy)phenyl]amino}carbonyl)amino]-1H-pyrazol-1-yl}benzyl)-2-methoxyacetamide
16. N-[3-tert-butyl-1-(4-{[(2-methoxyethyl)amino]methyl}phenyl)-1H-pyrazol-5-yl]-N'-[4-(pyridin-4-yloxy)phenyl]urea
17. N-[1-(4-{[bis(2-hydroxyethyl)amino]methyl}phenyl)-3-tert-butyl-1H-pyrazol-5-yl]-N'-[4-(pyridin-4-yloxy)phenyl]urea
18. N-(4-{3-tert-butyl-5-[({[4-(pyridin-4-yloxy)phenyl]amino}carbonyl)amino]-1H-pyrazol-1-yl}benzyl)glycinamide
19. 3-(3-tert-butyl-5-{[({2-fluoro-4-[(2-methylpyridin-4-yl)oxy]phenyl}amino)carbonyl]-amino}-1H-pyrazol-1-yl)-N-[(2,2-dimethyl-1,3-dioxolan-4-yl)methyl]benzamide
20. 3-{3-tert-butyl-5-[({[4-(pyridin-4-yloxy)phenyl]amino}carbonyl)amino]-1H-pyrazol-1-yl}-N-[(2,2-dimethyl-1,3-dioxolan-4-yl)methyl]benzamide
21. 3-(3-tert-butyl-5-{[({2-fluoro-4-[(2-methylpyridin-4-yl)oxy]phenyl}amino)carbonyl]-amino}-1H-pyrazol-1-yl)-N-(2,3-dihydroxypropyl)benzamide
22. 3-{3-tert-butyl-5-[({[4-(pyridin-4-yloxy)phenyl]amino}carbonyl)amino]-1H-pyrazol-1-yl}-N-(2,3-dihydroxypropyl)benzamide
23. N-{3-tert-butyl-1-[4-(hydroxymethyl)phenyl]-1H-pyrazol-5-yl}-N'-{2-fluoro-4-[(2-methylpyridin-4-yl)oxy]phenyl}urea
24. N-(3-tert-butyl-1-{4-[(2-methoxyethoxy)methyl]phenyl}-1H-pyrazol-5-yl)-N'-{2-fluoro-4-[(2-methylpyridin-4-yl)oxy]phenyl}urea
25. 4-(3-tert-butyl-5-{[({2-fluoro-4-[(2-methylpyridin-4-yl)oxy]phenyl}amino)carbonyl]-amino}-1H-pyrazol-1-yl)-2-methyl-N-(2-morpholin-4-ylethyl)benzenesulfonamide
26. ethyl(4-{3-tert-butyl-5-[({[4-(pyridin-4-yloxy)phenyl]amino}carbonyl)amino]-1H-pyrazol-1-yl}phenyl)acetate
27. (4-{3-tert-butyl-5-[({[4-(pyridin-4-yloxy)phenyl]amino}carbonyl)amino]-1H-pyrazol-1-yl}phenyl)acetic acid
28. N-{3-tert-butyl-1-[4-(2-hydroxyethyl)phenyl]-1H-pyrazol-5-yl}-N'-[4-(pyridin-4-yloxy)phenyl]urea
29. N-[3-tert-butyl-1-(4-{2-[(3S)-3-hydroxypyrrolidin-1-yl]-2-oxoethyl}phenyl)-1H-pyrazol-5-yl]-N'-[4-(pyridin-4-yloxy)phenyl]urea
30. N-[3-tert-butyl-1-(4-{2-[(3S)-3-hydroxypyrrolidin-1-yl]ethyl}phenyl)-1H-pyrazol-5-yl]-N'-[4-(pyridin-4-yloxy)phenyl]urea
31. methyl N-[(4-{3-tert-butyl-5-[({[4-(pyridin-4-yloxy)phenyl]amino}carbonyl)amino]-1H-pyrazol-1-yl}phenyl)acetyl]-L-serinate
32. N-[(4-{3-tert-butyl-5-[({[4-(pyridin-4-yloxy)phenyl]amino}carbonyl)amino]-1H-pyrazol-1-yl}phenyl)acetyl]-L-serine
33. N-{3-tert-butyl-1-[4-(2-{[2-hydroxy-1-(hydroxymethyl)ethyl]amino}ethyl)phenyl]-1H-pyrazol-5-yl}-N'-[4-(pyridin-4-yloxy)phenyl]urea
34. N-{3-tert-butyl-1-[4-(2-piperidin-1-ylethoxy)phenyl]-1H-pyrazol-5-yl}-N'-[4-(pyridin-4-yloxy)phenyl]urea
35. N-{3-tert-butyl-1-[4-(2-morpholin-4-ylethoxy)phenyl]-1H-pyrazol-5-yl}-N'-[4-(pyridin-4-yloxy)phenyl]urea
36. N-{3-tert-butyl-1-[4-(3-morpholin-4-ylpropoxy)phenyl]-1H-pyrazol-5-yl}-N'-{2-fluoro-4-[(2-methylpyridin-4-yl)oxy]phenyl}urea
37. N-{3-tert-butyl-1-[4-(3-morpholin-4-ylpropoxy)phenyl]-1H-pyrazol-5-yl}-N'-[4-(pyridin-4-yloxy)phenyl]urea
38. N-{3-tert-butyl-1-[4-(3-morpholin-4-ylpropoxy)phenyl]-1H-pyrazol-5-yl}-N'-[4-(pyridin-3-yloxy)phenyl]urea
39. N-{3-tert-butyl-1-[4-(tetrahydro-2H-pyran-4-ylmethoxy)phenyl]-1H-pyrazol-5-yl}-N'-[4-(pyridin-4-yloxy)phenyl]urea
40. N-{3-tert-butyl-1-[4-(tetrahydro-2H-pyran-4-ylmethoxy)phenyl]-1H-pyrazol-5-yl}-N'-[4-(pyridin-3-yloxy)phenyl]urea
41. N-{3-tert-butyl-1-[4-(tetrahydro-2H-pyran-4-ylmethoxy)phenyl]-1H-pyrazol-5-yl}-N'-{2-fluoro-4-[(2-methylpyridin-4-yl)oxy]phenyl}urea
42. N-{3-tert-butyl-1-[4-(3-hydroxypropoxy)phenyl]-1H-pyrazol-5-yl}-N'-{2-fluoro-4-[(2-methylpyridin-4-yl)oxy]phenyl}urea
43. N-{3-tert-butyl-1-[4-(3-hydroxypropoxy)phenyl]-1H-pyrazol-5-yl}-N'-[4-(pyridin-3-yloxy)phenyl]urea
44. N-{3-tert-butyl-1-[4-(3-hydroxypropoxy)phenyl]-1H-pyrazol-5-yl}-N'-[4-(pyridin-4-yloxy)phenyl]urea
45. N-{3-tert-butyl-1-[4-(2-pyrrolidin-1-ylethoxy)phenyl]-1H-pyrazol-5-yl}-N'-[4-(pyridin-4-yloxy)phenyl]urea
46. N-{3-tert-butyl-1-[4-(2-pyrrolidin-1-ylethoxy)phenyl]-1H-pyrazol-5-yl}-N'-[4-(pyridin-3-yloxy)phenyl]urea
47. N-{3-tert-butyl-1-[4-(2-pyrrolidin-1-ylethoxy)phenyl]-1H-pyrazol-5-yl}-N'-{2-fluoro-4-[(2-methylpyridin-4-yl)oxy]phenyl}urea
48. tert-butyl-4-{2-[4-(3-tert-butyl-5-{[({2-fluoro-4-[(2-methylpyridin-4-yl)oxy]phenyl}-amino)carbonyl]amino}-1H-pyrazol-1-yl)phenoxy]ethyl}piperidine-1-carboxylate
49. N-{3-tert-butyl-1-[4-(2-piperidin-4-ylethoxy)phenyl]-1H-pyrazol-5-yl}-N'-{2-fluoro-4-[(2-methylpyridin-4-yl)oxy]phenyl}urea
50. butyl4-(4-{3-tert-butyl-5-[({[4-(pyridin-4-yloxy)phenyl]amino}carbonyl)amino]-1H-pyrazol-1-yl}phenoxy)butanoate
51. butyl4-[4-(3-tert-butyl-5-{[({2-fluoro-4-[(2-methylpyridin-4-yl)oxy]phenyl}amino)-carbonyl]amino}-1H-pyrazol-1-yl)phenoxy]butanoate
52. tert-butyl {2-[4-(3-tert-butyl-5-{[({2-fluoro-4-[(2-methylpyridin-4-yl)oxy]phenyl}-amino)carbonyl]amino}-1H-pyrazol-1-yl)phenoxy]ethyl}carbamate
53. N-{1-[4-(2-aminoethoxy)phenyl]-3-tert-butyl-1H-pyrazol-5-yl}-N'-{2-fluoro-4-[(2-methylpyridin-4-yl)oxy]phenyl}urea
54. 4-[4-(3-tert-butyl-5-{[({2-fluoro-4-[(2-methylpyridin-4-yl)oxy]phenyl}amino)-carbonyl]amino}-1H-pyrazol-1-yl)phenoxy]butanoic acid 55. 4-(4-{3-tert-butyl-5-[({[4-(pyridin-4-yloxy)phenyl]amino}carbonyl)amino]-1H-pyrazol-1-yl}phenoxy)butanoic acid
56. tert-butyl 4-[2-(4-{3-tert-butyl-5-[({[4-(pyridin-4-yloxy)phenyl]amino}carbonyl)-amino]-1H-pyrazol-1-yl}phenoxy)ethyl]piperidine-1-carboxylate
57. N-{3-tert-butyl-1-[4-(2-piperidin-4-ylethoxy)phenyl]-1H-pyrazol-5-yl}-N'-[4-(pyridin-4-yloxy)phenyl]urea
58. tert-butyl 4-[2-(4-{3-tert-butyl-5-[({[4-(pyridin-3-yloxy)phenyl]amino}carbonyl)-amino]-1H-pyrazol-1-yl}phenoxy)ethyl]piperidine-1-carboxylate
59. tert-butyl[2-(4-{3-tert-butyl-5-[({[4-(pyridin-4-yloxy)phenyl]amino}carbonyl)amino]-1H-pyrazol-1-yl}phenoxy)ethyl]carbamate
60. N-{1-[4-(2-aminoethoxy)phenyl]-3-tert-butyl-1H-pyrazol-5-yl}-N'-[4-(pyridin-4-yloxy)phenyl]urea
61. tert-butyl[2-(4-{3-tert-butyl-5-[({[4-(pyridin-3-yloxy)phenyl]amino}carbonyl)amino]-1H-pyrazol-1-yl}phenoxy)ethyl]carbamate
62. N-{1-[4-(2-aminoethoxy)phenyl]-3-tert-butyl-1H-pyrazol-5-yl}-N'-[4-(pyridin-3-yloxy)phenyl]urea
63. N-{3-tert-butyl-1-[4-(2-hydroxyethoxy)phenyl]-1H-pyrazol-5-yl}-N'-[4-(pyridin-4-yloxy)phenyl]urea
64. N-{3-tert-butyl-1-[4-(2-hydroxyethoxy)phenyl]-1H-pyrazol-5-yl}-N'-{2-fluoro-4-[(2-methylpyridin-4-yl)oxy]phenyl}urea
65. N-{3-tert-butyl-1-[4-(2-hydroxyethoxy)phenyl]-1H-pyrazol-5-yl}-N'-[4-(pyridin-3-yloxy)phenyl]urea
66. N-{3-tert-butyl-1-[4-(2,3-dihydroxypropoxy)phenyl]-1H-pyrazol-5-yl}-N'-[4-(pyridin-4-yloxy)phenyl]urea
67. N-{3-tert-butyl-1-[4-(2,3-dihydroxypropoxy)phenyl]-1H-pyrazol-5-yl}-N'-{2-fluoro-4-[(2-methylpyridin-4-yl)oxy]phenyl}urea
68. N-{3-tert-butyl-1-[3-(3-morpholin-4-ylpropoxy)phenyl]-1H-pyrazol-5-yl}-N'-[4-(pyridin-4-yloxy)phenyl]urea
69. N-{3-tert-butyl-1-[3-(3-morpholin-4-ylpropoxy)phenyl]-1H-pyrazol-5-yl}-N'-[4-(pyridin-3-yloxy)phenyl]urea
70. N-{3-tert-butyl-1-[3-(3-morpholin-4-ylpropoxy)phenyl]-1H-pyrazol-5-yl}-N'-{2-fluoro-4-[(2-methylpyridin-4-yl)oxy]phenyl}urea
71. N-{3-tert-butyl-1-[3-(3-hydroxypropoxy)phenyl]-1H-pyrazol-5-yl}-N'-{2-fluoro-4-[(2-methylpyridin-4-yl)oxy]phenyl}urea
72. N-{3-tert-butyl-1-[3-(3-hydroxypropoxy)phenyl]-1H-pyrazol-5-yl}-N'-[4-(pyridin-3-yloxy)phenyl]urea
73. N-{3-tert-butyl-1-[3-(2-pyrrolidin-1-ylethoxy)phenyl]-1H-pyrazol-5-yl}-N'-{2-fluoro-4-[(2-methylpyridin-4-yl)oxy]phenyl}urea
74. N-{3-tert-butyl-1-[3-(2-pyrrolidin-1-ylethoxy)phenyl]-1H-pyrazol-5-yl}-N'-[4-(pyridin-3-yloxy)phenyl]urea
75. N-{3-tert-butyl-1-[3-(2-pyrrolidin-1-ylethoxy)phenyl]-1H-pyrazol-5-yl}-N'-[4-(pyridin-4-yloxy)phenyl]urea
76. N-[4-(3-tert-butyl-5-{[({2-fluoro-4-[(2-methylpyridin-4-yl)oxy]phenyl}amino)-carbonyl]amino}-1H-pyrazol-1-yl)phenyl]-3-methoxypropanamide
77. N-(4-{3-tert-butyl-5-[({[4-(pyridin-4-yloxy)phenyl]amino}carbonyl)amino]-1H-pyrazol-1-yl}phenyl)-2-methoxyacetamide
78. N-[4-(3-tert-butyl-5-{[({2-fluoro-4-[(2-methylpyridin-4-yl)oxy]phenyl}amino)-carbonyl]amino}-1H-pyrazol-1-yl)phenyl]-2-methoxyacetamide
79. 2-[(4-{3-tert-butyl-5-[({[4-(pyridin-4-yloxy)phenyl]amino}carbonyl)amino]-1H-pyrazol-1-yl}phenyl)amino]-2-oxoethyl acetate
80. 2-bromo-N-(4-{3-tert-butyl-5-[({[4-(pyridin-4-yloxy)phenyl]amino}carbonyl)amino]-1H-pyrazol-1-yl}phenyl)acetamide
81. N-(4-{3-tert-butyl-5-[({[4-(pyridin-4-yloxy)phenyl]amino}carbonyl)amino]-1H-pyrazol-1-yl}phenyl)-2-morpholin-4-ylacetamide
82. N-(4-{3-tert-butyl-5-[({[4-(pyridin-4-yloxy)phenyl]amino}carbonyl)amino]-1H-pyrazol-1-yl}phenyl)-2-pyrrolidin-1-ylacetamide
83. N-(3-tert-butyl-1-{4-[(2-morpholin-4-ylethyl)amino]phenyl}-1H-pyrazol-5-yl)-N'-[4-(pyridin-4-yloxy)phenyl]urea
84. N-(4-{3-tert-butyl-5-[({[4-(pyridin-3-yloxy)phenyl]amino}carbonyl)amino]-1H-pyrazol-1-yl}phenyl)-2-methoxyacetamide
85. N-(3-tert-butyl-1-{4-[(2-hydroxyethyl)amino]phenyl}-1H-pyrazol-5-yl)-N'-[4-(pyridin-4-yloxy)phenyl]urea
86. N-(3-tert-butyl-1-{4-[(2-hydroxyethyl)amino]phenyl}-1H-pyrazol-5-yl)-N'-[4-(pyridin-3-yloxy)phenyl]urea
87. N-(3-tert-butyl-1-{4-[(2-methoxyethyl)amino]phenyl}-1H-pyrazol-5-yl)-N'-[4-(pyridin-3-yloxy)phenyl]urea
88. N-(3-tert-butyl-1-{4-[(3-hydroxypropyl)amino]phenyl}-1H-pyrazol-5-yl)-N'-[4-(pyridin-4-yloxy)phenyl]urea
89. N-(3-tert-butyl-1-{4-[(3-hydroxypropyl)amino]phenyl}-1H-pyrazol-5-yl)-N'-[4-(pyridin-3-yloxy)phenyl]urea
90. 4-[(4-{3-tert-butyl-5-[({[4-(pyridin-4-yloxy)phenyl]amino}carbonyl)amino]-1H-pyrazol-1-yl}phenyl)amino]-4-oxobutanoic acid
91. 4-[(4-{3-tert-butyl-5-[({[4-(pyridin-3-yloxy)phenyl]amino}carbonyl)amino]-1H-pyrazol-1-yl}phenyl)amino]-4-oxobutanoic acid
92. 4-[(4-{3-tert-butyl-5-[({[4-(pyridin-3-yloxy)phenyl]amino}carbonyl)amino]-1H-pyrazol-1-yl}phenyl)amino]-2,2-dimethyl-4-oxobutanoic acid
93. N-(3-tert-butyl-1-{4-[(2-hydroxyethyl)amino]phenyl}-1H-pyrazol-5-yl)-N'-{2-fluoro-4-[(2-methylpyridin-4-yl)oxy]phenyl}urea
94. N-(3-tert-butyl-1-{4-[(3-hydroxypropyl)amino]phenyl}-1H-pyrazol-5-yl)-N'-{2-fluoro-4-[(2-methylpyridin-4-yl)oxy]phenyl}urea
95. N-(3-tert-butyl-1-{4-[(2-methoxyethyl)amino]phenyl}-1H-pyrazol-5-yl)-N'-{2-fluoro-4-[(2-methylpyridin-4-yl)oxy]phenyl}urea
96. N-(3-tert-butyl-1-{4-[[(dimethylamino)sulfonyl]-2-hydroxyethyl)amino]phenyl}-1H-pyrazol-5-yl)-N'-[4-(pyridin-4-yloxy)phenyl]urea
97. N-(3-{3-tert-butyl-5-[({[4-(pyridin-4-yloxy)phenyl]amino}carbonyl)amino]-1H-pyrazol-1-yl}phenyl)-2-methoxyacetamide
98. N-(3-{3-tert-butyl-5-[({[4-(pyridin-3-yloxy)phenyl]amino}carbonyl)amino]-1H-pyrazol-1-yl}phenyl)-2-methoxyacetamide
99. N-(3-tert-butyl-1-{3-[(2-hydroxyethyl)amino]phenyl}-1H-pyrazol-5-yl)-N'-[4-(pyridin-4-yloxy)phenyl]urea
100. N-(3-tert-butyl-1-{3-[(2-hydroxyethyl)amino]phenyl}-1H-pyrazol-5-yl)-N'-[4-(pyridin-3-yloxy)phenyl]urea
101. N-(3-tert-butyl-1-{3-[(2-methoxyethyl)amino]phenyl}-1H-pyrazol-5-yl)-N'-[4-(pyridin-4-yloxy)phenyl]urea
102. N-(3-tert-butyl-1-{3-[(2-methoxyethyl)amino]phenyl}-1H-pyrazol-5-yl)-N'-[4-(pyridin-3-yloxy)phenyl]urea
103. N-(3-tert-butyl-1-{3-[(3-hydroxypropyl)amino]phenyl}-1H-pyrazol-5-yl)-N'-[4-(pyridin-3-yloxy)phenyl]urea
104. 4-[(3-{3-tert-butyl-5-[({[4-(pyridin-4-yloxy)phenyl]amino}carbonyl)amino]-1H-pyrazol-1-yl}phenyl)amino]-4-oxobutanoic acid 105. 4-[(3-{3-tert-butyl-5-[({[4-(pyridin-4-yloxy)phenyl]amino}carbonyl)amino]-1H-pyrazol-1-yl}phenyl)amino]-2,2-dimethyl-4-oxobutanoic acid
106. 4-[(3-{3-tert-butyl-5-[({[4-(pyridin-3-yloxy)phenyl]amino}carbonyl)amino]-1H-pyrazol-1-yl}phenyl)amino]-4-oxobutanoic acid
107. 4-[(3-{3-tert-butyl-5-[({[4-(pyridin-3-yloxy)phenyl]amino}carbonyl)amino]-1H-pyrazol-1-yl}phenyl)amino]-2,2-dimethyl-4-oxobutanoic acid
108. N-[3-(3-tert-butyl-5-{[({2-fluoro-4-[(2-methylpyridin-4-yl)oxy]phenyl}amino)-carbonyl]amino}-1H-pyrazol-1-yl)phenyl]-2-methoxyacetamide
109. N-(3-tert-butyl-1-{3-[(2-hydroxyethyl)amino]phenyl}-1H-pyrazol-5-yl)-N'-{2-fluoro-4-[(2-methylpyridin-4-yl)oxy]phenyl}urea
110. N-(3-tert-butyl-1-{3-[(3-hydroxypropyl)amino]phenyl}-1H-pyrazol-5-yl)-N'-{2-fluoro-4-[(2-methylpyridin-4-yl)oxy]phenyl}urea
111. N-(3-tert-butyl-1-{3-[(2-methoxyethyl)amino]phenyl}-1H-pyrazol-5-yl)-N'-{2-fluoro-4-[(2-methylpyridin-4-yl)oxy]phenyl}urea
112. N-(3-{3-tert-butyl-5-[({[4-(pyridin-4-yloxy)phenyl]amino}carbonyl)amino]-1H-pyrazol-1-yl}phenyl)-2-morpholin-4-ylacetamide
113. N-(3-{3-tert-butyl-5-[({[4-(pyridin-4-yloxy)phenyl]amino}carbonyl)amino]-1H-pyrazol-1-yl}phenyl)-2-(1H-imidazol-1-yl)acetamide
114. N-(3-tert-butyl-1-{3-[[(dimethylamino)sulfonyl](2-hydroxyethyl)amino]phenyl}-1H-pyrazol-5-yl)-N'-[4-(pyridin-4-yloxy)phenyl]urea
115. N-(3-tert-butyl-1-{3-[(2-morpholin-4-ylethyl)amino]phenyl}-1H-pyrazol-5-yl)-N'-[4-(pyridin-4-yloxy)phenyl]urea
116. 4-{3-tert-butyl-5-[({[4-(pyridin-4-yloxy)phenyl]amino}carbonyl)amino]-1H-pyrazol-1-yl}-N-(2-methoxyethyl)benzamide
117. 4-{3-tert-butyl-5-[({[4-(pyridin-4-yloxy)phenyl]amino}carbonyl)amino]-1H-pyrazol-1-yl}-N-(2-methoxyethyl)-N-methylbenzamide
118. 4-{3-tert-butyl-5-[({[4-(pyridin-4-yloxy)phenyl]amino}carbonyl)amino]-1H-pyrazol-1-yl}-N-methyl-N-[2-(methylsulfonyl)ethyl]benzamide
119. 4-{3-tert-butyl-5-[({[4-(pyridin-4-yloxy)phenyl]amino}carbonyl)amino]-1H-pyrazol-1-yl}-N-(4-pyrrolidin-1-ylbutyl)benzamide
120. 4-{3-tert-butyl-5-[({[4-(pyridin-4-yloxy)phenyl]amino}carbonyl)amino]-1H-pyrazol-1-yl}-N-(2-morpholin-4-ylethyl)benzamide
121. 4-{3-tert-butyl-5-[({[4-(pyridin-4-yloxy)phenyl]amino}carbonyl)amino]-1H-pyrazol-1-yl}-N-[3-(diethylamino)propyl]benzamide
122. 4-{3-tert-butyl-5-[({[4-(pyridin-4-yloxy)phenyl]amino}carbonyl)amino]-1H-pyrazol-1-yl}-N-[2-(dimethylamino)ethyl]benzamide
123. 4-{3-tert-butyl-5-[({[4-(pyridin-4-yloxy)phenyl]amino}carbonyl)amino]-1H-pyrazol-1-yl}-N-(3-pyrrolidin-1-ylpropyl)benzamide
124. 4-{3-tert-butyl-5-[({[4-(pyridin-4-yloxy)phenyl]amino}carbonyl)amino]-1H-pyrazol-1-yl}-N-[2-(1H-pyrazol-1-yl)ethyl]benzamide
125. 4-{3-tert-butyl-5-[({[4-(pyridin-4-yloxy)phenyl]amino}carbonyl)amino]-1H-pyrazol-1-yl}-N-[3-(1H-imidazol-1-yl)propyl]benzamide
126. 4-(3-tert-butyl-5-{[({2-fluoro-4-[(2-methylpyridin-4-yl)oxy]phenyl}amino)-carbonyl]amino}-1H-pyrazol-1-yl)-N-(4-pyrrolidin-1-ylbutyl)benzamide
127. 4-(3-tert-butyl-5-{[({2-fluoro-4-[(2-methylpyridin-4-yl)oxy]phenyl}amino)-carbonyl]amino}-1H-pyrazol-1-yl)-N-[3-(diethylamino)propyl]benzamide
128. 4-(3-tert-butyl-5-{[({2-fluoro-4-[(2-methylpyridin-4-yl)oxy]phenyl}amino)-carbonyl]amino}-1H-pyrazol-1-yl)-N-(2-morpholin-4-ylethyl)benzamide
129. 4-(3-tert-butyl-5-{[({2-fluoro-4-[(2-methylpyridin-4-yl)oxy]phenyl}amino)-carbonyl]amino}-1H-pyrazol-1-yl)-N-(2-pyrrolidin-1-ylethyl)benzamide
130. 4-{3-tert-butyl-5-[({[4-(pyridin-3-yloxy)phenyl]amino}carbonyl)amino]-1H-pyrazol-1-yl}-N-[3-(diethylamino)propyl]benzamide
131. 4-{3-tert-butyl-5-[({[4-(pyridin-3-yloxy)phenyl]amino}carbonyl)amino]-1H-pyrazol-1-yl}-N-(2-morpholin-4-ylethyl)benzamide
132. 4-{3-tert-butyl-5-[({[4-(pyridin-3-yloxy)phenyl]amino}carbonyl)amino]-1H-pyrazol-1-yl}-N-(4-pyrrolidin-1-ylbutyl)benzamide
133. 4-{3-tert-butyl-5-[({[4-(pyridin-3-yloxy)phenyl]amino}carbonyl)amino]-1H-pyrazol-1-yl}-N-(2-pyrrolidin-1-ylethyl)benzamide
134. 4-{3-tert-butyl-5-[({[4-(pyridin-3-yloxy)phenyl]amino}carbonyl)amino]-1H-pyrazol-1-yl}-N-[2-(dimethylamino)ethyl]benzamide
135. 4-{3-tert-butyl-5-[({[4-(pyridin-3-yloxy)phenyl]amino}carbonyl)amino]-1H-pyrazol-1-yl}-N-methyl-N-[2-(methylsulfonyl)ethyl]benzamide
136. 3-{3-tert-butyl-5-[({[4-(pyridin-4-yloxy)phenyl]amino}carbonyl)amino]-1H-pyrazol-1-yl}-N-(2-pyrrolidin-1-ylethyl)benzamide
137. 3-{3-tert-butyl-5-[({[4-(pyridin-4-yloxy)phenyl]amino}carbonyl)amino]-1H-pyrazol-1-yl}-N-[3-(diethylamino)propyl]benzamide
138. 3-{3-tert-butyl-5-[({[4-(pyridin-4-yloxy)phenyl]amino}carbonyl)amino]-1H-pyrazol-1-yl}-N-(2-methoxyethyl)benzamide
139. 3-{3-tert-butyl-5-[({[4-(pyridin-4-yloxy)phenyl]amino}carbonyl)amino]-1H-pyrazol-1-yl}-N-(tetrahydrofuran-2-ylmethyl)benzamide
140. 3-{3-tert-butyl-5-[({[4-(pyridin-4-yloxy)phenyl]amino}carbonyl)amino]-1H-pyrazol-1-yl}-N-{[6-(trifluoromethyl)pyridin-3-yl]methyl}benzamide
141. N-[2-(acetylamino)ethyl]-3-{3-tert-butyl-5-[({[4-(pyridin-4-yloxy)phenyl]amino}-carbonyl)amino]-1H-pyrazol-1-yl}benzamide
142. 3-{3-tert-butyl-5-[({[4-(pyridin-4-yloxy)phenyl]amino}carbonyl)amino]-1H-pyrazol-1-yl}-N-[3-(1H-imidazol-1-yl)propyl]benzamide
143. 3-{3-tert-butyl-5-[({[4-(pyridin-4-yloxy)phenyl]amino}carbonyl)amino]-1H-pyrazol-1-yl}-N-[2-(2-hydroxyethoxy)ethyl]benzamide
144. 3-{3-tert-butyl-5-[({[4-(pyridin-4-yloxy)phenyl]amino}carbonyl)amino]-1H-pyrazol-1-yl}-N-[2-(1-methylpyrrolidin-2-yl)ethyl]benzamide
145. 3-{3-tert-butyl-5-[({[4-(pyridin-4-yloxy)phenyl]amino}carbonyl)amino]-1H-pyrazol-1-yl}-N-(3-hydroxy-2,2-dimethylpropyl)benzamide
146. tert-butyl 4-{[(3-{3-tert-butyl-5-[({[4-(pyridin-4-yloxy)phenyl]amino}carbonyl)-amino]-1H-pyrazol-1-yl}benzoyl)amino]methyl}piperidine-1-carboxylate
147. 3-{3-tert-butyl-5-[({[4-(pyridin-4-yloxy)phenyl]amino}carbonyl)amino]-1H-pyrazol-1-yl}-N-(piperidin-4-ylmethyl)benzamide
148. 3-{3-tert-butyl-5-[({[4-(pyridin-4-yloxy)phenyl]amino}carbonyl)amino]-1H-pyrazol-1-yl}-N-(3-hydroxypropyl)benzamide 149. 3-(3-tert-butyl-5-{[({2-fluoro-4-[(2-methylpyridin-4-yl)oxy]phenyl}amino)-carbonyl]amino}-1H-pyrazol-1-yl)-N-(3-hydroxypropyl)benzamide
150. 3-(3-tert-butyl-5-{[({2-fluoro-4-[(2-methylpyridin-4-yl)oxy]phenyl}amino)-carbonyl]amino}-1H-pyrazol-1-yl)-N-(2-hydroxyethyl)benzamide
151. 3-{3-tert-butyl-5-[({[4-(pyridin-4-yloxy)phenyl]amino}carbonyl)amino]-1H-pyrazol-1-yl}-N-(2-hydroxyethyl)benzamide
152. N-[2-(acetylamino)ethyl]-3-(3-tert-butyl-5-{[({2-fluoro-4-[(2-methylpyridin-4-yl)oxy]phenyl}amino)carbonyl]amino}-1H-pyrazol-1-yl)benzamide
153. 3-(3-tert-butyl-5-{[({2-fluoro-4-[(2-methylpyridin-4-yl)oxy]phenyl}amino)-carbonyl]amino}-1H-pyrazol-1-yl)-N-[3-(1H-imidazol-1-yl)propyl]benzamide
154. 3-(3-tert-butyl-5-{[({2-fluoro-4-[(2-methylpyridin-4-yl)oxy]phenyl}amino)-carbonyl]amino}-1H-pyrazol-1-yl)-N-(tetrahydrofuran-2-ylmethyl)benzamide
155. 3-(3-tert-butyl-5-{[({2-fluoro-4-[(2-methylpyridin-4-yl)oxy]phenyl}amino)-carbonyl]amino}-1H-pyrazol-1-yl)-N-(2-pyridin-4-ylethyl)benzamide
156. 3-(3-tert-butyl-5-{[({2-fluoro-4-[(2-methylpyridin-4-yl)oxy]phenyl}amino)-carbonyl]amino}-1H-pyrazol-1-yl)-N-[3-(diethylamino)propyl]benzamide
157. 3-(3-tert-butyl-5-{[({2-fluoro-4-[(2-methylpyridin-4-yl)oxy]phenyl}amino)-carbonyl]amino}-1H-pyrazol-1-yl)-N-[2-(1-methylpyrrolidin-2-yl)ethyl]benzamide
158. 3-(3-tert-butyl-5-{[({2-fluoro-4-[(2-methylpyridin-4-yl)oxy]phenyl}amino)-carbonyl]amino}-1H-pyrazol-1-yl)-N-(2-pyrrolidin-1-ylethyl)benzamide
159. 3-(3-tert-butyl-5-{[({2-fluoro-4-[(2-methylpyridin-4-yl)oxy]phenyl}amino)-carbonyl]amino}-1H-pyrazol-1-yl)-N-(4-pyrrolidin-1-ylbutyl)benzamide
160. 3-(3-tert-butyl-5-{[({2-fluoro-4-[(2-methylpyridin-4-yl)oxy]phenyl}amino)-carbonyl]amino}-1H-pyrazol-1-yl)-N-(3-hydroxy-2,2-dimethylpropyl)benzamide
161. tert-butyl 4-({[3-(3-tert-butyl-5-{[({2-fluoro-4-[(2-methylpyridin-4-yl)oxy]phenyl}-amino)carbonyl]amino}-1H-pyrazol-1-yl)benzoyl]amino}methyl)piperidine-1-carboxylate
162. 3-(3-tert-butyl-5-{[({2-fluoro-4-[(2-methylpyridin-4-yl)oxy]phenyl}amino)-carbonyl]amino}-1H-pyrazol-1-yl)-N-(piperidin-4-ylmethyl)benzamide
163. 4-{3-tert-butyl-5-[({[4-(pyridin-4-yloxy)phenyl]amino}carbonyl)amino]-1H-pyrazol-1-yl}-N-(tetrahydrofuran-2-ylmethyl)benzenesulfonamide
164. 4-{3-tert-butyl-5-[({[4-(pyridin-4-yloxy)phenyl]amino}carbonyl)amino]-1H-pyrazol-1-yl}-N-(2-morpholin-4-ylethyl)benzenesulfonamide
165. 4-(3-tert-butyl-5-{[({2-fluoro-4-[(2-methylpyridin-4-yl)oxy]phenyl}amino)-carbonyl]amino}-1H-pyrazol-1-yl)-N-(2-morpholin-4-ylethyl)benzenesulfonamide
166. 4-(3-tert-butyl-5-{[({2-fluoro-4-[(2-methylpyridin-4-yl)oxy]phenyl}amino)-carbonyl]amino}-1H-pyrazol-1-yl)-N-[2-(1-methylpyrrolidin-2-yl)ethyl]benzene-sulfonamide
167. 4-{3-tert-butyl-5-[({[4-(pyridin-4-yloxy)phenyl]amino}carbonyl)amino]-1H-pyrazol-1-yl}-N-[2-(1-methylpyrrolidin-2-yl)ethyl]benzenesulfonamide
168. 4-{3-tert-butyl-5-[({[4-(pyridin-4-yloxy)phenyl]amino}carbonyl)amino]-1H-pyrazol-1-yl}-2-methyl-N-(2-morpholin-4-ylethyl)benzenesulfonamide
169. 4-{3-tert-butyl-5-[({[4-(pyridin-4-yloxy)phenyl]amino}carbonyl)amino]-1H-pyrazol-1-yl}-N-(tetrahydrofuran-2-ylmethyl)-2-(trifluoromethoxy)benzene-sulfonamide
170. 4-(3-tert-butyl-5-{[({2-fluoro-4-[(2-methylpyridin-4-yl)oxy]phenyl}amino)-carbonyl]amino}-1H-pyrazol-1-yl)-N-(tetrahydrofuran-2-ylmethyl)-2-(trifluoro-methoxy)benzenesulfonamide
171. 4-{3-tert-butyl-5-[({[4-(pyridin-4-yloxy)phenyl]amino}carbonyl)amino]-1H-pyrazol-1-yl}-2-methyl-N-(tetrahydrofuran-2-ylmethyl)benzenesulfonamide
172. 4-(3-tert-butyl-5-{[({2-fluoro-4-[(2-methylpyridin-4-yl)oxy]phenyl}amino)-carbonyl]amino}-1H-pyrazol-1-yl)-2-methyl-N-(tetrahydrofuran-2-ylmethyl)-benzenesulfonamide
173. 4-(3-tert-butyl-5-{[({2-fluoro-4-[(2-methylpyridin-4-yl)oxy]phenyl}amino)carbonyl]amino}-1H-pyrazol-1-yl)-N-(tetrahydrofuran-2-ylmethyl)benzenesulfonamide
174. 3-{3-tert-butyl-5-[({[4-(pyridin-4-yloxy)phenyl]amino}carbonyl)amino]-1H-pyrazol-1-yl}-N-(2-methoxyethyl)benzenesulfonamide
175. 3-(3-tert-butyl-5-{[({2-fluoro-4-[(2-methylpyridin-4-yl)oxy]phenyl}amino)-carbonyl]amino}-1H-pyrazol-1-yl)-N-(2-methoxyethyl)benzenesulfonamide
176. 3-{3-tert-butyl-5-[({[4-(pyridin-3-yloxy)phenyl]amino}carbonyl)amino]-1H-pyrazol-1-yl}-N-(2-methoxyethyl)benzenesulfonamide
177. 3-{3-tert-butyl-5-[({[4-(pyridin-4-yloxy)phenyl]amino}carbonyl)amino]-1H-pyrazol-1-yl}-N-[2-(dimethylamino)ethyl]benzenesulfonamide
178. 3-(3-tert-butyl-5-{[({2-fluoro-4-[(2-methylpyridin-4-yl)oxy]phenyl}amino)-carbonyl]amino}-1H-pyrazol-1-yl)-N-[2-(dimethylamino)ethyl]benzenesulfonamide
179. N-{1-[4-(aminomethyl)phenyl]-3-tert-butyl-1H-pyrazol-5-yl}-N'-[4-(pyridin-3-yloxy)phenyl]urea
180. N-(4-{3-tert-butyl-5-[({[4-(pyridin-3-yloxy)phenyl]amino}carbonyl)amino]-1H-pyrazol-1-yl}benzyl)-2-methoxyacetamide
181. N-{1-[4-(aminomethyl)phenyl]-3-tert-butyl-1H-pyrazol-5-yl}-N'-{2-fluoro-4-[(2-methylpyridin-4-yl)oxy]phenyl}urea
182. N-[4-(3-tert-butyl-5-{[({2-fluoro-4-[(2-methylpyridin-4-yl)oxy]phenyl}amino)-carbonyl]amino}-1H-pyrazol-1-yl)benzyl]-2-methoxyacetamide
183. N-[3-tert-butyl-1-(4-{[(2-methoxyethyl)amino]methyl}phenyl)-1H-pyrazol-5-yl]-N'-{2-fluoro-4-[(2-methylpyridin-4-yl)oxy]phenyl}urea
184. N-[1-(4-{[bis(2-hydroxyethyl)amino]methyl}phenyl)-3-tert-butyl-1H-pyrazol-5-yl]-N'-[4-(pyridin-3-yloxy)phenyl]urea
185. N-[1-(4-{[bis(2-hydroxyethyl)amino]methyl}phenyl)-3-tert-butyl-1H-pyrazol-5-yl]-N'-{2-fluoro-4-[(2-methylpyridin-4-yl)oxy]phenyl}urea
186. N-[1-(4-{[bis(3-hydroxypropyl)amino]methyl}phenyl)-3-tert-butyl-1H-pyrazol-5-yl]-N'-[4-(pyridin-4-yloxy)phenyl]urea
187. N-[1-(4-{[bis(3-hydroxypropyl)amino]methyl}phenyl)-3-tert-butyl-1H-pyrazol-5-yl]-N'-[4-(pyridin-3-yloxy)phenyl]urea
188. N-[1-(4-{[bis(3-hydroxypropyl)amino]methyl}phenyl)-3-tert-butyl-1H-pyrazol-5-yl]-N'-{2-fluoro-4-[(2-methylpyridin-4-yl)oxy]phenyl}urea
189. N2-acetyl-N-(4-{3-tert-butyl-5-[({[4-(pyridin-4-yloxy)phenyl]amino}carbonyl)-amino]-1H-pyrazol-1-yl}benzyl)glycinamide
190. tert-butyl{2-[(4-{3-tert-butyl-5-[({[4-(pyridin-4-yloxy)phenyl]amino}carbonyl)-amino]-1H-pyrazol-1-yl}benzyl)amino]-2-oxoethyl}carbamate
191. tert-butyl{2-[(4-{3-tert-butyl-5-[({[4-(pyridin-4-yloxy)phenyl]amino}carbonyl)-amino]-1H-pyrazol-1-yl}benzyl)amino]-1-methyl-2-oxoethyl}carbamate 192. N-(4-{3-tert-butyl-5-[({[4-(pyridin-4-yloxy)phenyl]amino}carbonyl)amino]-1H-pyrazol-1-yl}benzyl)-2-(1-methyl-1H-imidazol-4-yl)acetamide
193. N-(4-{3-tert-butyl-5-[({[4-(pyridin-3-yloxy)phenyl]amino}carbonyl)amino]-1H-pyrazol-1-yl}benzyl)glycinamide
194. N-[4-(3-tert-butyl-5-{[({2-fluoro-4-[(2-methylpyridin-4-yl)oxy]phenyl}amino)-carbonyl]amino}-1H-pyrazol-1-yl)benzyl]acetamide
195. N2-acetyl-N-[4-(3-tert-butyl-5-{[({2-fluoro-4-[(2-methylpyridin-4-yl)oxy]phenyl}-amino)carbonyl]amino}-1H-pyrazol-1-yl)benzyl]glycinamide
196. tert-butyl(2-{[4-(3-tert-butyl-5-{[({2-fluoro-4-[(2-methylpyridin-4-yl)oxy]phenyl}-amino)carbonyl]amino}-1H-pyrazol-1-yl)benzyl]amino}-2-oxoethyl)carbamate
197. tert-butyl(2-{[4-(3-tert-butyl-5-{[({2-fluoro-4-[(2-methylpyridin-4-yl)oxy]phenyl}-amino)carbonyl]amino}-1H-pyrazol-1-yl)benzyl]amino}-1-methyl-2-oxoethyl)carbamate
198. N-[4-(3-tert-butyl-5-{[({2-fluoro-4-[(2-methylpyridin-4-yl)oxy]phenyl}amino)-carbonyl]amino}-1H-pyrazol-1-yl)benzyl]-2-(1-methyl-1H-imidazol-4-yl)acetamide
199. N-[4-(3-tert-butyl-5-{[({2-fluoro-4-[(2-methylpyridin-4-yl)oxy]phenyl}amino)-carbonyl]amino}-1H-pyrazol-1-yl)benzyl]-1-methyl-1H-imidazole-4-carboxamide
200. N2-acetyl-N-(4-{3-tert-butyl-5-[({[4-(pyridin-3-yloxy)phenyl]amino}carbonyl)-amino]-1H-pyrazol-1-yl}benzyl)glycinamide
201. tert-butyl {2-[(4-{3-tert-butyl-5-[({[4-(pyridin-3-yloxy)phenyl]amino}carbonyl)-amino]-1H-pyrazol-1-yl}benzyl)amino]-2-oxoethyl}carbamate
202. N-[4-(3-tert-butyl-5-{[({2-fluoro-4-[(2-methylpyridin-4-yl)oxy]phenyl}amino)-carbonyl]amino}-1H-pyrazol-1-yl)benzyl]alaninamide
203. N-[4-(3-tert-butyl-5-{[({2-fluoro-4-[(2-methylpyridin-4-yl)oxy]phenyl}amino)-carbonyl]amino}-1H-pyrazol-1-yl)benzyl]glycinamide
204. N-(4-{3-tert-butyl-5-[({[4-(pyridin-4-yloxy)phenyl]amino}carbonyl)amino]-1H-pyrazol-1-yl}benzyl)alaninamide
205. N-[3-tert-butyl-1-(3-{[(2-hydroxyethyl)amino]methyl}phenyl)-1H-pyrazol-5-yl]-N'-[4-(pyridin-4-yloxy)phenyl]urea
206. N-{1-[3-(aminomethyl)phenyl]-3-tert-butyl-1H-pyrazol-5-yl}-N'-[4-(pyridin-4-yloxy)phenyl]urea
207. N{-1-[3-(aminomethyl)phenyl]-3-tert-butyl-1H-pyrazol-5-yl}-N'-{2-fluoro-4-[(2-methylpyridin-4-yl)oxy]phenyl}urea
208. N-(3-{3-tert-butyl-5-[({[4-(pyridin-4-yloxy)phenyl]amino}carbonyl)amino]-1H-pyrazol-1-yl}benzyl)acetamide
209. N-[3-(3-tert-butyl-5-{[({2-fluoro-4-[(2-methylpyridin-4-yl)oxy]phenyl}amino)carbonyl]amino}-1H-pyrazol-1-yl)benzyl]acetamide
210. N2-acetyl-N-(3-{3-tert-butyl-5-[({[4-(pyridin-4-yloxy)phenyl]amino}carbonyl)-amino]-1H-pyrazol-1-yl}benzyl)glycinamide
211. N-(3-{3-tert-butyl-5-[({[4-(pyridin-4-yloxy)phenyl]amino}carbonyl)amino]-1H-pyrazol-1-yl}benzyl)-2-methoxyacetamide
212. N2-acetyl-N-[3-(3-tert-butyl-5-{[({2-fluoro-4-[(2-methylpyridin-4-yl)oxy]phenyl}-amino)carbonyl]amino}-1H-pyrazol-1-yl)benzyl]glycinamide
213. N-[3-(3-tert-butyl-5-{[({2-fluoro-4-[(2-methylpyridin-4-yl)oxy]phenyl}amino)-carbonyl]amino}-1H-pyrazol-1-yl)benzyl]-2-methoxyacetamide
214. N-[3-tert-butyl-1-(3-{[(2,3-dihydroxypropyl)amino]methyl}phenyl)-1H-pyrazol-5-yl]-N'-{2-fluoro-4-[(2-methylpyridin-4-yl)oxy]phenyl}urea
215. N-{3-tert-butyl-1-[3-(hydroxymethyl)phenyl]-1H-pyrazol-5-yl}-N'-{2-fluoro-4-[(2-methylpyridin-4-yl)oxy]phenyl}urea
216. N-(3-tert-butyl-1-{4-[(2-morpholin-4-ylethoxy)methyl]phenyl}-1H-pyrazol-5-yl)-N'-{2-fluoro-4-[(2-methylpyridin-4-yl)oxy]phenyl}urea
217. N-{3-tert-butyl-1-[4-(methoxymethyl)phenyl]-1H-pyrazol-5-yl}-N'-{2-fluoro-4-[(2-methylpyridin-4-yl)oxy]phenyl}urea
218. N-(3-tert-butyl-1-{4-[(2-morpholin-4-ylethoxy)methyl]phenyl}-1H-pyrazol-5-yl)-N'-{2-fluoro-4-[(2-methylpyridin-4-yl)oxy]phenyl}urea
219. N-{3-tert-butyl-1-[4-(methoxymethyl)phenyl]-1H-pyrazol-5-yl}-N'-{2-fluoro-4-[(2-methylpyridin-4-yl)oxy]phenyl}urea
220. N-(3-tert-butyl-1-{4-[(2-methoxyethoxy)methyl]phenyl}-1H-pyrazol-5-yl)-N'-{2-fluoro-4-[(2-methylpyridin-4-yl)oxy]phenyl}urea
221. ethyl[4-(3-tert-butyl-5-{[({2-fluoro-4-[(2-methylpyridin-4-yl)oxy]phenyl}amino)-carbonyl]amino}-1H-pyrazol-1-yl)phenyl]acetate
222. [4-(3-tert-butyl-5-{[({2-fluoro-4-[(2-methylpyridin-4-yl)oxy]phenyl}amino)-carbonyl]amino}-1H-pyrazol-1-yl)phenyl]acetic acid
223. N-{3-tert-butyl-1-[4-(2-hydroxyethyl)phenyl]-1H-pyrazol-5-yl}-N'-{2-fluoro-4-[(2-methylpyridin-4-yl)oxy]phenyl}urea
224. N-{3-tert-butyl-1-[4-(2-morpholin-4-yl-2-oxoethyl)phenyl]-1H-pyrazol-5-yl}-N'-[4-(pyridin-4-yloxy)phenyl]urea
225. N-{3-tert-butyl-1-[4-(2-oxo-2-pyrrolidin-1-ylethyl)phenyl]-1H-pyrazol-5-yl}-N'-[4-(pyridin-4-yloxy)phenyl]urea
226. tert-butyl 4-[(4-{3-tert-butyl-5-[({[4-(pyridin-4-yloxy)phenyl]amino}carbonyl)-amino]-1H-pyrazol-1-yl}phenyl)acetyl]piperazine-1-carboxylate
227. N-(3-tert-butyl-1-{4-[2-(4-methylpiperazin-1-yl)-2-oxoethyl]phenyl}-1H-pyrazol-5-yl)-N'-[4-(pyridin-4-yloxy)phenyl]urea
228. 2-(4-{3-tert-butyl-5-[({[4-(pyridin-4-yloxy)phenyl]amino}carbonyl)amino]-1H-pyrazol-1-yl}phenyl)-N-[(2,2-dimethyl-1,3-dioxolan-4-yl)methyl]acetamide
229. 2-(4-{3-tert-butyl-5-[({[4-(pyridin-4-yloxy)phenyl]amino}carbonyl)amino]-1H-pyrazol-1-yl}phenyl)-N-(2-methoxyethyl)acetamide
230. 2-(4-{3-tert-butyl-5-[({[4-(pyridin-4-yloxy)phenyl]amino}carbonyl)amino]-1H-pyrazol-1-yl}phenyl)-N-(2-morpholin-4-ylethyl)acetamide
231. N-[3-tert-butyl-1-(4-{2-[(3R)-3-hydroxypyrrolidin-1-yl]-2-oxoethyl}phenyl)-1H-pyrazol-5-yl]-N'-[4-(pyridin-4-yloxy)phenyl]urea
232. N-{3-tert-butyl-1-[4-(2-morpholin-4-ylethyl)phenyl]-1H-pyrazol-5-yl}-N'-[4-(pyridin-4-yloxy)phenyl]urea
233. N-{3-tert-butyl-1-[4-(2-pyrrolidin-1-ylethyl)phenyl]-1H-pyrazol-5-yl}-N'-[4-(pyridin-4-yloxy)phenyl]urea
234. 2-(4-{3-tert-butyl-5-[({[4-(pyridin-4-yloxy)phenyl]amino}carbonyl)amino]-1H-pyrazol-1-yl}phenyl)-N-(2-hydroxyethyl)acetamide
235. N-[3-tert-butyl-1-(4-{2-[(2-hydroxyethyl)amino]ethyl}phenyl)-1H-pyrazol-5-yl]-N'-[4-(pyridin-4-yloxy)phenyl]urea
236. N-{3-tert-butyl-1-[4-(2-oxo-2-piperazin-1-ylethyl)phenyl]-1H-pyrazol-5-yl}-N'-[4-(pyridin-4-yloxy)phenyl]urea 237. N-[3-tert-butyl-1-(4-{2-[(3R)-3-hydroxypyrrolidin-1-yl]ethyl}phenyl)-1H-pyrazol-5-yl]-N'-[4-(pyridin-4-yloxy)phenyl]urea
238. N-{3-tert-butyl-1-[4-(2-piperazin-1-ylethyl)phenyl]-1H-pyrazol-5-yl}-N'-[4-(pyridin-4-yloxy)phenyl]urea
239. 2-(4-{3-tert-butyl-5-[({[4-(pyridin-4-yloxy)phenyl]amino}carbonyl)amino]-1H-pyrazol-1-yl}phenyl)-N-(2,3-dihydroxypropyl)acetamide
240. N-[3-tert-butyl-1-(4-{2-[(2,3-dihydroxypropyl)amino]ethyl}phenyl)-1H-pyrazol-5-yl]-N'-[4-(pyridin-4-yloxy)phenyl]urea
241. N-[3-tert-butyl-1-(4-{2-[(2-methoxyethyl)amino]ethyl}phenyl)-1H-pyrazol-5-yl]-N'-[4-(pyridin-4-yloxy)phenyl]urea
242. N-(3-tert-butyl-1-{4-[2-(4-methylpiperazin-1-yl)ethyl]phenyl}-1H-pyrazol-5-yl)-N'-[4-(pyridin-4-yloxy)phenyl]urea
243. N-[3-tert-butyl-1-(4-{2-[(2-morpholin-4-ylethyl)amino]ethyl}phenyl)-1H-pyrazol-5-yl]-N'-[4-(pyridin-4-yloxy)phenyl]urea

| Ex. No. | Structure | IUPAC name | LC-MS m/z (MH+) | Ret. time (min) |
|---|---|---|---|---|
| 1 | 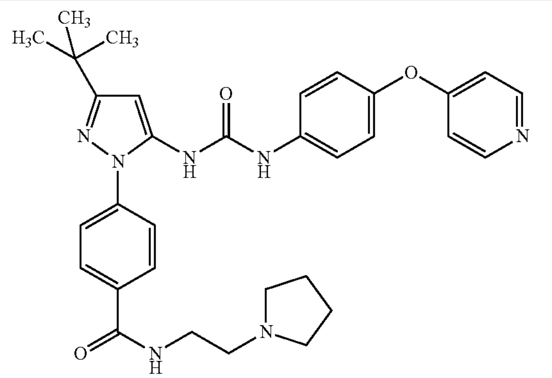 | 4-{3-tert-butyl-5-[({[4-(pyridin-4-yloxy)phenyl]amino}carbonyl)amino]-1H-pyrazaol-1-yl}-N-(2-pyrrolidin-1-ylethyl)benzamide | 568 | 2.48 |
| 2 | 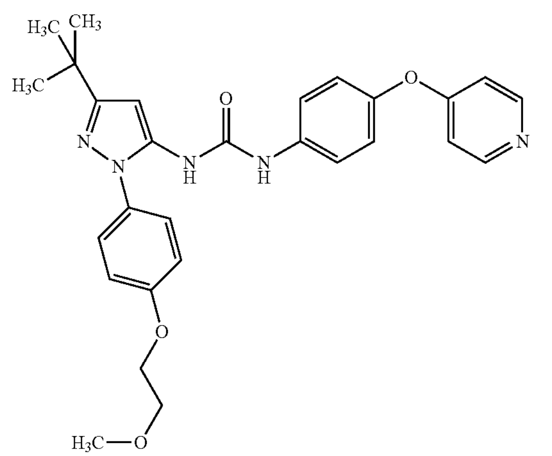 | N-{3-tert-butyl-1-[4-(2-methoxyethoxy)phenyl]-1H-pyrazol-5-yl}-N'-[4-(pyridin-4-yloxy)phenyl]urea | 502 | 2.84 |
| 3 | 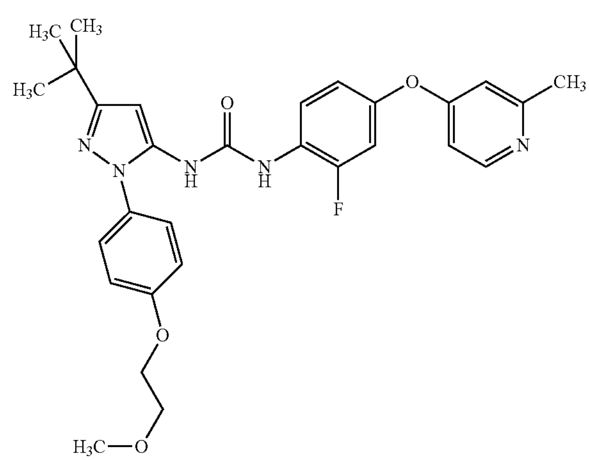 | N-{3-tert-butyl-1-[4-(2-methoxyethoxy)phenyl]-1H-pyrazol-5-yl}-N'-{2-fluoro-4-[(2-methylpyridin-4-yl)oxy]phenyl}urea | 534 | 2.39 |

-continued

| Ex. No. | Structure | IUPAC name | LC-MS m/z (MH+) | Ret. time (min) |
|---|---|---|---|---|
| 4 | 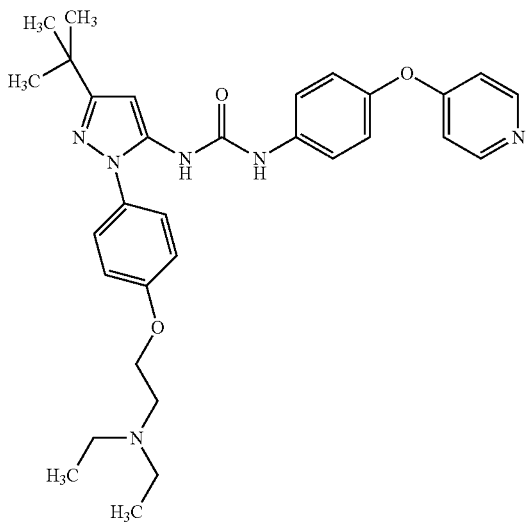 | N-(3-tert-butyl-1-{4-[2-(diethylamino)ethoxy]phenyl}-1H-pyrazol-5-yl)-N'-[4-(pyridin-4-yloxy)phenyl]urea | 543 | 2.16 |
| 5 | 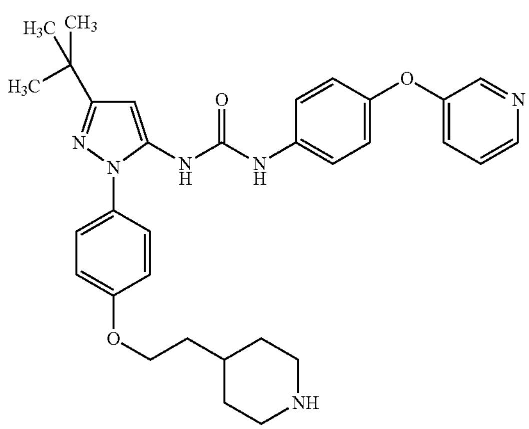 | N-{3-tert-butyl-1-[4-(2-piperidin-4-ylethoxy)phenyl]-1H-pyrazol-5-yl}-N'-[4-(pyridin-3-yloxy)phenyl]urea | 555 | 2.73 |
| 6 | 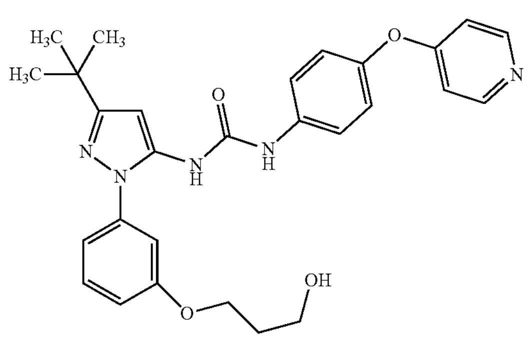 | N-{3-tert-butyl-1-[3-(3-hydroxypropoxy)phenyl]-1H-pyrazol-5-yl}-N'-[4-(pyridin-4-yloxy)phenyl]urea | 502 | 2.36 |

-continued

| Ex. No. | Structure | IUPAC name | LC-MS m/z (MH+) | Ret. time (min) |
|---|---|---|---|---|
| 7 | 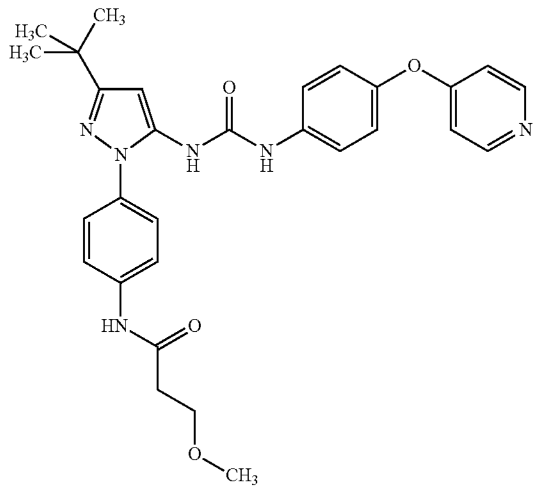 | N-(4-{3-tert-butyl-5-[({[4-(pyridin-4-yloxy)phenyl]amino}carbonyl)amino]-1H-pyrazol-1-yl}phenyl)-3-methoxypropanamide | 529 | 2.20 |
| 8 | 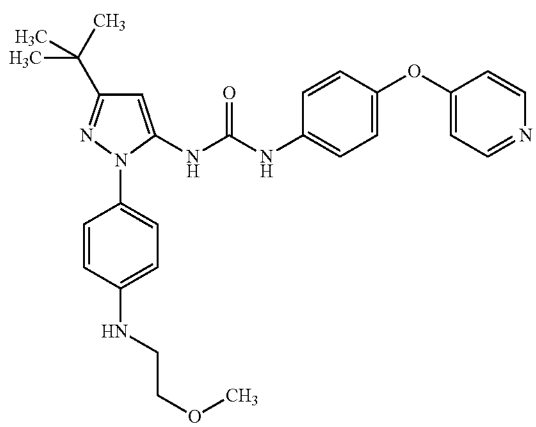 | N-(3-tert-butyl-1-{4-[(2-methoxyethyl)amino]phenyl}-1H-pyrazol-5-yl)-N'-[4-(pyridin-4-yloxy)phenyl]urea | 501 | 2.39 |
| 9 | 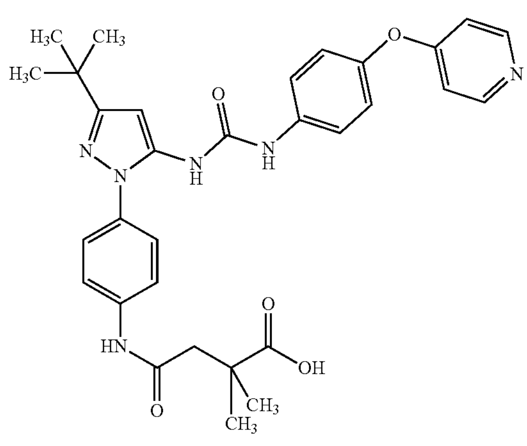 | 4-[(4-{3-tert-butyl-5-[({[4-(pyridin-4-yloxy)phenyl]amino}carbonyl)amino]-1H-pyrazol-1-yl}phenyl)amino]-2,2-dimethyl-4-oxobutanoic acid | 571 | 2.49 |

-continued

| Ex. No. | Structure | IUPAC name | LC-MS m/z (MH+) | Ret. time (min) |
|---|---|---|---|---|
| 10 | 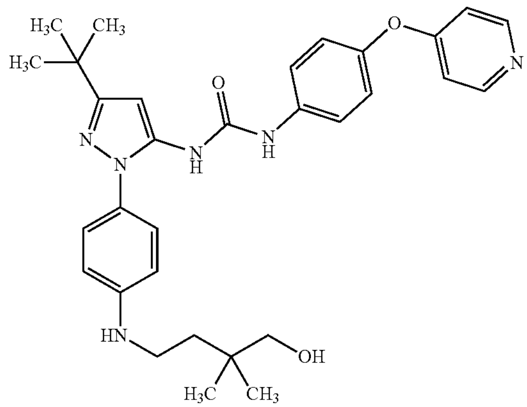 | N-(3-tert-butyl-1-{4-[(4-hydroxy-3,3-dimethylbutyl)amino]phenyl}-1H-pyrazol-5-yl)-N'-[4-(pyridin-4-yloxy)phenyl]urea | 543 | 2.31 |
| 11 | 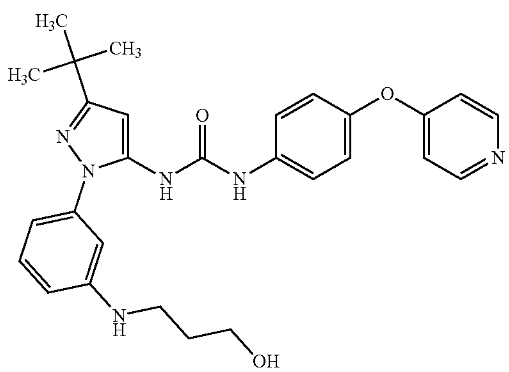 | N-(3-tert-butyl-1-{3-[(3-hydroxypropyl)amino]phenyl}-1H-pyrazol-5-yl)-N'-[4-(pyridin-4-yloxy)phenyl]urea | 501 | 2.29 |
| 12 | 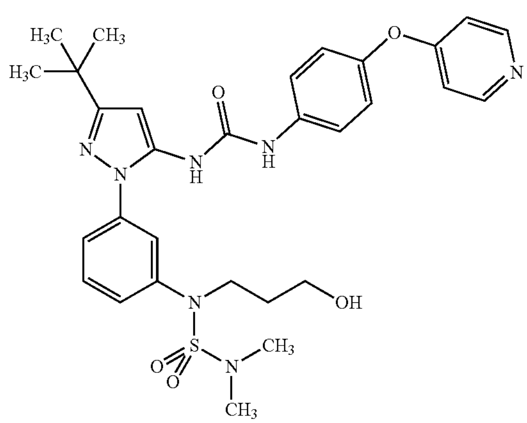 | N-(3-tert-butyl-1-{3-[[(dimethylamino)sulfonyl](3-hydroxypropyl)amino]phenyl}-1H-pyrazol-5-yl)-N'-[4-(pyridin-4-yloxy)phenyl]urea | 608 | 2.45 |

-continued

| Ex. No. | Structure | IUPAC name | LC-MS m/z (MH+) | Ret. time (min) |
|---|---|---|---|---|
| 13 | 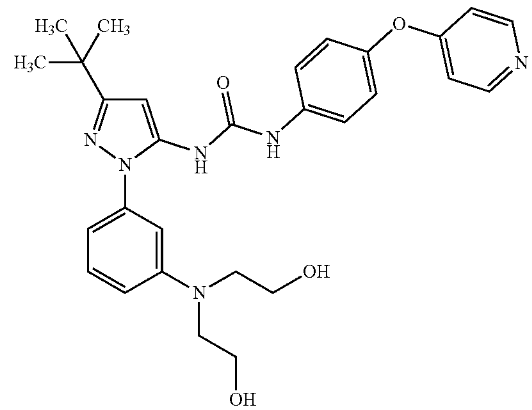 | N-(1-{3-[bis(2-hydroxyethyl) amino]phenyl}-3-tert-butyl-1H-pyrazol-5-yl)-N'-[4-(pyridin-4-yloxy)phenyl]urea | 531 | 2.27 |
| 14 | 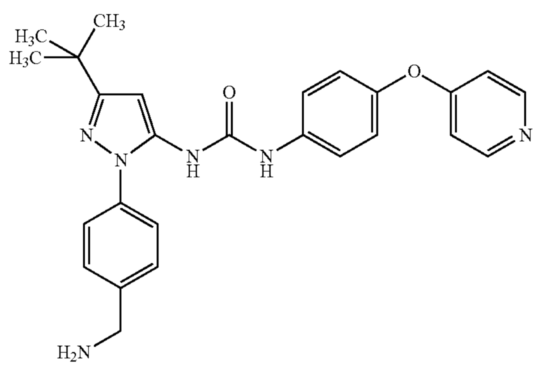 | N-{1-[4-(aminomethyl)phenyl]-3-tert-butyl-1H-pyrazol-5-yl}-N'-[4-(pyridin-4-yloxy)phenyl]urea | 457 | 1.96 |
| 15 | 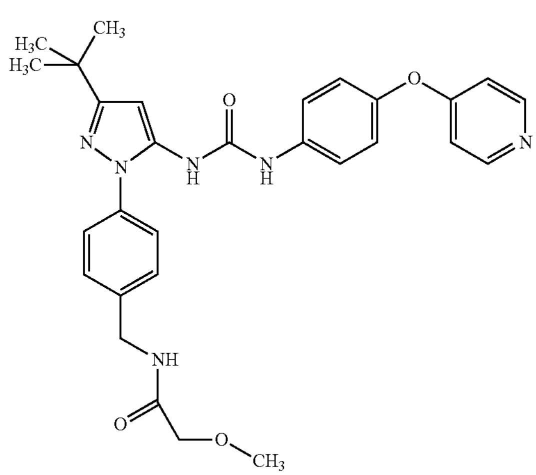 | N-(4-{3-tert-butyl-5-[({[4-(pyridin-4-yloxy)phenyl]amino}carbonyl)amino]-1H-pyrazol-1-yl}benzyl)-2-methoxyacetamide | 529 | 2.29 |

-continued

| Ex. No. | Structure | IUPAC name | LC-MS m/z (MH+) | Ret. time (min) |
|---|---|---|---|---|
| 16 | 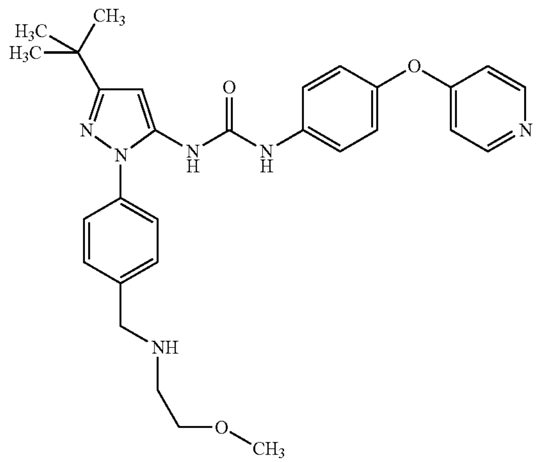 | N-[3-tert-butyl-1-(4-{[(2-methoxyethyl)amino]methyl}phenyl)-1H-pyrazol-5-yl]-N'-[4-(pyridin-4-yloxy)phenyl]urea | 515 | 2.02 |
| 17 | 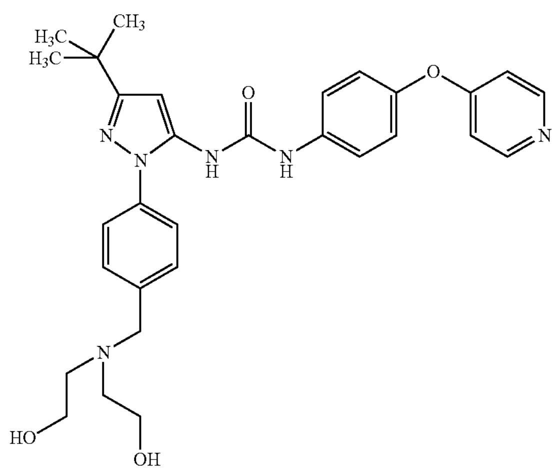 | N-[1-(4-{[bis(2-hydroxyethyl)amino]methyl}phenyl)-3-tert-butyl-1H-pyrazol-5-yl]-N'-[4-(pyridin-4-yloxy)phenyl]urea | 545 | 2.03 |
| 18 | 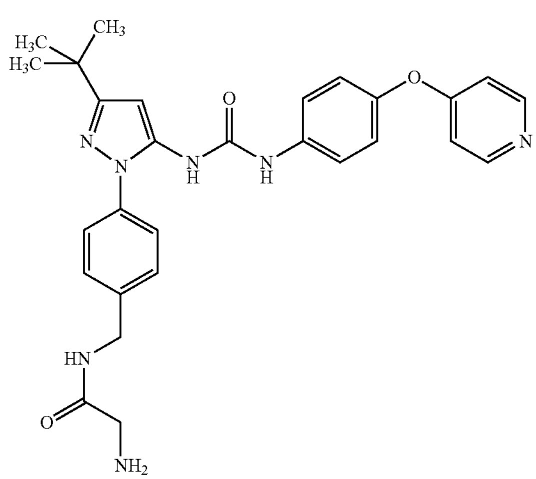 | N-(4-{3-tert-butyl-5-[({[4-(pyridin-4-yloxy)phenyl]amino}carbonyl)amino]-1H-pyrazol-1-yl}benzyl)glycinamide | 514 | 2.01 |

-continued

| Ex. No. | Structure | IUPAC name | LC-MS m/z (MH+) | Ret. time (min) |
|---|---|---|---|---|
| 19 | 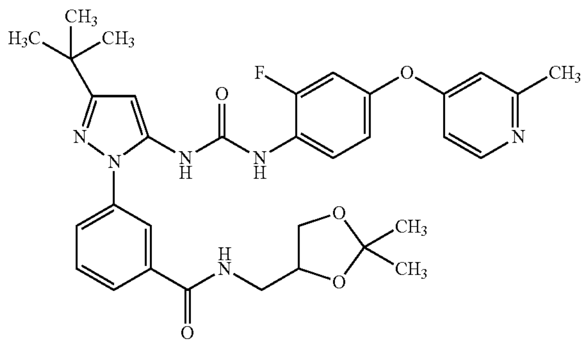 | 3-(3-tert-butyl-5-{[({2-fluoro-4-[(2-methylpyridin-4-yl)oxy]phenyl}amino)carbonyl]amino}-1H-pyrazol-1-yl)-N-[(2,2-dimethyl-1,3-dioxolan-4-yl)methyl]benzamide | 617 | 2.54 |
| 20 | 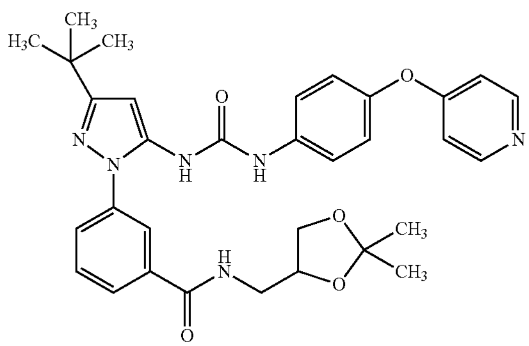 | 3-{3-tert-butyl-5-[({[4-(pyridin-4-yloxy)phenyl]amino}carbonyl)amino]-1H-pyrazol-1-yl}-N-[(2,2-dimethyl-1,3-dioxolan-4-yl)methyl]benzamide | 585 | 2.59 |
| 21 | 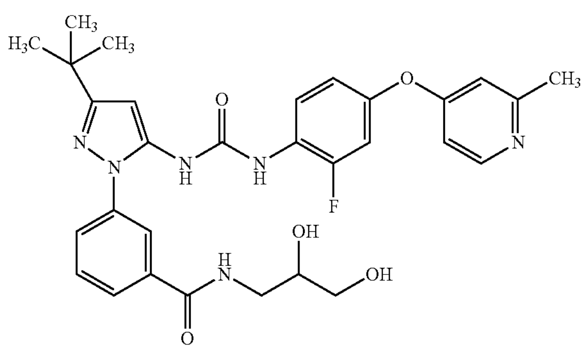 | 3-(3-tert-butyl-5-{[({2-fluoro-4-[(2-methylpyridin-4-yl)oxy]phenyl}amino)carbonyl]amino}-1H-pyrazol-1-yl)-N-(2,3-dihydroxypropyl)benzamide | 577 | 1.54 |
| 22 | 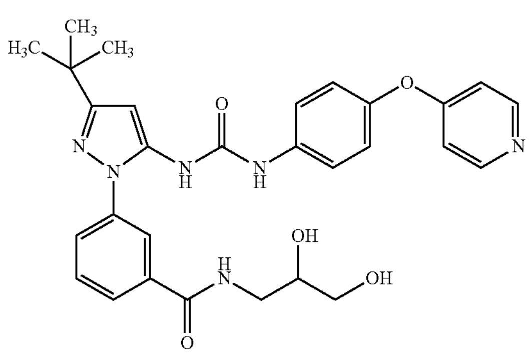 | 3-{3-tert-butyl-5-[({[4-pyridin-4-yloxy)phenyl]amino}carbonyl)amino]-1H-pyrazol-1-yl}-N-(2,3-dihydroxypropyl)benzamide | 545 | 2.21 |

-continued

| Ex. No. | Structure | IUPAC name | LC-MS m/z (MH+) | Ret. time (min) |
|---|---|---|---|---|
| 23 | 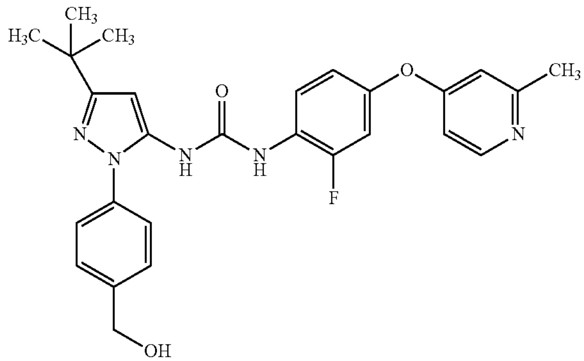 | N-{3-tert-butyl-1-[4-(hydroxymethyl)phenyl]-1H-pyrazol-5-yl}-N'-{2-fluoro-4-[(2-methylpyridin-4-yl)oxy]phenyl}urea | 490 | 2.41 |
| 24 | 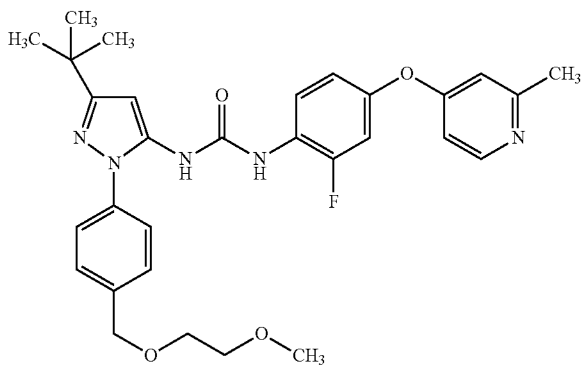 | N-(3-tert-butyl-1-{4-[(2-methoxyethoxy)methyl]phenyl}-1H-pyrazol-5-yl)-N'-{2-fluoro-4-[(2-methylpyridin-4-yl)oxy]phenyl}urea | 548 | 2.69 |
| 25 | 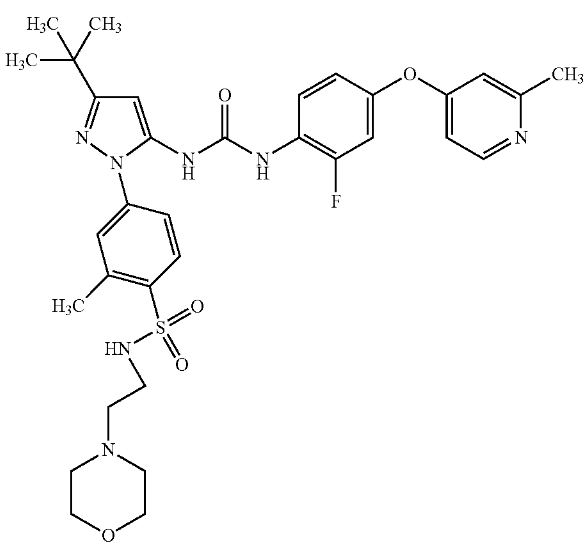 | 4-(3-tert-butyl-5-{[({2-fluoro-4-[(2-methylpyridin-4-yl)oxy]phenyl}amino)carbonyl]amino}-1H-pyrazol-1-yl)-2-methyl-N-(2-morpholin-4-ylethyl)benzenesulfonamide | 666 | 2.26 |

-continued

| Ex. No. | Structure | IUPAC name | LC-MS m/z (MH+) | Ret. time (min) |
|---|---|---|---|---|
| 26 | 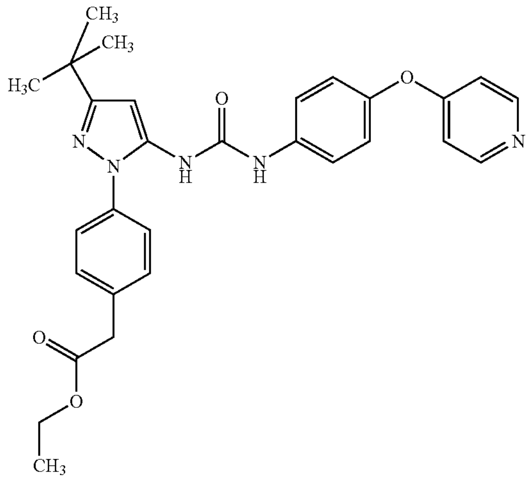 | ethyl (4-{3-tert-butyl-5-[({[4-(pyridin-4-yloxy)phenyl]amino}carbonyl)amino]-1H-pyrazol-1-yl}phenyl)acetate | 514 | 2.66 |
| 27 | 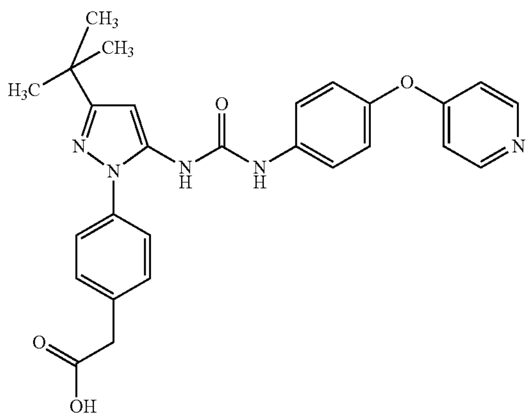 | (4-{3-tert-butyl-5-[({[4-(pyridin-4-yloxy)phenyl]amino}carbonyl)amino]-1H-pyrazol-1-yl}phenyl)acetic acid | 486 | 2.39 |
| 28 | 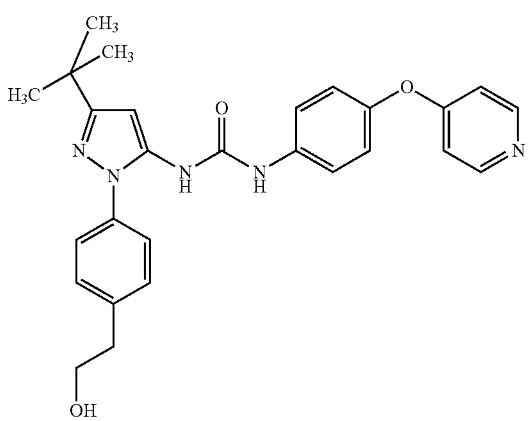 | N-{3-tert-butyl-1-[4-(2-hydroxyethyl)phenyl]-1H-pyrazol-5-yl}-N'-[4-(pyridin-4-yloxy)phenyl]urea | 472 | 2.36 |

-continued
| Ex. No. | Structure | | IUPAC name | LC-MS m/z (MH+) | Ret. time (min) |
|---|---|---|---|---|---|
| 29 | 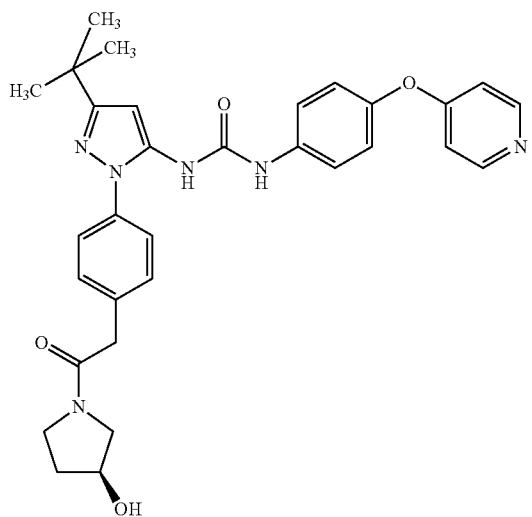 | Chiral | N-[3-tert-butyl-1-(4-{2-[(3S)-3-hydroxypyrrolidin-1-yl]-2-oxoethyl}phenyl)-1H-pyrazol-5-yl]-N'-[4-(pyridin-4-yloxy)phenyl]urea | 555 | 2.28 |
| 30 | 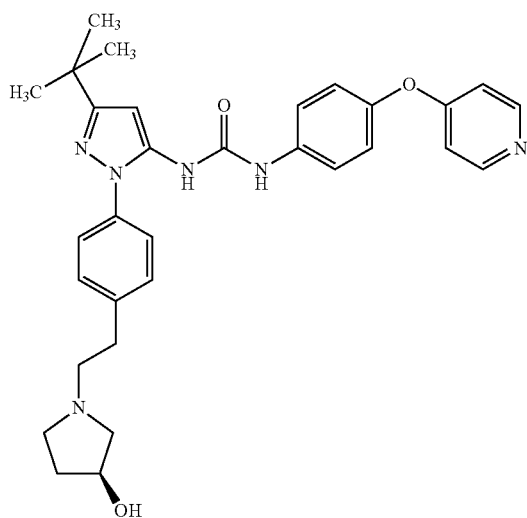 | Chiral | N-[3-tert-butyl-1-(4-{2-[(3S)-3-hydroxypyrrolidin-1-yl]ethyl}phenyl)-1H-pyrazol-5-yl]-N'-[4-(pyridin-4-yloxy)phenyl]urea | 541 | 2.04 |

-continued

| Ex. No. | Structure | IUPAC name | LC-MS m/z (MH+) | Ret. time (min) |
|---|---|---|---|---|
| 31 | 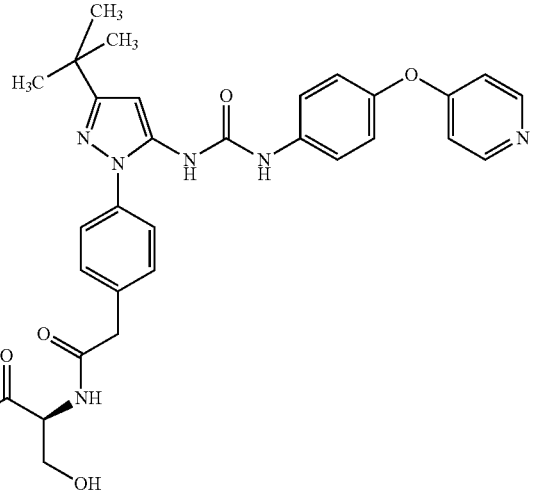 Chiral | methyl N-[(4-{3-tert-butyl-5-[({[4-(pyridin-4-yloxy)phenyl]amino}carbonyl)amino]-1H-pyrazol-1-yl}phenyl)acetyl]-L-serinate | 587 | 2.27 |
| 32 | 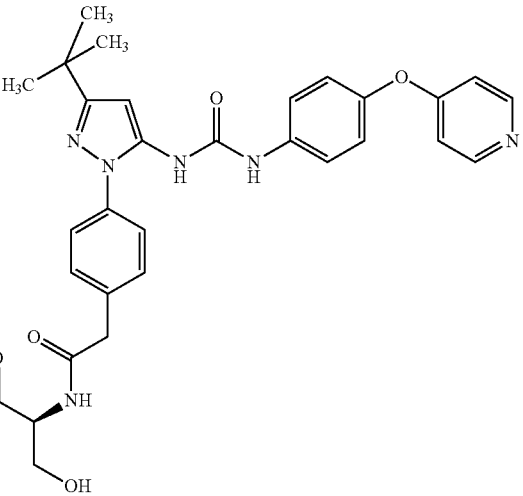 Chiral | N-[(4-{3-tert-butyl-5-[({[4-(pyridin-4-yloxy)phenyl]amino}carbonyl)amino]-1H-pyrazol-1-yl}phenyl)acetyl]-L-serine | 573 | 2.22 |
| 33 | 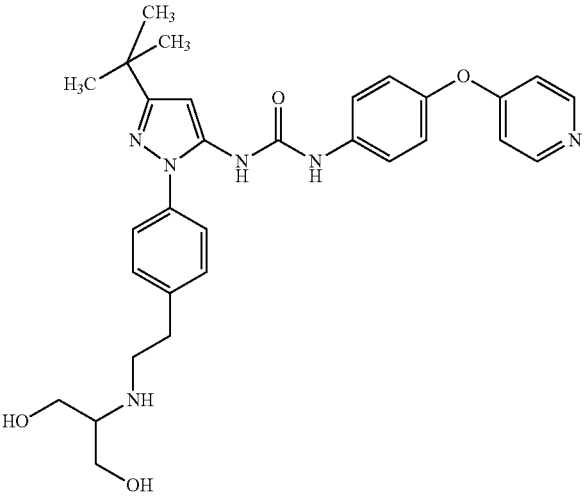 | N-{3-tert-butyl-1-[4-(2-{[2-hydroxy-1-(hydroxymethyl)ethyl]amino}ethyl)phenyl]-1H-pyrazol-5-yl}-N'-[4-(pyridin-4-yloxy)phenyl]urea | 545 | 2.14 |

-continued

| Ex. No. | Structure | IUPAC name | LC-MS m/z (MH+) | Ret. time (min) |
|---|---|---|---|---|
| 34 | 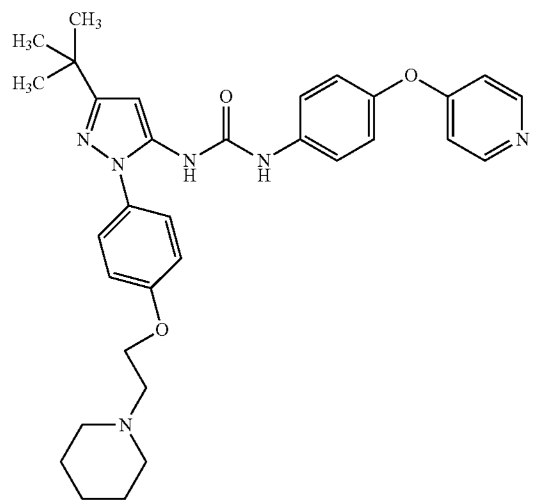 | N-{3-tert-butyl-1-[4-(2-piperidin-1-ylethoxy)phenyl]-1H-pyrazol-5-yl}-N'-[4-(pyridin-4-yloxy)phenyl]urea | 555 | 1.78 |
| 35 | 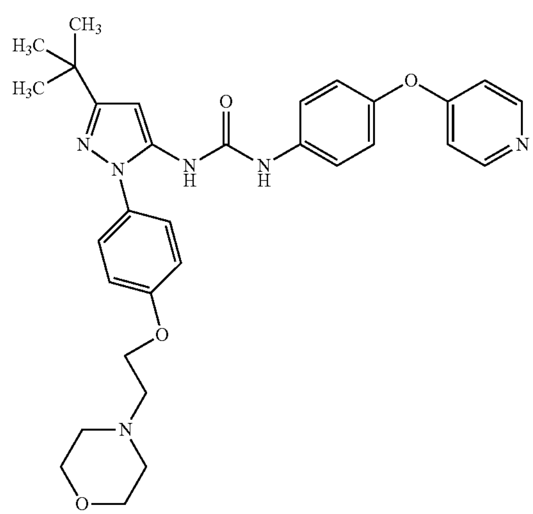 | N-{3-tert-butyl-1-[4-(2-morpholin-4-ylethoxy)phenyl]-1H-pyrazol-5-yl}-N'-[4-(pyridin-4-yloxy)phenyl]urea | 557 | 1.97 |
| 36 | 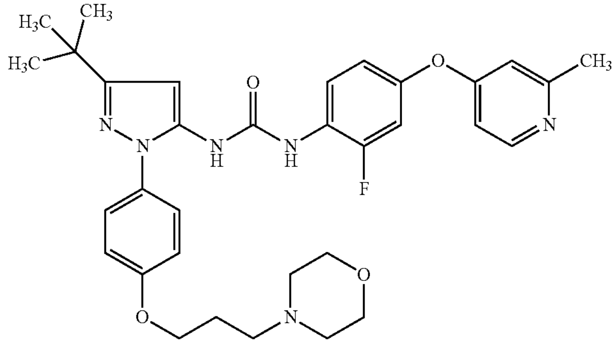 | N-{3-tert-butyl-1-[4-(3-morpholin-4-ylpropoxy)phenyl]-1H-pyrazol-5-yl}-N'-{2-fluoro-4-[(2-methylpyridin-4-yl)oxy]phenyl}urea | 603 | 2.12 |

| Ex. No. | Structure | IUPAC name | LC-MS m/z (MH+) | Ret. time (min) |
|---|---|---|---|---|
| 37 | 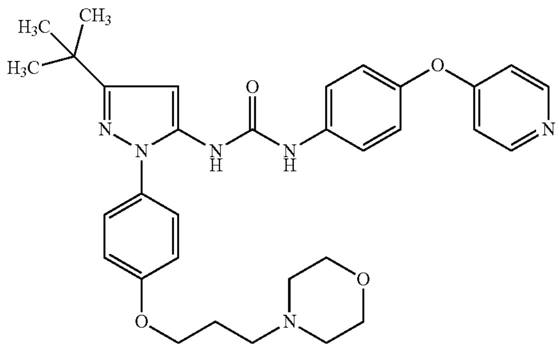 | N-{3-tert-butyl-1-[4-(3-morpholin-4-ylpropoxy)phenyl]-1H-pyrazol-5-yl}-N'-[4-(pyridin-4-yloxy)phenyl]urea | 571 | 2.47 |
| 38 | 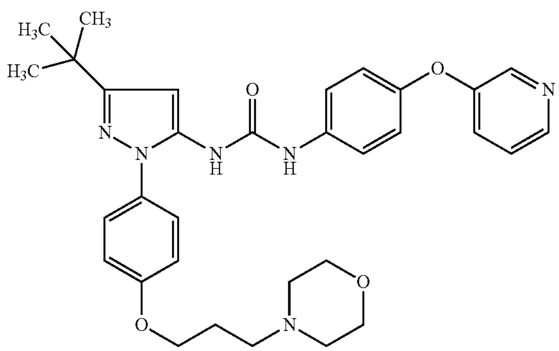 | N-{3-tert-butyl-1-[4-(3-morpholin-4-ylpropoxy)phenyl]-1H-pyrazol-5-yl}-N'-[4-(pyridin-3-yloxy)phenyl]urea | 571 | 2.73 |
| 39 | 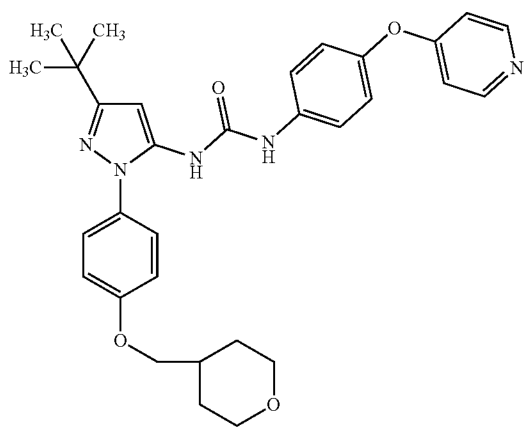 | N-{3-tert-butyl-1-[4-(tetrahydro-2H-pyran-4-ylmethoxy)phenyl]-1H-pyrazol-5-yl}-N'-[4-(pyridin-4-yloxy)phenyl]urea | 542 | 2.57 |
| 40 | 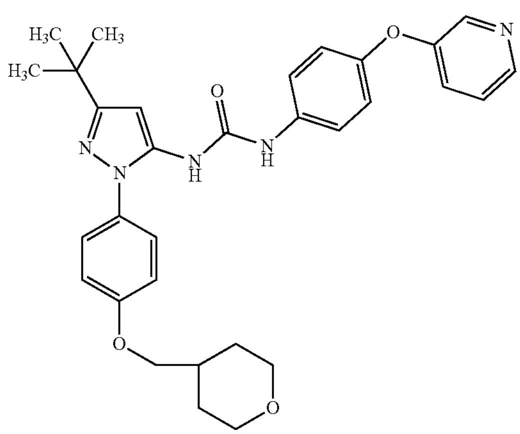 | N-{3-tert-butyl-1-[4-(tetrahydro-2H-pyran-4-ylmethoxy)phenyl]-1H-pyrazol-5-yl}-N'-[4-(pyridin-3-yloxy)phenyl]urea | 0 | 2.87 |

-continued

| Ex. No. | Structure | IUPAC name | LC-MS m/z (MH+) | Ret. time (min) |
|---|---|---|---|---|
| 41 | 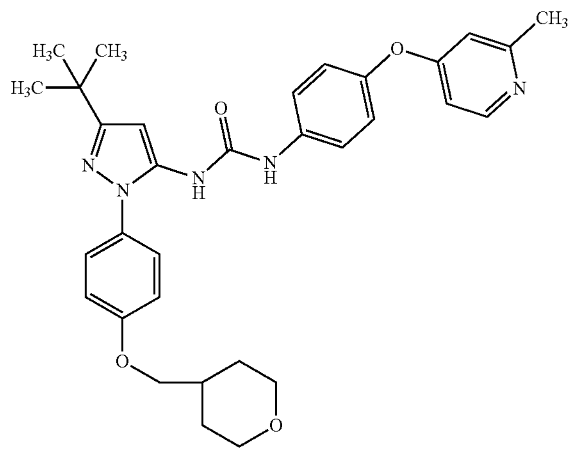 | N-{3-tert-butyl-1-[4-(tetrahydrohydro-2H-pyran-4-ylmethoxy)phenyl]-1H-pyrazol-5-yl}-N'-{2-fluoro-4-[(2-methylpyridin-4-yl)oxy]phenyl}urea | 574 | 2.67 |
| 42 | 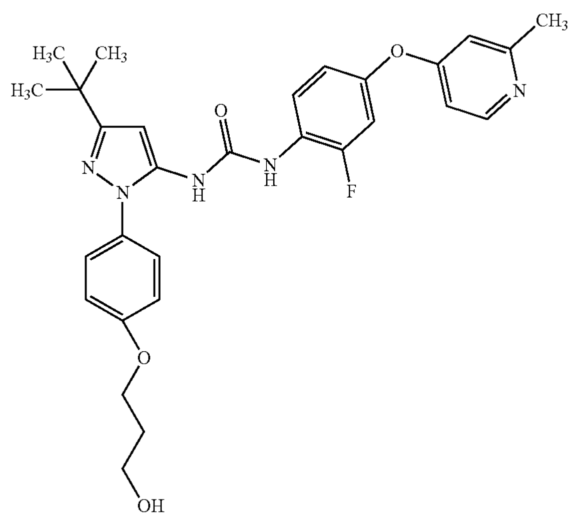 | N-{3-tert-butyl-1-[4-(3-hydroxypropoxy)phenyl]-1H-pyrazol-5-yl}-N'-{2-fluoro-4-[(2-methylpyridin-4-yl)oxy]phenyl}urea | 534 | 2.85 |
| 43 | 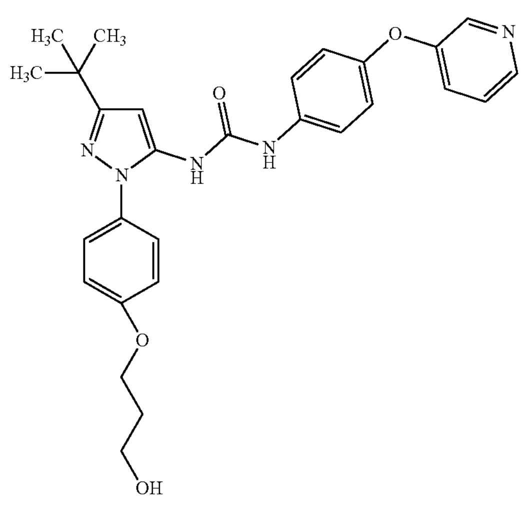 | N-{3-tert-butyl-1-[4-(3-hydroxypropoxy)phenyl]-1H-pyrazol-5-yl}-N'-[4-(pyridin-3-yloxy)phenyl]urea | 502 | 2.88 |

-continued

| Ex. No. | Structure | IUPAC name | LC-MS m/z (MH+) | Ret. time (min) |
|---|---|---|---|---|
| 44 | 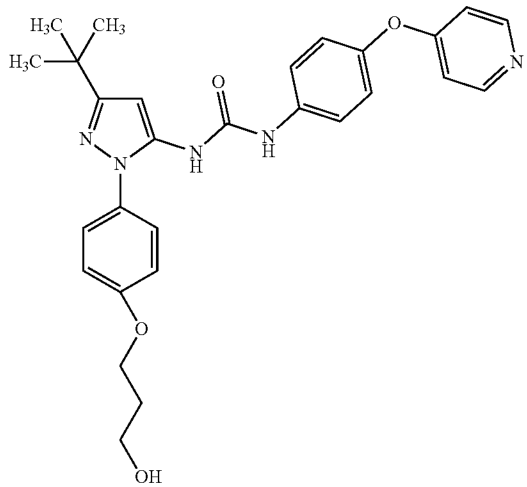 | N-{3-tert-butyl-1-[4-(3-hydroxypropoxy)phenyl]-1H-pyrazol-5-yl}-N'-[4-(pyridin-4-yloxy)phenyl]urea | 502 | 2.53 |
| 45 | 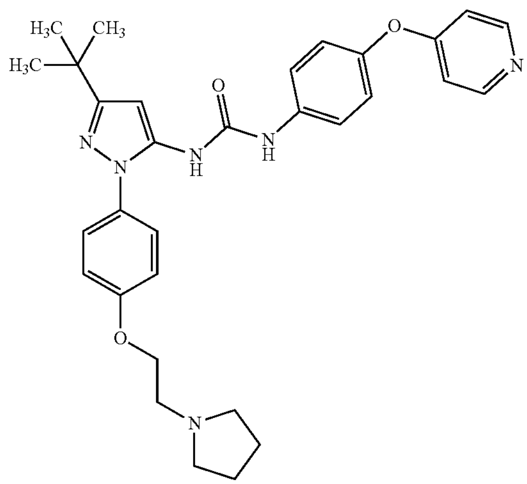 | N-{3-tert-butyl-1-[4-(2-pyrrolidin-1-ylethoxy)phenyl]-1H-pyrazol-5-yl}-N'-[4-(pyridin-4-yloxy)phenyl]urea | 541 | 2.52 |
| 46 | 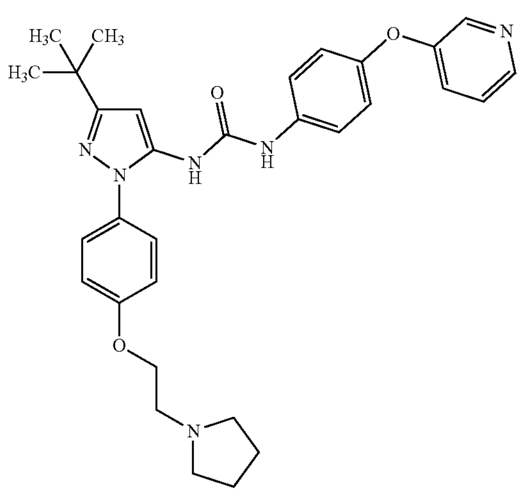 | N-{3-tert-butyl-1-[4-(2-pyrrolidin-1-ylethoxy)phenyl]-1H-pyrazol-5-yl}-N'-4-(pyridin-3-yloxy)phenyl]urea | 541 | 2.68 |

-continued

| Ex. No. | Structure | IUPAC name | LC-MS m/z (MH+) | Ret. time (min) |
| --- | --- | --- | --- | --- |
| 47 | 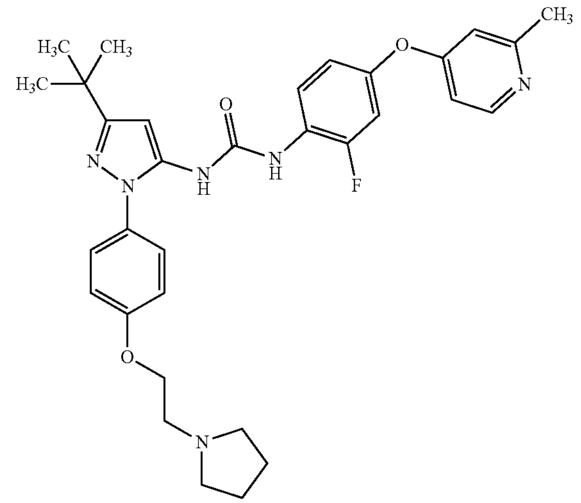 | N-{3-tert-butyl-1-[4-(2-pyrrolidin-1-ylethoxy)phenyl]-1H-pyrazol-5-yl}-N'-{2-fluoro-4-[(2-methylpyridin-4-yl)oxy]phenyl}urea | 573 | 2.57 |
| 48 | 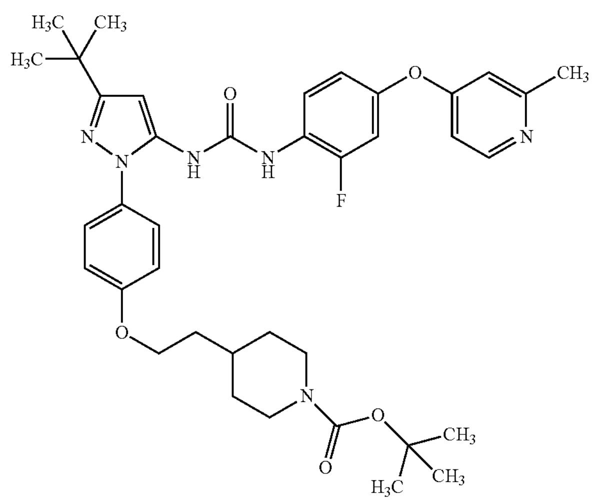 | tert-butyl 4-{2-[4-(3-tert-butyl-5-{[({2-fluoro-4-[(2-methylpyridin-4-yl)oxy]phenyl}amino)carbonyl]amino}-1H-pyrazol-1-yl)phenoxy]ethyl}piperidin-1-carboxylate | 687 | 3.24 |
| 49 | 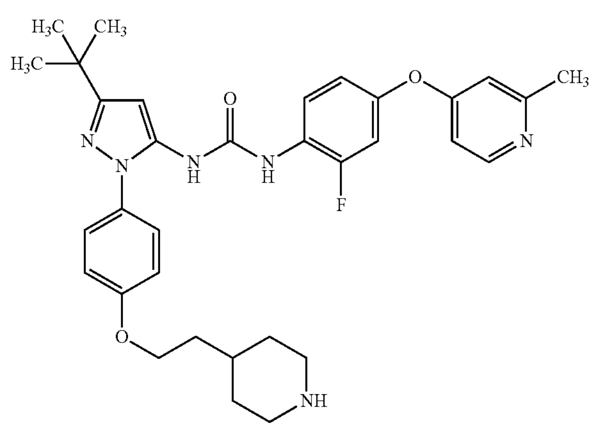 | N-{3-tert-butyl-1-[4-(2-piperidin-4-ylethoxy)phenyl]-1H-pyrazol-5-yl}-N'-{2-fluoro-4-[(2-methylpyridin-4-yl)oxy]phenyl}urea | 587 | 2.74 |

| Ex. No. | Structure | IUPAC name | LC-MS m/z (MH+) | Ret. time (min) |
|---|---|---|---|---|
| 50 | 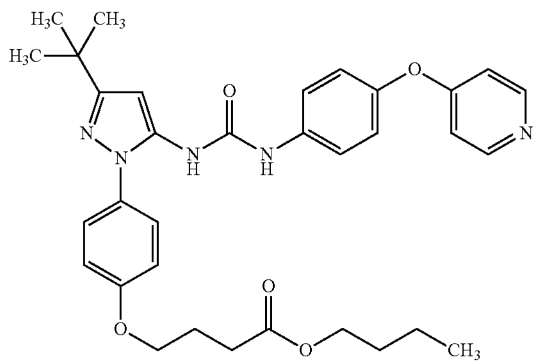 | butyl 4-(4-{3-tert-butyl-5-[({[4-(pyridin-4-yloxy)phenyl]amino}carbonyl)amino]-1H-pyrazol-1-yl}phenoxy)butanoate | 586 | 3.40 |
| 51 | 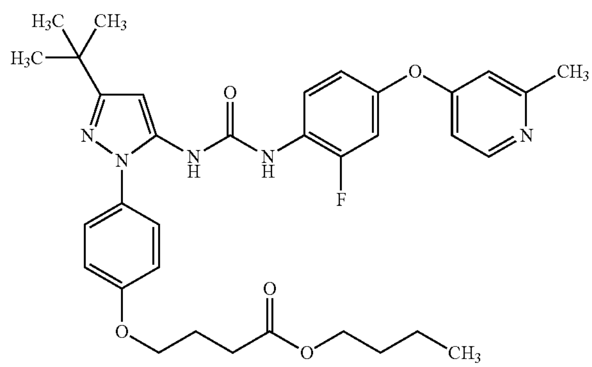 | butyl 4-[4-(3-tert-butyl-5-{[({2-fluoro-4-[(2-methylpyridin-4-yl)oxy]phenyl}amino)carbonyl]amino}-1H-pyrazol-1-yl)phenoxy]butanoate | 618 | 3.42 |
| 52 | 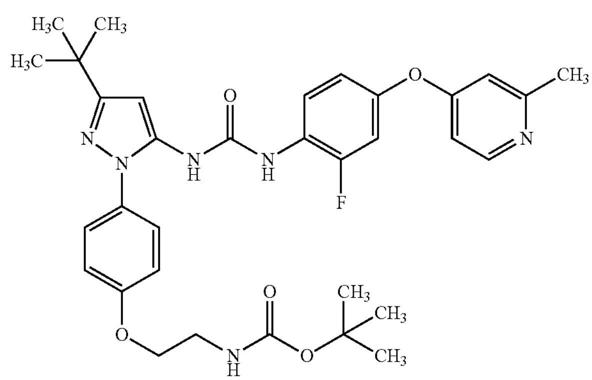 | tert-butyl {2-[4-(3-tert-butyl-5-{[({2-fluoro-4-[(2-methylpyridin-4-yl)oxy]phenyl}amino)carbonyl]amino}-1H-pyrazol-1-yl)phenoxy]ethyl}carbamate | 619 | 3.20 |
| 53 | 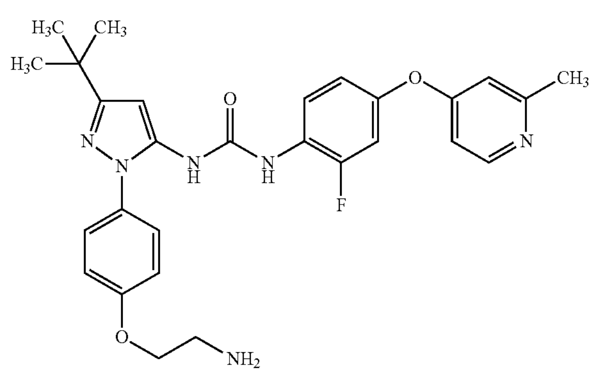 | N-{1-[4-(2-aminoethoxy)phenyl]-3-tert-butyl-1H-pyrazol-5-yl}-N'-{2-fluoro-4-[(2-methylpyridin-4-yl)oxy]phenyl}urea | 519 | 0.36 |

-continued

| Ex. No. | Structure | IUPAC name | LC-MS m/z (MH+) | Ret. time (min) |
|---|---|---|---|---|
| 54 | 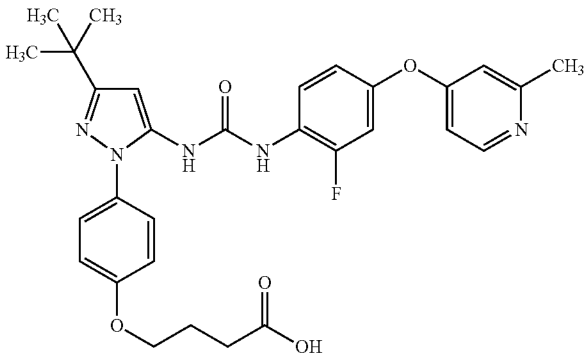 | 4-[4-(3-tert-butyl-5-{[({2-fluoro-4-[(2-methylpyridin-4-yl)oxy]phenyl}amino)carbonyl]amino}-1H-pyrazol-1-yl)phenoxy]butanoic acid | 562 | 2.95 |
| 55 | 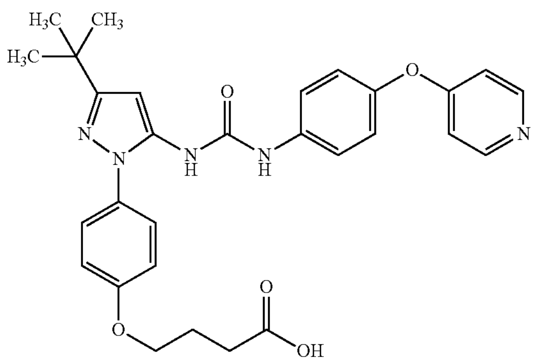 | 4-(4-{3-tert-butyl-5-[({[4-pyridin-4-yloxy)phenyl]amino}carbonyl)amino]-1H-pyrazol-1-yl}phenoxy)butanoic acid | 530 | 2.51 |
| 56 | 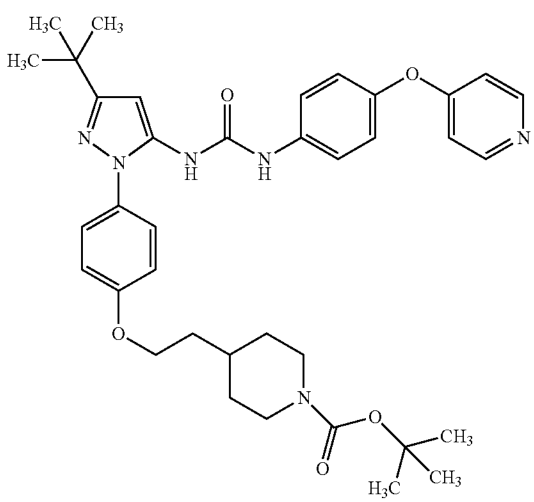 | tert-butyl 4-[2-(4-{3-tert-butyl-5-[({[4-(pyridin-4-yloxy)phenyl]amino}carbonyl)amino]-1H-pyrazol-1-yl}phenoxy)ethyl]piperidine-1-carboxylate | 655 | 3.48 |

| Ex. No. | Structure | IUPAC name | LC-MS m/z (MH+) | Ret. time (min) |
|---|---|---|---|---|
| 57 | 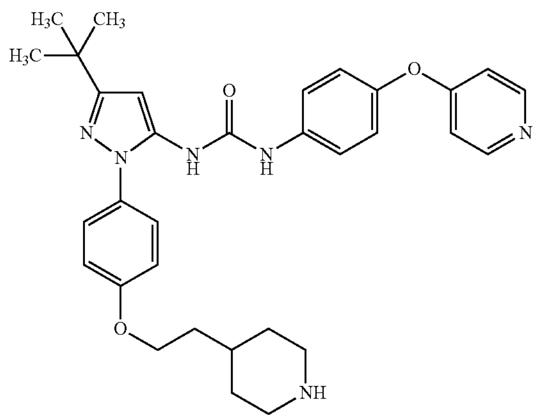 | N-{3-tert-butyl-1-[4-(2-piperidin-4-ylethoxy)phenyl]-1H-pyrazol-5-yl}-N'-[4-(pyridin-4-yloxy)phenyl]urea | 555 | 2.28 |
| 58 | 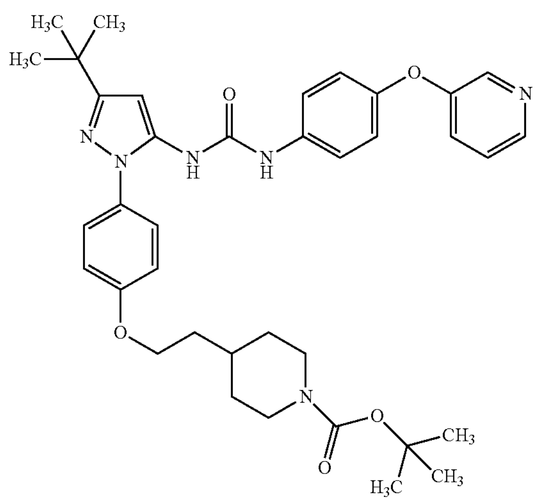 | tert-butyl 4-[2-(4-{3-tert-butyl-5-[({[4-(pyridin-3-yloxy)phenyl]amino}carbonyl)amino]-1H-pyrazol-1-yl}phenoxy)ethyl]piperidine-1-carboxylate | 655 | 3.51 |
| 59 | 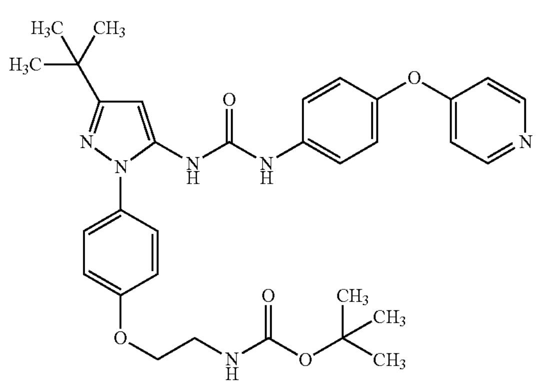 | tert-butyl [2-(4-{3-tert-butyl-5-[({[4-(pyridin-4-yloxy)phenyl]amino}carbonyl)amino]-1H-pyrazol-1-yl}phenoxy)ethyl]carbamate | 587 | 3.13 |

| Ex. No. | Structure | IUPAC name | LC-MS m/z (MH+) | Ret. time (min) |
|---|---|---|---|---|
| 60 | 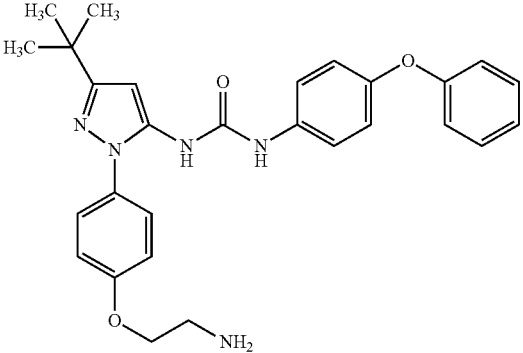 | N-{1-[4-(2-aminoethoxy)phenyl]-3-tert-butyl-1H-pyrazol-5-yl}-N'-[4-(pyridin-4-yloxy)phenyl]urea | 487 | 2.12 |
| 61 | 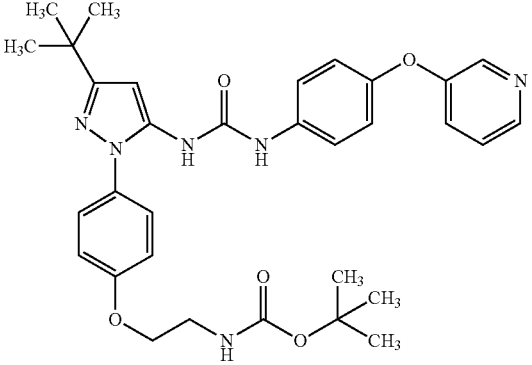 | tert-butyl [2-(4-{3-tert-butyl-5-[({[4-(pyridin-3-yloxy)phenyl]amino}carbonyl)amino]-1H-pyrazol-1-yl}phenoxy)ethyl]carbamate | 587 | 3.31 |
| 62 | 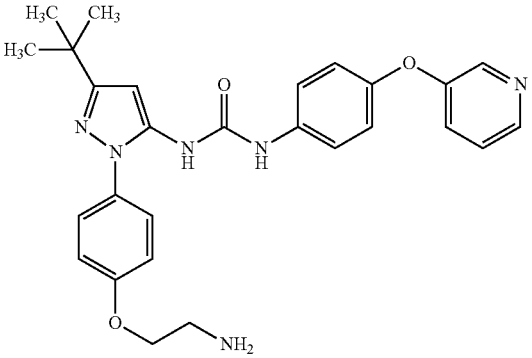 | N-{1-[4-(2-aminoethoxy)phenyl]-3-tert-butyl-1H-pyrazol-5-yl}-N'-[4-(pyridin-3-yloxy)phenyl]urea | 487 | 2.25 |

-continued

| Ex. No. | Structure | IUPAC name | LC-MS m/z (MH+) | Ret. time (min) |
|---|---|---|---|---|
| 63 | 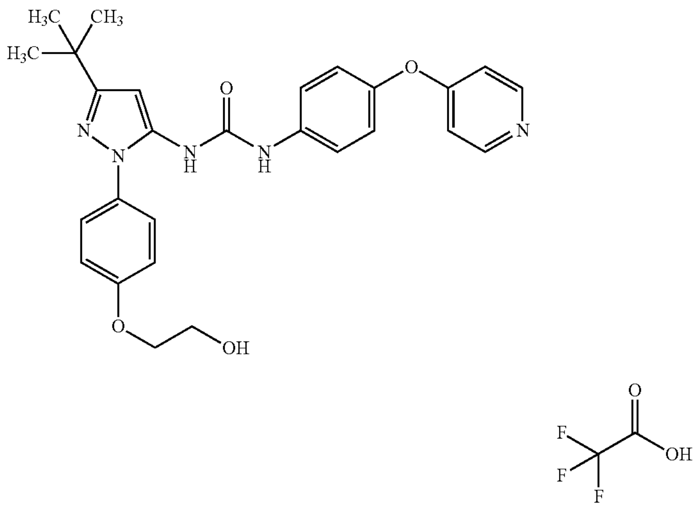 | N-{3-tert-butyl-1-[4-(2-hydroxyethoxy)phenyl]-1H-pyrazol-5-yl}-N'-[4-(pyridin-4-yloxy)phenyl]urea trifluoroacetate (salt) | 488 | 2.29 |
| 64 | 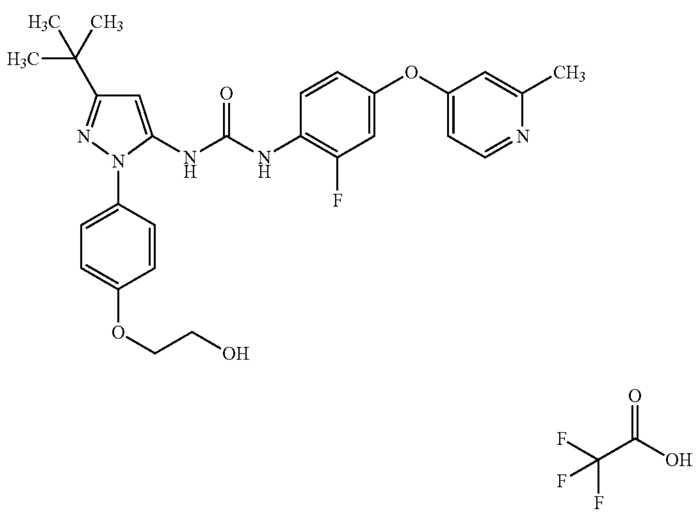 | N-{3-tert-butyl-1-[4-(2-hydroxyethoxy)phenyl]-1H-pyrazol-5-yl}-N'-{2-fluoro-4-[(2-methylpyridin-4-yl)oxy]phenyl}urea trifluoroacetate (salt) | 520 | 2.80 |
| 65 | 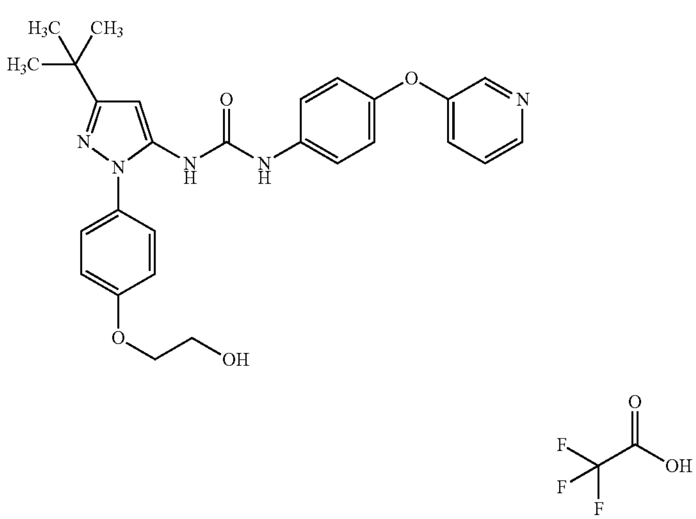 | N-{3-tert-butyl-1-[4-(2-hydroxyethoxy)phenyl]-1H-pyrazol-5-yl}-N'-[4-(pyridin-3-yloxy)phenyl]urea trifluoroacetate (salt) | 488 | 2.49 |

-continued

| Ex. No. | Structure | IUPAC name | LC-MS m/z (MH+) | Ret. time (min) |
|---|---|---|---|---|
| 66 | | N-{3-tert-butyl-1-[4-(2,3-dihydroxypropoxy)phenyl]-1H-pyrazol-5-yl}-N'-[4-pyridin-4-yloxy)phenyl]urea trifluoroacetate (salt) | 518 | 2.30 |
| 67 | | N-{3-tert-butyl-1-[4-(2,3-dihydroxypropoxy)phenyl]-1H-pyrazol-5-yl}-N'-{2-fluoro-4-[(2-methylpyridin-4-yl)oxy]phenyl}urea trifluoroacetate (salt) | 550 | 2.47 |
| 68 | 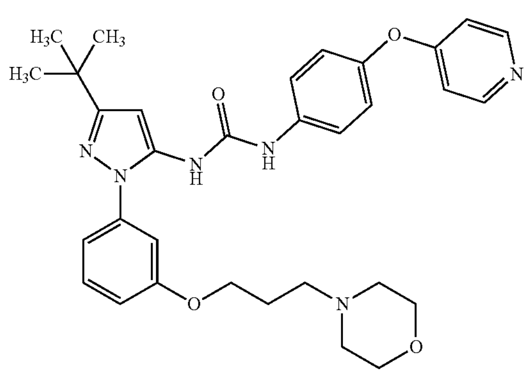 | N-{3-tert-butyl-1-[3-(3-morpholin-4-ylpropoxy)phenyl]-1H-pyrazol-5-yl}-N'-[4-(pyridin-4-yloxy)phenyl]urea | 571 | 2.53 |

-continued

| Ex. No. | Structure | IUPAC name | LC-MS m/z (MH+) | Ret. time (min) |
|---|---|---|---|---|
| 69 | 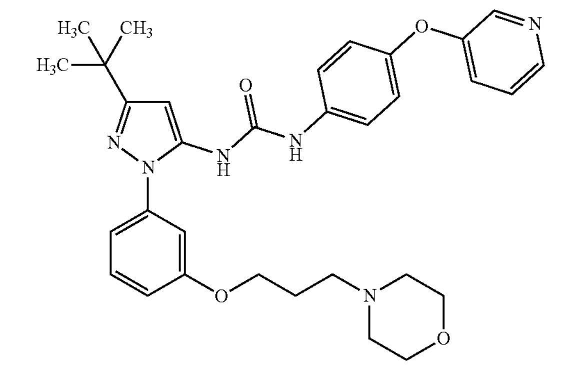 | N-{3-tert-butyl-1-[3-(3-morpholin-4-ylpropoxy)phenyl]-1H-pyrazol-5-yl}-N'-[4-(pyridin-3-yloxy)phenyl]urea | 571 | 2.32 |
| 70 | 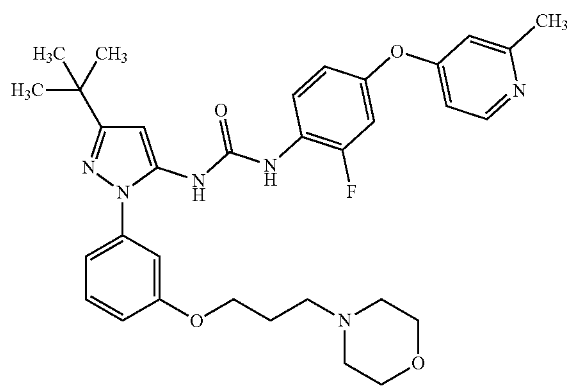 | N-{3-tert-butyl-1-[3-(3-morpholin-4-ylpropoxy)phenyl]-1H-pyrazol-5-yl}-N'-{2-fluoro-4-[(2-methylpyridin-4-yl)oxy]phenyl}urea | 603 | 2.21 |
| 71 | 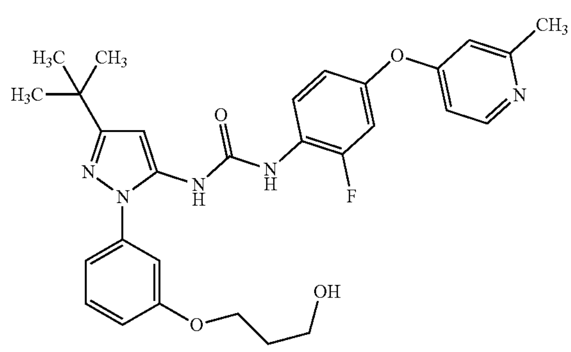 | N-{3-tert-butyl-1-[3-(3-hydroxypropoxy)phenyl]-1H-pyrazol-5-yl}-N'-{2-fluoro-4-[(2-methylpyridin-4-yl)oxy]phenyl}urea | 534 | 2.43 |
| 72 | 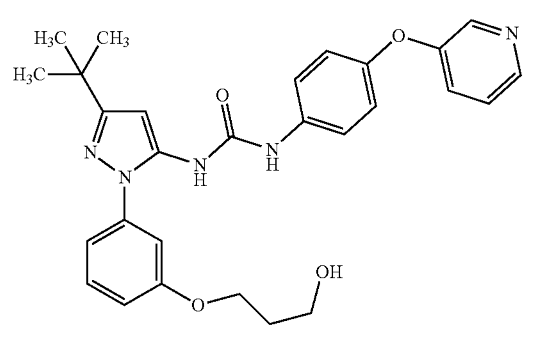 | N-{3-tert-butyl-1-[3-(3-hydroxypropoxy)phenyl]-1H-pyrazol-5-yl}-N'-[4-(pyridin-3-yloxy)phenyl]urea | 502 | 2.91 |

| Ex. No. | Structure | IUPAC name | LC-MS m/z (MH+) | Ret. time (min) |
|---|---|---|---|---|
| 73 | 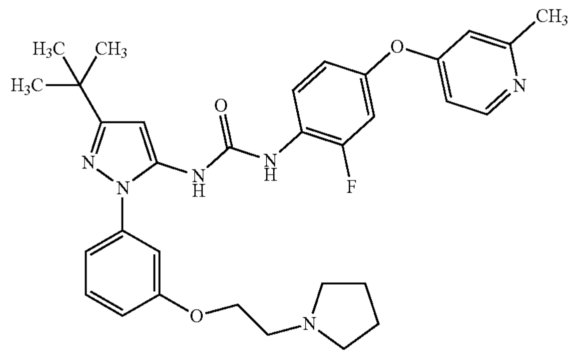 | N-{3-tert-butyl-1-[3-(2-pyrrolidin-1-ylethoxy)phenyl]-1H-pyrazol-5-yl}-N'-{2-fluoro-4-[(2-methylpyridin-4-yl)oxy]phenyl}urea | 573 | 2.12 |
| 74 | 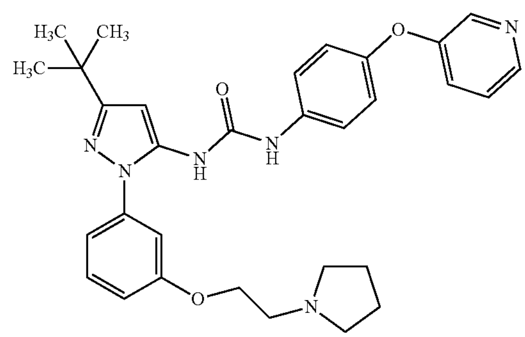 | N-{3-tert-butyl-1-[3-(2-pyrrolidin-1-ylethoxy)phenyl]-1H-pyrazol-5-yl}-N'-[4-(pyridin-3-yloxy)phenyl]urea | 541 | 2.24 |
| 75 | 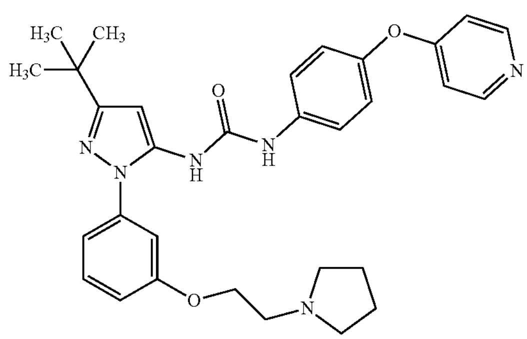 | N-{3-tert-butyl-1-[3-(2-pyrrolidin-1-ylethoxy)phenyl]-1H-pyrazol-5-yl}-N'-[4-(pyridin-4-yloxy)phenyl]urea | 541 | 2.06 |
| 76 | 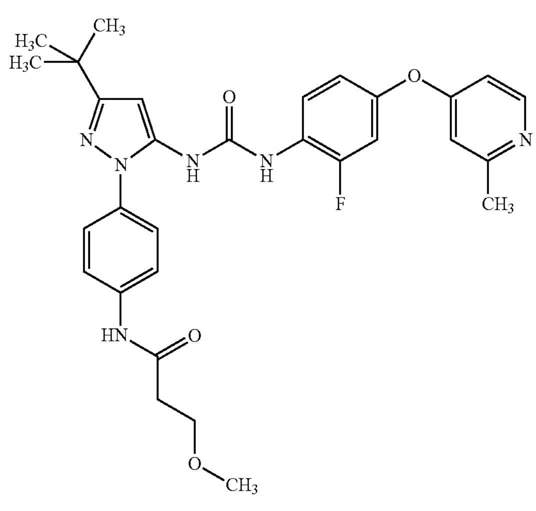 | N-[4-(3-tert-butyl-5-{[({2-fluoro-4-[(2-methylpyridin-4-yl)oxy]phenyl}amino)carbonyl]amino}-1H-pyrazol-1-yl)phenyl]-3-methoxypropanamide | 561 | 2.27 |

| Ex. No. | Structure | IUPAC name | LC-MS m/z (MH+) | Ret. time (min) |
|---|---|---|---|---|
| 77 | 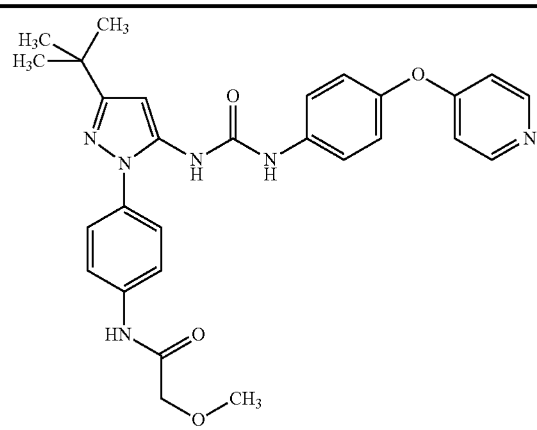 | N-(4-{3-tert-butyl-5-[({[4-(pyridin-4-yloxy)phenyl]amino}carbonyl)amino]-1H-pyrazol-1-yl}phenyl)-2-methoxyacetamide | 515 | 2.28 |
| 78 | 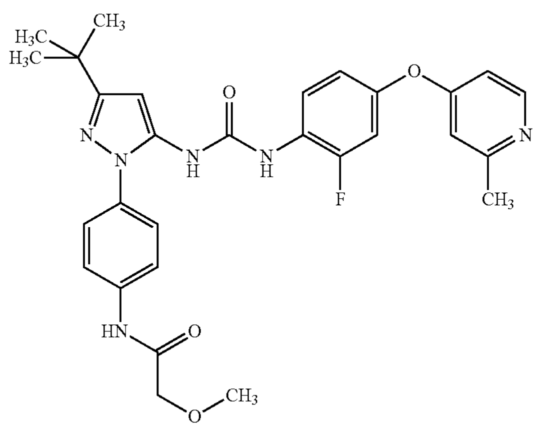 | N-[4-(3-tert-butyl-5-{[({2-fluoro-4-[(2-methylpyridin-4-yl)oxy]phenyl}amino)carbonyl]amino}-1H-pyrazol-1-yl)phenyl]-2-methoxyacetamide | 547 | 1.65 |
| 79 | 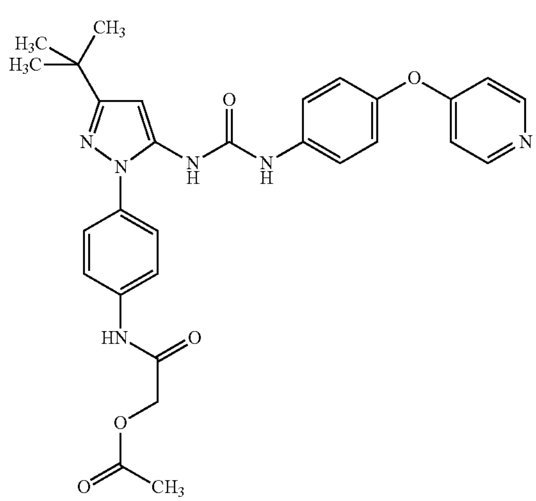 | 2-[(4-{3-tert-butyl-5-[({[4-(pyridin-4-yloxy)phenyl]amino}carbonyl)amino]-1H-pyrazol-1-yl}phenyl)amino]-2-oxoethyl acetate | 543 | 2.78 |

| Ex. No. | Structure | IUPAC name | LC-MS m/z (MH+) | Ret. time (min) |
|---|---|---|---|---|
| 80 | 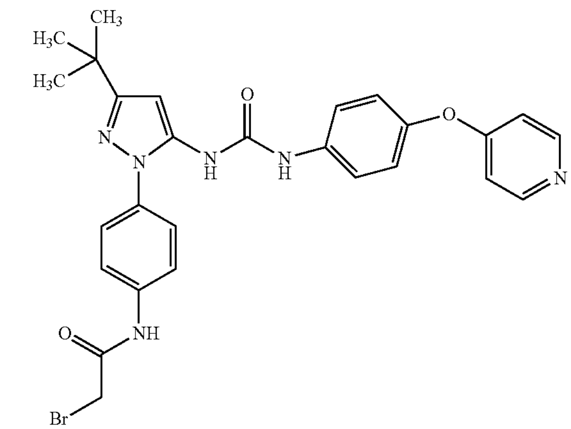 | 2-bromo-N-(4-{3-tert-butyl-5-[({[4-(pyridin-4-yloxy)phenyl]amino}carbonyl)amino]-1H-pyrazol-1-yl}phenyl)acetamide | 563 | 2.13 |
| 81 | 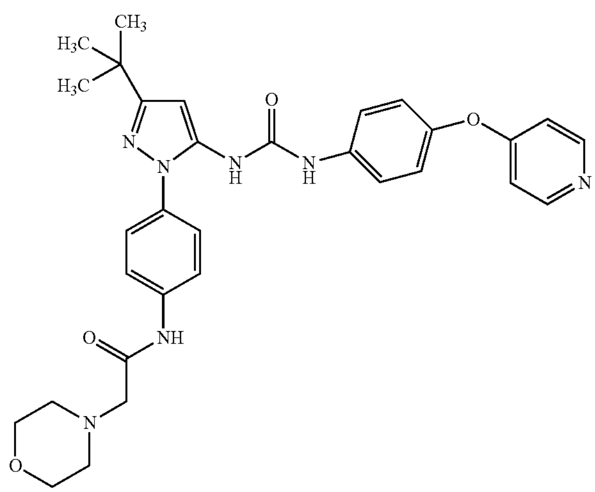 | N-(4-{3-tert-butyl-5-[({[4-(pyridin-4-yloxy)phenyl]amino}carbonyl)amino]-1H-pyrazol-1-yl}phenyl)-2-morpholin-4-ylacetamide | 570 | 1.96 |
| 82 | 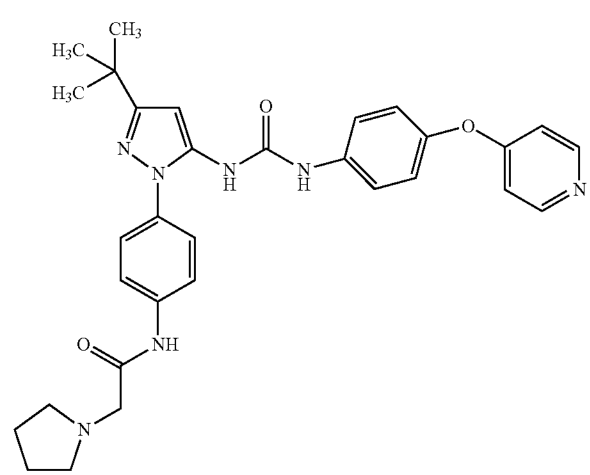 | N-(4-{3-tert-butyl-5-[({[4-(pyridin-4-yloxy)phenyl]amino}carbonyl)amino]-1H-pyrazol-1-yl}phenyl)-2-pyrrolidin-1-ylacetamide | 554 | 1.91 |

-continued

| Ex. No. | Structure | IUPAC name | LC-MS m/z (MH+) | Ret. time (min) |
|---|---|---|---|---|
| 83 | 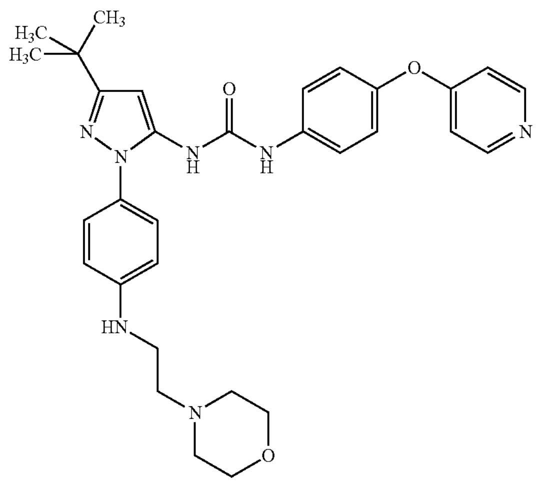 | N-(3-tert-butyl-1-{4-[(2-morpholin-4-ylethyl)amino]phenyl}-1H-pyrazol-5-yl)-N'-[4-(pyridin-4-yloxy)phenyl]urea | 556 | 1.53 |
| 84 | 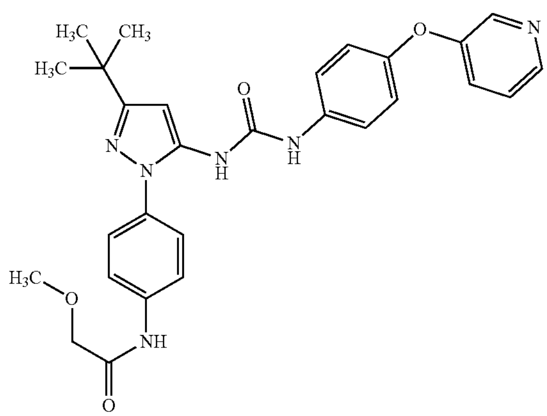 | N-(4-{3-tert-butyl-5-[({[4-(pyridin-3-yloxy)phenyl]amino}carbonyl)amino]-1H-pyrazol-1-yl}phenyl)-2-methoxyacetamide | 515 | 2.56 |
| 85 | 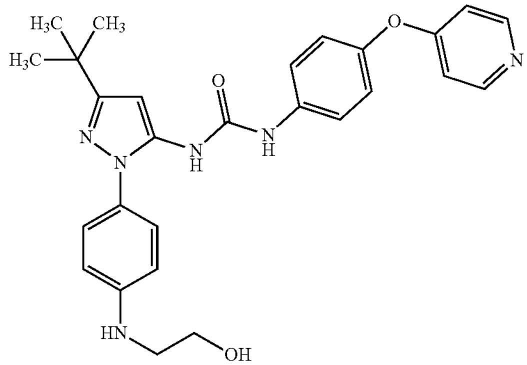 | N-(3-tert-butyl-1-{4-[(2-hydroxyethyl)amino]phenyl}-1H-pyrazol-5-yl)-N'-[4-(pyridin-4-yloxy)phenyl]urea | 487 | 2.22 |

-continued

| Ex. No. | Structure | IUPAC name | LC-MS m/z (MH+) | Ret. time (min) |
|---|---|---|---|---|
| 86 | 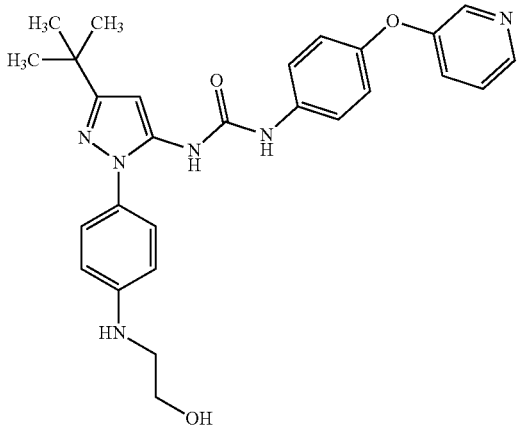 | N-(3-tert-butyl-1-{4-[(2-hydroxyethyl)amino]phenyl}-1H-pyrazol-5-yl)-N'-[4-(pyridin-3-yloxy)phenyl]urea | 487 | 2.44 |
| 87 | 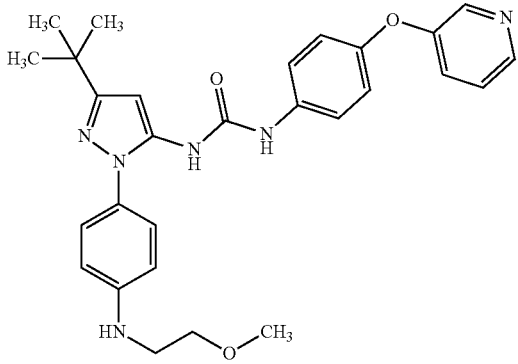 | N-(3-tert-butyl-1-{4-[(2-methoxyethyl)amino]phenyl}-1H-pyrazol-5-yl)-N'-[4-(pyridin-3-yloxy)phenyl]urea | 501 | 2.61 |
| 88 | 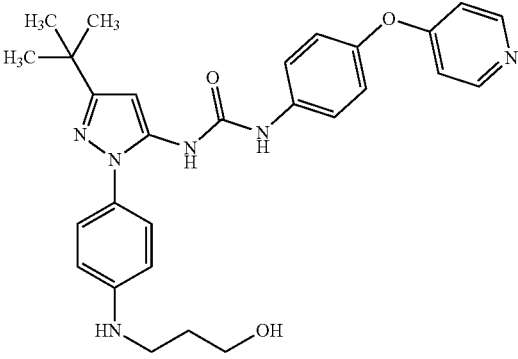 | N-(3-tert-butyl-1-{4-[(3-hydroxypropyl)amino]phenyl}-1H-pyrazol-5-yl)-N'-[4-(pyridin-4-yloxy)phenyl]urea | 501 | 2.26 |
| 89 | 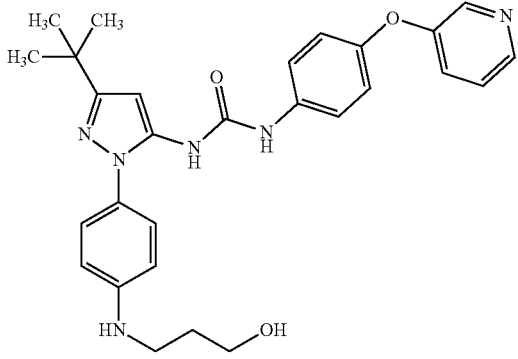 | N-(3-tert-butyl-1-{4-[(3-hydroxypropyl)amino]phenyl}-1H-pyrazol-5-yl)-N'-[4-(pyridin-3-yloxy)phenyl]urea | 501 | 2.45 |

-continued

| Ex. No. | Structure | IUPAC name | LC-MS m/z (MH+) | Ret. time (min) |
|---|---|---|---|---|
| 90 | 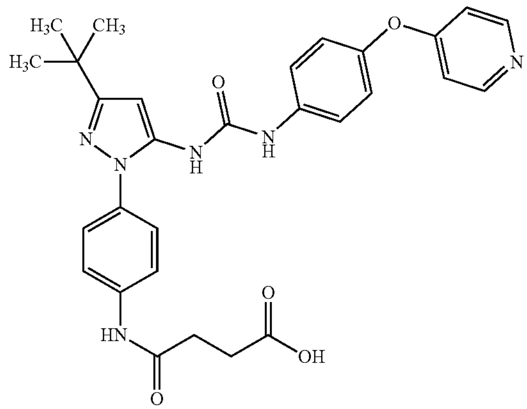 | 4-[(4-{3-tert-butyl-5-[({[4-(pyridin-4-yloxy)phenyl]amino}carbonyl)amino]-1H-pyrazol-1-yl}phenyl)amino]-4-oxobutanoic acid | 543 | 2.37 |
| 91 | 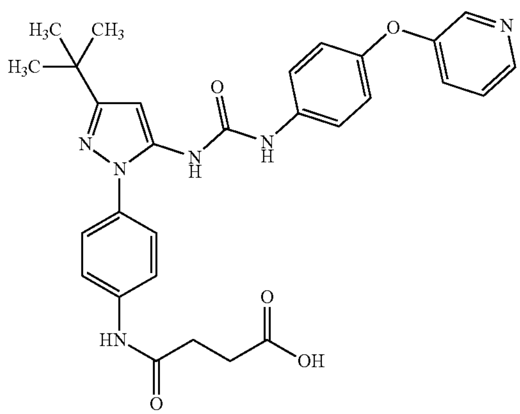 | 4-[(4-{3-tert-butyl-5-[({[4-(pyridin-3-yloxy)phenyl]amino}carbonyl)amino]-1H-pyrazol-1-yl}phenyl)amino]-4-oxobutanoic acid | 543 | 2.53 |
| 92 | 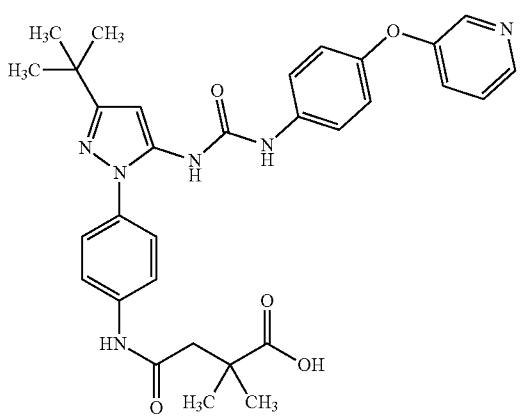 | 4-[(4-{3-tert-butyl-5-[({[4-(pyridin-3-yloxy)phenyl]amino}carbonyl)amino]-1H-pyrazol-1-yl}phenyl)amino]-2,2-dimethyl-4-oxobutanoic acid | 571 | 2.65 |

| Ex. No. | Structure | IUPAC name | LC-MS m/z (MH+) | Ret. time (min) |
|---|---|---|---|---|
| 93 | 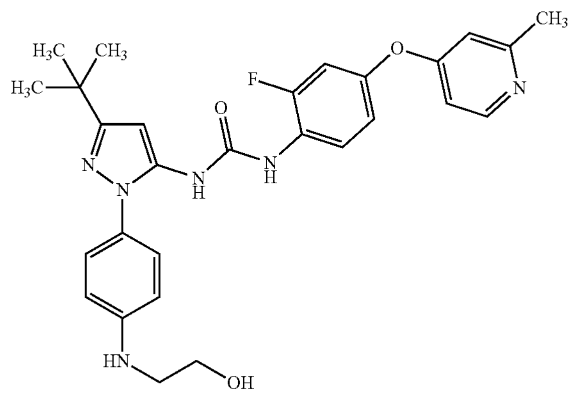 | N-(3-tert-butyl-1-{4-[(2-hydroxyethyl)amino]phenyl}-1H-pyrazol-5-yl)-N'-{2-fluoro-4-[(2-methylpyridin-4-yl)oxy]phenyl}urea | 519 | 1.69 |
| 94 | 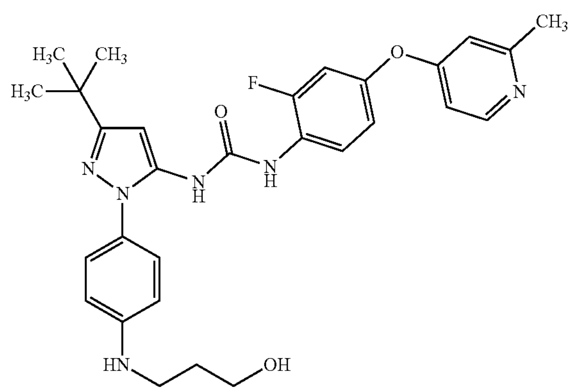 | N-(3-tert-butyl-1-{4-[(3-hydroxypropyl)amino]phenyl}-1H-pyrazol-5-yl)-N'-{2-fluoro-4-[(2-methylpyridin-4-yl)oxy]phenyl}urea | 533 | 2.30 |
| 95 | 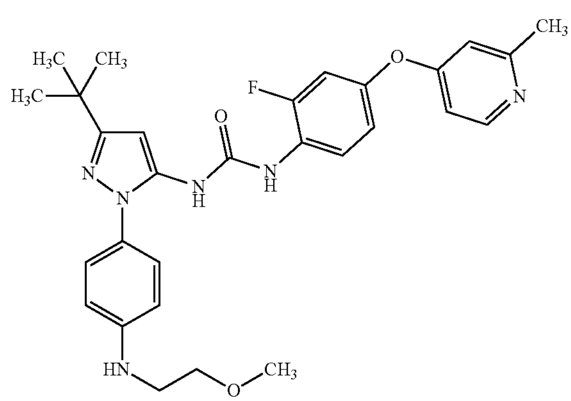 | N-(3-tert-butyl-1-{4-[(2-methoxyethyl)amino]phenyl}-1H-pyrazol-5-yl)-N'-{2-fluoro-4-[(2-methylpyridin-4-yl)oxy]phenyl}urea | 533 | 2.46 |

-continued

| Ex. No. | Structure | IUPAC name | LC-MS m/z (MH+) | Ret. time (min) |
|---|---|---|---|---|
| 96 | 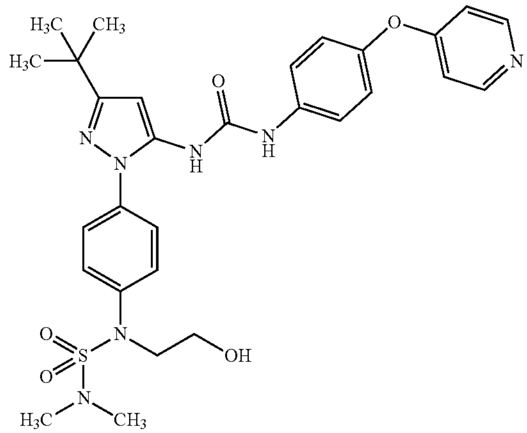 | N-(3-tert-butyl-1-{4-[[(dimethylamino)sulfonyl](2-hydroxyethyl)amino]phenyl}-1H-pyrazol-5-yl)-N'-[4-(pyridin-4-yloxy)phenyl]urea | 594 | 2.40 |
| 97 | 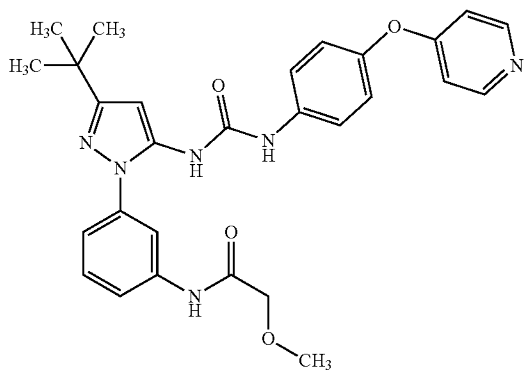 | N-(3-{3-tert-butyl-5-[({[4-(pyridin-4-yloxy)phenyl]amino}carbonyl)amino]-1H-pyrazol-1-yl}phenyl)-2-methoxyacetamide | 515 | 2.42 |
| 98 | 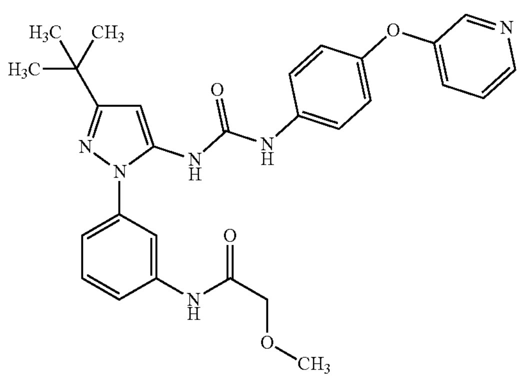 | N-(3-{3-tert-butyl-5-[({[4-(pyridin-3-yloxy)phenyl]amino}carbonyl)amino]-1H-pyrazol-1-yl}phenyl)-2-methoxyacetamide | 515 | 2.59 |
| 99 | 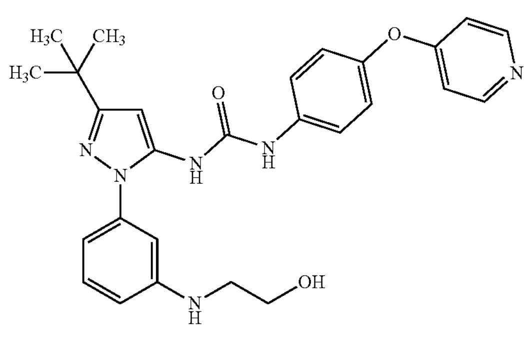 | N-(3-tert-butyl-1-{3-[(2-hydroxyethyl)amino]phenyl}-1H-pyrazol-5-yl)-N'-[4-(pyridin-4-yloxy)phenyl]urea | 487 | 2.30 |

-continued

| Ex. No. | Structure | IUPAC name | LC-MS m/z (MH+) | Ret. time (min) |
|---|---|---|---|---|
| 100 | 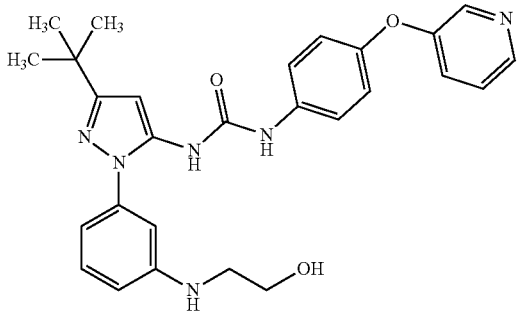 | N-(3-tert-butyl-1-{3-[(2-hydroxyethyl)amino]phenyl}-1H-pyrazol-5-yl)-N'-[4-(pyridin-3-yloxy)phenyl]urea | 487 | 2.49 |
| 101 | 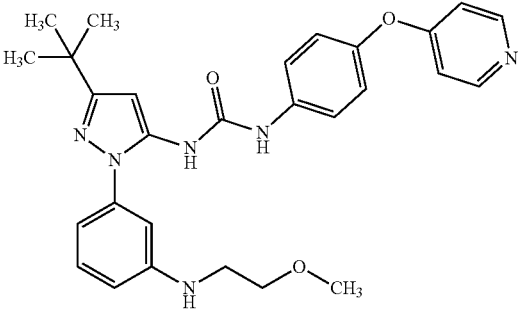 | N-(3-tert-butyl-1-{3-[(2-methoxyethyl)amino]phenyl}-1H-pyrazol-5-yl)-N'-[4-(pyridin-4-yloxy)phenyl]urea | 501 | 2.46 |
| 102 | 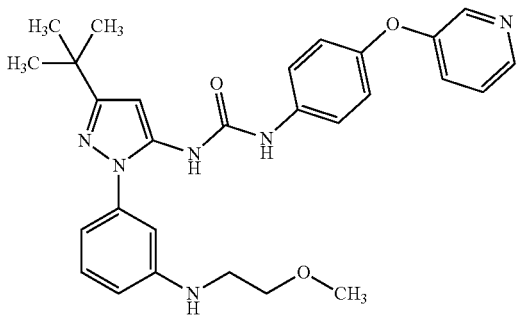 | N-(3-tert-butyl-1-{3-[(2-methoxyethyl)amino]phenyl}-1H-pyrazol-5-yl)-N'-[4-(pyridin-3-yloxy)phenyl]urea | 501 | 2.70 |
| 103 | 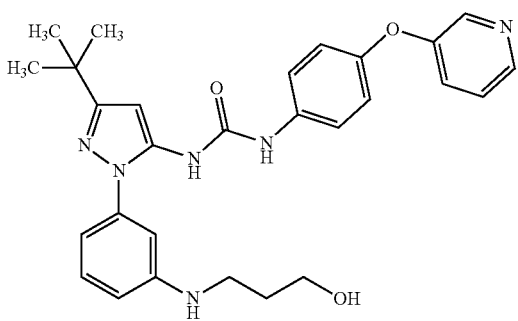 | N-(3-tert-butyl-1-{3-[(3-hydroxypropyl)amino]phenyl}-1H-pyrazol-5-yl)-N'-[4-(pyridin-3-yloxy)phenyl]urea | 501 | 2.48 |

-continued

| Ex. No. | Structure | IUPAC name | LC-MS m/z (MH+) | Ret. time (min) |
|---|---|---|---|---|
| 104 | 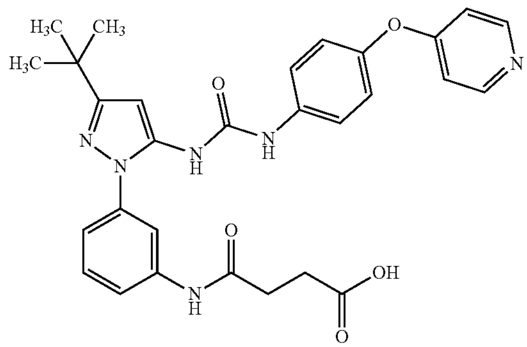 | 4-[(3-{3-tert-butyl-5-[({[4-(pyridin-4-yloxy)phenyl]amino}carbonyl)amino]-1H-pyrazol-1-yl}phenyl)amino]-4-oxobutanoic acid | 543 | 2.32 |
| 105 | 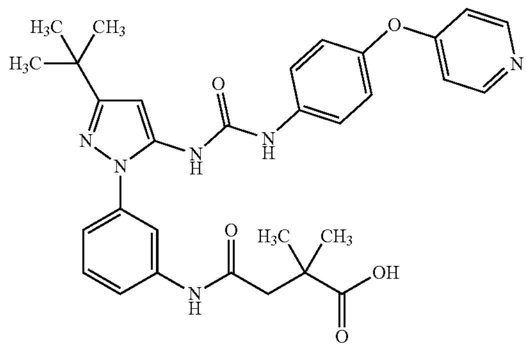 | 4-[(3-{3-tert-butyl-5-[({[4-(pyridin-4-yloxy)phenyl]amino}carbonyl)amino]-1H-pyrazol-1-yl}phenyl)amino]-2,2-dimethyl-4-oxobutanoic acid | 571 | 2.48 |
| 106 | 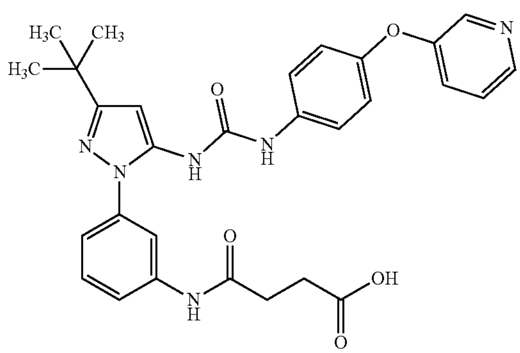 | 4-[(3-{3-tert-butyl-5-[({[4-(pyridin-3-yloxy)phenyl]amino}carbonyl)amino]-1H-pyrazol-1-yl}phenyl)amino]-4-oxobutanoic acid | 543 | 2.54 |
| 107 | 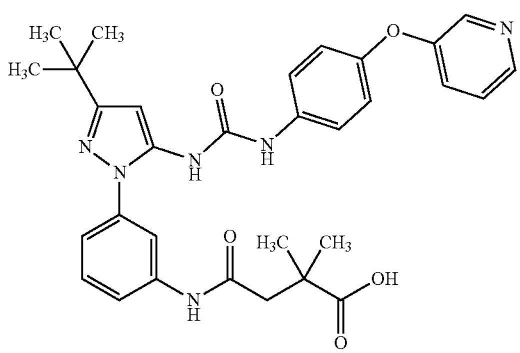 | 4-[(3-{3-tert-butyl-5-[({[4-(pyridin-3-yloxy)phenyl]amino}carbonyl)amino]-1H-pyrazol-1-yl}phenyl)amino]-2,2-dimethyl-4-oxobutanoic acid | 571 | 2.71 |

-continued

| Ex. No. | Structure | IUPAC name | LC-MS m/z (MH+) | Ret. time (min) |
|---|---|---|---|---|
| 108 | 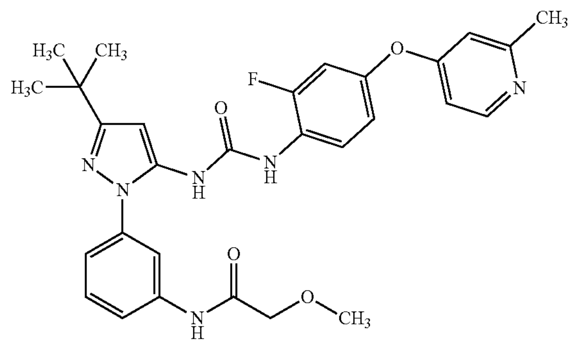 | N-[3-(3-tert-butyl-5-{[({2-fluoro-4-[(2-methylpyridin-4-yl)oxy]phenyl}amino)carbonyl]amino}-1H-pyrazol-1-yl)phenyl]-2-methoxyacetamide | 547 | 2.55 |
| 109 | 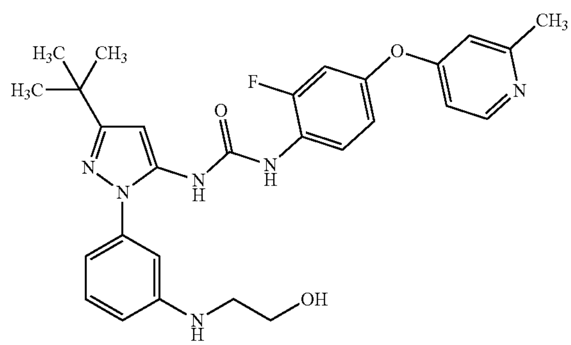 | N-(3-tert-butyl-1-{3-[(2-hydroxyethyl)amino]phenyl}-1H-pyrazol-5-yl)-N'-{2-fluoro-4-[(2-methylpyridin-4-yl)oxy]phenyl}urea | 519 | 1.80 |
| 110 | 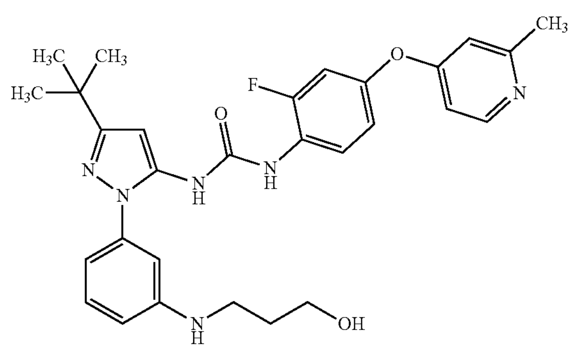 | N-(3-tert-butyl-1-{3-[(3-hydroxypropyl)amino]phenyl}-1H-pyrazol-5-yl)-N'-{2-fluoro-4-[(2-methylpyridin-4-yl)oxy]phenyl}urea | 533 | 2.35 |
| 111 | 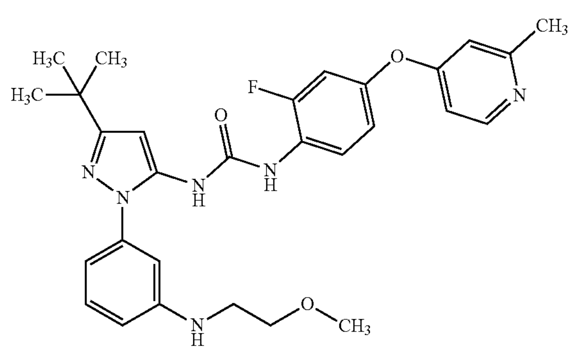 | N-(3-tert-butyl-1-{3-[(2-methoxyethyl)amino]phenyl}-1H-pyrazol-5-yl)-N'-{2-fluoro-4-[(2-methylpyridin-4-yl)oxy]phenyl}urea | 533 | 2.51 |

-continued

| Ex. No. | Structure | IUPAC name | LC-MS m/z (MH+) | Ret. time (min) |
|---|---|---|---|---|
| 112 | 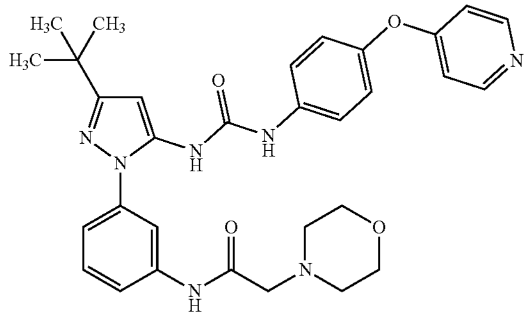 | N-(3-{3-tert-butyl-5-[({[4-(pyridin-4-yloxy)phenyl]amino}carbonyl)amino]-1H-pyrazol-1-yl}phenyl)-2-morpholin-4-ylacetamide | 570 | 2.11 |
| 113 | 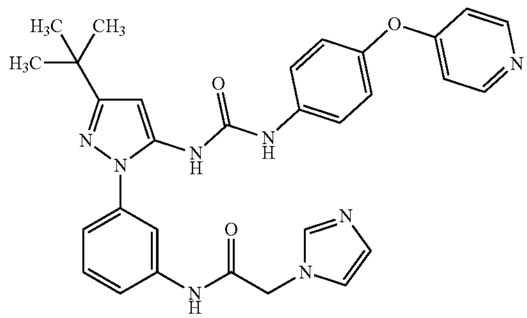 | N-(3-{3-tert-butyl-5-[({[4-(pyridin-4-yloxy)phenyl]amino}carbonyl)amino]-1H-pyrazol-1-yl}phenyl)-2-(1H-imidazol-1-yl)acetamide | 551 | 2.08 |
| 114 | 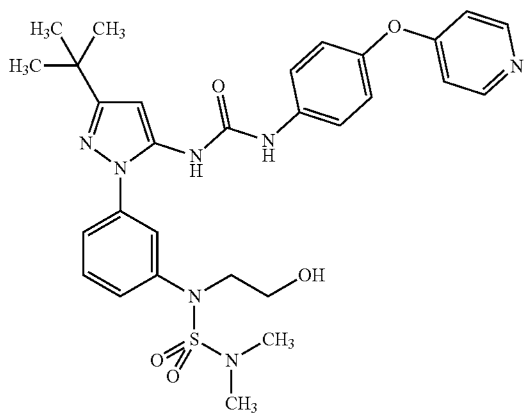 | N-(3-tert-butyl-1-{3-[[(dimethylamino)sulfonyl](2-hydroxyethyl)amino]phenyl]-1H-pyrazol-5-yl)-N'-[4-(pyridin-4-yloxy)phenyl]urea | 594 | 2.42 |
| 115 | 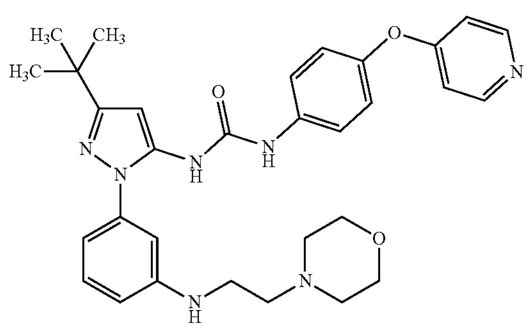 | N-(3-tert-butyl-1-{3-[(2-morpholin-4-ylethyl)amino]phenyl}-1H-pyrazol-5-yl)-N'-[4-(pyridin-4-yloxy)phenyl]urea | 556 | 2.07 |

-continued

| Ex. No. | Structure | IUPAC name | LC-MS m/z (MH+) | Ret. time (min) |
|---|---|---|---|---|
| 116 | 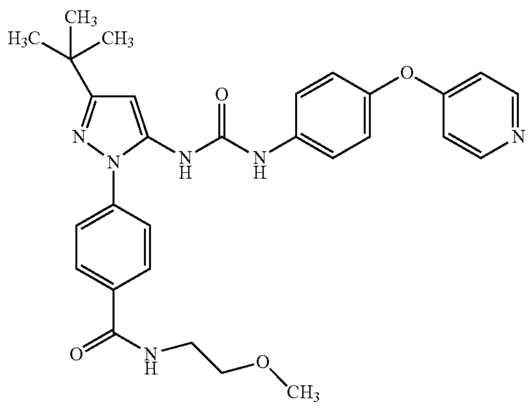 | 4-{3-tert-butyl-5-[({[4-(pyridin-4-yloxy)phenyl]amino}carbonyl)amino]-1H-pyrazol-1-yl}-N-(2-methoxyethyl)benzamide | 529 | 2.17 |
| 117 | 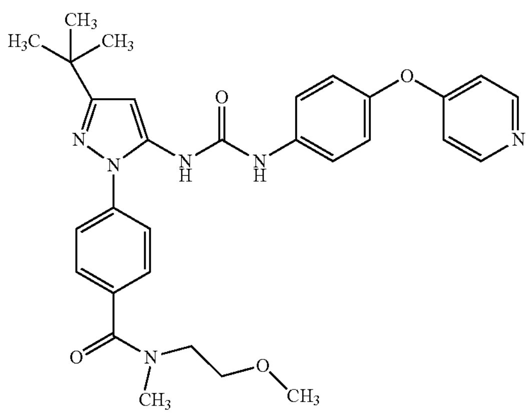 | 4-{3-tert-butyl-5-[({[4-(pyridin-4-yloxy)phenyl]amino}carbonyl)amino]-1H-pyrazol-1-yl}-N-(2-methoxyethyl)-N-methylbenzamide | 543 | 2.25 |
| 118 | 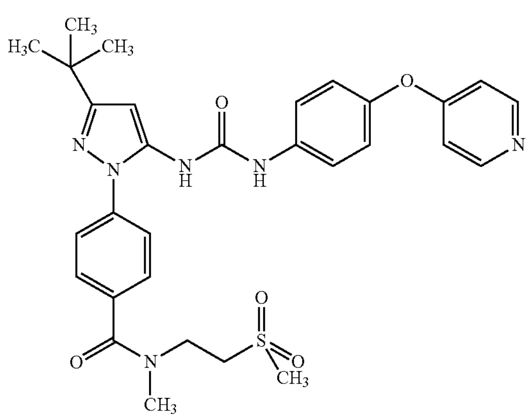 | 4-{3-tert-butyl-5-[({[4-(pyridin-4-yloxy)phenyl]amino}carbonyl)amino]-1H-pyrazol-1-yl}-N-methyl-N-[2-(methylsulfonyl)ethyl]benzamide | 591 | 2.08 |

-continued

| Ex. No. | Structure | IUPAC name | LC-MS m/z (MH+) | Ret. time (min) |
|---|---|---|---|---|
| 119 | 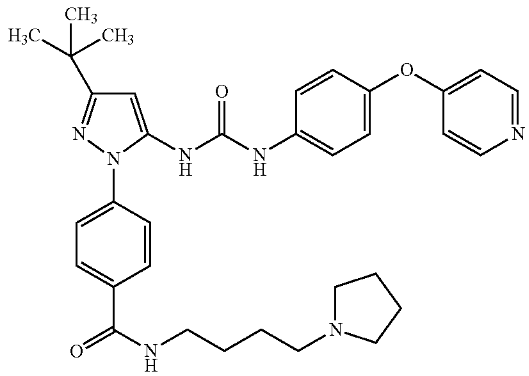 | 4-{3-tert-butyl-5-[({[4-(pyridin-4-yloxy)phenyl]amino}carbonyl)amino]-1H-pyrazol-1-yl}-N-(4-pyrrolidin-1-ylbutyl)benzamide | 586 | 2.05 |
| 120 | 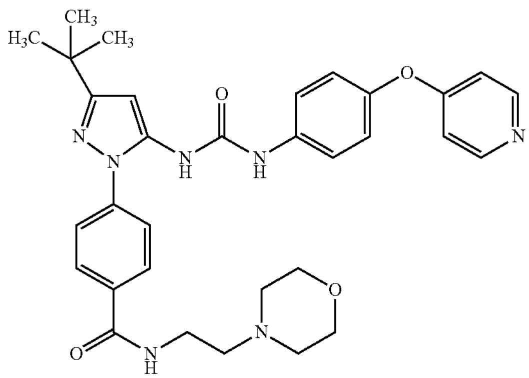 | 4-{3-tert-butyl-5-[({[4-(pyridin-4-yloxy)phenyl]amino}carbonyl)amino]-1H-pyrazol-1-yl}-N-(2-morpholin-4-ylethyl)benzamide | 584 | 2.03 |
| 121 | 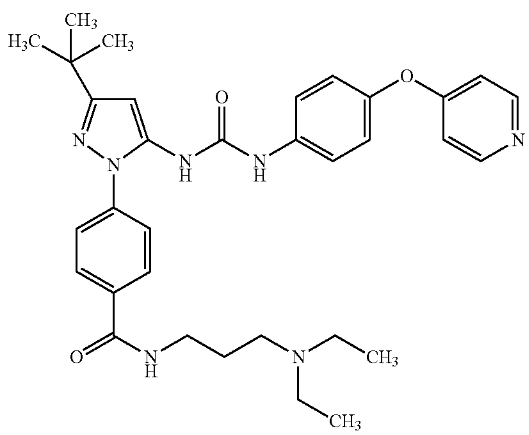 | 4-{3-tert-butyl-5-[({[4-(pyridin-4-yloxy)phenyl]amino}carbonyl)amino]-1H-pyrazol-1-yl}-N-[3-(diethylamino)propyl]benzamide | 584 | 1.17 |
| 122 | 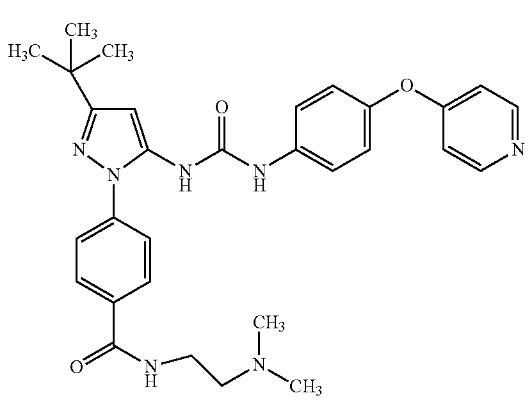 | 4-{3-tert-butyl-5-[({[4-(pyridin-4-yloxy)phenyl]amino}carbonyl)amino]-1H-pyrazol-1-yl}-N-[2-(dimethylamino)ethyl]benzamide | 542 | 1.89 |

-continued

| Ex. No. | Structure | IUPAC name | LC-MS m/z (MH+) | Ret. time (min) |
|---|---|---|---|---|
| 123 | 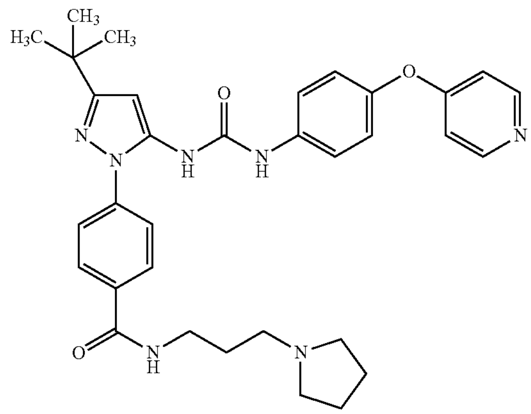 | 4-{3-tert-butyl-5-[({[4-(pyridin-4-yloxy)phenyl]amino}carbonyl)amino]-1H-pyrazol-1-yl}-N-(3-pyrrolidin-1-ylpropyl)benzamide | 582 | 2.48 |
| 124 | 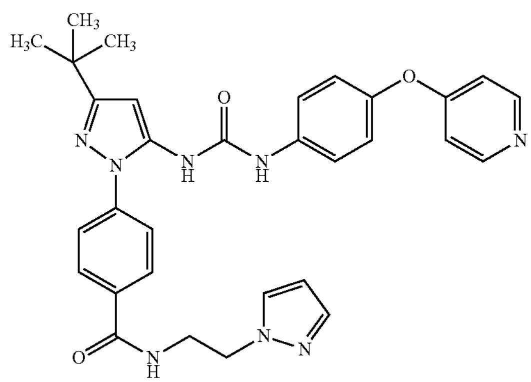 | 4-{3-tert-butyl-5-[({[4-(pyridin-4-yloxy)phenyl]amino}carbonyl)amino]-1H-pyrazol-1-yl}-N-[2-(1H-pyrazol-1-yl)ethyl]benzamide | 565 | 1.82 |
| 125 | 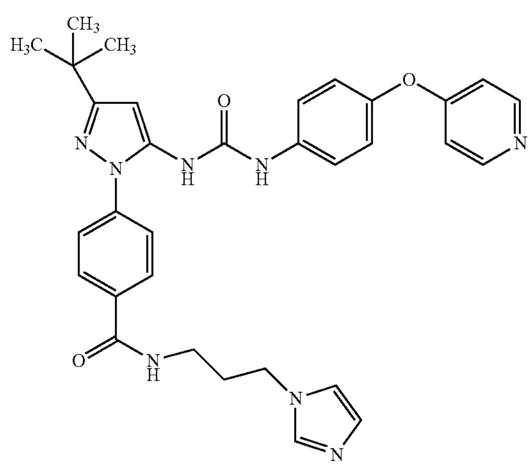 | 4-{3-tert-butyl-5-[({[4-(pyridin-4-yloxy)phenyl]amino}carbonyl)amino]-1H-pyrazol-1-yl}-N-[3-(1H-imidazol-1-yl)propyl]benzamide | 579 | 2.46 |

-continued

| Ex. No. | Structure | IUPAC name | LC-MS m/z (MH+) | Ret. time (min) |
|---|---|---|---|---|
| 126 | 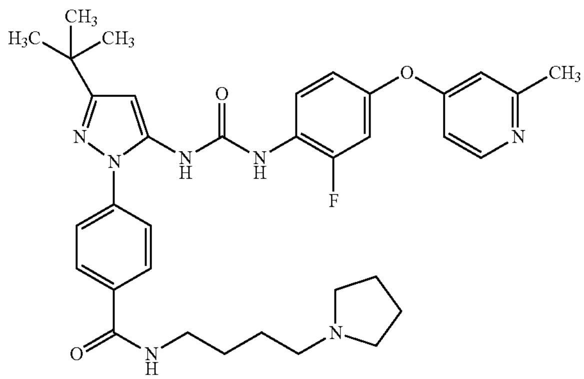 | 4-(3-tewrt-butyl-5-{[({2-fluoro-4-[(2-methylpyridin-4-yl)oxy]phenyl}amino)carbonyl]amino}-1H-pyrazol-1-yl)-N-(4-pyrrolidin-1-ylbutyl)benzamide | 628 | 2.54 |
| 127 | 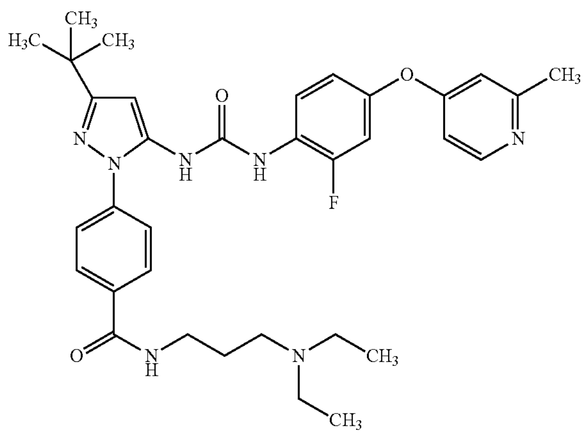 | 4-(3-tert-butyl-5-{[({2-fluoro-4-[(2-methylpyridin-4-yl)oxy]phenyl}amino)carbonyl]amino}-1H-pyrazol-1-yl)-N-[3-(diethylamino)propyl]benzamide | 616 | 2.52 |
| 128 | 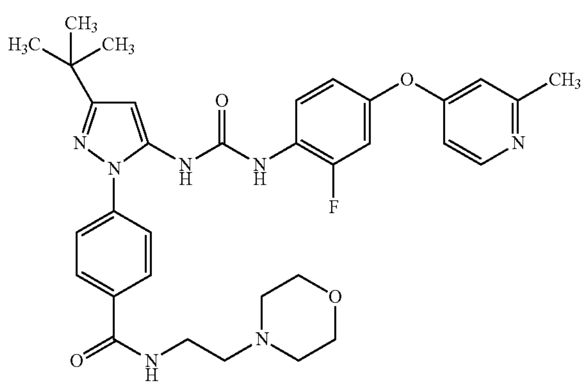 | 4-(3-tert-butyl-5-{[({2-fluoro-4-[(2-methylpyridin-4-yl)oxy]phenyl}amino)carbonyl]amino}-1H-pyrazol-1-yl)-N-(2-morpholin-4-ylethyl)benzamide | 616 | 2.06 |
| 129 | 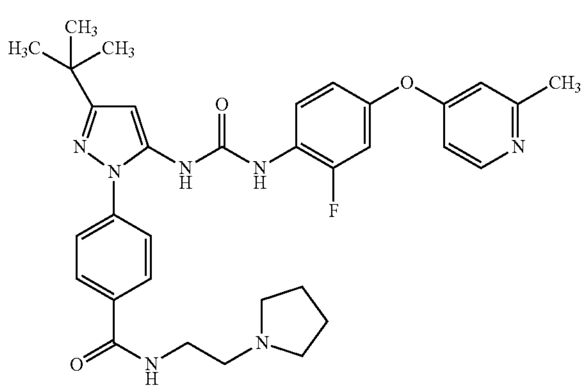 | 4-(3-tert-butyl-5-{[({2-fluoro-4-[(2-methylpyridin-4-yl)oxy]phenyl}amino)carbonyl]amino}-1H-pyrazol-1-yl)-N-(2-pyrrolidin-1-ylethyl)benzamide | 600 | 2.09 |

| Ex. No. | Structure | IUPAC name | LC-MS m/z (MH+) | Ret. time (min) |
|---|---|---|---|---|
| 130 | 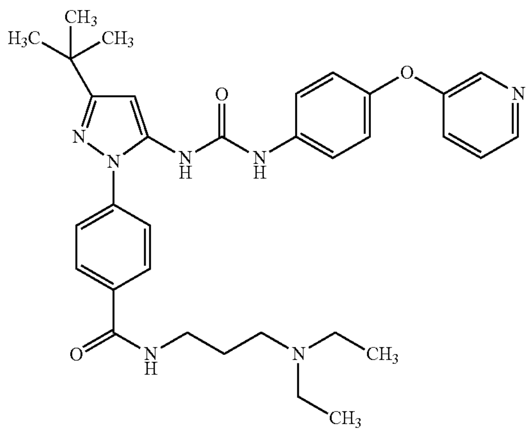 | 4-{3-tert-butyl-5-[({[4-(pyridin-3-yloxy)phenyl]amino}carbonyl)amino]-1H-pyrazol-1-yl}-N-[3-(diethylamino)propyl]benzamide | 584 | 2.15 |
| 131 | 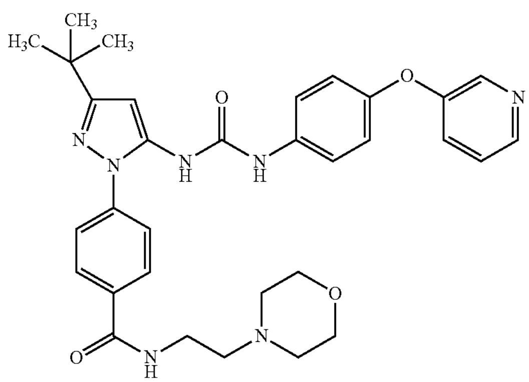 | 4-{3-tert-butyl-5-[({[4-(pyridin-3-yloxy)phenyl]amino}carbonyl)amino]-1H-pyrazol-1-yl}-N-(2-morpholin-4-ylethyl)benzazmide | 584 | 2.13 |
| 132 | 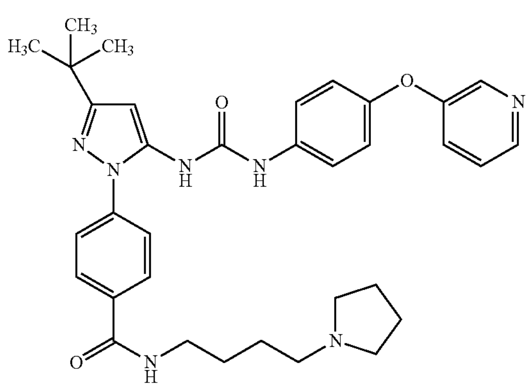 | 4-{3-tert-butyl-5-[({[4-(pyridin-3-yloxy)phenyl]amino}carbonyl)amino]-1H-pyrazol-1-yl}-N-(4-pyrrolidin-1-ylbutyl)benzamide | 596 | 2.65 |

| Ex. No. | Structure | IUPAC name | LC-MS m/z (MH+) | Ret. time (min) |
|---|---|---|---|---|
| 133 | 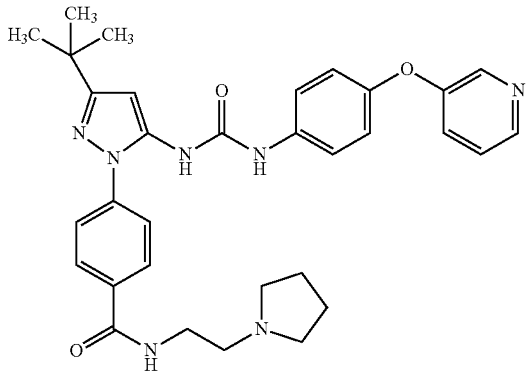 | 4-{3-tert-butyl-5-[({[4-(pyridin-3-yloxy)phenyl]amino}carbonyl)amino]-1H-pyrqazol-1-yl}-N-(2-pyrrolidin-1-ylethyl)benzamide | 568 | 2.62 |
| 134 | 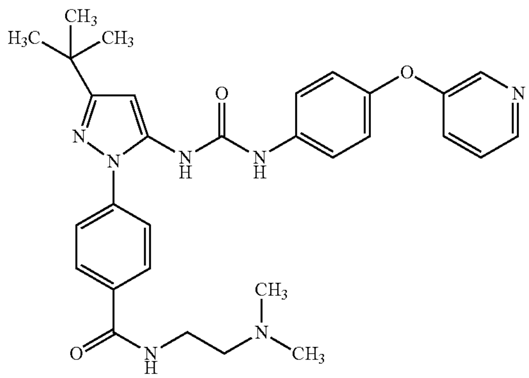 | 4-{3-tert-butyl-5-[({[4-(pyridin-3-yloxy)phenyl]amino}carbonyl)amino]-1H-pyrazol-1-yl}-N-[2-(dimethylamino)ethyl]benzamide | 542 | 2.59 |
| 135 | 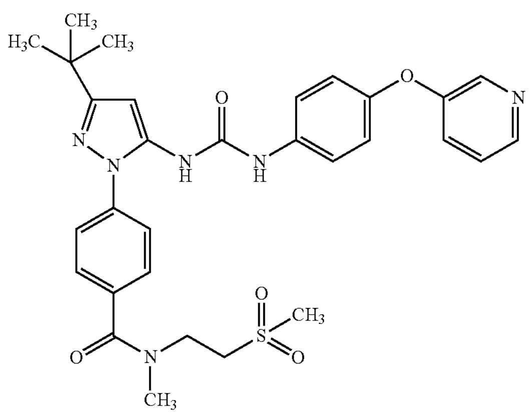 | 4-{3-tert-butyl-5-[({[4-(pyridin-3-yloxy)phenyl]amino}carbonyl)amino]-1H-pyrazol-1-yl}-N-methyl-N-[2-(methylsulfonyl)ethyl]benzamide | 591 | 2.92 |
| 136 | 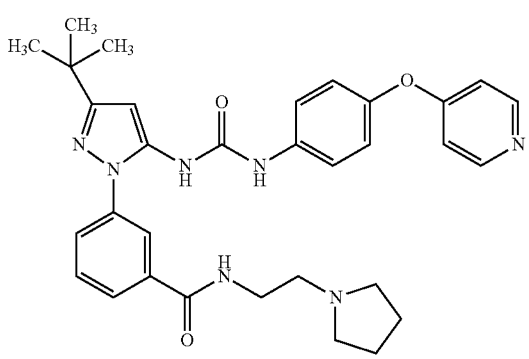 | 3-{3-tert-butyl-5-[({[4-(pyridin-4-yloxy)phenyl]amino}carbonyl)amino]-1H-pyrazol-1-yl}-N-(2-pyrrolidin-1-ylethyl)benzamide | 568 | 2.11 |

-continued

| Ex. No. | Structure | IUPAC name | LC-MS m/z (MH+) | Ret. time (min) |
|---|---|---|---|---|
| 137 | 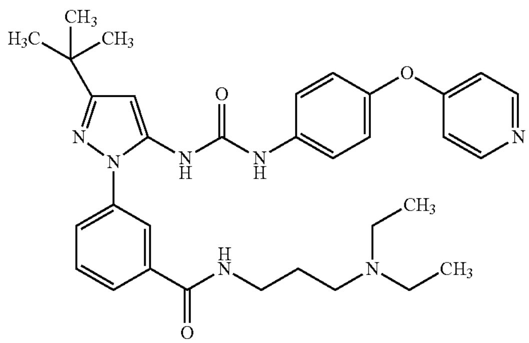 | 3-{3-tert-butyl-5-[({[4-(pyridin-4-yloxy)phenyl]amino}carbonyl)amino]-1H-pyrazol-1-yl}-N-[3-(diethylamino)propyl]benzamide | 584 | 2.12 |
| 138 | 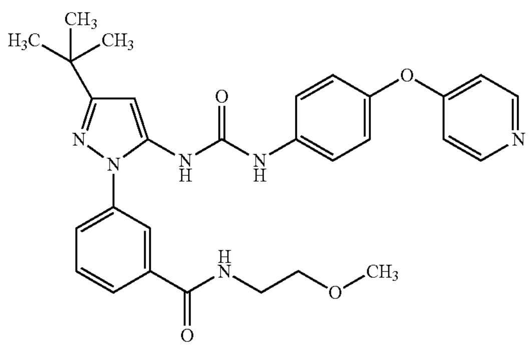 | 3-{3-tert-butyl-5-[({[4-(pyridin-4-yloxy)phenyl]amino}carbonyl)amino]-1H-pyrazol-1-yl}-N-(2-methoxyethyl)benzamide | 530 | 2.60 |
| 139 | 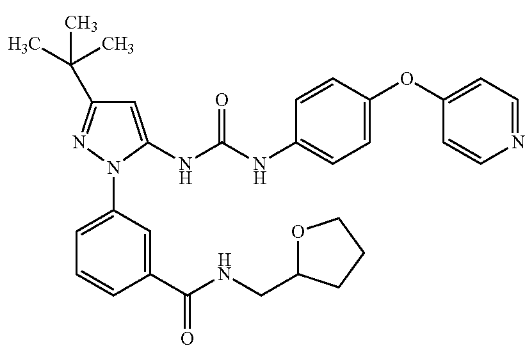 | 3-{3-tert-butyl-5-[({[4-(pyriudin-4-yloxy)phenyl]amino}carbonyl)amino]-1H-pyrazol-1-yl}-N-(tetrahydrofuran-2-ylmethyl)benzamide | 582 | 2.12 |
| 140 | 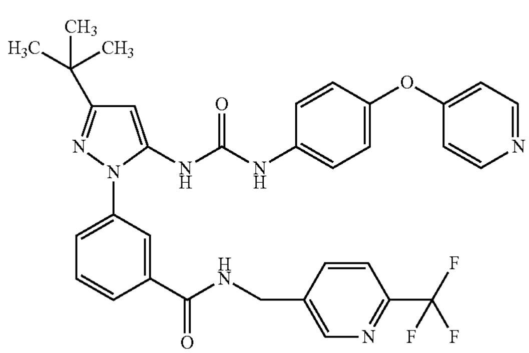 | 3-{3-tert-butyl-5-[({[4-(pyridin-4-yloxy)phenyl]amino}carbonyl)amino]-1H-pyrazol-1-yl}-N-{[6-(trifluoromethyl)pyridin-3-yl]methyl}benzamide | 630 | 2.73 |

| Ex. No. | Structure | IUPAC name | LC-MS m/z (MH+) | Ret. time (min) |
|---|---|---|---|---|
| 141 | 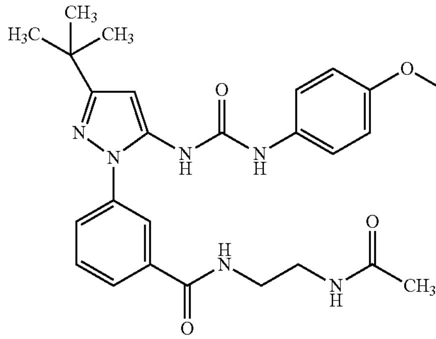 | N-[2-(acetylamino)ethyl]-3-{3-tert-butyl-5-[({[4-(pyridin-4-yloxy)phenyl]amino}carbonyl)amino]-1H-pyrazol-1-yl}benzamide | 556 | 2.35 |
| 142 | 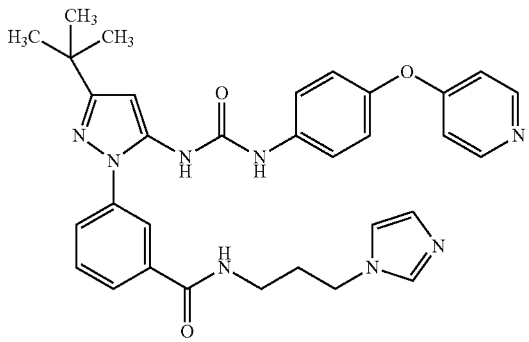 | 3-{3-tert-butyl-5-[({[4-(pyridin-4-yloxy)phenyl]amino}carbonyl)amino]-1H-pyrazol-1-yl}-N-[3-(1H-imidazol-1-yl)propyl]benzamide | 579 | 2.15 |
| 143 | 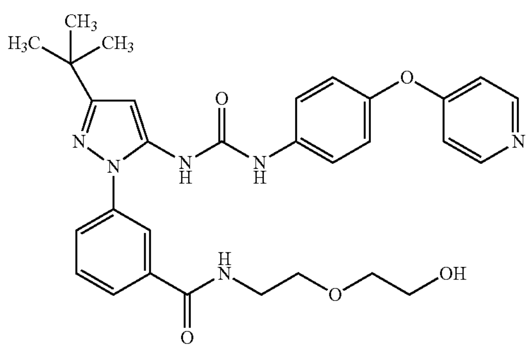 | 3-{3-tert-butyl-5-[({[4-(pyridin-4-yloxy)phenyl]amino}carbonyl)amino]-1H-pyrazol-1-yl}-N-[2-(2-hydroxyethoxy)ethyl]benzamide | 559 | 2.38 |
| 144 | 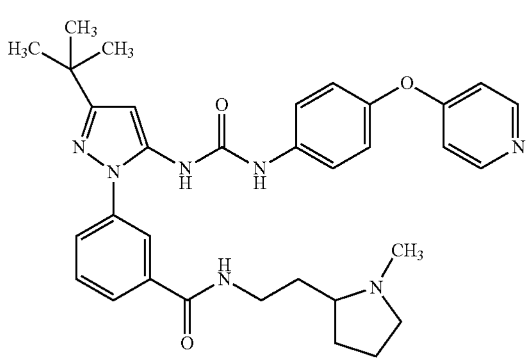 | 3-{3-tert-butyl-5-[({[4-(pyridin-4-yloxy)phenyl]amino}carbonyl)amino]-1H-pyrazol-1-yl}-N-[2-(1-methylpyrrolidin-2-yl)ethyl]benzamide | 582 | 2.13 |

-continued

| Ex. No. | Structure | IUPAC name | LC-MS m/z (MH+) | Ret. time (min) |
|---|---|---|---|---|
| 145 | 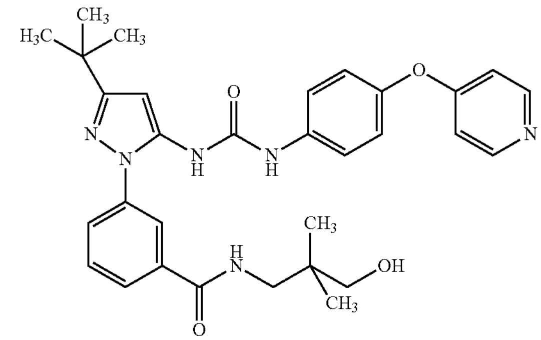 | 3-{3-tert-butyl-5-[({[4-(pyridin-4-yloxy)phenyl]amino}carbonyl)amino]-1H-pyrazol-1-yl}-N-(3-hydroxy-2,2-dimethylpropyl)benzamide | 557 | 2.45 |
| 146 | 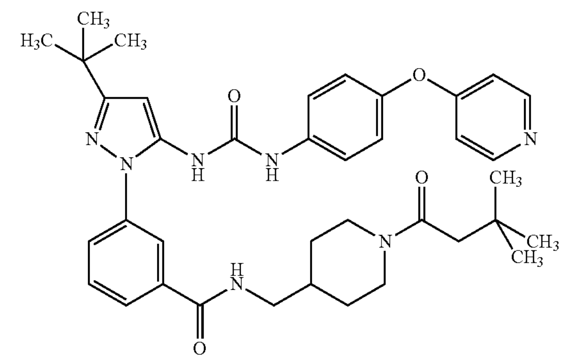 | tert-butyl 4-{[(3-{3-tert-butyl-5-[({[4-(pyridin-4-yloxy)phenyl]amino}carbonyl)amino]-1H-pyrazol-1-yl}benzoyl)amino]methyl}piperidine-1-carboxylate | 668 | 2.79 |
| 147 | 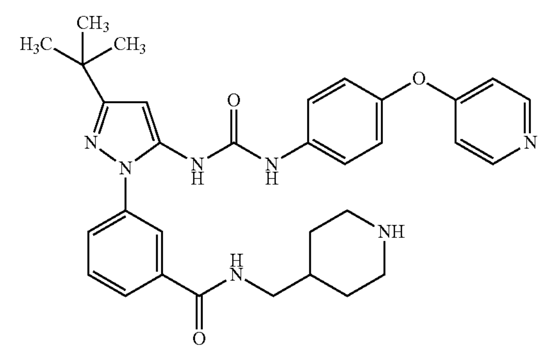 | 3-{3-tert-butyl-5-[({[4-(pyridin-4-yloxy)phenyl]amino}carbonyl)amino]-1H-pyrazol-1-yl}-N-(piperidin-4-ylmethyl)benzamide | 568 | 2.44 |
| 148 | 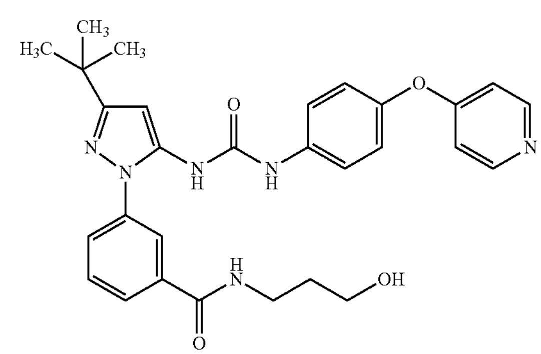 | 3-{3-tert-butyl-5-[({[4-(pyridin-4-yloxy)phenyl]amino}carbonyl)amino]-1H-pyrazol-1-yl}-N-(3-hydroxypropyl)benzamide | 529 | 2.26 |

-continued

| Ex. No. | Structure | IUPAC name | LC-MS m/z (MH+) | Ret. time (min) |
|---|---|---|---|---|
| 149 | 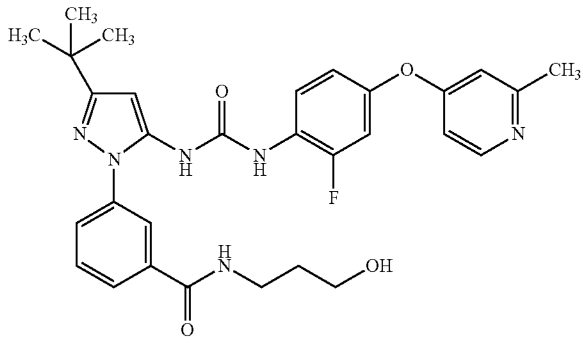 | 3-(3-tert-butyl-5-{[({2-fluoro-4-[(2-methylpyridin-4-yl)oxy]phenyl}amino)carbonyl]amino}-1H-pyrazol-1-yl)-N-(3-hydroxypropyl)benzamide | 561 | 2.32 |
| 150 | 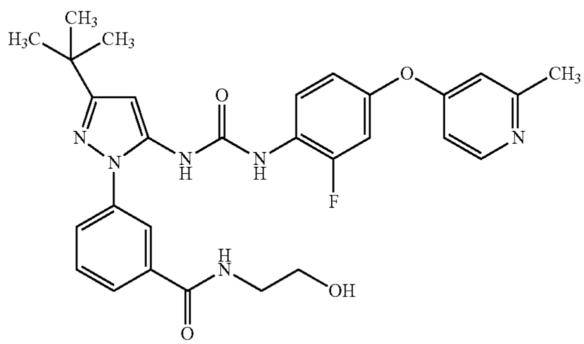 | 3-(3-tert-butyl-5-{[({2-fluoro-4-[(2-methylpyridin-4-yl)oxy]phenyl}amino)carbonyl]amino}-1H-pyrazol-1-yl)-N-(2-hydroxyethyl)benzamide | 547 | 2.72 |
| 151 | 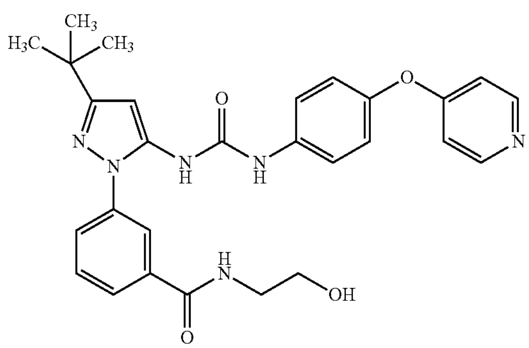 | 3-{3-tert-butyl-5-[({[4-(pyridin-4-yloxy)phenyl]amino}carbonyl)amino]-1H-pyrazol-1-yl}-N-(2-hydroxyethyl)benzamide | 515 | 2.66 |
| 152 | 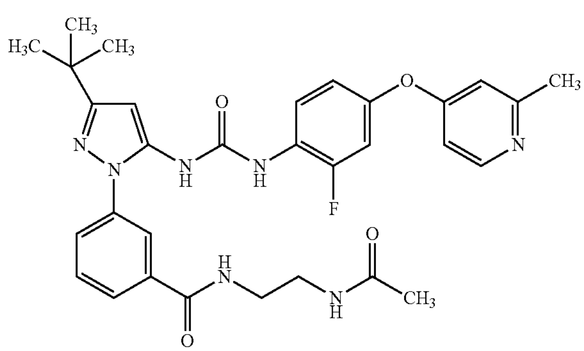 | N-[2-(acetylamino)ethyl]-3-(3-tert-butyl-5-{[({2-fluoro-4-[(2-methylpyridin-4-yl)oxy]phenyl}amino)carbonyl]amino}-1H-pyrazol-1-)benzamide | 588 | 1.82 |

-continued

| Ex. No. | Structure | IUPAC name | LC-MS m/z (MH+) | Ret. time (min) |
|---|---|---|---|---|
| 153 | 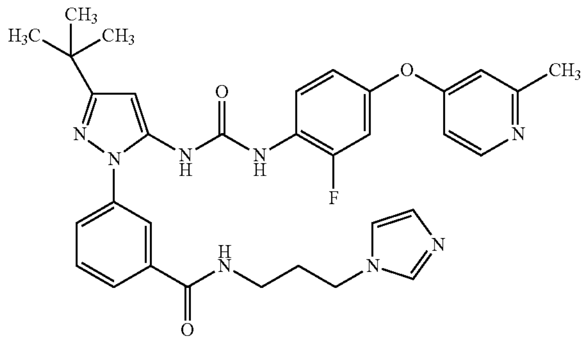 | 3-(3-tert-butyl-5-{[({2-fluoro-4-[(2-methylpyridin-4-yl)oxy]phenyl}amino)carbonyl]amino}-1H-pyrazol-1-yl)-N-[3-(1H-imidazol-1-yl)propyl]benzamide | 611 | 2.59 |
| 154 | 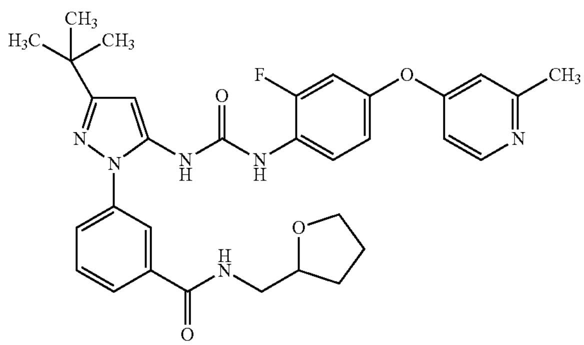 | 3-(3-tert-butyl-5-{[({2-fluoro-4-[(2-methylpyridin-4-yl)oxy]phenyl}amino)carbonyl]amino}-1H-pyrazol-1-yl)-N-(tetrahydrofuran-2-ylmethyl)benzamide | 587 | 2.47 |
| 155 | 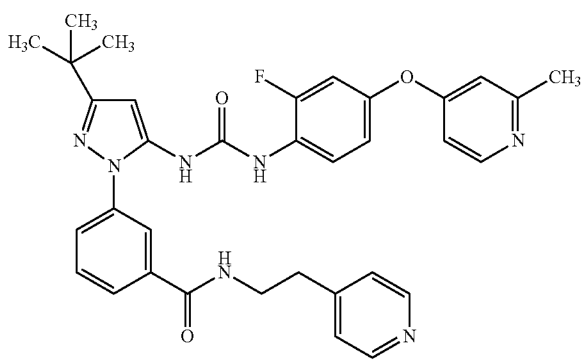 | 3-(3-tert-butyl-5-{[({2-fluoro-4-[(2-methylpyridin-4-yl)oxy]phenyl}amino)carbonyl]amino}-1H-pyrazol-1-yl)-N-(2-pyridin-4-ylethyl)benzamide | 608 | 2.16 |
| 156 | 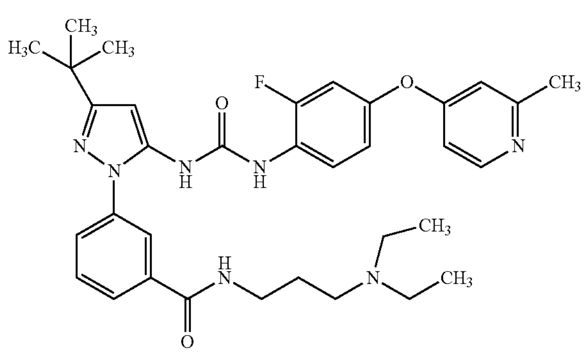 | 3-(3-tert-butyl-5-{[({2-fluoro-4-[(2-methylpyridin-4-yl)oxy]phenyl}amino)carbonyl]amino}-1H-pyrazol-1-yl)-N-[3-(diethylamino)propyl]benzamide | 616 | 2.18 |

-continued

| Ex. No. | Structure | IUPAC name | LC-MS m/z (MH+) | Ret. time (min) |
|---|---|---|---|---|
| 157 | 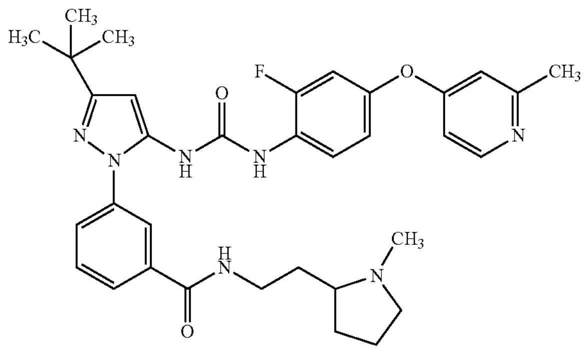 | 3-(3-tert-butyl-5-{[({2-fluoro-4-[(2-methylpyridin-4-yl)oxy]phenyl}amino)carbonyl]amino}-1H-pyrazol-1-yl)-N-[2-(1-methylpyrrolidin-2-yl)ethyl]benzamide | 614 | 2.16 |
| 158 | 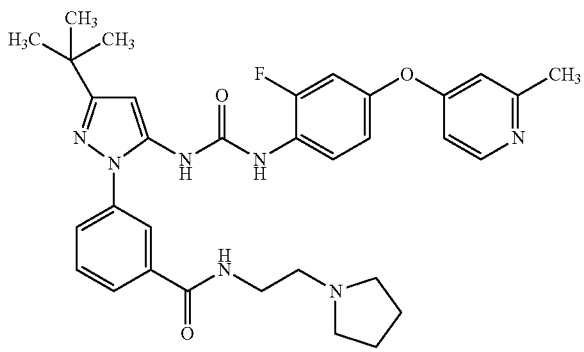 | 3-(3-tert-butyl-5-{[({2-fluoro-4-[(2-methylpyridin-4-yl)oxy]phenyl}amino)carbonyl]amino}-1H-pyrazol-1-yl)-N-(2-pyrrolidin-1-ylethyl)benzamide | 600 | 2.17 |
| 159 | 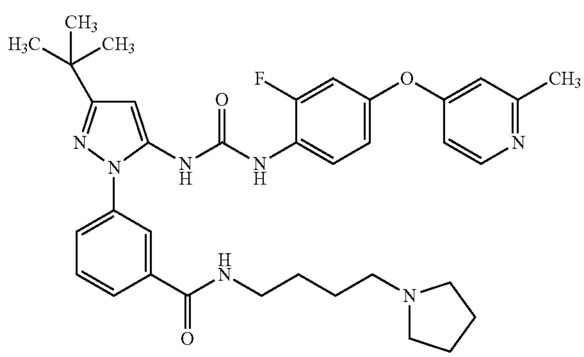 | 3-(3-tert-butyl-5-{[({2-fluoro-4-[(2-methylpyridin-4-yl)oxy]phenyl}amino)carbonyl]amino}-1H-pyrazol-1-yl)-N-(4-pyrrolidin-1-ylbutyl)benzamide | 628 | 2.22 |
| 160 | 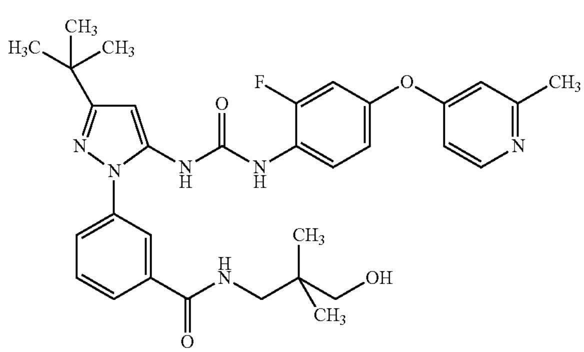 | 3-(3-tert-butyl-5-{[({2-fluoro-4-[(2-methylpyridin-4-yl)oxy]phenyl}amino)carbonyl]amino}-1H-pyrazol-1-yl)-N-(3-hydroxy-2,2-dimethylpropyl)benzamide | 589 | 2.76 |

| Ex. No. | Structure | IUPAC name | LC-MS m/z (MH+) | Ret. time (min) |
|---|---|---|---|---|
| 161 | 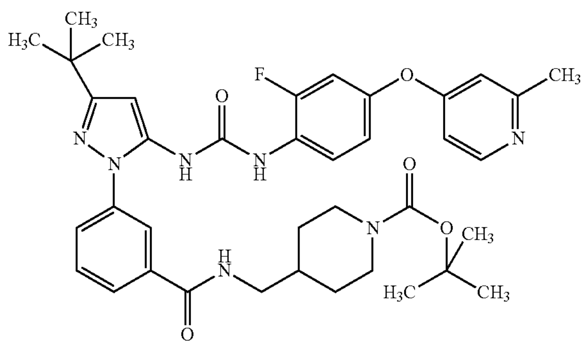 | tert-butyl 4-({[3-(3-tert-butyl-5-{[({2-fluoro-4-[(2-methylpyridin-4-yl)oxy]phenyl}amino)carbonyl]amino}-1H-pyrazol-1-yl)benzoyl]amino}methyl)piperidine-1-carboxylate | 700 | 2.86 |
| 162 | 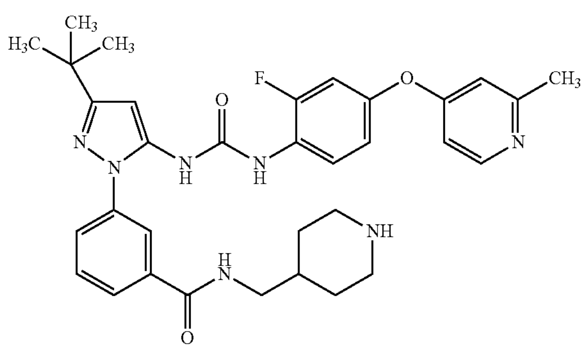 | 3-(3-tert-butyl-5-{[({2-fluoro-4-[(2-methylpyridin-4-yl)oxy]phenyl}amino)carbonyl]amino}-1H-pyrazol-1-yl)-N-(piperidin-4-ylmethyl)benzamide | 600 | 2.08 |
| 163 | 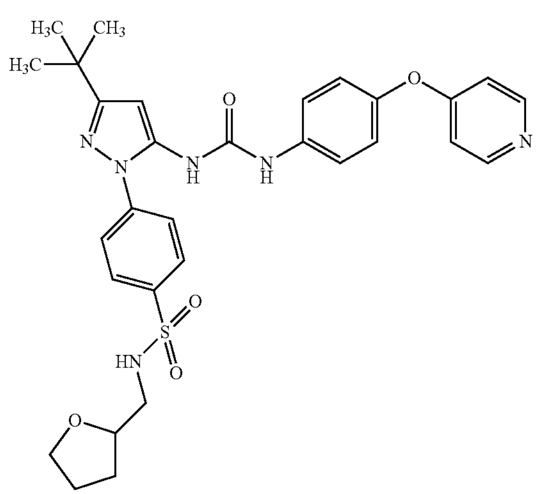 | 4-{3-tert-butyl-5-[({[4-(pyridin-4-yloxy)phenyl]amino}carbonyl)amino]-1H-pyrazol-1-yl}-N-(tetrahydrofuran-2-ylmethyl)benzenesulfonamide | 591 | 2.91 |

| Ex. No. | Structure | IUPAC name | LC-MS m/z (MH+) | Ret. time (min) |
|---|---|---|---|---|
| 164 | 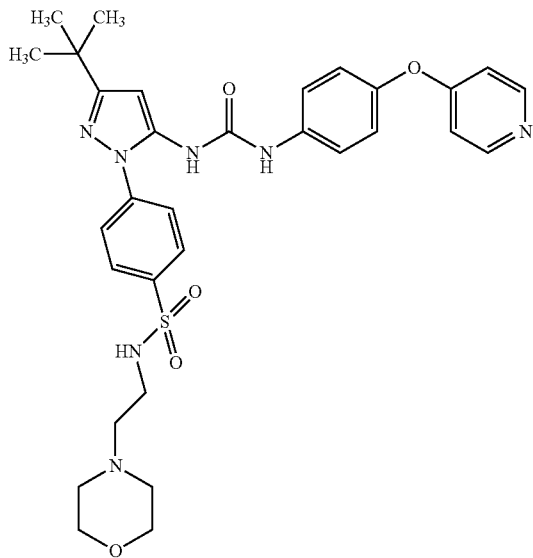 | 4-{3-tert-butyl-5-[({[4-(pyridin-4-yloxy)phenyl]amino}carbonyl)amino]-1H-pyrazol-1-yl}-N-(2-morpholin-4-ylethyl)benzenesulfonamide | 620 | 2.15 |
| 165 | 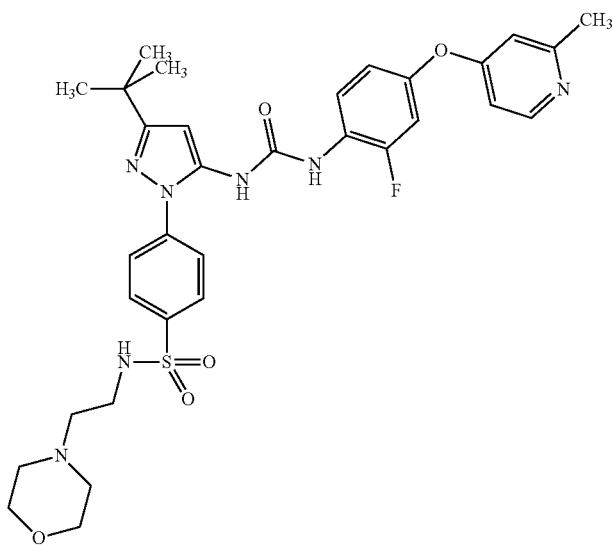 | 4-(3-tert-butyl-5-{[({2-fluoro-4-[(2-methylpyridin-4-yl)oxy]phenyl}amino)carbonyl]amino}-1H-pyrazol-1-yl)-N-(2-morpholin-4-ylethyl)benzenesulfonamide | 652 | 2.21 |

| Ex. No. | Structure | IUPAC name | LC-MS m/z (MH+) | Ret. time (min) |
|---|---|---|---|---|
| 166 | 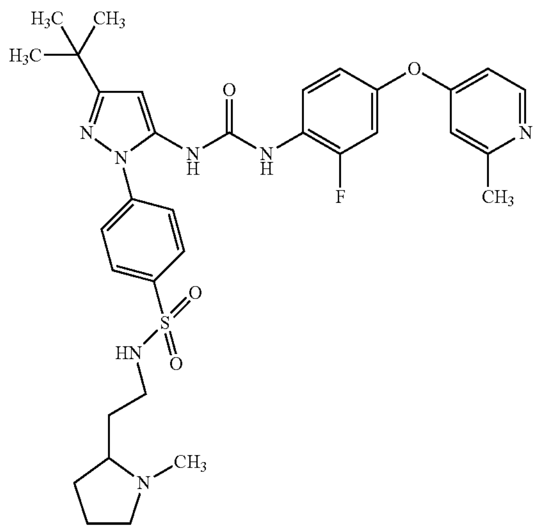 | 4-(3-tert-butyl-5-{[({2-fluoro-4-[(2-methylpyridin-4-yl)oxy]phenyl}amino)carbonyl]amino}-1H-pyrazol-1-yl)-N-[2-(1-methylpyrrolidin-2-yl)ethyl]benzenesulfonamide | 650 | 2.22 |
| 167 | 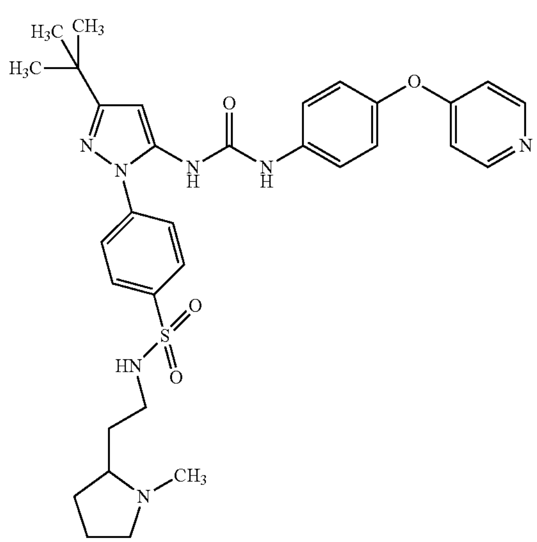 | 4-{3-tert-butyl-5-[({[4-(pyridin-4-yloxy)phenyl]amino}carbonyl)amino]-1H-pyrazol-1-yl}-N-[2-(1-methylpyrrolidin-2-yl)ethyl]benzenesulfonamide | 618 | 2.16 |

| Ex. No. | Structure | IUPAC name | LC-MS m/z (MH+) | Ret. time (min) |
|---|---|---|---|---|
| 168 | 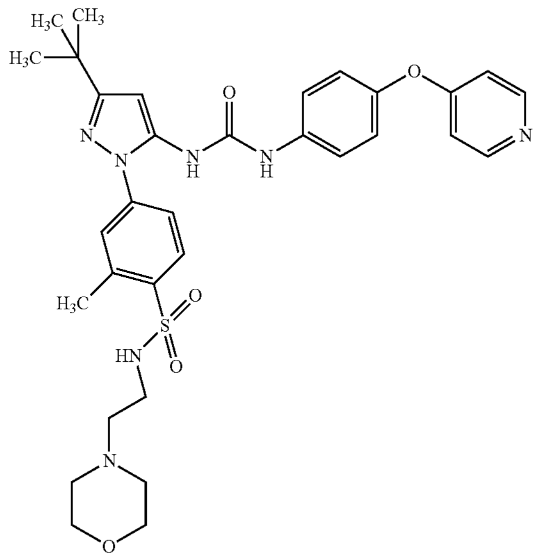 | 4-{3-tert-butyl-5-[({[4-(pyridin-4-yloxy)phenyl]amino}carbonyl)amino]-1H-pyrazol-1-yl}-2-methyl-N-(2-morpholin-4-ylethyl)benzenesulfonamide | 634 | 2.21 |
| 169 | 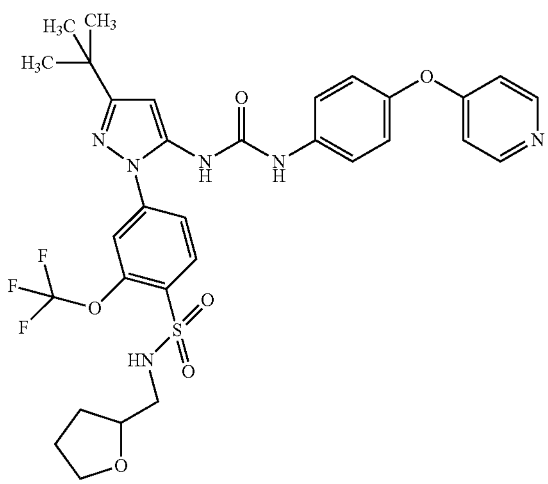 | 4-{3-tert-butyl-5-[({[4-(pyridin-4-yloxy)phenyl]amino}carbonyl)amino]-1H-pyrazol-1-yl}-N-(tetrahydrofuran-2-ylmethyl)-2-(trifluoromethoxy)benzenesulfonamide | 675 | 3.11 |
| 170 | 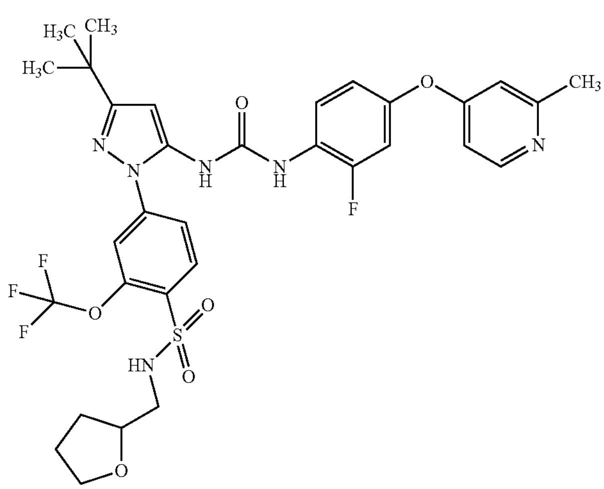 | 4-(3-tert-butyl-5-{[({2-fluoro-4-[(2-methylpyridin-4-yl)oxy]phenyl}amino)carbonyl]amino}-1H-pyrazol-1-yl)-N-(tetrahydrofuran-2-ylmethyl)-2-(trifluoromethoxy)benzenesulfonamide | 707 | 3.18 |

| Ex. No. | Structure | IUPAC name | LC-MS m/z (MH+) | Ret. time (min) |
|---|---|---|---|---|
| 171 | 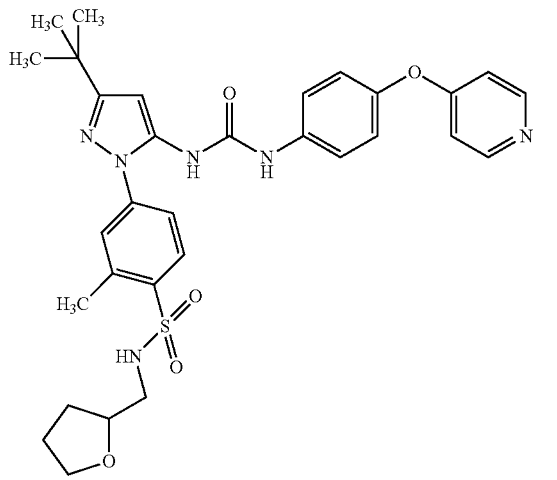 | 4-{3-tert-butyl-5-[({[4-(pyridin-4-yloxy)phenyl]amino}carbonyl)amino]-1H-pyrazol-1-yl}-2-methyl-N-(tetrahydrofuran-2-ylmethyl)benzenesulfonamide | 605 | 2.59 |
| 172 | 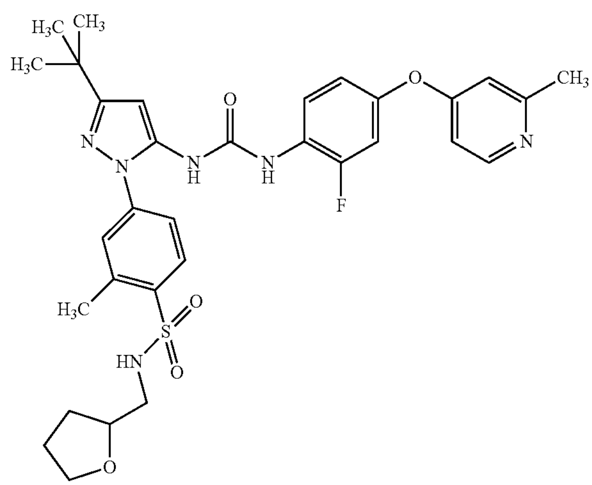 | 4-(3-tert-butyl-5-{[({2-fluoro-4-[(2-methylpyridin-4-yl)oxy]phenyl}amino)carbonyl]amino}-1H-pyrazol-1-yl)-2-methyl-N-(tetrahydrofuran-2-ylmethyl)benzenesulfonamide | 637 | 2.69 |
| 173 | 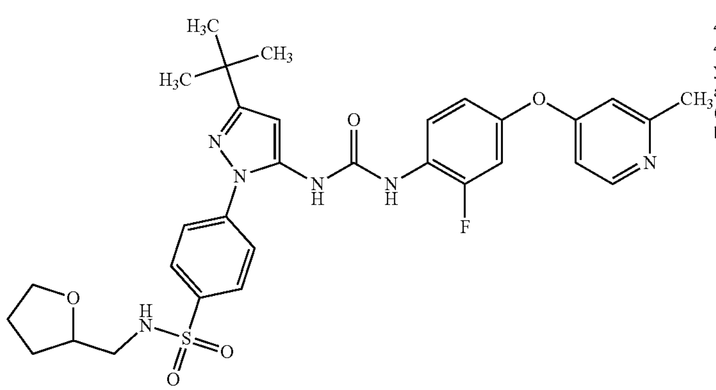 | 4-(3-tert-butyl-5-{[({2-fluoro-4-[(2-methylpyridin-4-yl)oxy]phenyl}amino)carbonyl]amino}-1H-pyrazol-1-yl)-N-(tetrahydrofuran-2-ylmethyl)benzenesulfonamide | 623 | 2.66 |

-continued

| Ex. No. | Structure | IUPAC name | LC-MS m/z (MH+) | Ret. time (min) |
|---|---|---|---|---|
| 174 | 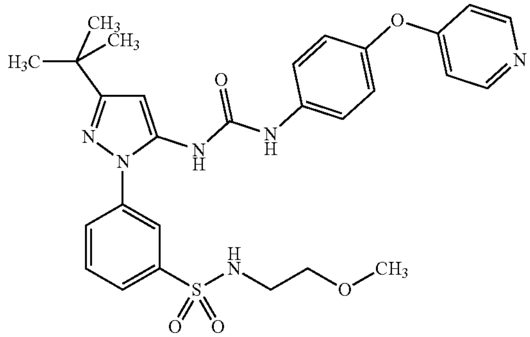 | 3-{3-tert-butyl-5-[({[4-(pyridin-4-yloxy)phenyl]amino}carbonyl)amino]-1H-pyrazol-1-yl}-N-(2-methoxyethyl)benzenesulfonamide | 565 | 2.41 |
| 175 | 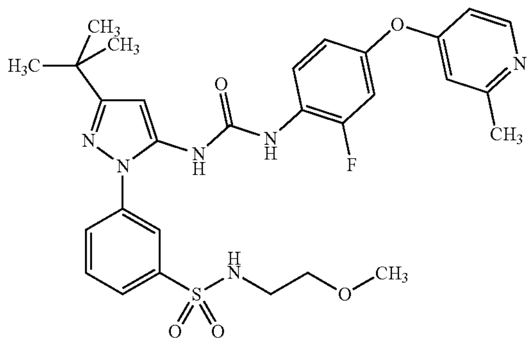 | 3-(3-tert-butyl-5-{[({2-fluoro-4-[(2-methylpyridin-4-yl)oxy]phenyl}amino)carbonyl]amino}-1H-pyrazol-1-yl)-N-(2-methoxyethyl)benzenesulfonamide | 597 | 2.48 |
| 176 | 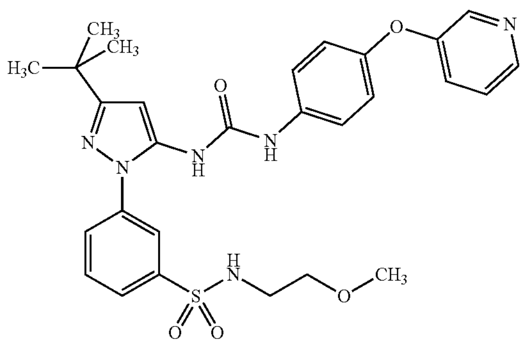 | 3-{3-tert-butyl-5-[({[4-(pyridin-3-yloxy)phenyl]amino}carbonyl)amino]-1H-pyrazol-1-yl}-N-(2-methoxyethyl)benzenesulfonamide | 565 | 2.63 |
| 177 | 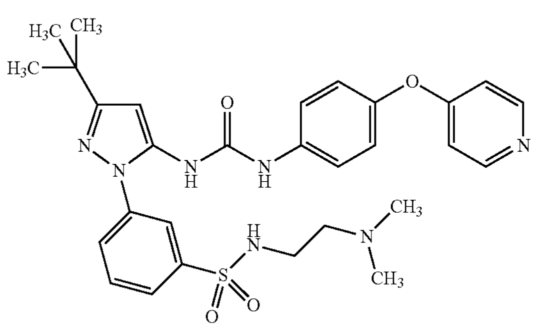 | 3-{3-tert-butyl-5-[({[4-(pyridin-4-yloxy)phenyl]amino}carbonyl)amino]-1H-pyrazol-1-yl}-N-[2-(dimethylamino)ethyl]benzenesulfonamide | 600 (M + Na) | 2.11 |

| Ex. No. | Structure | IUPAC name | LC-MS m/z (MH+) | Ret. time (min) |
|---|---|---|---|---|
| 178 | 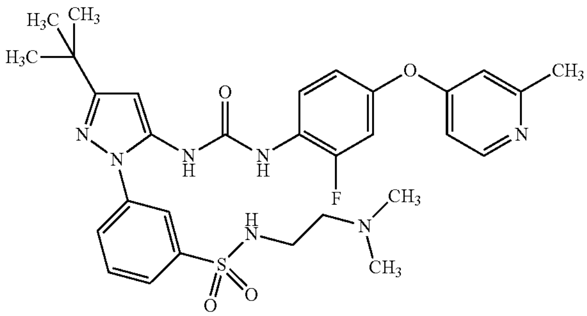 | 3-(3-tert-butyl-5-{[({2-fluoro-4-[(2-methylpyridin-4-yl)oxy]phenyl}amino)carbonyl]amino}-1H-pyrazol-1-yl)-N-[2-(dimethylamino)ethyl]benzenesulfonamide | 610 | 2.20 |
| 179 | 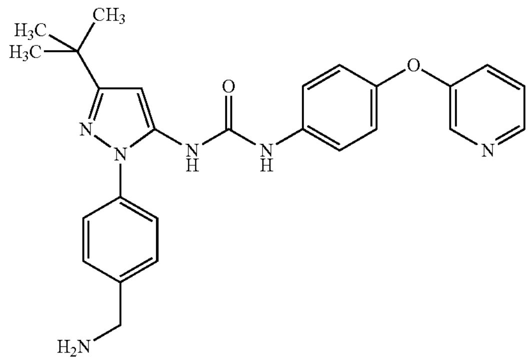 | N-{1-[4-(aminomethyl)phenyl]-3-tert-butyl-1H-pyrazol-5-yl}-N'-[4-(pyridin-3-yloxy)phenyl]urea | 457 | 2.55 |
| 180 | 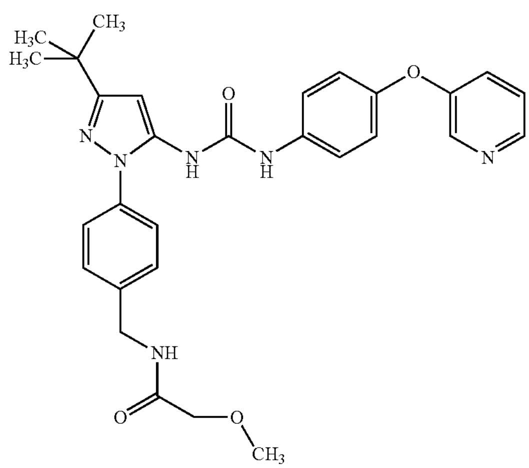 | N-(4-{3-tert-butyl-5-[({[4-(pyridin-3-yloxy)phenyl]amino}carbonyl)amino]-1H-pyrazol-1-yl}benzyl)-2-methoxyacetamide | 529 | 2.52 |
| 181 | 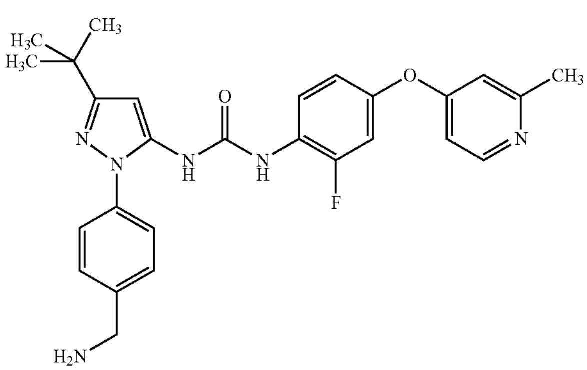 | N-{1-[4-(aminomethyl)phenyl]-3-tert-butyl-1H-pyrazol-5-yl}-N'-{2-fluoro-4-[(2-methylpyridin-4-yl)oxy]phenyl}urea | 489 | 2.06 |

-continued

| Ex. No. | Structure | IUPAC name | LC-MS m/z (MH+) | Ret. time (min) |
|---|---|---|---|---|
| 182 | 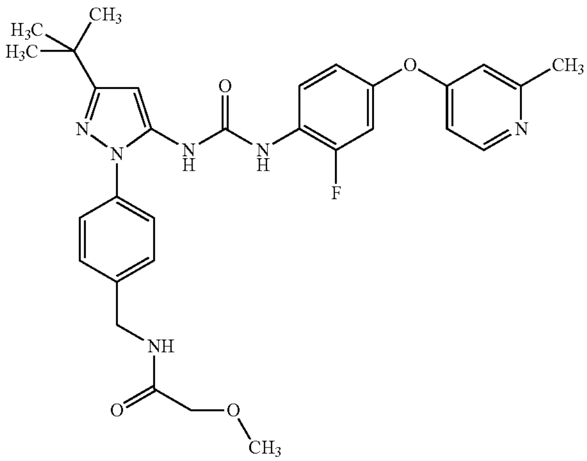 | N-[4-(3-tert-butyl-5-{[({2-fluoro-4-[(2-methylpyridin-4-yl)oxy]phenyl}amino)carbonyl]amino}-1H-pyrazol-1-yl)benzyl]-2-methoxyacetamide | 561 | 2.38 |
| 183 | 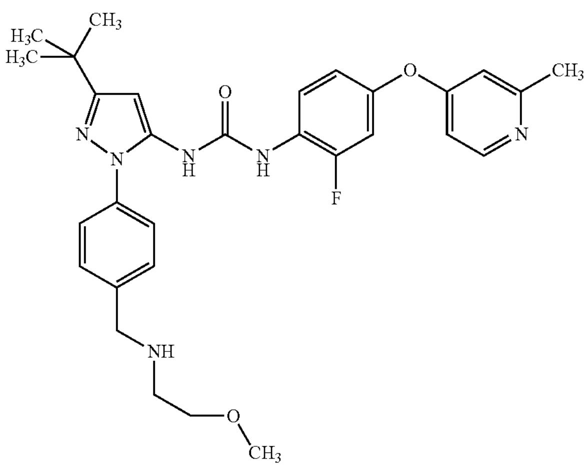 | N-[3-tert-butyl-1-(4-{[(2-methoxyethyl)amino]methyl}phenyl)-1H-pyrazol-5-yl]-N'-{2-fluoro-4-[(2-methylpyridin-4-yl)oxy]phenyl}urea | 547 | 2.14 |
| 184 | 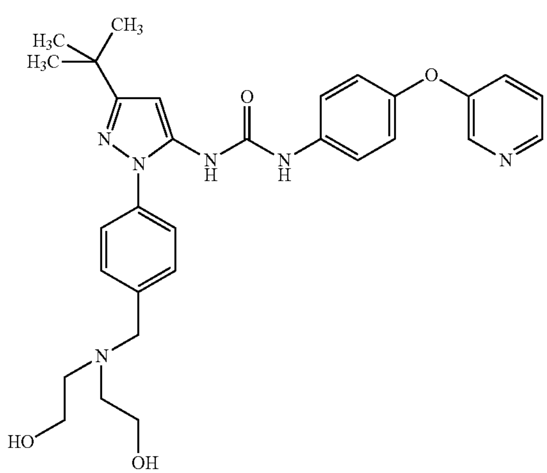 | N-[1-(4-{[bis(2-hydroxyethyl)amino]methyl}phenyl)-3-tert-butyl-1H-pyrazol-5-yl]-N'-[4-(pyridin-3-yloxy)phenyl]urea | 545 | 2.56 |

-continued

| Ex. No. | Structure | IUPAC name | LC-MS m/z (MH+) | Ret. time (min) |
|---|---|---|---|---|
| 185 | 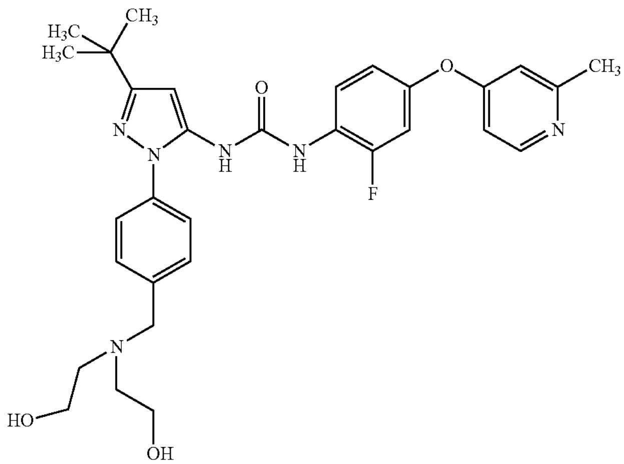 | N-[1-(4-bis{[(2-hydroxyethyl)amino]methyl}phenyl)-3-tert-butyl-1H-pyrazol-5-yl]-N'-{2-fluoro-4-[(2-methylpyridin-4-yl)oxy]phenyl}urea | 577 | 2.44 |
| 186 | 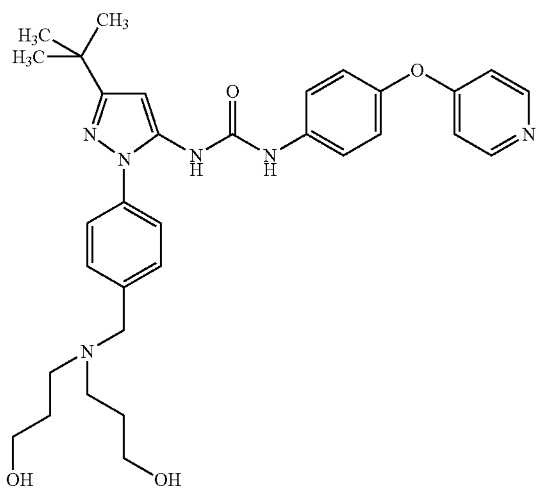 | N-[1-(4-{[bis(3-hydroxypropyl)amino]methyl}phenyl)-3-tert-butyl-1H-pyrazol-5-yl]-N'-[4-(pyridin-4-yloxy)phenyl]urea | 573 | 2.04 |
| 187 | 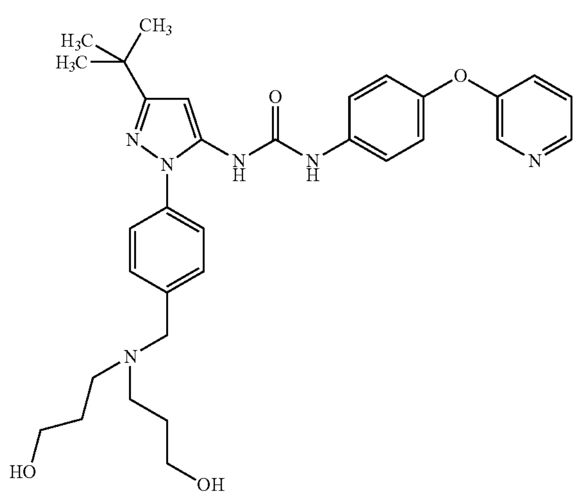 | N-[1-(4-{[bis(3-hydroxypropyl)amino]methyl}phenyl)-3-tert-butyl-1H-pyrazol-5-yl]-N'-[4-(pyridin-3-yloxy)phenyl]urea | 573 | 2.21 |

| Ex. No. | Structure | IUPAC name | LC-MS m/z (MH+) | Ret. time (min) |
|---|---|---|---|---|
| 188 | 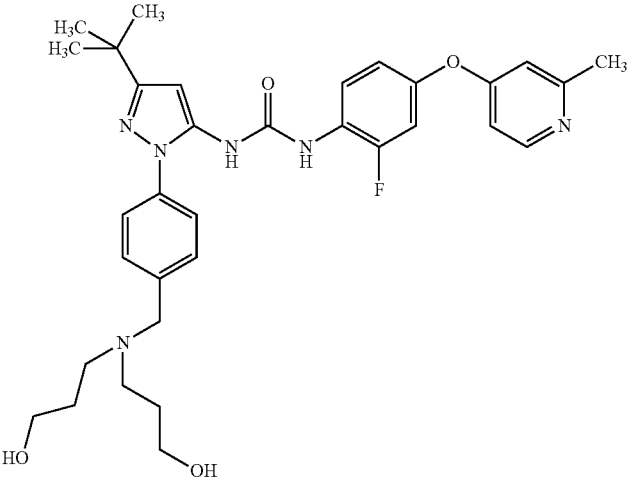 | N-[1-(4-{[bis(3-hydroxypropyl)amino]methyl}phenyl)-3-tert-butyl-1H-pyrazol-5-yl]-N'-{2-fluoro-4-[(2-methylpyridin-4-yl)oxy]phenyl}urea | 605 | 2.09 |
| 189 | 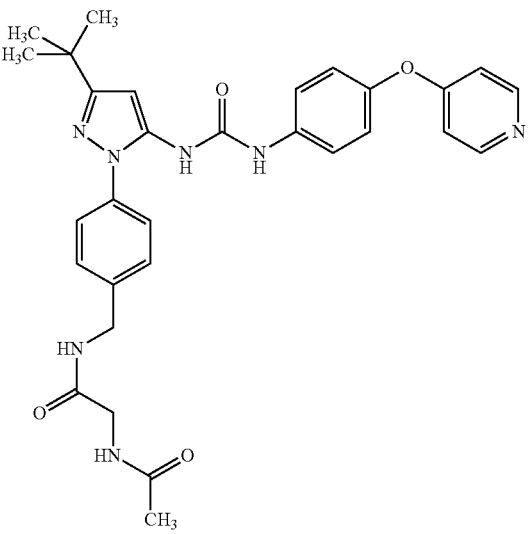 | N2-acetyl-N-(4-{3-tert-butyl-5-[({[4-pyridin-4-yloxy)phenyl]amino}carbonyl)amino]-1H-pyrazol-1-yl}benzyl)glycinamide | 556 | 2.62 |

| Ex. No. | Structure | IUPAC name | LC-MS m/z (MH+) | Ret. time (min) |
|---|---|---|---|---|
| 190 | 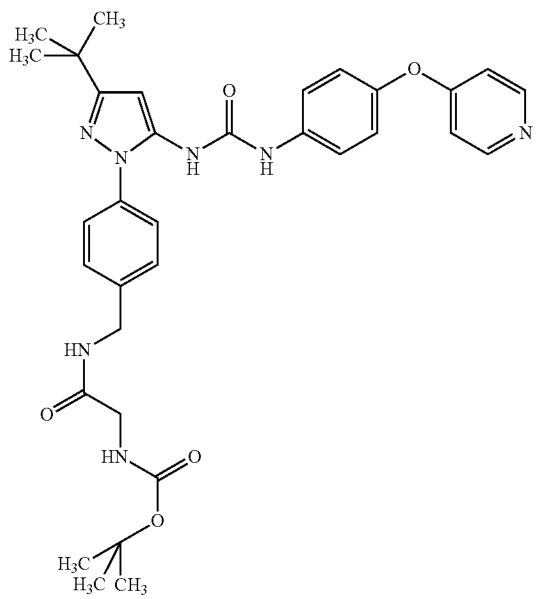 | tert-butyl {2-[(4-{3-tert-butyl-5-[({[4-(pyridin-4-yloxy)phenyl]amino}carbonyl)amino]-1H-pyrazol-1-yl}benzyl)amino]-2-oxoethyl}carbamate | 614 | 2.89 |
| 191 | 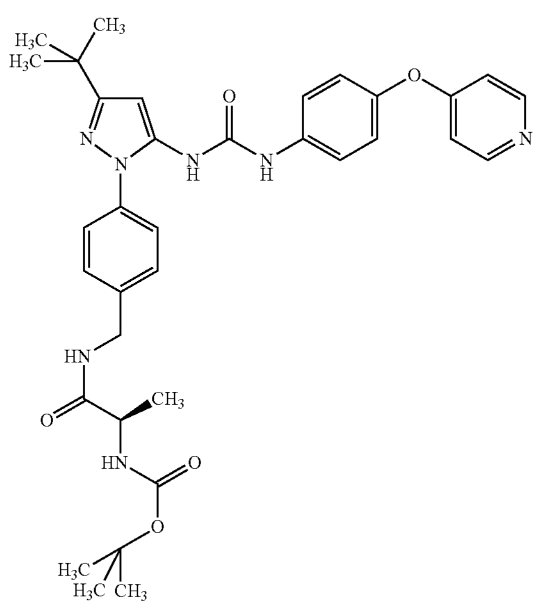 | tert-butyl {2-[(4-{3-tert-butyl-5-[({[4-(pyridin-4-yloxy)phenyl]amino}carbonyl)amino]-1H-pyrazol-1-yl}benzyl)amino]-1-methyl-2-oxoethyl}carbamate | 628 | 2.62 |

-continued
| Ex. No. | Structure | IUPAC name | LC-MS m/z (MH+) | Ret. time (min) |
|---|---|---|---|---|
| 192 | 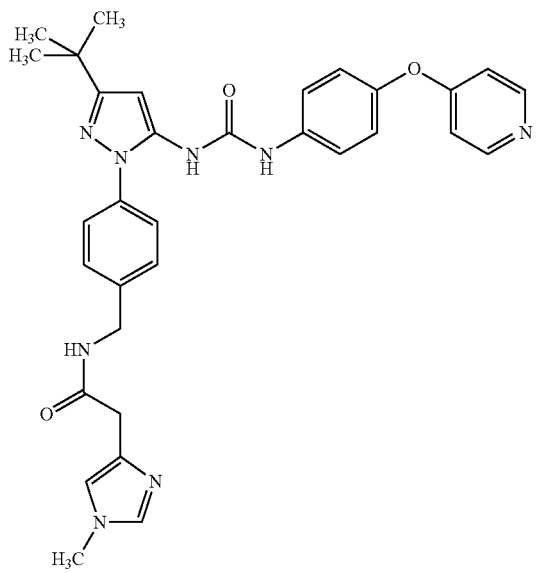 | N-(4-{3-tert-butyl-5-[({[4-(pyridin-4-yloxy)phenyl]amino}carbonyl)amino]-1H-pyrazol-1-yl}benzyl)-2-(1-methyl-1H-imidazol-4-yl)acetamide | 579 | 2.45 |
| 193 | 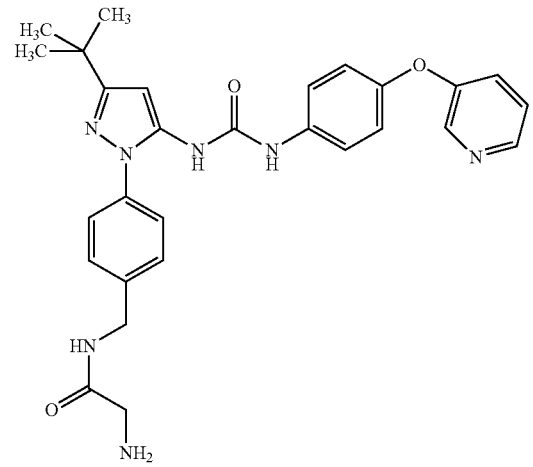 | N-(4-{3-tert-butyl-5-[({[4-(pyridin-3-yloxy)phenyl]amino}carbonyl)amino]-1H-pyrazol-1-yl}benzyl)glycinamide | 514 | 2.21 |
| 194 | 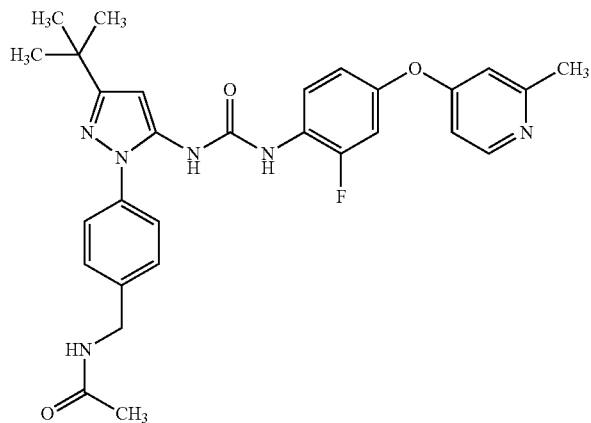 | N-[4-(3-tert-butyl-5-{[({2-fluoro-4-[(2-methylpyridin-4-yl)oxy]phenyl}amino)carbonyl]amino}-1H-pyrazol-1-yl)benzyl]acetamide | 531 | 2.79 |

-continued
| Ex. No. | Structure | IUPAC name | LC-MS m/z (MH+) | Ret. time (min) |
|---|---|---|---|---|
| 195 | 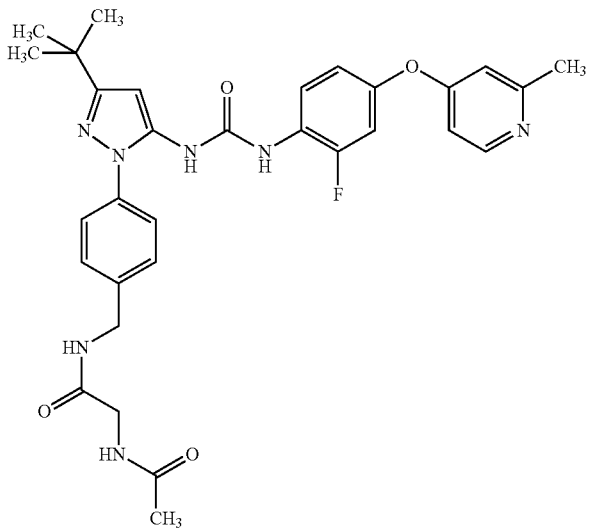 | N2-acetyl-N-[4-(3-tert-butyl-5-{[({2-fluoro-4-[(2-methylpyridin-4-yl)oxy]phenyl}amino)carbonyl]amino}-1H-pyrazol-1-yl)benzyl]glycinamide | 588 | 2.26 |
| 196 | 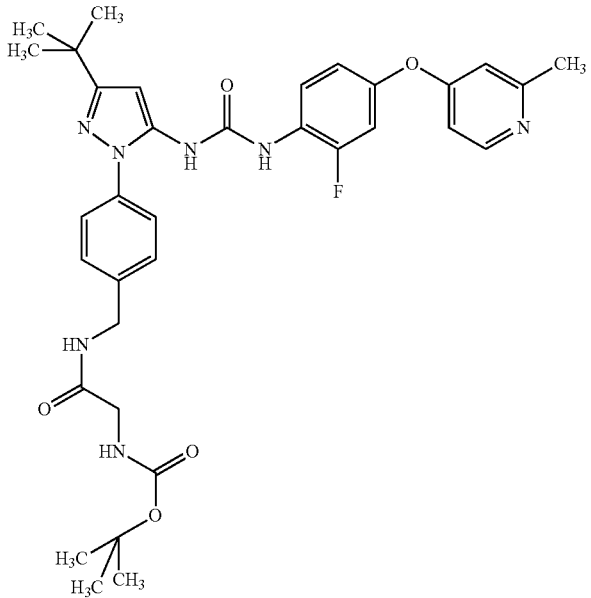 | tert-butyl (2-{[4-(3-tert-butyl-5-{[({2-fluoro-4-[(2-methylpyridin-4-yl)oxy]phenyl}amino)carbonyl]amino}-1H-pyrazol-1-yl)benzyl]amino}-2-oxoethyl)carbamate | 646 | 2.55 |

| Ex. No. | Structure | IUPAC name | LC-MS m/z (MH+) | Ret. time (min) |
|---|---|---|---|---|
| 197 | 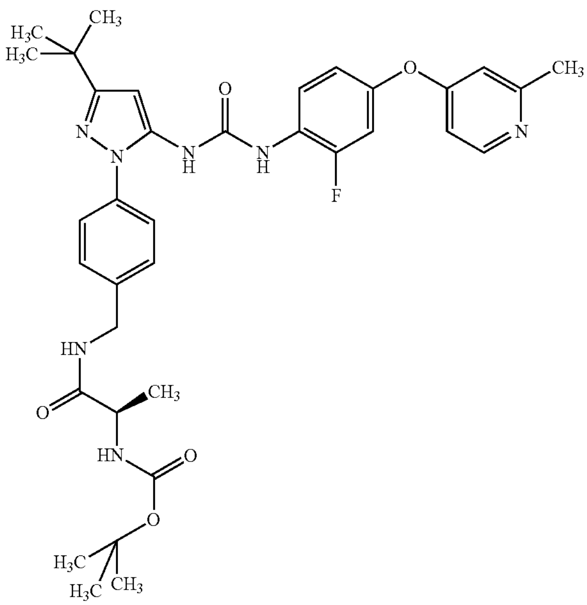 | tert-butyl (2-{[4-(3-tert-butyl-5-{[({2-fluoro-4-[(2-methylpyridin-4-yl)oxy]phenyl}amino)carbonyl]amino}-1H-pyrazol-1-yl)benzyl]amino}-1-methyl-2-oxoethyl)carbamate | 660 | 2.58 |
| 198 | 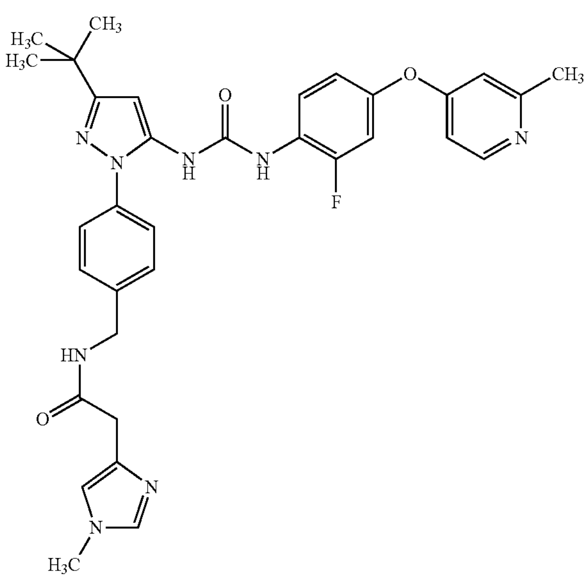 | N-[4-(3-tert-butyl-5-{[({2-fluoro-4-[(2-methylpyridin-4-yl)oxy]phenyl}amino)carbonyl]amino}-1H-pyrazol-1-yl)benzyl]-2-(1-methyl-1H-imidazol-4-yl)acetamide | 611 | 2.06 |

| Ex. No. | Structure | IUPAC name | LC-MS m/z (MH+) | Ret. time (min) |
|---|---|---|---|---|
| 199 | 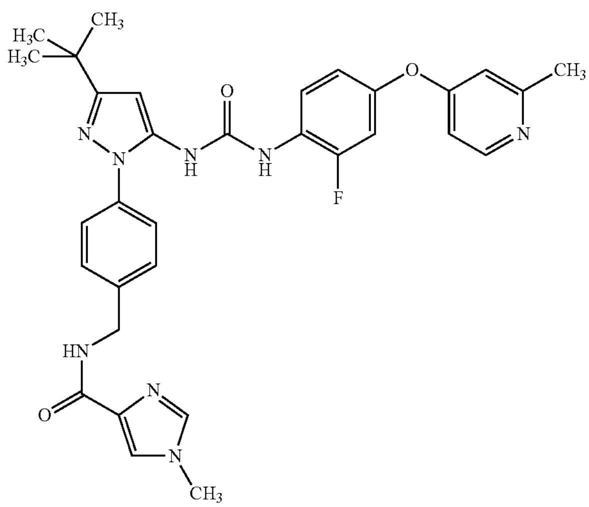 | N-[4-(3-tert-butyl-5-{[({2-fluoro-4-[(2-methylpyridin-4-yl)oxy]phenyl}amino)carbonyl]amino}-1H-pyrazol-1-yl)benzyl]-1-methyl-1H-imidazole-4-carboxamide | 597 | 2.22 |
| 200 | 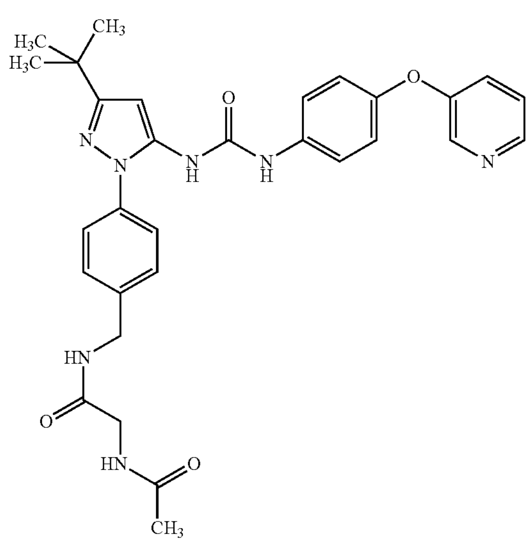 | N2-acetyl-N-(4-{3-tert-butyl-5-[({[4-(pyridin-3-yloxy)phenyl]amino}carbonyl)amino]-1H-pyrazol-1-yl}benzyl)glycinamide | 556 | 2.38 |

| Ex. No. | Structure | IUPAC name | LC-MS m/z (MH+) | Ret. time (min) |
|---|---|---|---|---|
| 201 | 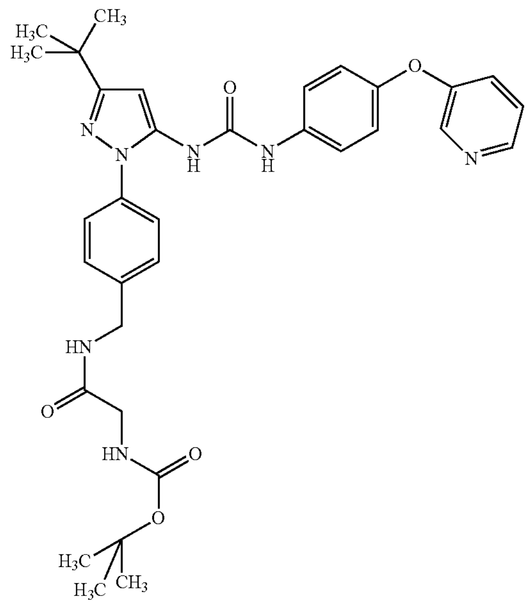 | tert-butyl {2-[(4-{3-tert-butyl-5-[({[4-(pyridin-3-yloxy)phenyl]amino}carbonyl)amino]-1H-pyrazol-1-yl}benzyl)amino]-2-oxoethyl}carbamate | 613 | 2.74 |
| 202 | 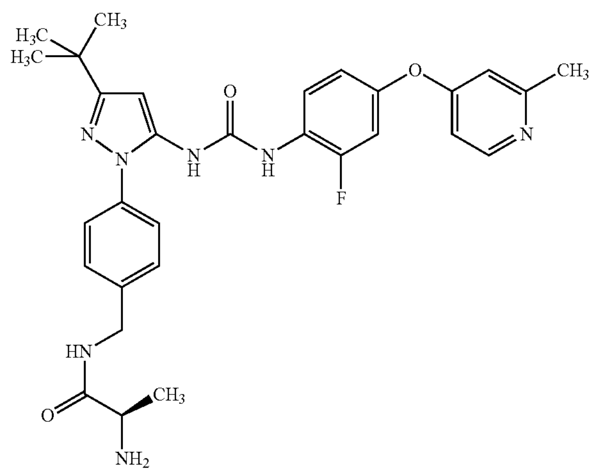 | N-[4-(3-tert-butyl-5-{[({2-fluoro-4-[(2-methylpyridin-4-yl)oxy]phenyl}amino)carbonyl]amino}-1H-pyrazol-1-yl)benzyl]alaninamide | 560 | 2.05 |
| 203 | 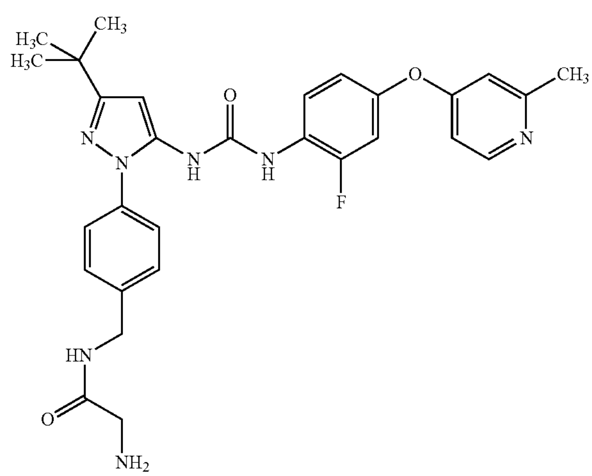 | N-[4-(3-tert-butyl-5-{[({2-fluoro-4-[(2-methylpyridin-4-yl)oxy]phenyl}amino)carbonyl]amino}-1H-pyrazol-1-yl)benzyl]glycinamide | 546 | 2.10 |

-continued

| Ex. No. | Structure | IUPAC name | LC-MS m/z (MH+) | Ret. time (min) |
|---|---|---|---|---|
| 204 | 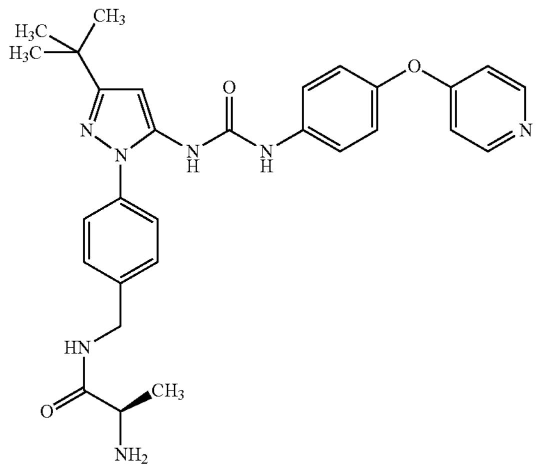 | N-(4-{3-tert-butyl-5-[({[4-(pyridin-4-yloxy)phenyl]amino}carbonyl)amino]-1H-pyrazol-1-yl}benzyl)alaninamide | 528 | 2.02 |
| 205 | 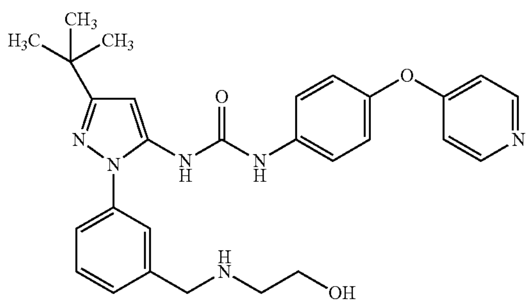 | N-[3-tert-butyl-1-(3-{[(2-hydroxyethyl)amino]methyl}phenyl)-1H-pyrazol-5-yl]-N'-[4-(pyridin-4-yloxy)phenyl]urea | 501 | 2.11 |
| 206 | 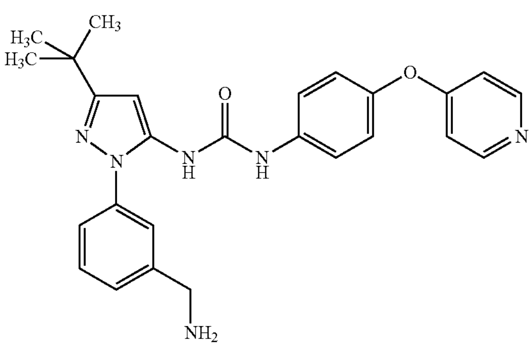 | N-{1-[3-(aminomethyl)phenyl]-3-tert-butyl-1H-pyrazol-5-yl}-N'-[4-(pyridin-4-yloxy)phenyl]urea | 457 | 2.00 |
| 207 | 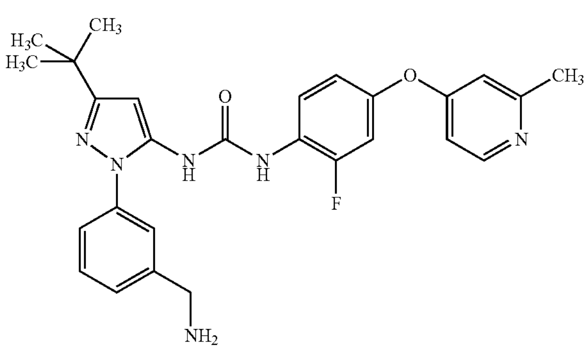 | N-{1-[3-(aminomethyl)phenyl]-3-tert-butyl-1H-pyrazol-5-yl}-N'-{2-fluoro-4-[(2-methylpyridin-4-yl)oxy]phenyl}urea | 489 | 2.09 |

| Ex. No. | Structure | IUPAC name | LC-MS m/z (MH+) | Ret. time (min) |
|---|---|---|---|---|
| 208 | 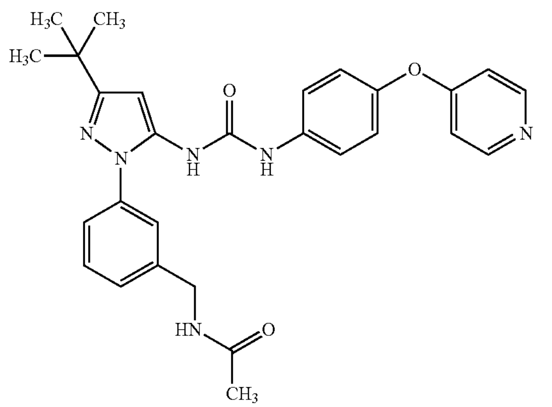 | N-(3-{3-tert-butyl-5-[({[4-(pyridin-4-yloxy)phenyl]amino}carbonyl)amino]-1H-pyrazol-1-yl}benzyl)acetamide | 499 | 2.30 |
| 209 | 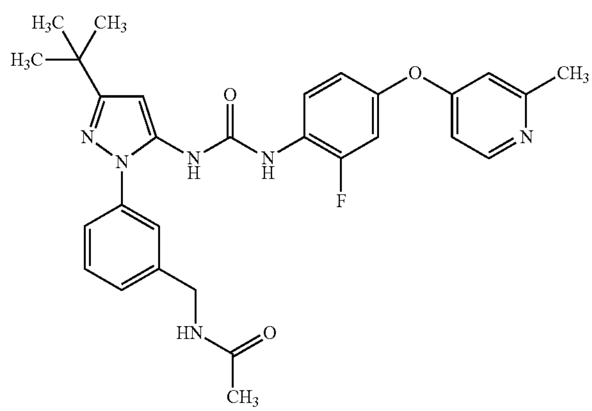 | N-[3-(3-tert-butyl-5-{[({2-fluoro-4-[(2-methylpyridin-4-yl)oxy]phenyl}amino)carbonyl]amino}-1H-pyrazol-1-yl)benzyl]acetamide | 531 | 2.36 |
| 210 | 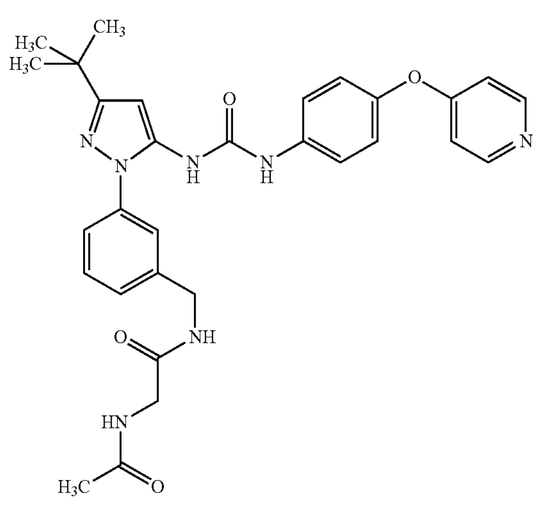 | N2-acetyl-N-(3-{3-tert-butyl-5-[({[4-(pyridin-4-yloxy)phenyl]amino}carbonyl)amino]-1H-pyrazol-1-yl}benzyl)glycinamide | 556 | 1.61 |

| Ex. No. | Structure | IUPAC name | LC-MS m/z (MH+) | Ret. time (min) |
|---|---|---|---|---|
| 211 | 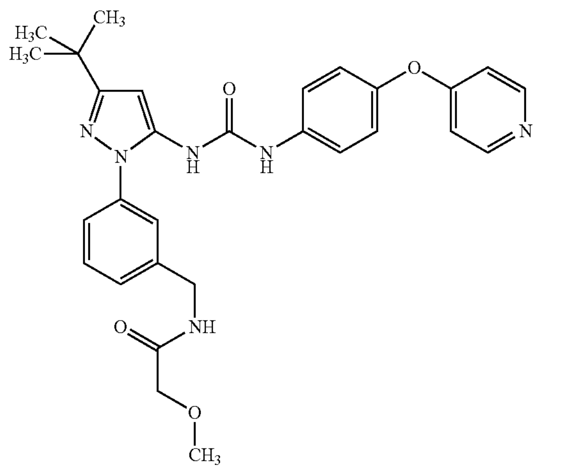 | N-(3-{3-tert-butyl-5-[({[4-(pyridin-4-yloxy)phenyl]amino}carbonyl)amino]-1H-pyrazol-1-yl}benzyl)-2-methoxyacetamide | 529 | 1.82 |
| 212 | 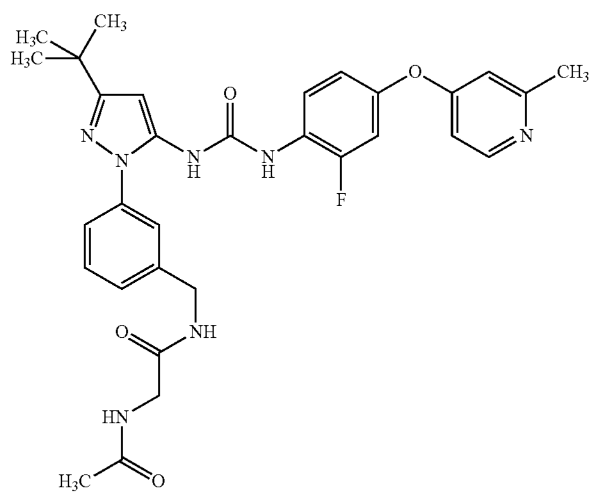 | N2-acetyl-N-[3-(3-tert-butyl-5-{[({2-fluoro-4-[(2-methylpyridin-4-yl)oxy]phenyl}amino)carbonyl]amino}-1H-pyrazol-1-yl)benzyl]glycinamide | 588 | 1.68 |
| 213 | 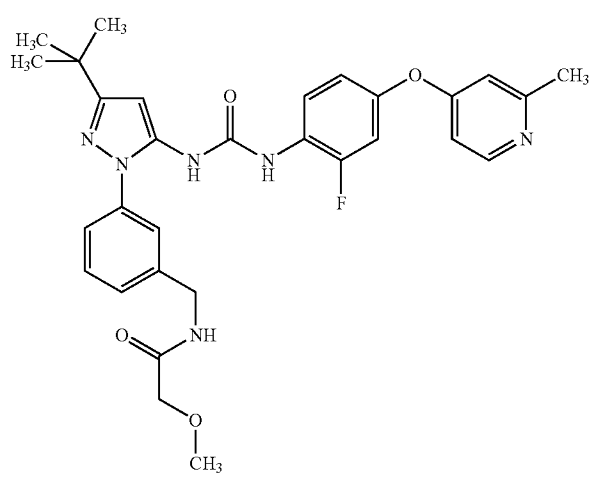 | N-[3-(3-tert-butyl-5-{[({2-fluoro-4-[(2-methylpyridin-4-yl)oxy]phenyl}amino)carbonyl]amino}-1H-pyrazol-1-yl)benzyl]-2-methoxyacetamide | 561 | 1.86 |

| Ex. No. | Structure | IUPAC name | LC-MS m/z (MH+) | Ret. time (min) |
|---|---|---|---|---|
| 214 | 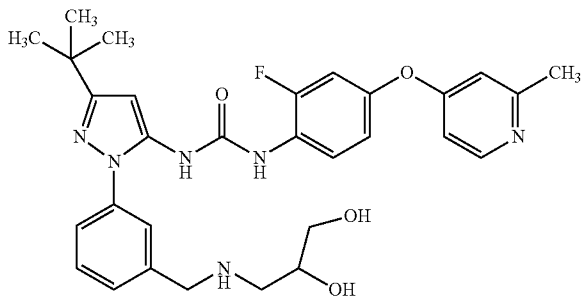 | N-[3-tert-butyl-1-(3-{[(2,3-dihydroxypropyl)amino]methyl}phenyl)-1H-pyrazol-5-yl]-N'-{2-fluoro-4-[(2-methylpyridin-4-yl)oxy]phenyl}urea | 563 | 2.03 |
| 215 | 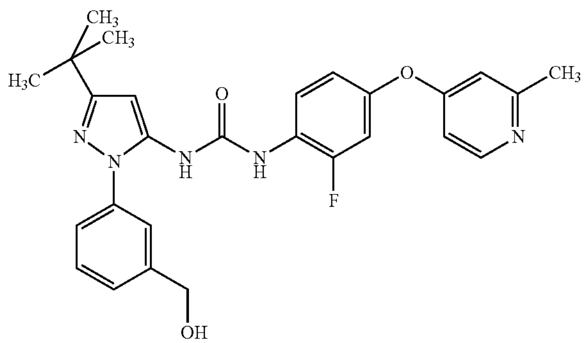 | N-{3-tert-butyl-1-[3-(hydroxymethyl)phenyl]-1H-pyrazol-5-yl}-N'-{2-fluoro-4-[(2-methylpyridin-4-yl)oxy]phenyl}urea | 490 | 2.36 |
| 216 | 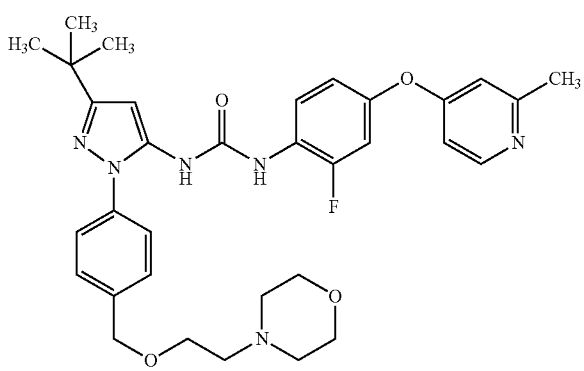 | N-(3-tert-butyl-1-{4-[(2-morpholin-4-ylethoxy)methyl]phenyl}-1H-pyrazol-5-yl)-N'-{2-fluoro-4-[(2-methylpyridin-4-yl)oxy]phenyl}urea | 603 | 2.05 |
| 217 | 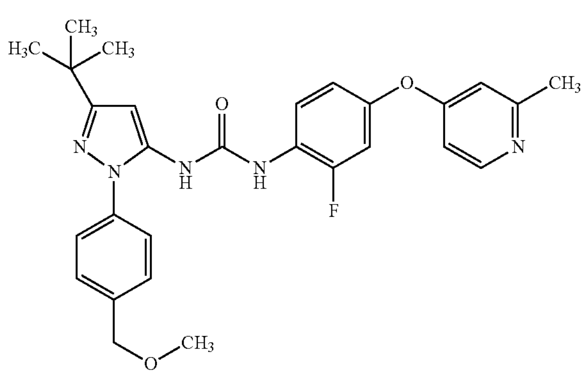 | N-{3-tert-butyl-1-[4-(methoxymethyl)phenyl]-1H-pyrazol-5-yl}-N'-{2-fluoro-4-[(2-methylpyridin-4-yl)oxy]phenyl}urea | 504 | 2.60 |

| Ex. No. | Structure | IUPAC name | LC-MS m/z (MH+) | Ret. time (min) |
|---|---|---|---|---|
| 218 | 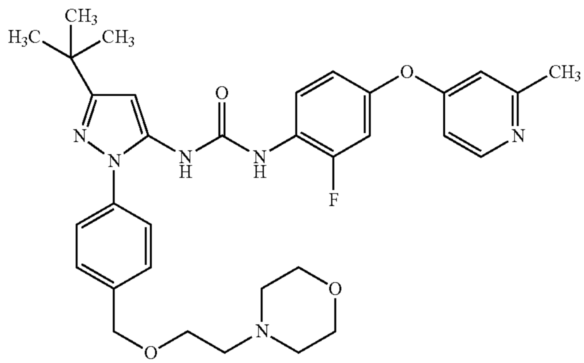 | N-(3-tert-butyl-1-{4-[(2-morpholin-4-ylethoxy)methyl]phenyl}-1H-pyrazol-5-yl)-N'-{2-fluoro-4-[(2-methylpyridin-4-yl)oxy]phenyl}urea | 603 | 2.05 |
| 219 | 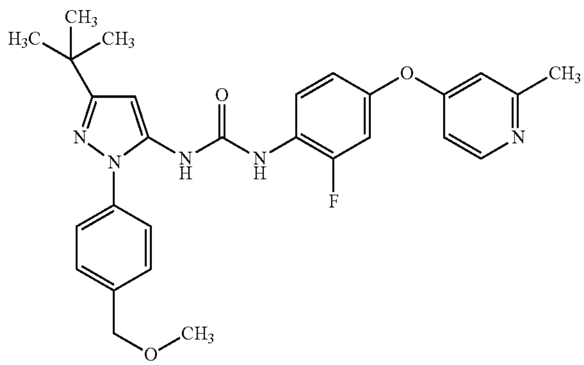 | N-{3-tert-butyl-1-[4-(methoxymethyl)phenyl]-1H-pyrazol-5-yl}-N'-{2-fluoro-4-[(2-methoxypyridin-4-yl)oxy]phenyl}urea | 504 | 2.60 |
| 220 | 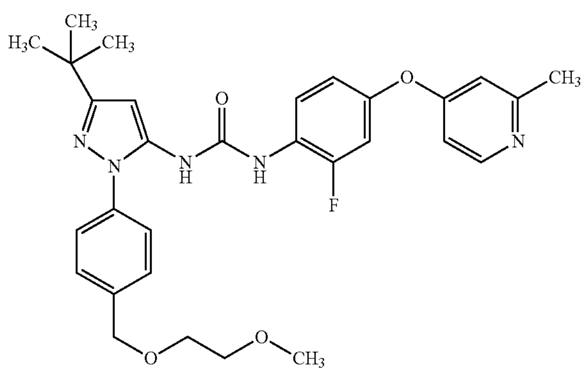 | N-(3-tert-butyl-1-{4-[(2-methoxyethoxy)methyl]phenyl}-1H-pyrazol-5-yl)-N'-{2-fluoro-4-[(2-methylpyridin-4-yl)oxy]phenyl}urea | 548 | 2.69 |
| 221 | 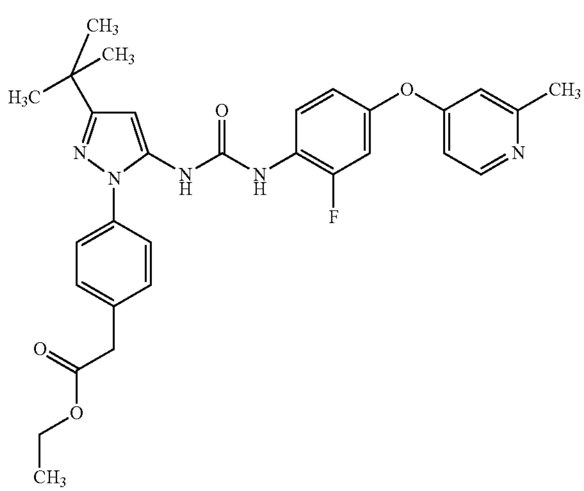 | ethyl [4-(3-tert-butyl-5-{[({2-fluoro-4-[(2-methylpyridin-4-yl)oxy]phenyl}amino)carbonyl]amino}-1H-pyrazol-1-yl)phenyl]acetate | 546 | 2.73 |

| Ex. No. | Structure | IUPAC name | LC-MS m/z (MH+) | Ret. time (min) |
|---|---|---|---|---|
| 222 | 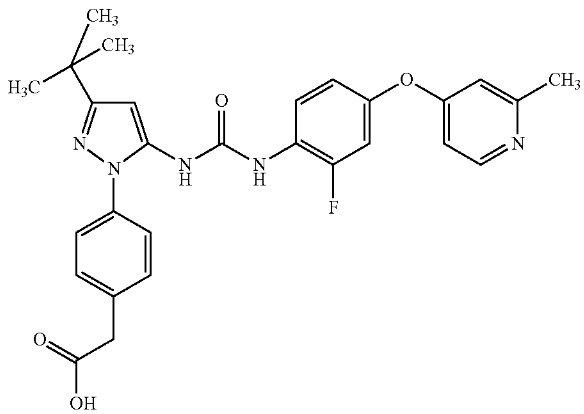 | [4-(3-tert-butyl-5-{[({2-fluoro-4-[(2-methylpyridin-4-yl)oxy]phenyl}amino)carbonyl]amino}-1H-pyrazol-1-yl)phenyl]acetic acid | 518 | 2.44 |
| 223 | 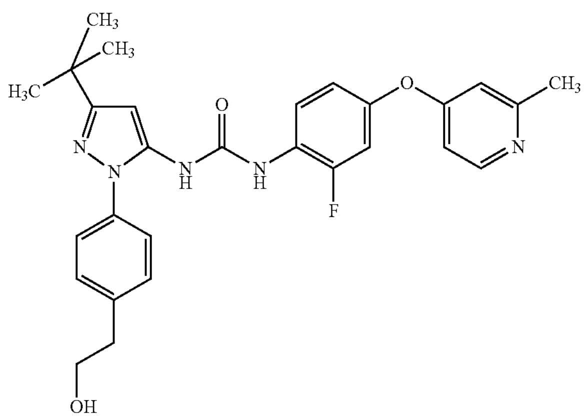 | N-{3-tert-butyl-1-[4-(2-hydroxyethyl)phenyl]-1H-pyrazol-5-yl}-N'-{2-fluoro-4-[(2-methylpyridin-4-yl)oxy]phenyl}urea | 504 | 2.44 |
| 224 | 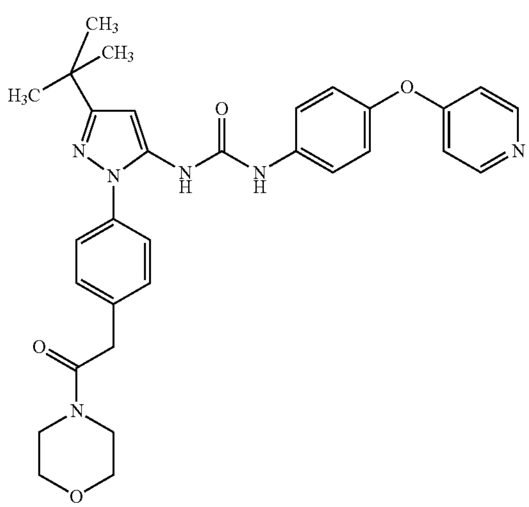 | N-{3-tert-butyl-1-[4-(2-morpholin-4-yl-2-oxoethyl)phenyl]-1H-pyrazol-5-yl}-N'-[4-(pyridin-4-yloxy)phenyl]urea | 555 | 2.36 |

| Ex. No. | Structure | IUPAC name | LC-MS m/z (MH+) | Ret. time (min) |
|---|---|---|---|---|
| 225 | 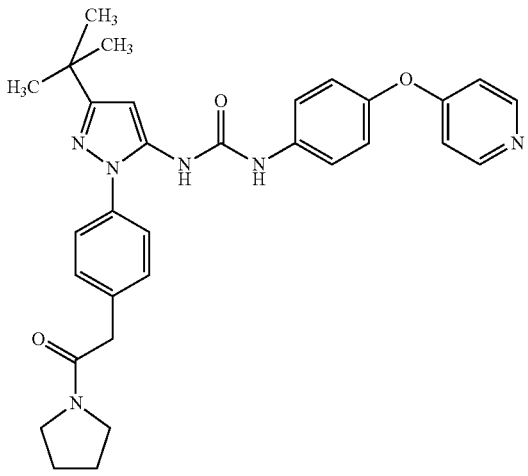 | N-{3-tert-butyl-1-[4-(2-oxo-2-pyrrolidin-1-ylethyl)phenyl]-1H-pyrazol-5-yl}-N'-[4-(pyridin-4-yloxy)phenyl]urea | 539 | 2.46 |
| 226 | 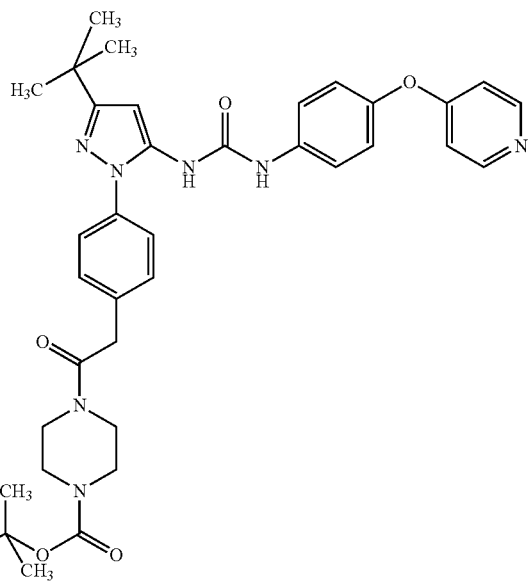 | tert-butyl 4-[(4-{3-tert-butyl-5-[({[4-(pyridin-4-yloxy)phenyl]amino}carbonyl)amino]-1H-pyrazol-1-yl}phenyl)acetyl]piperazine-1-carboxylate | 654 | 2.72 |

-continued
| Ex. No. | Structure | IUPAC name | LC-MS m/z (MH+) | Ret. time (min) |
|---|---|---|---|---|
| 227 | 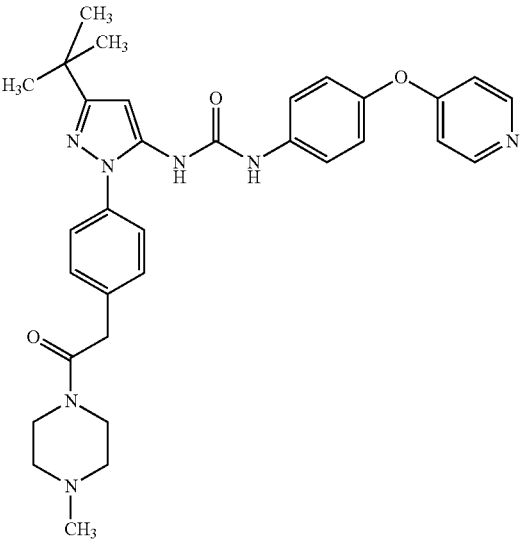 | N-(3-tert-butyl-1-{4-[2-(4-methylpiperazin-1-yl)-2-oxoethyl]phenyl}-1H-pyrazol-5-yl)-N'-[4-(pyridin-4-yloxy)phenyl]urea | 568 | 2.10 |
| 228 | 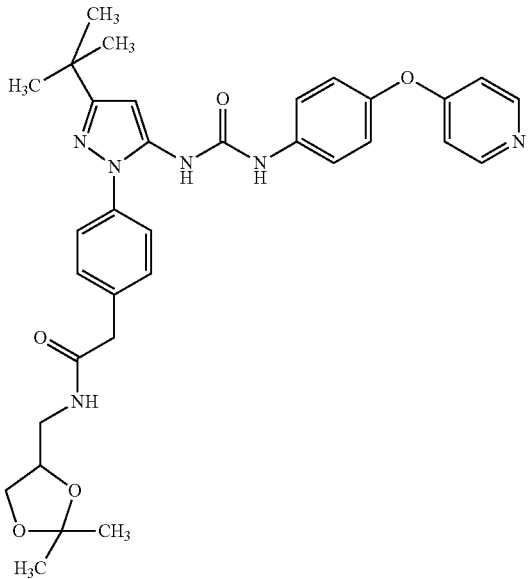 | 2-(4-{3-tert-butyl-5-[({[4-(pyridin-4-yloxy)phenyl]amino}carbonyl)amino]-1H-pyrazol-1-yl}phenyl)-N-[(2,2-dimethyl-1,3-dioxolan-4-yl)methyl]acetamide | 599 | 2.86 |

| Ex. No. | Structure | IUPAC name | LC-MS m/z (MH+) | Ret. time (min) |
|---|---|---|---|---|
| 229 | 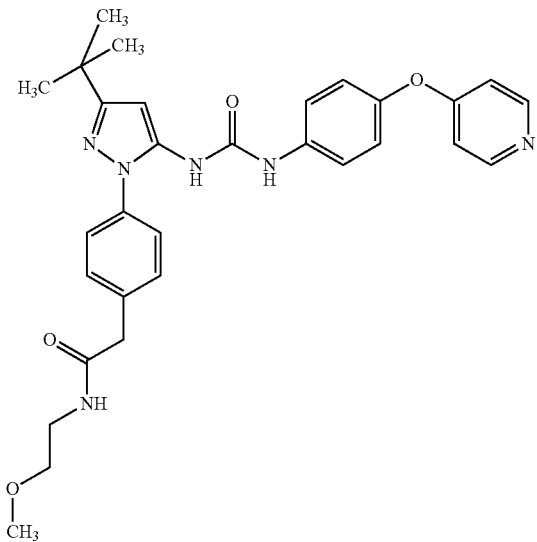 | 2-(4-{3-tert-butyl-5-[({[4-(pyridin-4-yloxy)phenyl]amino}carbonyl)amino]-1H-pyrazol-1-yl}phenyl)-N-(2-methoxyethyl)acetamide | 543 | 2.75 |
| 230 | 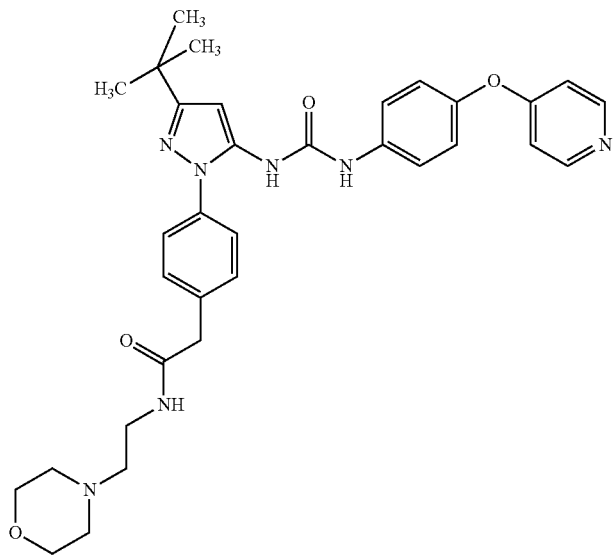 | 2-(4-{3-tert-butyl-5-[({[4-(pyridin-4-yloxy)phenyl]amino}carbonyl)amino]-1H-pyrazol-1-yl}phenyl)-N-(2-morpholin-4-ylethyl)acetamide | 598 | 2.12 |

| Ex. No. | Structure | IUPAC name | LC-MS m/z (MH+) | Ret. time (min) |
|---|---|---|---|---|
| 231 | Chiral | N-[3-tert-butyl-1-(4-{2-[(3R)-3-hydroxypyrrolidin-1-yl]-2-oxoethyl}phenyl)-1H-pyrazol-5-yl]-N'-[4-(pyridin-4-yloxy)phenyl]urea | 555 | 2.28 |
| 232 | 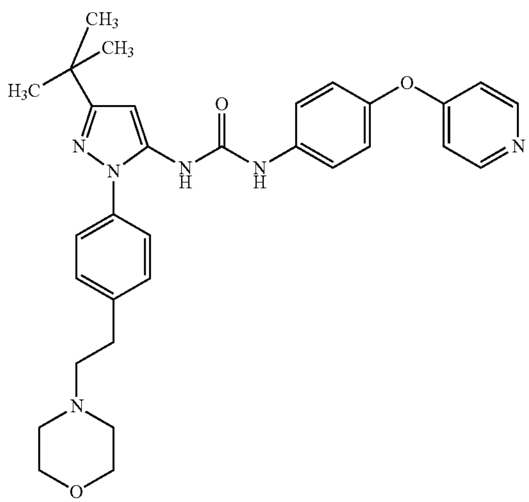 | N-{3-tert-butyl-1-[4-(2-morpholin-4-ylethyl)phenyl]-1H-pyrazol-5-yl}-N'-[4-(pyridin-4-yloxy)phenyl]urea | 541 | 1.65 |
| 233 | 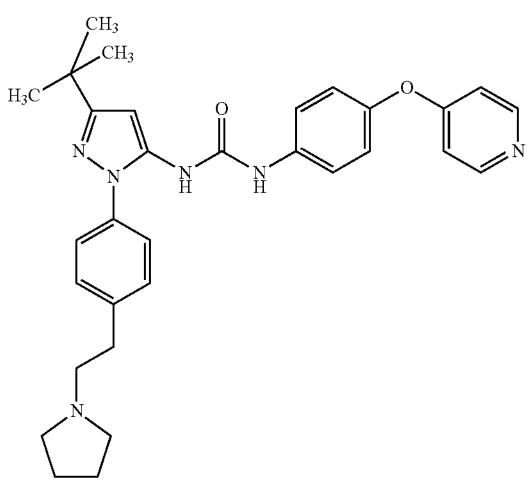 | N-{3-tert-butyl-1-[4-(2-pyrrolidin-1-ylethyl)phenyl]-1H-pyrazol-5-yl}-N'-[4-(pyridin-4-yloxy)phenyl]urea | 525 | 1.69 |

-continued
| Ex. No. | Structure | IUPAC name | LC-MS m/z (MH+) | Ret. time (min) |
|---|---|---|---|---|
| 234 | 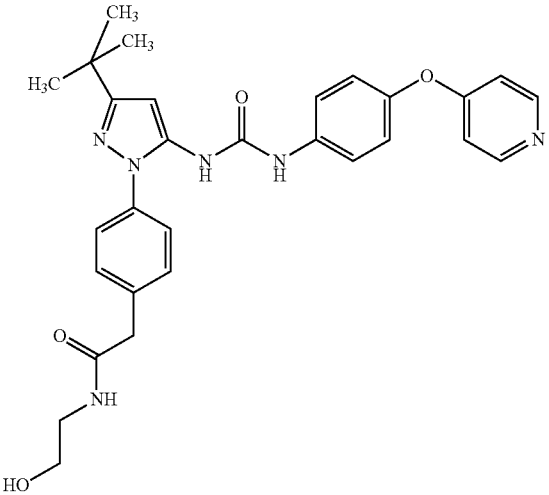 | 2-(4-{3-tert-butyl-5-[({[4-(pyridin-4-yloxy)phenyl]amino}carbonyl)amino]-1H-pyrazol-1-yl}phenyl)-N-(2-hydroxyethyl)acetamide | 529 | 2.20 |
| 235 | 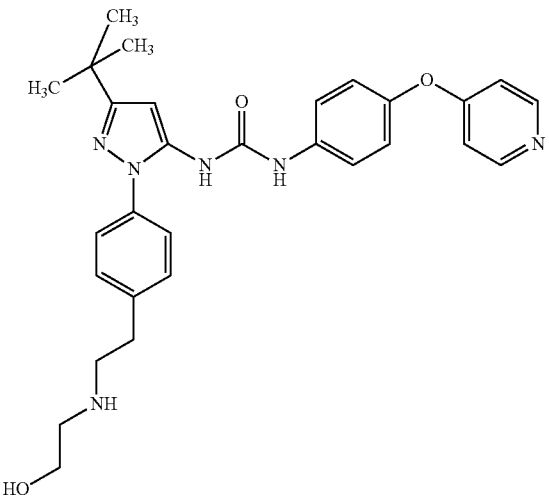 | N-[3-tert-butyl-1-(4-{2-[(2-hydroxyethyl)amino]ethyl}phenyl)-1H-pyrazol-5-yl]-N'-[4-(pyridin-4-yloxy)phenyl]urea | 515 | 2.02 |
| 236 | 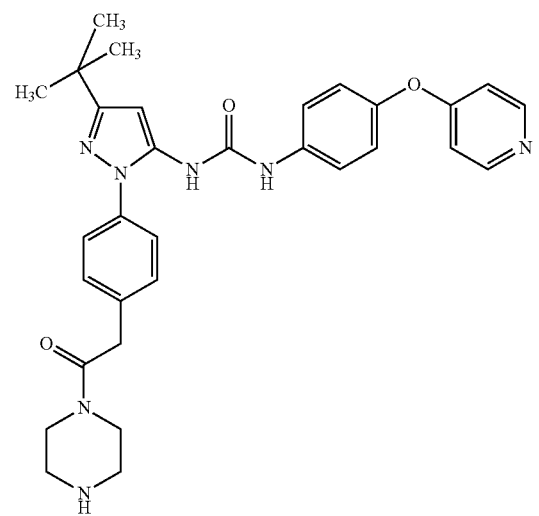 | N-{3-tert-butyl-1-[4-(2-oxo-2-piperazin-1-ylethyl)phenyl]-1H-pyrazol-5-yl}-N'-[4-(pyridin-4-yloxy)phenyl]urea | 554 | 2.02 |

| Ex. No. | Structure | IUPAC name | LC-MS m/z (MH+) | Ret. time (min) |
|---|---|---|---|---|
| 237 | Chiral 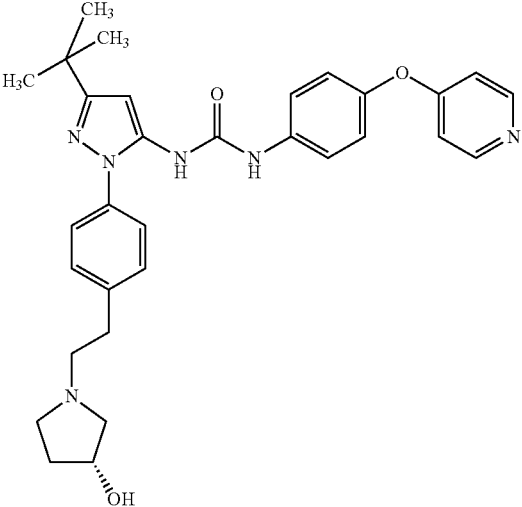 | N-[3-tert-butyl-1-(4-{2-[(3R)-3-hydroxypyrrolidin-1-yl]ethyl}phenyl)-1H-pyrazol-5-yl]-N'-[4-(pyridin-4-yloxy)phenyl]urea | 541 | 2.04 |
| 238 | 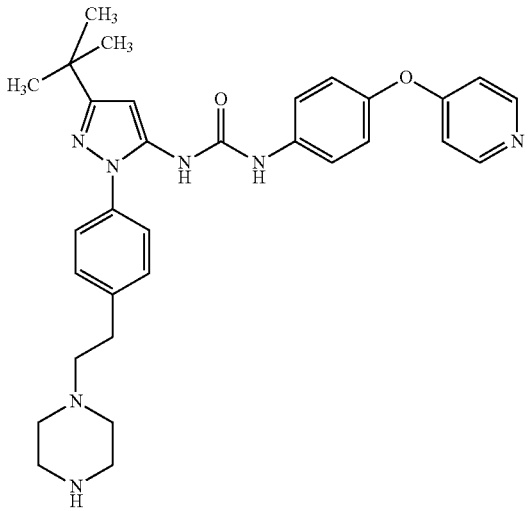 | N-{3-tert-butyl-1-[4-(2-piperazin-1-ylethyl)phenyl]-1H-pyrazol-5-yl}-N'-[4-(pyridin-4-yloxy)phenyl]urea | 540 | 1.92 |

-continued

| Ex. No. | Structure | IUPAC name | LC-MS m/z (MH+) | Ret. time (min) |
|---|---|---|---|---|
| 239 | 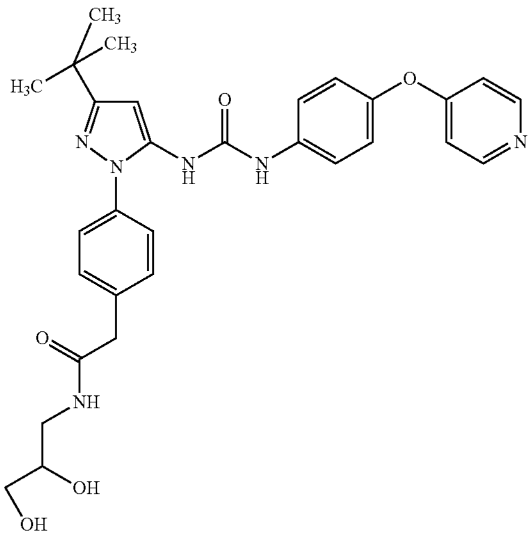 | 2-(4-{3-tert-butyl-5-[({[4-(pyridin-4-yloxy)phenyl]amino}carbonyl)amino]-1H-pyrazol-1-yl}phenyl)-N-(2,3-dihydroxypropyl)acetamide | 559 | 2.18 |
| 240 | 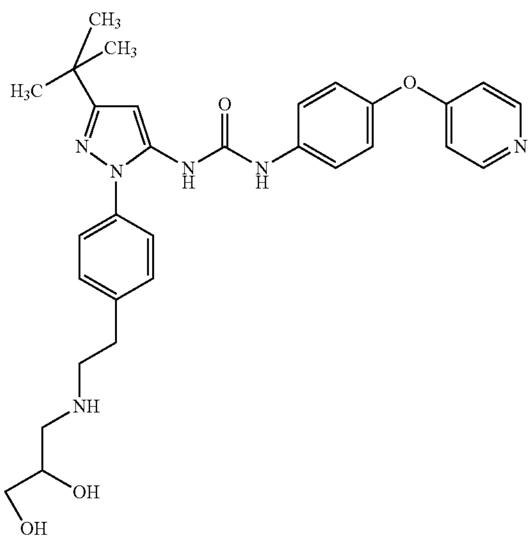 | N-[3-tert-butyl-1-(4-{2-[(2,3-dihydroxypropyl)amino]ethyl}phenyl)-1H-pyrazol-5-yl]-N'-[4-(pyridin-4-yloxy)phenyl]urea | 545 | 2.01 |
| 241 | 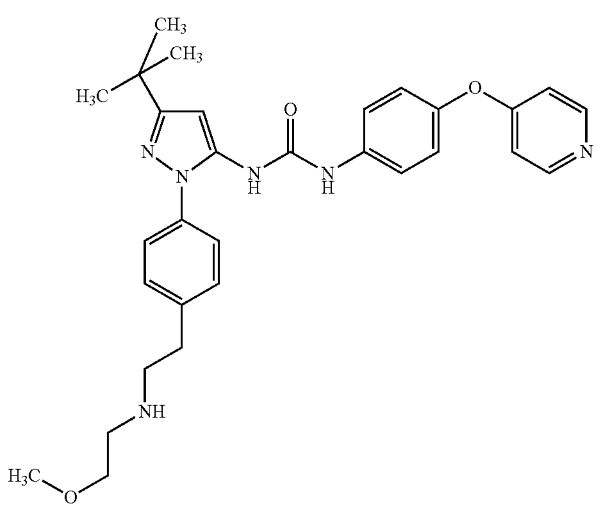 | N-[3-tert-butyl-1-(4-{2-[(2-methoxyethyl)amino]ethyl}phenyl)-1H-pyrazol-5-yl]-N'-[4-(pyridin-4-yloxy)phenyl]urea | 529 | 2.06 |

| Ex. No. | Structure | IUPAC name | LC-MS m/z (MH+) | Ret. time (min) |
|---|---|---|---|---|
| 242 | 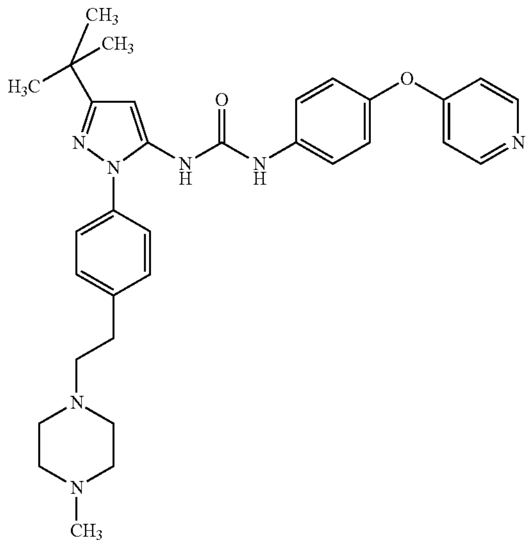 | N-(3-tert-butyl-1-{4-[2-(4-methylpiperazin-1-yl)ethyl]phenyl}-1H-pyrazol-5-yl)-N'-[4-(pyridin-4-yloxy)phenyl]urea | 554 | 2.00 |
| 243 | 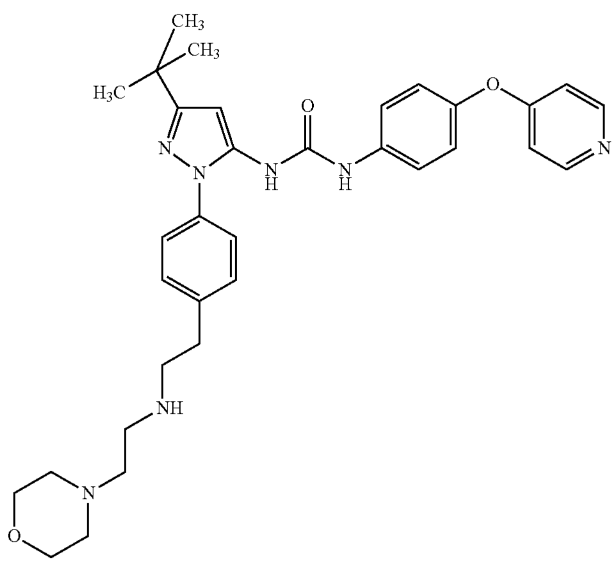 | N-[3-tert-butyl-1-(4-{2-[(2-morpholin-4-ylethyl)amino]ethyl}phenyl)-1H-pyrazol-5-yl]-N'-[4-(pyridin-4-yloxy)phenyl]urea | 584 | 1.97 |

What is claimed is:

1. A method of treating ovarian cancer, breast cancer, pancreatic cancer, and prostate cancer comprising administering to a mammal in need thereof a therapeutically effective amount of a compound of formula I or a pharmaceutically acceptable salt stereoisomer, alkyl ester prodrug or phenyl($C_1$-$C_5$) alkyl ester prodrug thereof,

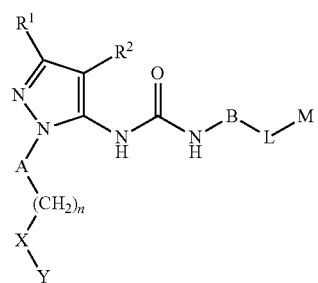

Formula I wherein $R^1$ and $R^2$ are independently:
(a) hydrogen;
(b) $(C_1-C_5)$alkyl, optionally substituted with one or more of hydroxy or fluoro; or
(c) halogen;

A is phenyl, pyridine, or pyrimidine, optionally substituted with 1 or 2 substituents that are independently $(C_1-C_5)$alkyl, $(C_1-C_5)$alkoxy, $(C_1-C_5)$haloalkyl, $(C_1-C_5)$haloalkoxy, or halogen;

B is phenylene or naphthalene, optionally substituted with 1 to 4 substituents that are independently $(C_1-C_5)$alkyl, $(C_1-C_5)$alkoxy, $(C_1-C_5)$haloalkyl, $(C_1-C_5)$haloalkoxy, or halogen;

L is a bridging group which is —O—, —S—, or —$CH_2$—;

M is phenyl, pyridine or pyrimidine, optionally substituted with 1 to 3 substituents that are independently:
(1) $(C_1-C_5)$alkyl;
(2) $(C_1-C_5)$haloalkyl;
(3) —O—$R^3$;
(4) —$NR^3R^4$;
(5) halogen;
(6) —C(O)$NR^3R^4$;
(7) cyano;
(8) C(O)$R^3$;
(9) —C≡C—$R^3$ or
(10) nitro;

n is zero or one and

X is:
(1) —O—;
(2) —$SO_2$—;
(3) —$NR^5$—;
(4) —$NR^5$—$SO_2$—;
(5) —N($SO_2NR^7R^8$)—;
(6) —$SO_2$—$NR^5$—;
(7) —$NR^5$—C(O)—;
(8) —C(O)—$NR^5$—;
(9) —C(O)— or
(10) a single bond;

Y is a linear or branched $C_1$ to $C_6$ alkyl fragment that is substituted with one or two Z groups, where each Z group is independently:
(1) —$OR^6$;
(2) —O—C(O)—$R^6$;
(3) —$NR^7R^8$;
(4) —$SO_2$—$(C_1-C_5)$alkyl;
(5) —C(O)—O—$R^6$;
(6) —NH—C(O)—$R^6$;
(7) —C(O)—$NR^7R^8$ or
(8) a monocyclic, saturated, partially saturated, or aromatic heterocycle of 5-7 ring atoms containing at least one heteroatom selected from N, O, or S, that is optionally substituted with 1 to 3 substituents selected from $(C_1-C_5)$alkyl, $(C_1-C_5)$haloalkyl, hydroxy, amino, halogen, or oxo;

with the proviso that when n is zero and X is —O—, —$NR^3$—, or a single bond, then Z is not morpholine, piperidine, imidazole, or tetrazole;

with the further proviso that when n is zero and X is a single bond, then Z is not —$NR^7R^8$;

$R^3$, $R^4$, $R^5$ and $R^6$ are each independently hydrogen or $(C_1-C_5)$alkyl optionally substituted with hydroxy; and $R^7$ and $R^8$ are independently hydrogen, or $(C_1-C_5)$alkyl optionally substituted with hydroxy; or the group —$NR^7R^8$ forms a monocyclic saturated heterocyclic ring having 5 to 7 ring atoms optionally substituted on a carbon atom with hydroxy, where, in addition to the nitrogen atom in the group —$NR^7R^8$, zero to two of the other ring atoms is a hetero atom selected from N, O and S, and the remaining ring atoms are carbon.

2. A method according to claim 1, wherein said cancer is of the breast.

3. A method according to claim 2, wherein said breast cancer is invasive ductal carcinoma, invasive lobular carcinoma, ductal carcinoma in situ, or lobular carcinoma in situ.

4. A method according to claim 1, wherein said cancer is prostate cancer.

5. A method according to claim 1, wherein said cancer is pancreatic cancer.

6. A method of treating diabetic retinopathy, ischemic retinal-vein occlusion, retinopathy of prematurity, age-related macular degeneration, neovascular glaucoma, psoriasis, retrolental fibroplasias, angiofibroma, rheumatoid arthritis, restenosis, in-stent restenosis, or vascular graft restenosis, comprising administering to a mammal in need thereof a therapeutically effective amount of a compound of formula I or a pharmaceutically acceptable salt stereoisomer, alkyl ester prodrug or phenyl$(C_1-C_5)$ alkyl ester prodrug thereof, Formula I wherein $R^1$ and $R^2$ are independently:
(a) hydrogen;
(b) $(C_1-C_5)$alkyl, optionally substituted with one or more of hydroxy or fluoro; or
(c) hydrogen;

A is phenyl, pyridine, or pyrimidine, optionally substituted with 1 or 2 substituents that are independently $(C_1-C_5)$alkyl, $(C_1-C_2)$alkoxy, $(C_1-C_5)$haloalkyl, $(C_1-C_5)$haloalkoxy, or halogen;

B is phenylene or naphthylene optionally substituted with 1 to 4 substituents that are independently $(C_1-C_5)$alkyl, $(C_1-C_5)$alkoxy, $(C_1-C_5)$haloalkyl, $(C_1-C_5)$haloalkoxy, or halogen;

L is a bridging group which is —O—, —S—, or —$CH_2$—;

M is phenyl, pyridine or pyrimidine, optionally substituted with 1 to 3 substituents that are independently:
(1) $(C_1-C_5)$alkyl;
(2) $(C_1-C_5)$haloalkyl;
(3) —O—$R^3$;
(4) —$NR^3R^4$;
(5) halogen;
(6) —C(O)$NR^3R^4$;
(7) cyano;
(8) C(O)$R^3$;
(9) —C≡C—$R^3$ or
(10) nitro;

n is zero or one and

X is:
(1) —O—;
(2) —$SO_2$;

(3) —$NR^5$;
(4) —$NR^5$—$SO_2$—;
(5) —$N(SO_2NR^7R^8)$—;
(6) —$SO_2$—$NR^5$—;
(7) —$NR^5$—C(O)—;
(8) —C(O)—$NR^5$—;
(9) —C(O)— or
(10) a single bond;

Y is a linear or branched $C_1$ to $C_6$ alkyl fragment that is substituted with one or two groups, where each Z group is independently:
(1) —$OR^6$;
(2) —O—C(O)—$R^6$;
(3) —$NR^7R^8$;
(4) —$SO_2$—($C_1$-$C_5$)alkyl;
(5) —C(O)—O—$R^6$;
(6) —NH—C(O)—$R^6$;
(7) —C(O)—$NR^7R^8$ or
(8) a monocyclic, saturated, partially saturated, or aromatic heterocycle of 5-7 ring atoms containing at least one heteroatom selected from N, O, or S, that is optionally substituted with 1 to 3 substituents selected from ($C_1$-$C_5$)alkyl, ($C_1$-$C_5$)haloalkyl, hydroxy, amino, halogen, or oxo;

with the proviso that when n is zero and X is —O—, —$NR^3$—, or a single bond, then Z is not morpholine, piperidine, imidazole, or tetrazole;

with the further proviso that when n is zero and X is a single bond, then Z is not —$NR^7R^8$;

$R^3$, $R^4$, $R^5$ and $R^6$ are each independently hydrogen or ($C_1$-$C_5$)alkyl optionally substituted with hydroxy; and $R^7$ and $R^8$ are independently hydrogen, or ($C_1$-$C_5$)alkyl optionally substituted with hydroxy; or the group —$NR^7R^8$ forms a monocyclic saturated heterocyclic ring having 5 to 7 ring atoms optionally substituted on a carbon atom with hydroxy, where, in addition to the nitrogen atom in the group —$NR^7R^8$, zero to two of the other ring atoms is a hetero atom selected from N, O and S, and the remaining ring atoms are carbon.

* * * * *